(12) United States Patent
Korb et al.

(10) Patent No.: US 8,915,592 B2
(45) Date of Patent: Dec. 23, 2014

(54) APPARATUSES AND METHODS OF OCULAR SURFACE INTERFEROMETRY (OSI) EMPLOYING POLARIZATION AND SUBTRACTION FOR IMAGING, PROCESSING, AND/OR DISPLAYING AN OCULAR TEAR FILM

(71) Applicant: TearScience, Inc., Morrisville, NC (US)

(72) Inventors: Donald R. Korb, Boston, MA (US); William L. Weber, Olivebridge, NY (US); Randal B. Chinnock, Southbridge, MA (US); Benjamin T. Gravely, Raleigh, NC (US); Stephen M. Grenon, Durham, NC (US)

(73) Assignee: TearScience, Inc., Morrisville, NC (US)

( * ) Notice: Subject to any disclaimer, the term of this patent is extended or adjusted under 35 U.S.C. 154(b) by 0 days.

(21) Appl. No.: 13/870,054

(22) Filed: Apr. 25, 2013

(65) Prior Publication Data

US 2013/0308095 A1    Nov. 21, 2013

Related U.S. Application Data

(63) Continuation-in-part of application No. 12/798,325, filed on Apr. 1, 2010, now Pat. No. 8,545,017.

(60) Provisional application No. 61/638,231, filed on Apr. 25, 2012, provisional application No. 61/211,596, filed on Apr. 1, 2009.

(51) Int. Cl.
*A61B 3/14*   (2006.01)
*A61B 3/10*   (2006.01)
(Continued)

(52) U.S. Cl.
CPC ............... *A61B 3/101* (2013.01); *A61B 3/0025* (2013.01); *G06T 2207/20224* (2013.01);
(Continued)

(58) Field of Classification Search
USPC ......... 351/206, 200, 205, 209–210, 221–223, 351/245–246, 212, 208, 160 R, 159, 247; 600/356, 346, 476, 425
See application file for complete search history.

(56) References Cited

U.S. PATENT DOCUMENTS

| | | |
|---|---|---|
| 3,941,901 A | 3/1976 | Harsch |
| 3,971,952 A | 7/1976 | Inbar et al. |

(Continued)

FOREIGN PATENT DOCUMENTS

| | | |
|---|---|---|
| DE | 3108878 A1 | 9/1982 |
| EP | 0943288 A1 | 9/1999 |

(Continued)

OTHER PUBLICATIONS

Author Unknown, "Tonney's RT-7000 is new and improved," Instruments—New Product Gallery, Vision Care Product News (VCPN), Jul. 2008, 1 page.

(Continued)

*Primary Examiner* — Dawayne A Pinkney
(74) *Attorney, Agent, or Firm* — Withrow & Terranova PLLC

(57) ABSTRACT

Apparatuses and methods employing ocular surface interferometry (OSI) employing polarization and subtraction for imaging, processing, and/or displaying an ocular tear film are disclosed. The apparatuses and methods can be employed for measuring tear film layer thickness (TFLT) of the ocular tear film, which includes lipid layer thickness (LLT) and/or aqueous layer thickness (ALT). An imaging device is focused on the lipid layer of the tear film to capture optical wave interference interactions of specularly reflected light from the tear film combined with a background signal(s) in a first image. The imaging device is focused on the lipid layer of the tear film to capture a second image containing background signal(s) in the first image. The second image can be subtracted from the first image to reduce and/or eliminate background signal(s) in the first image to produce a resulting image that can be analyzed to measure tear film layer thickness (TFLT).

32 Claims, 64 Drawing Sheets
(27 of 64 Drawing Sheet(s) Filed in Color)

(51) Int. Cl.

| | | |
|---|---|---|
| *A61B 3/02* | (2006.01) | |
| *A61B 5/05* | (2006.01) | |
| *A61B 3/00* | (2006.01) | |
| *G06T 7/00* | (2006.01) | |
| *G01B 11/06* | (2006.01) | |
| *G06T 5/00* | (2006.01) | |
| *G06T 5/50* | (2006.01) | |

(52) U.S. Cl.
CPC .... *G06T 2207/10016* (2013.01); *G06T 7/0012* (2013.01); *G01B 11/0675* (2013.01); *G06T 5/002* (2013.01); *G06T 5/50* (2013.01); *G06T 2207/30041* (2013.01)
USPC .......... 351/206; 351/210; 351/221; 351/222; 600/425

(56) References Cited

U.S. PATENT DOCUMENTS

| | | | |
|---|---|---|---|
| 4,122,348 | A | 10/1978 | Bruck |
| 4,533,223 | A | 8/1985 | Duparchy |
| 4,597,648 | A | 7/1986 | Feldon et al. |
| 4,705,037 | A | 11/1987 | Peyman et al. |
| 4,747,683 | A | 5/1988 | Doane |
| 4,842,401 | A | 6/1989 | Maurice |
| 4,885,352 | A | 12/1989 | Erickson |
| 4,938,584 | A | 7/1990 | Suematsu et al. |
| 5,110,200 | A | 5/1992 | Snook |
| D330,769 | S | 11/1992 | Blaha et al. |
| 5,258,791 | A | 11/1993 | Penney et al. |
| 5,268,305 | A | 12/1993 | Ribi et al. |
| 5,427,915 | A | 6/1995 | Ribi et al. |
| 5,475,452 | A | 12/1995 | Kuhn et al. |
| 5,491,097 | A | 2/1996 | Ribi et al. |
| 5,494,829 | A | 2/1996 | Sandstrom et al. |
| 5,571,568 | A | 11/1996 | Ribi et al. |
| 5,621,523 | A | 4/1997 | Oobayashi et al. |
| 5,622,872 | A | 4/1997 | Ribi |
| 5,625,428 | A | 4/1997 | Isogai |
| 5,626,134 | A | 5/1997 | Zuckerman |
| 5,642,137 | A | 6/1997 | Kitazumi |
| 5,647,032 | A | 7/1997 | Jutamulia |
| 5,712,721 | A | 1/1998 | Large |
| 5,719,659 | A | 2/1998 | Suzuki |
| D394,505 | S | 5/1998 | Hayashi |
| 5,760,950 | A | 6/1998 | Maly et al. |
| 5,886,767 | A | 3/1999 | Snook |
| 5,988,815 | A | 11/1999 | Maus et al. |
| 6,059,773 | A | 5/2000 | Maloney et al. |
| 6,127,183 | A | 10/2000 | Ivarsson et al. |
| 6,198,540 | B1 | 3/2001 | Ueda et al. |
| 6,213,605 | B1 | 4/2001 | D'Souza et al. |
| 6,236,459 | B1 | 5/2001 | Negahdaripour |
| 6,299,305 | B1 | 10/2001 | Miwa |
| 6,394,603 | B2 | 5/2002 | Miwa et al. |
| 6,447,119 | B1 | 9/2002 | Stewart et al. |
| 6,450,641 | B2 | 9/2002 | D'Souza et al. |
| D465,850 | S | 11/2002 | Takizawa |
| D472,637 | S | 4/2003 | Cooper et al. |
| 6,659,613 | B2 | 12/2003 | Applegate et al. |
| 6,685,320 | B2 | 2/2004 | Hirohara et al. |
| 6,736,507 | B2 | 5/2004 | Kudryashov et al. |
| 6,964,814 | B2 | 11/2005 | Fujii et al. |
| 7,073,906 | B2 | 7/2006 | Portney |
| 7,121,666 | B2 | 10/2006 | Tseng et al. |
| 7,144,111 | B1 | 12/2006 | Ross, III et al. |
| D552,736 | S | 10/2007 | Yamaoka |
| 7,431,458 | B2 | 10/2008 | Jongsma et al. |
| D582,556 | S | 12/2008 | Yamaoka |
| 7,611,245 | B2 | 11/2009 | Carbonari |
| D607,562 | S | 1/2010 | Heine et al. |
| 7,654,669 | B2 | 2/2010 | Suzuki |
| 7,688,453 | B2 | 3/2010 | Williby et al. |
| 7,758,190 | B2 | 7/2010 | Korb et al. |
| 7,771,353 | B2 | 8/2010 | Luce |
| 7,982,881 | B2 | 7/2011 | Fercher et al. |
| 7,988,294 | B2 | 8/2011 | Korb et al. |
| 8,092,023 | B2 | 1/2012 | Korb et al. |
| 8,192,026 | B2 | 6/2012 | Gravely et al. |
| 8,215,774 | B2 | 7/2012 | Korb et al. |
| 8,249,695 | B2 | 8/2012 | Grenon et al. |
| 8,255,039 | B2 | 8/2012 | Gravely et al. |
| 8,545,017 | B2 | 10/2013 | Korb et al. |
| 8,585,204 | B2 | 11/2013 | Gravely et al. |
| 8,591,033 | B2 | 11/2013 | Korb et al. |
| 8,602,557 | B2 | 12/2013 | Huth et al. |
| 8,617,229 | B2 | 12/2013 | Korb et al. |
| 8,641,194 | B2 | 2/2014 | Primeau et al. |
| 2001/0055095 | A1 | 12/2001 | D'Souza et al. |
| 2002/0180929 | A1 | 12/2002 | Tseng et al. |
| 2003/0056281 | A1 | 3/2003 | Hasegawa |
| 2004/0212781 | A1 | 10/2004 | Mihashi et al. |
| 2005/0096431 | A1 | 5/2005 | Fujii et al. |
| 2005/0119737 | A1 | 6/2005 | Bene et al. |
| 2005/0159657 | A1 | 7/2005 | Cappo et al. |
| 2006/0055956 | A1 | 3/2006 | Takahashi et al. |
| 2006/0103724 | A1 | 5/2006 | Jongsma et al. |
| 2006/0109423 | A1 | 5/2006 | Wang |
| 2006/0140454 | A1 | 6/2006 | Northcott et al. |
| 2006/0159722 | A1 | 7/2006 | Braithwaite et al. |
| 2006/0270802 | A1 | 11/2006 | Washizu et al. |
| 2008/0002202 | A1 | 1/2008 | Hall et al. |
| 2008/0161741 | A1 | 7/2008 | Bene et al. |
| 2008/0273171 | A1 | 11/2008 | Huth et al. |
| 2008/0285043 | A1 | 11/2008 | Fercher et al. |
| 2008/0287808 | A1 | 11/2008 | Tearney et al. |
| 2008/0309855 | A1 | 12/2008 | Yan et al. |
| 2008/0316499 | A1 | 12/2008 | Korb et al. |
| 2008/0319323 | A1 | 12/2008 | Gravely et al. |
| 2009/0161090 | A1 | 6/2009 | Campbell et al. |
| 2009/0201465 | A1 | 8/2009 | Huth |
| 2009/0225276 | A1 | 9/2009 | Suzuki |
| 2009/0275929 | A1 | 11/2009 | Zickler |
| 2010/0026323 | A1 | 2/2010 | Tiefenthaler |
| 2010/0102211 | A1 | 4/2010 | Murooka et al. |
| 2010/0253907 | A1 | 10/2010 | Korb et al. |
| 2010/0259721 | A1 | 10/2010 | Korb et al. |
| 2010/0315591 | A1 | 12/2010 | Gratton et al. |
| 2011/0007321 | A1 | 1/2011 | Everett et al. |
| 2011/0043661 | A1 | 2/2011 | Podoleanu |
| 2011/0053283 | A1 | 3/2011 | Hood et al. |
| 2011/0096292 | A1 | 4/2011 | Saito |
| 2011/0181836 | A1 | 7/2011 | Rowe |
| 2011/0206291 | A1 | 8/2011 | Kashani et al. |
| 2011/0237999 | A1 | 9/2011 | Muller et al. |
| 2011/0273550 | A1 | 11/2011 | Amano et al. |
| 2011/0292395 | A1 | 12/2011 | Fercher et al. |
| 2013/0010257 | A1 | 1/2013 | Primeau et al. |
| 2013/0141698 | A1 | 6/2013 | Huth et al. |
| 2013/0293842 | A1 | 11/2013 | Grenon et al. |
| 2014/0104574 | A1 | 4/2014 | Grenon et al. |
| 2014/0118699 | A1 | 5/2014 | Huth et al. |

FOREIGN PATENT DOCUMENTS

| | | |
|---|---|---|
| EP | 1900320 A1 | 3/2008 |
| EP | 2189108 A1 | 5/2010 |
| EP | 2695570 A1 | 2/2014 |
| EP | 1900320 B1 | 4/2014 |
| GB | 2407378 B | 9/2006 |
| JP | 6269412 A | 9/1994 |
| JP | 7002647 A | 1/1995 |
| JP | 7136120 A | 5/1995 |
| JP | 07313464 A | 12/1995 |
| JP | 07313465 A | 12/1995 |
| JP | 8052112 A | 2/1996 |
| JP | 8098811 A | 4/1996 |
| JP | 2001309889 A | 11/2001 |
| JP | 2005211173 A | 8/2005 |
| JP | 2005211633 A | 8/2005 |
| JP | 2005230328 A | 9/2005 |
| JP | 2007068928 A | 3/2007 |
| JP | 2007209370 A | 8/2007 |

(56) References Cited

FOREIGN PATENT DOCUMENTS

| | | | |
|---|---|---|---|
| JP | 2007523382 A | 8/2007 | |
| JP | 2008246004 A | 10/2008 | |
| JP | 2009134276 A | 6/2009 | |
| KR | 101259056 B1 | 4/2013 | |
| WO | 0026614 A1 | 5/2000 | |
| WO | 2005044099 A1 | 5/2005 | |
| WO | 2007004348 A | 1/2007 | |
| WO | 2008137863 A2 | 11/2008 | |
| WO | 2008156883 A2 | 12/2008 | |
| WO | 2012137545 A1 | 10/2012 | |
| WO | 2013082356 A2 | 6/2013 | |
| WO | 2013082356 A3 | 6/2013 | |
| WO | 2013166352 A2 | 11/2013 | |
| WO | 2013166477 A2 | 11/2013 | |
| WO | 2014018640 A1 | 1/2014 | |

OTHER PUBLICATIONS

Author Unknown, "Tearscope Plus: Introduction and guided tour to the benefits of the Keeler Tearscope-plus," Keeler Instruments, bon Optic, created Jan. 24, 2006, www.bon.de/download/TearscopeE. pdf, 22 pages.

Australian Patent Examination Report No. 1 for Australian patent application 2011235961, mailed Jan. 2, 2013, 3 pages.

Alonso-Caneiro, D. et al., "Context-Based Modelling of Interferometric Signals for the Assessment of Tear-Film Surface Quality," 2009 IEEE/SP 15th Workshop on Statistical Signal Processing (SSP), 2009, pp. 553-556.

An, Yang et al., "Contrast Sensitivity Measurement in Dry Eyes," Int J Ophthalmol, vol. 10, No. 3, Mar. 2010, pp. 488-491.

Arndt, G. Dickey et al., "Microwave Treatment of Prostate Cancer and Hyperplasia," NASA Tech Briefs, Jun. 2005, 1 page.

Author Unknown, "Blepharitis," The Eye Digest, The Dry Eye Research Center, University of Illinois at Chicago, 2003, 3 pages.

Author Unknown, "Introduction to the Report of the International Dry Eye WorkShop (2007)," The Ocular Surface, vol. 5, No. 2, Apr. 2007, pp. 69-70.

Author Unknown, "Keratoconjunctivitis Sicca" Wikipedia, http://en.wikipedia.org/wiki/keratoconjunctivitis_sicca, Nov. 2006, 4 pages.

Author Unknown, "Measurement of Intraocular Pressure" Biomedical Foundations of Ophthalmology, Intraocular Pressure, vol. 2, Chapter 7, Circa 1982, 6 pages (pp. 11-16).

Author Unknown, "Thermographic Camera" Wikipedia, http://en.wikipedia.org/wiki/thermographic_camera, Sep. 2006, 4 pages.

Bartlett, Hannah, et al. "New Perspectives on the Investigation and Treatment of Dry Eye Syndrome13 Part 1" Optician, vol. 231, No. 6038, Feb. 2006, 9 pages (pp. 27-37).

Begley, Carolyn, G., et al., "Relationship Between Symptom Profile and Clinical Signs Among Dry Eye Patients" Circa 2003, 1 page.

Begley, Carolyn, G., et al., "The Relationship Between Habitual Patient-Reported Symptoms and Clinical Signs among Patients with Dry Eye of Varying Severity" Investigative Ophthalmology & Visual Science, vol. 44, No. 11, Nov. 2003, 9 pages (pp. 4753-4761).

Behrens, Ashley, MD, "Interferometry for the Detection of Dry Eye," Cataract & Refractive Surgery Today Europe, Nov./Dec. 2008. pp. 57-58.

Behrens, Ashley, MD, "Multiwave Interferometry is Creating a New Understanding of the Tear Film," Refractive Eyecare, Oct. 2009, from www.refractiveeyecare.com, 5 pages.

Berliner, M. L., M.D., "The Margins of the Eyelid" Chapter Eight, Biomicroscopy of the Eye, Slit Lamp Microscopy of the Living Eye, vol. 1, Medical Book Department of Harper & Brothers, NYC, Paul B. Hoeber, Inc., 1949, 5 pages (pp. 252-257).

Blackie, Caroline et al., "The Relationship Between Dry Eye Symptoms and Lipid Layer Thickness," Cornea, vol. 28, No. 7, Aug. 2009, pp. 789-794.

Borchman, Douglas, et al., "Temperature-Induced Conformational Changes in Human Tear Lipids Hydrocarbon Chains" Biopolymers, vol. 87, No. 2-3, Jun. 13, 2007, pp. 124-133 (10 pages).

Boyer, Kim L. et al., "Resilient Subclass Discriminant Analysis with Application to Prelens Tear Film Interferometry," Proceedings, Lecture Notes in Computer Science, vol. 6718/2011, MCPR, Cancun, Mexico, Jun. 29-Jul. 2, 2011, pp. 1-11.

Bron, A.J. et al., "Functional Aspects of the Tear Film Lipid Layer," Experimental Eye Research, vol. 78, 2004, pp. 347-360.

Bron, A.J. et al., "The Contribution of Meibomian Disease to Dry Eye," Ocul. Surf., vol. 2, 2004, pp. 149-164.

Bron, Anthony J., BSc, FRCS, FCOphth, et al., "The Ocular Appendages: Eyelids, Conjunctiva and Lacrimal Apparatus" Chapter 2, Wolff's Anatomy of the Eye and Orbit, Eighth Edition, Chapman & Hall Medical, Jan. 1997, 12 pages (pp. 30-42).

Carrington, S. D., et al., "Polarized Light Biomicroscopic Observations on the Pre-Corneal Tear Film" J. Small Anim. Pract., vol. 28, 1987, 20 pages (pp. 605-622).

Craig, J.P. et al. "Importance of the Lipid Layer in Human Tear Film Stability and Evaporation," Optometry and Visual Science, vol. 70, No. 1, 1997, pp. 8-14.

Cruz, Daniele, "Dry Eye Syndrome More Widespread than Predicted" Ocular Surgery News, U.S. Edition, May 2007, 1 page.

Cruz, Daniele, "Surgeon: Early Treatment Key to Avoiding Dry Eye Progression" Ocular Surgery News, U.S. Edition, May 2007, 1 page.

Danjo, Yukitaka, et al., "Measurement of the Precorneal Tear Film Thickness with a Non-Contact Optical Interferometry Film Thickness Measurement System" Jpn J Ophthal., vol. 38, 1994, 7 pages (pp. 260-266).

De Paiva, Cintia S., et al., "Diagnostic Approaches to Lacrimal Keratoconjunctivitis," Dry Eye and Ocular Surface Disorders, New York, NY: Marcel Dekker, 2004, pp. 269-270.

Di Pascuale, Mario A., M.D., et al., "Lipid Tear Deficiency in Persistent Dry Eye After Laser in Situ Keratomileusis and Treatment Results of New Eye-Warming Device" J Cataract Refract. Surg., vol. 31, ASCRS and ESCRS, Elsevier Inc., 2005, 9 pages (pp. 1741-1749).

Di Pascuale, Mario A., M.D., et al., "Sequential Changes of Lipid Tear Film after the Instillation of a Single Drop of a New Emulsion Eye Drop in Dry Eye Patients" American Academy of Ophthalmology, vol. 111, 2004, 9 pages (pp. 783-791).

Doane, Marshall G., "Abnormalities of the Structure of the Superficial Lipid Layer on the in Vivo Dry-Eye Tear Film" (and critique of same) Lacrimal Gland, Tear Film, and Dry Eye Syndromes, Plenum Press, New York, 1994, 11 pages (pp. 489-493).

Doane, Marshall G., "An Instrument for in Vivo Tear Film Interferometry" (and critique of same), Optometry and Vision Science, vol. 66, No. 6, 1989, 10 pages (pp. 383-388).

Doane, Marshall G., et al., "Tear Film Interferometry as a Diagnostic Tool for Evaluating Normal and Dry-Eye Tear Film" Lacrimal Gland, Tear Film, and Dry Eye Syndromes 2, Plenum Press, New York, 1998, 7 pages (pp. 397-303).

Dogru, M. et al., "New Insights into the Diagnosis and Treatment of Dry Eye," Ocular Surface, vol. 2, No. 2, 2004, pp. 59-74.

Dogru, M. et al., "Strip Meniscometry: A New and Simple Method of Tear Meniscus Evaluation," Invest. Ophthalmol. Vis. Sci., vol. 47, No. 5, May 2006, pp. 1895-1901.

Driver, Paul J., et al., "Meibomian Gland Dysfunction" Major Review, Survey of Ophthalmology, vol. 40, No. 5, Mar.-Apr. 1996, 25 pages (pp. 343-367).

Dubra, Alfredo, et al., "Double Lateral Shearing Interferometer for the Quantitative Measurement of Tear Film Topography" Applied Optics, vol. 44, No. 7, Mar. 2005, 9 pages (pp. 1191-1199).

Elizondo, A.E. et al., "Detection of Blink Related Microtrauma by Kinetic Analysis of Tear Interference Images in Patients with Steven Johnson Syndrome and Toxic Epidermal Necrolysis Syndrome," IOVS, vol. 46, Supp. S, 2005, E-Abstract 2654, 2 pages.

English translation of Japanese patent application announcement 2007-209370, 14 pages.

Eom et al., "Correlation Between Quantitative Measurements of Tear Film Lipid Layer Thickness and Meibomian Gland Loss in Patients with Obstructive Meibomian Gland Dysfunction and Normal Controls," American Journal of Ophthalmology, Jun. 2013, vol. 155, No. 6, Elsevier Inc., pp. 1104-1110.

(56) References Cited

OTHER PUBLICATIONS

Ernest, J. Terry, M.D. et al., "Ocular Massage Before Cataract Surgery" Tr. Am. Ophth. Soc., vol. LXXXIII, 1985, 13 pages (pp. 205-217).
European Search Report issued Jan. 20, 2012, for European Patent Application No. 11183259.8, 7 pages.
European Search Report for patent application 08732520.5 mailed Feb. 24, 2012, 8 pages.
Extended European Search Report and Written Opinion for patent application 10759411.1-1657 mailed May 14, 2013, 9 pages.
Examination Report for European patent application 11183259.8-1657 mailed May 8, 2013, 7 pages.
Fanning, Gary L., M.D., "Ocular Compression: A Review," OASIS Newsletter, Ophthalmic Anesthesia Society, Summer 2006, http://www.eyeanesthesia.org/newsletter/pdf/oasis_summer06.pdf, 7 pages.
Fenimore, C.P., et al., "Assessment of Resolution and Dynamic Range for Digital Cinema" National Institute of Standards and Technology, Gaithersburg, MD, Circa 2002, 8 pages.
Finlayson, Graham, et al., "Hue that is Invariant to Brightness and Gamma" School of Information Systems, University of East Anglia, Norwich, United Kingdom, Circa 2002, 9 pages (pp. 303-312).
First Office Action for Chinese patent application 201080024927.9 mailed May 13, 2013, 16 pages.
Fogt, Nick, et al., "Interferometric Measurement of Tear Film Thickness by use of Spectral Oscillations" J. Opt. Soc. Am. A., vol. 15, No. 1, Jan. 1998, 8 pages (pp. 268-275).
Foulks, G.N. et al., "Meibomian Gland Dysfunction: a Clinical Scheme for Description, Diagnosis, Classification, and Grading," The Ocular Surface, vol. 1, No. 3, Jul. 2003, pp. 107-126.
Foulks, G.N., "The Correlation Between the Tear Film Lipid Layer and Dry Eye Disease," Survey of Ophthalmology, vol. 52, No. 4, Jul.-Aug. 2007, pp. 369-374.
Foulks, G., "Ocular surface cell biology—from the light to the dark side," Ocular Surface, vol. 10, No. 4, Oct. 2012, 1 page.
Garcia, Julius, "Research Report; Tear Film Measurement" Report No. 09354231-1; Aug. 2006, 46 pages.
Garcia-Resua, C., et al., "Clinical Evaluation of the Tears Lipid Layer in a Young University Population" Rev. Esp. Contact, vol. 12, 2005, 6 pages.
Garncarz, B.E. et al., "Corneal Topography Measurement by Means of Radial Shearing Interference II—Experiment Results," Optik, vol. 113, No. 1, 2002, pp. 46-50.
Goto, E. et al., "Differentiation of Lipid Tear Deficiency Dry Eye by Kinetic Analysis of Tear Interference Images," Archives of Ophthalmology, vol. 121, No. 2 Feb. 2003, pp. 173-180.
Goto, E. et al., "Successful Tear Lipid Layer Treatment for Refractory Dry Eye in Office Workers by Low-Dose Lipid Application on the Full-Length Eyelid Margin," American Journal of Ophthalmology, vol. 142, No. 2, Aug. 2006, pp. 264-270.
Goto, E. et al., "Tear Evaporation Dynamics in Normal Subjects and Subjects with Obstructive Meibomian Gland Dysfunction," Investigative Ophthalmology abnd Visual Science, vol. 44, 2003, pp. 533-539.
Goto, E., et al. "Treatment of Non-Inflamed Obstructive Meibomian Gland Dysfunction by an Infrared Warm Compression Device" British Journal of Ophthalmology, BJO Online, http://www.bmjjournals.com/cgi/reprintform, vol. 26, 2002, 6 pages (pp. 1402-1407).
Goto, Eiki, et al. "Computer-Synthesis of an Interference Color Chart of Human Tear Lipid Layer, by a Colorimetric Approach" Investigative Ophthalmology & Visual Science, vol. 44, No. 11, Nov. 2003, 5 pages (pp. 4693-4697).
Goto, Eiki, et al., "Kinetic Analysis of Tear Interference Images in Aqueous Tear Deficiency Dry Eye Before and After Punctual Occlusion" Investigative Ophthalmology & Visual Science, vol. 44, No. 5, May 2003, 9 pages (pp. 1897-1905).
Goto, Eiki, M.D., "Quantification of Tear Interference Image; Tear Fluid Surface Nanotechnology" Cornea, vol. 23, Suppl. 1, Nov. 2004, 5 pages (pp. S20-S24).
Gravely, Ben, "Observations from TFA3" Aug. 2006, 4 pages.
Greiner, Jack V., et al., "Effect of Meibomian Gland Occlusion on Tear Film Lipid Layer Thickness" Lacrimal Gland, Tear Film, and Dry Eye Syndromes 2, Plenum Press, New York, 1998, 4 pages (pp. 345-348).
Greiner, Jack V., et al., "Meibomian Gland Phospholipids" Current Eye Research, Oxford University Press, 1995, 5 pages (pp. 371-375).
Greiner, Jack V., et al., "Volume of the Human and Rabbit Meibomian Gland System" Lacrimal Gland, Tear Film, and Dry Eye Syndromes 2, Plenum Pres, New York, 1998, 5 pages (pp. 339-343).
Guillon, J.P. et al., "Preocular Tear Film Characteristics of Nonwearers and Soft Contact Lens Wearers," Optometry and Vision Science, vol. 74, No. 5, 1997, pp. 273-279.
Guillon, J.P., "Tear Film Photography and Contact Lens Wear," Journal of the British Contact Lens Association, 1982, pp. 84-87.
Guillon, J.P., "The Tear Film Structure of the Contact Lens Wearer," Dept. of Optometry and Visual Science, City University, London, 1987, 398 pages.
Guillon, Jean-Pierre, "Non-Invasive Tearscope Plus Routine for Contact Lens Fitting," Contact Lens and Anterior Eye, (Supplement) 21, 1998, pp. S31-S40.
Guillon, Jean-Pierre, "Use of the Tearscope Plus and Attachments in the Routine Examination of the Marginal Dry Eye Contact Lens Patient," Lacrimal Gland, Tear Film, and Dry Eye Syndrome 2, 1998, pp. 859-867.
Hamilton, Dr. Roy C., "Ocular Explosion; a Dreaded Complication of Ophthalmic Regional Anaesthesia" Ophthalmic Anaesthesia News, Issue 4, Apr. 2001, 43 pages.
Hayreh, Sohan Singh, et al., "Parapapillary Chorioretinal Atrophy in Chronic High-Pressure Experimental Glaucoma in Rhesus Monkeys" Investigative Ophthalmology & Visual Science, vol. 39, No. 12, Nov. 1998, 8 pages (pp. 2296-1303).
Hellmuth, T. et al., "Non-Contact Measurement of the Optical Imaging Quality of an Eye," Proc. SPIE—Int. Soc. Opt. Eng. vol. 4431, 2001, pp. 52-58.
Hickson, Ian, "The Eye" Ian Hickson's Description of the Eye, http://academia.hixie.ch/bath/eye/home.html, 1998, 11 pages.
Author Unknown, Honan Balloon Intraocular Pressure Reducer with Valve—Complete, Ambler Surgical, Ambler Product No. HBC-120, Nov. 19, 2007, http://www.amblersurgical.com/store/product.cfm/pID:2456_5961E, 1 page.
Hosaka, Eri et al., "Interferometry in the Evaluation of Precorneal Tear Film Thickness in Dry Eye," American Journal of Opthalmology, vol. 151, No. 1, Jan. 2011, pp. 18-23.
International Search Report and Written Opinion for PCT/US2013/038116 mailed Sep. 12, 2013, 13 pages.
International Search Report and Written Opinion for PCT/US2013/038149 mailed Sep. 12, 2013, 18 pages.
International Search Report and Written Opinion for PCT/US2013/039395 mailed Oct. 11, 2013, 11 pages.
Ishida, Reiko et al., "Tear Film with 'Orgahexa Eyemasks' in Patients with Meibomian Gland Dysfunction," Optometry and Visions Science, vol. 85, No. 8, Aug. 2008, pp. E684-E691.
Iskander, D. Robert, PhD., et al., "Applications of High-Speed Videokeratoscopy" Clinical and Experimental Optometry, vol. 88, vol. 4, Jul. 2005, 9 pages (pp. 223-231).
Isreb, M.A. et al., "Correlation of Lipid Layer Thickness Measurements with Fluorescein Tear Film Breakup Time and Schirmer's Test," Eye, vol. 17, 2003, pp. 79-83.
Kaisheva, M et al., "Thin Liquid Films from Water-Based Dispersions of Cellulose Acethophthalate in the Presence of Pilocarpine Hydrochloride," J. Dispersion Sci. Technol., 1997.
Khamene, Ali, et al., "A Spectral-Discrimination Method for Tear-Film Lipid-Layer Thickness Estimation from Fringe Pattern Images" IEEE Transactions on Biomedical Engineering, vol. 47, No. 2, Jan. 2000, 10 pages (pp. 249-258).
Kilp, H. et al., "Tear Film Observation by Reflecting Microscopy and Differential Interference Contrast Microscopy," The Dry Eye Institute, Inc., 1986, pp. 564-569.
Kimball, S., et al., "Evidence for the major contribution of evaporation to tear film thinning between blinks," Investigative Ophthalmology and Visual Science, vol. 51, No. 12, Dec. 2010, http://www.iovs.org/content/51/12/6294.full.pdf+html, pp. 6294-6297.

(56) References Cited

OTHER PUBLICATIONS

King-Smith, P. Ewen et al., "The Thickness of the Human Precorneal Tear Film: Evidence from Reflection Spectra," Investigative Ophthalmology & Visual Science, Oct. 2000, vol. 41, No. 11, pp. 3348-3359.
King-Smith, P. Ewen, et al., "Application of a novel interferometric method to investigate the relation between lipid layer thickness and tear film thinning," Investigative Ophthalmology and Visual Science, vol. 51, No. 5, May 2010, http://www.iovs.org/content/51/5/2418.full.pdf+html, pp. 2418-2423.
King-Smith, P. Ewen, et al., "Evaporation from the Human Tear Film Studied by Interferometry" Lacrimal Gland, Tear Film, and Dry Eye Syndromes 3, Kluwer Academic/Plenum Publishers, 2002, 5 pages (pp. 425-429).
King-Smith, P. Ewen, et al., "Interferometric Imaging of the Full Thickness of the Precorneal Tear Film" J. Opt. Soc. Am. A, vol. 23, No. 9, Sep. 2006, 8 pages (pp. 2097-2104).
King-Smith, P. Ewen, et al., "Three Interferometric Methods for Measuring the Thickness of Layers of the Tear Film" Optometry and Vision Science, vol. 76, No. 1, Jan. 1999, 14 pages (pp. 19-32).
King-Smith, P.E. et al., "Can the Mucus Layer of the Tear Film be Demonstrated by Interferometry?," IOVS, vol. 45, Supp. 2, Apr. 2004, E-Abstract 3882. 2 pages.
King-Smith, P.E. et al., "Human Tear Film Breakup Studied by a New Imaging Interferometer: Preliminary Observations," IOVS, vol. 46, Supp. S, 2005, E-Abstract 4400, 2 pages.
Kojima, Takashi et al.., "A New Noninvasive Tear Stability Analysis System for the Assessment of Dry Eyes," Investigative Ophthalmology & Visual Science, May 2004, vol. 45, No. 5, pp. 1369-1374.
Korb, D. et al., "Lipid Layer Thickness Changes Following the Instillation of Two Novel Lubricant Eye Drops," IOVS, vol. 46, Supp. S, 2005, E-Abstract 2036, 2 pages.
Korb, Donald R. et al., "Meibomian Gland Diagnostic Expressibility: Correlation With Dry Eye Symptoms and Gland Location," Cornea, vol. 27, No. 10, Dec. 2008, pp. 1142-1147.
Korb, Donald R. et al., "Effect of Periocular Humidity on the Tear Film Lipid Layer," Cornea, vol. 15, No. 2, 1996, pp. 129-134.
Patel, S. et al., "Corneal Sensitivity and Some Properties of the Tear Film After Laser in Situ Keratomileusis, "Journal of Refractive Surgery, Vo. 17, No. 1, 2001, pp. 17-24.
Patel, Sudi, PhD, FCOptom, FAAO, et al., "Tear Meniscus Height, Lower Punctum Lacrimale, and Tear Lipid Layer in Normal Aging" Optometry and Vision Science, vol. 83, No. 10, Oct. 2006, 9 pages (pp. 732-739).
Paugh, J.R. et al., "White Light Tear Film Interferometry in Dry Eye Sub-Types," IOVS, vol. 45, Supp. 1, Apr. 2004, E-Abstract 93, 2 pages.
Pflugfelder, S.C. et al., "Evaluation of Subjective Assessments and Objective Diagnostic Tests for Diagnosing Tear-Film Disorders Known to Cause Ocular Irritation," Cornea, vol. 17, No. 1, 1998, pp. 38-56.
Pimenidi, M.K., et al., "Meibomian Gland Disfunction in Computer Vision Syndrome (abstract)," Annals of Ophthalmology (Vestn Oftalmol.) (Russia), Nov.-Dec. 2010, 126(6), http://www.medlit.ru/medeng/vof/vof10e0649.htm, 3 pages.
Primeau et al., "Interferometer for measuring the dynamic surface topography of a human tear film," Design and Quality for Biomedical Technologies V, vol. 8215, Feb. 2012, 11 pages.
Prydal, J.I. et al., "In Vivo Confocal Microscopy of the Cornea and Tear Film," Scanning, vol. 17, 1995, pp. 133-135.
Prydal, J.I. et al., "Study of Precorneal Tear Film Thickness and Structure by Interferometry and Confocal Microscopy," Investigative Ophthalmology and Visual Science, vol. 33, No. 6, May 1992, pp. 1996-2005.
Prydal, Jeremy I. et al., "Study of Human Precorneal Tear Film Thickness and Structure Using Laser Interferometry," Investigative Ophthalmology & Visual Science, vol. 33, No. 6, May 1992, pp. 2006-2011.

Remeseiro et al., "Automatic classification of the interferential tear film lipid layer using colour texture analysis," Computer Methods and Programs in Biomedicine, vol. 111, No. 1, Elsevier Ireland Ltd., Jul. 2013, pp. 93-103.
Rolando, M. et al., "The Dynamic Lipid Interference Pattern (DLIP) Test in Normal and Dry Eyes," IOVS, vol. 46, Supp. S, 2005, E-Abstract 4422, 2 pages.
Rolando, Maurizio et al., "New Test to Quantify Lipid Layer Behavior in Healthy Subjects and Patients with Keratoconjunctivitis Sicca," Cornea, vol. 27, No. 8, Sep. 2008, pp. 866-870.
Scaffidi, R.C. et al., "Lipid Layer Thickness and Dry Eye Symptoms," IOVS, vol. 46, Supp. S, 2005, E-Abstract 4444, 2 pages.
Schaumberg, D.A. et al., "Development and Validation of a Short Global Dry Eye Symptom Index," The Ocular Surface, vol. 5, No. 1, Jan. 2007, pp. 50-57.
Shiel, William C., Jr., MD, FACP, FACR, "Sjogren's Syndrome" MedicineNet.com, http:www.medicinenet.com, Sep. 2006, 3 pages.
Sullivan, David A., et al., "Androgen Influence on the Meibomian Gland" Investigative Ophthalmology & Visual Science, vol. 41, No. 12, Nov. 2000, 11 pages (pp. 3732-3742).
Sullivan, David A., et al., "Androgen Regulation of the Meibomian Gland" Lacrimal Gland, Tear Film, and Dry Eye Syndromes 2, Plenum Press, New York, 1998, 5 pages (pp. 327-331).
Szczesna-Iskander, D. et al., "Future Directions in Non-Invasive Measurements of Tear Film Surface Kinetics," Optometry and Vision Science, vol. 89, No. 5, May 2012 pp. 749-759.
Szczesna, D. et al., "Numerical Analysis of Interferograms of Tear Film Build-Up Time," Ophthalmic and Physiological Optics, vol. 29, No. 3, May 2009, pp. 211-218.
Szczesna, D., et al., "Predicting dry eye using noninvasive techniques of tear film surface assessment," Investigative Ophthalmology and Visual Science, vol. 52, No. 2, Feb. 2011, http://www.iovs.org/content/52/2/751.full.pdf+html, pp. 751-756.
Szczesna, D.H. et al., "Interferometric Measurements of the Tear Film Irregularities on the Human Cornea," Proceedings of the SPIE, vol. 5959, 2005, 10 pages.
Szczesna, Dorota H., et al., "Assessing Tear Film on Soft Contact Lenses With Lateral Shearing Interferometry," Eye & Contact Lens: Science & Clinical Practices, vol. 37, Issue 6, Nov. 2011, pp. 342-347.
Szczesna, Dorota H., et al., "Lateral Shearing Interferometry for Analysis of Tear Film Surface Kinetics," Optom. Vis. Sci., vol. 87, No. 7, Jul. 2010, pp. 513-517.
Szczesna, Dorota H., et al., "Robust estimation of tear film surface quality in lateral shearing interferometry," Journal of Biomedical Optics, vol. 14, No. 6, Nov./Dec. 2009, 4 pages.
Thai, Lee Choon, BSc, MCOptom, et al., "Contact Lens Drying and Visual Performance: The Vision Cycle with Contact Lenses" Optometry and Vision Science, vol. 79, No. 6, Jun. 2002, 8 pages (pp. 381-388).
Thai, Lee Choon, BSc, MCOptom, et al., "Effect of Contact Lens Materials on Tear Physiology" Optometry and Vision Science, vol. 81, No. 3, Mar. 2004, 11 pages (pp. 194-204).
Tomlinson, Alan, et al., "Reliability of Measurements of Tear Physiology" Lacrimal Gland, Tear Film, and Dry Eye Syndromes 3, Kluwer Academic/Plenum Publishers, 2002, 9 pages (pp. 1097-1105).
Tomlinson, Alan, et al., "Tear Film Osmolarity: Determination of a Referent for Dry Eye Diagnosis" Investigative Ophthalmology & Visual Science, vol. 47, No. 10, Oct. 2006, 7 pages (pp. 4309-4315).
Tseng, S.C. et al., "Changes of Lipid Tear Film in Dry Eye Patients and Normal Subjects Following One Drop of a New Emulsion Eye Drop Using Kinetic Analysis of Tear Interference Images," ARVO, vol. 44, 2003, E-Abstract 2457, 2 pages.
Uchida, A. et al., "Nonivasive Interference Tear Meniscometry in Dry Eye Patients with Sjogren Syndrome," Am. J. Ophthalmol., vol. 144, No. 2, Aug. 2007, pp. 232-237.
van Veen, R. L. P., et al., "Determination of VIS- NIR Absorption Coefficients of Mammalian Fat, with Time- and Spatially Resolved Diffuse Reflectance and Transmission Spectroscopy" Circa 2004, 3 pages.

(56) References Cited

OTHER PUBLICATIONS

Veres, A., et al., "Imaging lid-parallel conjunctival folds with OCT and comparing its grading with the slit lamp classification in dry eye patients and normal subjets," Investigative Ophthalmology and Visual Science, vol. 52, No. 6, May 2011, http://www.iovs.org/content/52/6/2945.full.pdf+html, pp. 2945-2951.

Wang, Jianhua et al., "Relationships between Central Tear Film Thickness and Tear Menisci of the Upper and Lower Eyelids" Investigative Ophthalmology & Visual Science, vol. 47, No. 10, Oct. 2006, 7 pages (pp. 4349-4355).

Wu, Dijia et al., "Sign Ambiguity Resolution for Phase Demodulation in Interferometry with Application to Prelens Tear Film Analysis," 2010 IEEE Computer Society Conference on Computer Visions and Pattern Recognition, CVPR 2010, 2010, pp. 2807-2814.

Wu, Dijia et al., "Texture Based Prelens Tear Film Segmentation in Interferometry Images," Machine Vision and Applications, vol. 21, No. 3, Apr. 2010, pp. 253-259.

Yokoi, N, et al., "Development of Automated Rheological Analysis for Tear Film Lipid Layer Spread Using the Cross-Correlation Method" Association for Research in Vision and Ophthalmology, 2007, 1 page.

Yokoi et al., "A Newly Developed Video-Meibography System Featuring a Newly Designed Probe," Japan Journal of Ophthalmology, vol. 51, Jan. 2007, pp. 53-56.

Yokoi, N. et al., "Assessment of Meibomian Gland Function in Dry Eye Using Meibometry," Arch. Ophthalmol., No. 117, Jun. 1999, pp. 723-729.

Yokoi, N. et al., "Correlation of Tear Lipid Layer Interference Patterns with the Diagnosis and Severity of Dry Eye," Amercian Journal of Ophthalmology, vol. 122, Dec. 1996, pp. 818-824.

Yokoi, N. et al., "New Instruments for Dry Eye Diagnosis," Seminars in Opthalmology, vol. 20, 2004, pp. 63-70.

Yokoi, Norihiko, et al., "Non-Invasive Methods of Assessing the Tear Film" Experimental Eye Research, vol. 78, Elsevier Ltd., 2003, 9 pages (pp. 399-407).

Young, G. et al., "Characteristics of the Pre-Lens Tear Films During Hydrogel Contact Lens Wear," Ophthal. Physiol. Opt., vol. 11, Jan. 1991, pp. 53-58.

Oculus, "Oculus Keratograph 5M Der Revolutionar," Oculus, 2 pages.

Bon, "Meibographie: mit der PHOENIX Analyse-Software," bon Optic Vertriebsgesellschaft mbH, Nov. 2011, 4 pages.

Yokoi, N. et al., "Relationship between tear volume and tear meniscus curvature," Arch. Ophthalmology, vol. 122, Sep. 2004 ,pp. 1265-1269.

Notice of Allowance for U.S. Appl. No. 11/820,664 mailed May 27, 2010, 10 pages.

Notice of Allowance for U.S. Appl. No. 11/820,664 mailed Mar. 25, 2010, 10 pages.

Final Office Action for U.S. Appl. No. 11/820,664 mailed Dec. 29, 2009, 7 pages.

Non-final Office Action for U.S. Appl. No. 11/820,664 mailed Jun. 5, 2009, 9 pages.

Notice of Allowance for U.S. Appl. No. 12/633,057 mailed Jun. 9, 2011, 8 pages.

Final Office Action for U.S. Appl. No. 12/633,057 mailed Apr. 6, 2011, 6 pages.

Non-final Office Action for U.S. Appl. No. 12/633,057 mailed Aug. 19, 2010, 8 pages.

Notice of Allowance for U.S. Appl. No. 11/900,314 mailed Jan. 25, 2012, 7 pages.

Non-final Office Action for U.S. Appl. No. 11/900,314 Aug. 22, 2011, 26 pages.

Non-final Office Action for U.S. Appl. No. 12/798,325 mailed Jan. 27, 2012, 15 pages.

Non-final Office Action for U.S. Appl. No. 12/798,325 mailed Aug. 30, 2012, 16 pages.

Notice of Allowance for U.S. Appl. No. 12/798,325 mailed Feb. 15, 2013, 9 pages.

Notice of Allowance for U.S. Appl. No. 12/798,325 mailed May 29, 2013, 10 pages.

Notice of Allowance for U.S. Appl. No. 29/329,613 mailed Feb. 4, 2010, 7 pages.

Notice of Allowance for U.S. Appl. No. 29/329,613 mailed Nov. 13, 2009, 7 pages.

Non-Final Rejection mailed Apr. 20, 2012, for U.S. Appl. No. 12/798,275, 15 pages.

Final Office Action for U.S. Appl. No. 12/798,275 mailed Nov. 20, 2012, 16 pages.

Reply to Final Office Action for U.S. Appl. No. 12/798,275, filed Jan. 29, 2013, 6 pages.

Advisory Action for U.S. Appl. No. 12/798,275 mailed Feb. 5, 2013, 9 pages.

Non-final Office Action for U.S. Appl. No. 12/798,275 mailed Jul. 30, 2013, 15 pages.

Notice of Allowance for U.S. Appl. No. 12/798,326 mailed Aug. 29, 2011, 9 pages.

Non-final Office Action for U.S. Appl. No. 12/798,326 mailed Jun. 28, 2011, 19 pages.

Non-final Office Action for U.S. Appl. No. 12/798,326 mailed Mar. 29, 2011, 23 pages.

Notice of Allowance for U.S. Appl. No. 12/798,324 mailed Apr. 2, 2012, 9 pages.

Non-final Office Action for U.S. Appl. No. 12/798,324 mailed Dec. 15, 2011, 27 pages.

Non-final Office Action for U.S. Appl. No. 13/455,628 mailed Aug. 29, 2012, 18 pages.

Final Office Action for U.S. Appl. No. 13/455,628 mailed May 10, 2013, 9 pages.

Notice of Allowance for U.S. Appl. No. 13/455,628 mailed Jul. 12, 2013, 8 pages.

Translation of Notice of Rejection for Japanese patent application 2010-513285 mailed Nov. 6, 2012, 4 pages.

Non-final Office Action for U.S. Appl. No. 13/195,353 mailed May 3, 2013, 5 pages.

Notice of Allowance for U.S. Appl. No. 13/195,353 mailed Jul. 26, 2013, 9 pages.

Finis et al., "Evaluation of lipid layer thickness measurement of the tear film as a diagnostic tool for Meibomian gland dysfunction," Cornea, vol. 32, No. 12, Dec. 2013, Lippincott Williams & Wilkins, 5 pages.

Primeau et al., "Interferometer and analysis methods for the in vitro characterization of dynamic fluid layers on contact lenses," Optical Engineering, vol. 51, No. 6, SPIE, Jun. 1, 2012, 9 pages.

Notice of Allowance for U.S. Appl. No. 12/798,275 mailed Jan. 2, 2014, 8 pages.

Korb, Donald R. et al., "Increase in Tear Film Lipid Layer Thickness Following Treatment of Meibomian Gland Dysfunction," Adv. Exp. Med. Biol., vol. 350, 1994, pp. 293-298.

Korb, Donald R. et al., "Tear Film Lipid Layer Thickness as a Function of Blinking," Cornea, vol. 13, No. 4, 1994, pp. 354-359.

Korb, Donald R. O.D., et al., "Comparison of Fluorescein Break-Up Time Measurement Reproducibility Using Standard Fluorescein Strips Versus the Dry Eye Test (DET) Method," Cornea, vol. 20(8), Philadelphia, 2001, 8 pages.

Korb, Donald R., "Alleviation of Computer-Induced Eye Discomfort Syndrome and Associated Lipid Layer Changes," Lacrimal Gland, Tear Film, and Dry Eye Syndrome 3, 2002, pp. 501-506.

Korb, Donald R., "The Tear Film—Its Role Today and in the Future," 2002, 52 pages.

Korb, Donald R., et al., "Human and Rabbit Lipid Layer and Interference Pattern Observations," Lacrimal Gland, Tear Film, and Dry Eye Syndromes 2, Plenum Press, New York, 1998, pp. 305-308.

Korb, Donald R., et al., "Tear Film Lipid Layer Formation: Implications for Contact Lens Wear," Review, Optometry and Vision Science, vol. 73, No. 3, 1996, pp. 189-192.

Korb, Donald R., et al., "The Effects of Anionic and Zwitterionic Phospholipids on the Tear Film Lipid Layer," Lacrimal Gland, Tear Film, and Dry Eye Syndromes 3, Kluwer Academic/Plenum Publishers, 2002, pp. 495-499.

(56) References Cited

OTHER PUBLICATIONS

Korb, Donald R., et al., "The Tear Film Structure, Function and Clinical Examination," British Contact Lens Association, Butterworth Heinemann, Circa 1999, pp. 154-179.

Korb, Donald R., O.D. et al., "The Phenomenon of Central Circular Clouding; the loss of corneal transparency unique to contact lens practice requiring specialized techniques for early recognition," Journal of American Optometric Association, vol. 39, No. 3, Mar. 1968, pp. 223-230.

Korb, Donald R., O.D., et al., "Lid Wiper Epitheliopathy and Dry Eye Symptoms," Eye & Contact Lens, vol. 31, No. 1, 2005, pp. 2-8.

Korb, Donald R., O.D., et al., "Meibomian Gland Dysfunction and Contact Lens Intolerance" Jnl American Optometric Association, vol. 51, No. 3, Mar. 1980, 9 pages (pp. 243-251).

Korb, Donald R., OD, et al., "A Device to Standardize and Quantify the Force Used to Diagnose Meibomian Gland Obstruction and Dysfunction" 2007, 1 page.

Korb, Donald R., OD, et al., "A New Device for the Diagnosis of Meibomian Gland Dysfunction and Obstruction" 2007, 1 page.

Korb, Donald, "Survey of Preferred tests for Diagnosis of the Tear Film and Dry Eye," Cornea, vol. 19, 2000, pp. 483-486.

Kowalik, W. et al., "Corneal Topography Measurement of the Eye by Means of Radial Shearing Interferometer," Proc. SPIE—Int. Soc. Opt. Eng. vol. 4356, 2001. pp. 375-380.

Kronemyer, Bob, "Dry Eye Experts Unveil New Treatment Guidelines, Terminology" Ocular Surgery News, U.S. Edition, May 2007, 1 page.

Leibovitch, Larry S., Ph.D., "The Shape of the Eye: Why the Eye is Round" Florida Atlantic University, Boca Raton, FL, Circa 1986, 28 pages (pp. 1-27).

Licznerski, T.J. et al., "Application of Twyman-Green Interferometer for Evaluation of in Vivio Breakup Characteristic of the Human Tear Film," Journal of Biomedical Optics, vol. 4, No. 1, Jan. 1999, pp. 176-182.

Licznerski, T.J. et al., "Interference and Model Study of the Human Tear Film," Politechnika Wroclawska, Source DAI-C 60/04, Winter 1999, p. 782 (Abstract only).

Licznerski, T.J. et al., "Novel Double Path Shearing Interferometer in Corneal Topography Measurements," Proceedings of the SPIE, vol. 5959, 2005, 6 pages.

Licznerski, Tomasz J., et al., "Analysis of Shearing Interferograms of Tear Film Using Fast Fourier Transforms" Journal of Biomedical Optics, vol. 3, No. 1, Jan. 1998, pp. 32-37.

Lopez Garcia, J.S. et al., "Measure of the Fatty Layer Thickness of Precorneal Tear Film by Interference Colours in Different Types of Dry Eye," Sociedad Espanola de Oftalmologia, vol. 78, Part 5, Jan. 2003, pp. 257-264.

Lorentz, Holly Irene, "Lipid Deposition on Hydrogel Contact Lenses" Master's Thesis, University of Waterloo, Ontario, Canada, 2006, 175 pages.

Loveridge, Ron, "Effective Management of Induced Dry Eye Syndrome with Soft CLs" www.optometry.co.uk, Apr. 2000,pp. 35-38.

Lui, Haixia, MD, et al., "Temporal Progression and Spatial Repeatability of Tear Breakup" Optometry and Vision Science, vol. 83, No. 10, Oct. 2006, pp. 723-730.

Mathers, W.D., "Assessment of the Tear Film with Tandem Scanning Confocal Microscopy," Cornea, vol. 16, No. 2, 1997, pp. 162-168.

Mathers, W.D., "Ocular Evaporation in Meibomian Gland Dysfunction and Dry Eye," Ophthalmology, vol. 100, No. 3, Mar. 1993, pp. 347-351.

Matsumoto, Yukihiro, et al., "Efficacy of a New Warm Moist Air Device on Tear Functions of Patients with Simple Meibomian Gland Dysfunction" Cornea, vol. 25, No. 6, Jul. 2006, 1 page.

McCarty, C.A. et al., "The Epidemiology of Dry Eye in Melbourne, Australia," Ophthalmology, vol. 105, No. 6, Jun. 1998, pp. 1114-1119.

McDonald, James E., "Surface Phenomena of the Tear Films," Tr. Am. Opth. Soc., vol. 66, 1968, pp. 905-939.

McGrath, Dermot, "Iris diaphragm IOLs safe and effective in treating aniridia," EuroTimes, European Society of Cataract & Refractive Surgeons, May 2007, http://www.escrs.org/Publications/Eurotimes/07May/ Irisdiaphragmiols.Pdf, p. 42.

Miano, Fausto, et al., "Interface Properties of Simplified Tear-Like Fluids in Relation to Lipid and Aqueous Layers Composition" Lacrimal Gland, Tear Film, and Dry Eye Syndromes 3, Kluwer Academic/Plenum Publishers, 2002, 13 pages (pp. 405-417).

Millar, et al., "Analysis of comparison of human meibomian lipid films and mixtures with cholestryl esters in vitro films using high resolution color microscopy," Cornea, vol. 53, No. 8, Jul. 2012, pp. 4710-4719.

Miller, David "Pressure of the Lid on the Eye" Arch. Opthalmology, vol. 78, 1967, 7 pages (pp. 382-330).

Mitra, M. et al., "Tear Film Lipid Layer Thickness and Ocular Comfort after Meibomian Therapy via Latent Heat with a Novel Device in Normal Subjects" Eye, vol. 19, 2005, 4 pages (pp. 657-660).

Mori, Asako, M.D., et al., "Efficacy and Safety of Infrared Warming of the Eyelids" Cornea, vol. 18(2), 1999, 6 pages (pp. 188-193).

Nichols, Jason J., et al., "The Impact of Hydrogel Lens Settling on the Thickness of the Tears and Contact Lens" Investigative Ophthalmology & Visual Science, vol. 45, No. 8, Aug. 2004, pp. 2549-2554.

Nichols, Jason J., et al., "The Thickness of the Post-Lens Tear Film Measured by Interferometry" Lacrimal Gland, Tear Film, and Dry Eye Syndromes 3, Kluwer Academic/Plenum Publishers, 2002, pp. 929-933.

Nichols, Jason J., et al., "Thickness of the Pre- and Post-Contact Lens Tear Film Measured in Vivo by Interferometry" Investigative Ophthalmology & Visual Science, vol. 44, No. 1, Jan. 2003, pp. 68-77.

Nichols, Jason J., OD, MS, Faao, et al., "Evaluation of Tear Film Interference Patterns and Measures of Tear Break-Up Time" Optometry and Vision Science, vol. 79, No. 6, Jun. 2002, pp. 363-369.

Nichols, Jason J., OD, MS, MPH, et al., "The Effect of Eye Closure on the Post-Lens Tear Film Thickness During Silicone Hydrogel Contact Lens Wear" Cornea, vol. 22, No. 6, 2003, pp. 539-544.

Nichols, K.K. et al., "The Lack of Association Between Signs and Symptoms in Patients with Dry Eye Disease," Cornea, vol. 23, No. 8, Nov. 2004, pp. 762-770.

Nichols, K.K. et al., "The Repeatability of Clinical Measurements of Dry Eye," Cornea, vol. 23, No. 3, Apr. 2004, pp. 272-285.

Norn, M.S., "Semiquantitative Interference Study of Fatty Layer of Precorneal Film," ACTA Ophthalmologica, vol. 57, 1979, pp. 766-774.

Corrected Notice of Acceptance for Australian patent application 2011235961 mailed Sep. 19, 2013, 2 pages.

Notice of Acceptance for Australian patent application 2011235961 mailed Sep. 11, 2013, 2 pages.

Ohashi, Yoshiki, et al., "Laboratory Findings in Tear Fluid Analysis," Clinica Chimica Acta 369, 2006, 12 pages (pp. 17-28).

Olson, Mary Catherine, B.A., et al., "Increase in Tear Film Lipid Layer Thickness Following Treatment with Warm Compresses in Patients with Meibomian Gland Dysfunction" Eye & Contact Lens, vol. 29(2), 2003, 6 pages.

Ong, B. L., et al., "Meibomian Gland Dysfunction: Some Clinical, Biochemical and Physical Observations" Ophthal. Physiol. Opt., vol. 10, Apr. 1990, 5 pages (pp. 144-148).

Lu, Hui et al., "Combination of Optical Coherence Tomography and Reflectometry Technique for Eye Measurement," Proceedings of SPIE, vol. 8567, Ophthalmic Technologies XXIII, 85672C, Mar. 26, 2013, 6 pages.

Translation of Notice of Rejection for Japanese patent application 2010-513285 mailed Dec. 3, 2013, 8 pages.

Translation of Notice of Rejection for Japanese patent application 2012-503707 mailed Dec. 3, 2013, 3 pages.

Sweeney, Deborah F., et al., "Tear film stability: A review," Experimental Eye Research, vol. 117, Elsevier Ltd., Dec. 2013, pp. 28-38.

Fagehi, Raied et al., "Contact Lens in Vitro Wettability by Interferometry Measures of Drying Dynamics," Eye & Contact Lens, vol. 39, No. 6, Contact Lens Association of Ophthalmologists, Nov. 2013, pp. 365-375.

International Search Report and Written Opinion for PCT/US2013/077117 mailed Mar. 18, 2014, 34 pages.

(56) References Cited

OTHER PUBLICATIONS

Lu, Hui et al., "Tear film measurement by optical reflectometry technique," Journal of Biomedical Optics, vol. 19, No. 2, Feb. 2014, 8 pages.

Szczesna, Dorota H. et al., "Interferometric measurements of dynamic changes of tear film," Journal of Biomedical Optics, vol. 11, No. 3, May 2006, 8 pages.

Second Office Action for Chinese patent application 201080024927.9 issued Mar. 21, 2014, 15 pages.

Lam, Sin Man et al., "Longitudinal changes in tear fluid lipidome brought about by eyelid-warming treatment in a cohort of meibomian gland dysfunction," Journal of Lipid Research, vol. 55, No. 9, Sep. 2014, American Society for Biochemistry and Molecular Biology, Inc., pp. 1959-1969.

Corrected Notice of Allowance for U.S. Appl. No. 14/137,105, mailed Sep. 25, 2014, 4 pages.

Szczesna et al., "Application of interferometry for evaluation of the effect of contact lens material on tear film quality," Proceedings of SPIE, vol. 7064, Aug. 11, 2008, SPIE, 9 pages.

International Search Report and Written Opinion for PCT/US2014/036636, mailed Oct. 2, 2014, 9 pages.

King-Smith, P.E. et al., "Tear film interferometry and corneal surface roughness," Investigative Ophthalmology & Visual Science, vol. 55, No. 4, Apr. 1, 2014, Association for Research in Vision and Ophthalmology Inc., pp. 2614-2618.

Qazi, Yureeda et al., "Image-guided evaluation and monitoring of treatment response in patients with dry eye disease," Graefe's Archive for Clinical and Experimental Ophthalmology, vol. 252, Issue 6, Jun. 2014, Springer Verlag, pp. 857-872.

Wu, Yuan et al., "Correlation between measurement of tear meniscus by anterior segment module of OCT with dry eye signs and symptoms," Chinese Journal of Experimental Ophthalmology, vol. 32, No. 6, Jun. 2014, Henan Institute of Ophthalmology, pp. 541-545.

Notice of Allowance for U.S. Appl. No. 14/137,105 mailed Jul. 18, 2014, 9 pages.

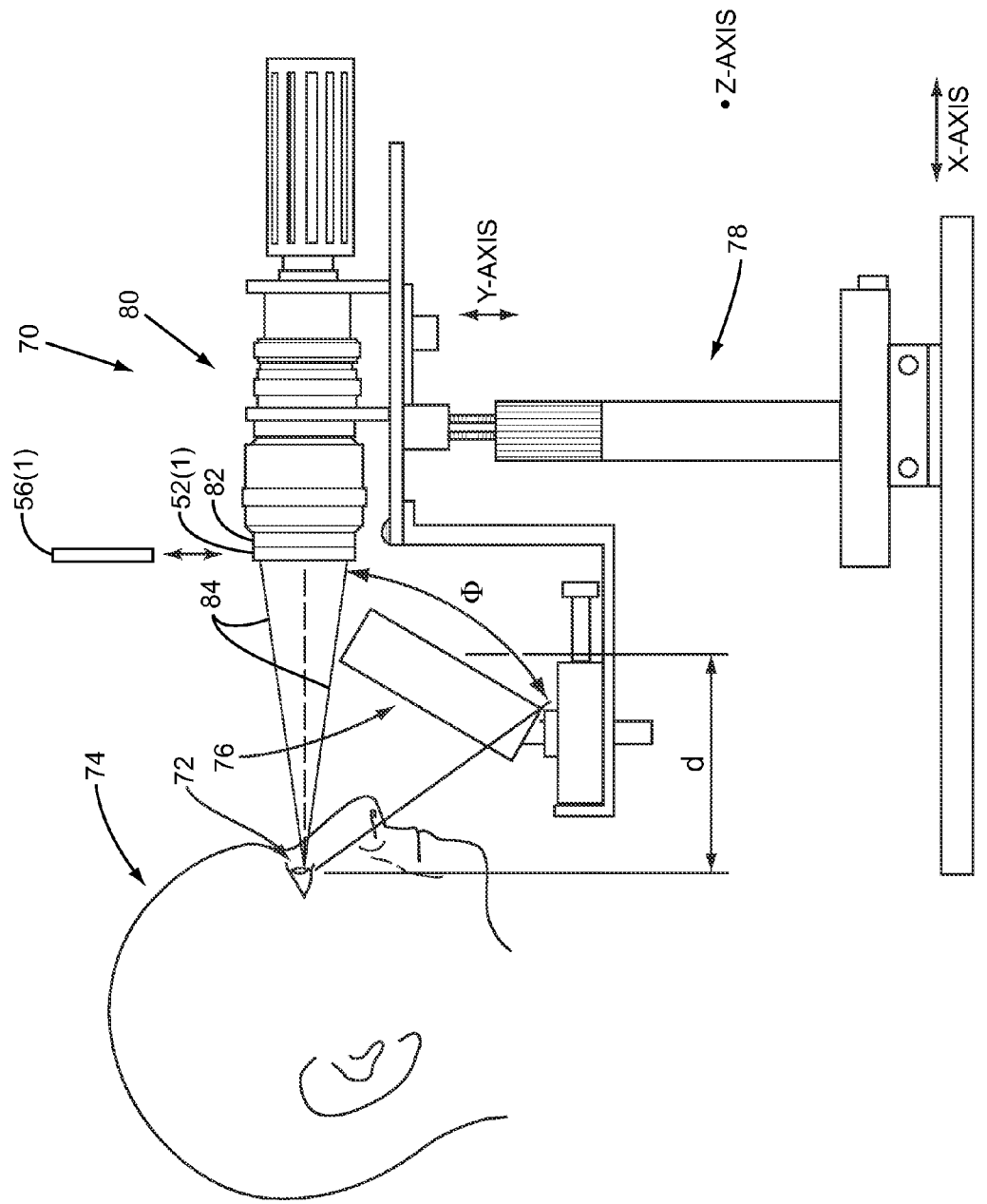

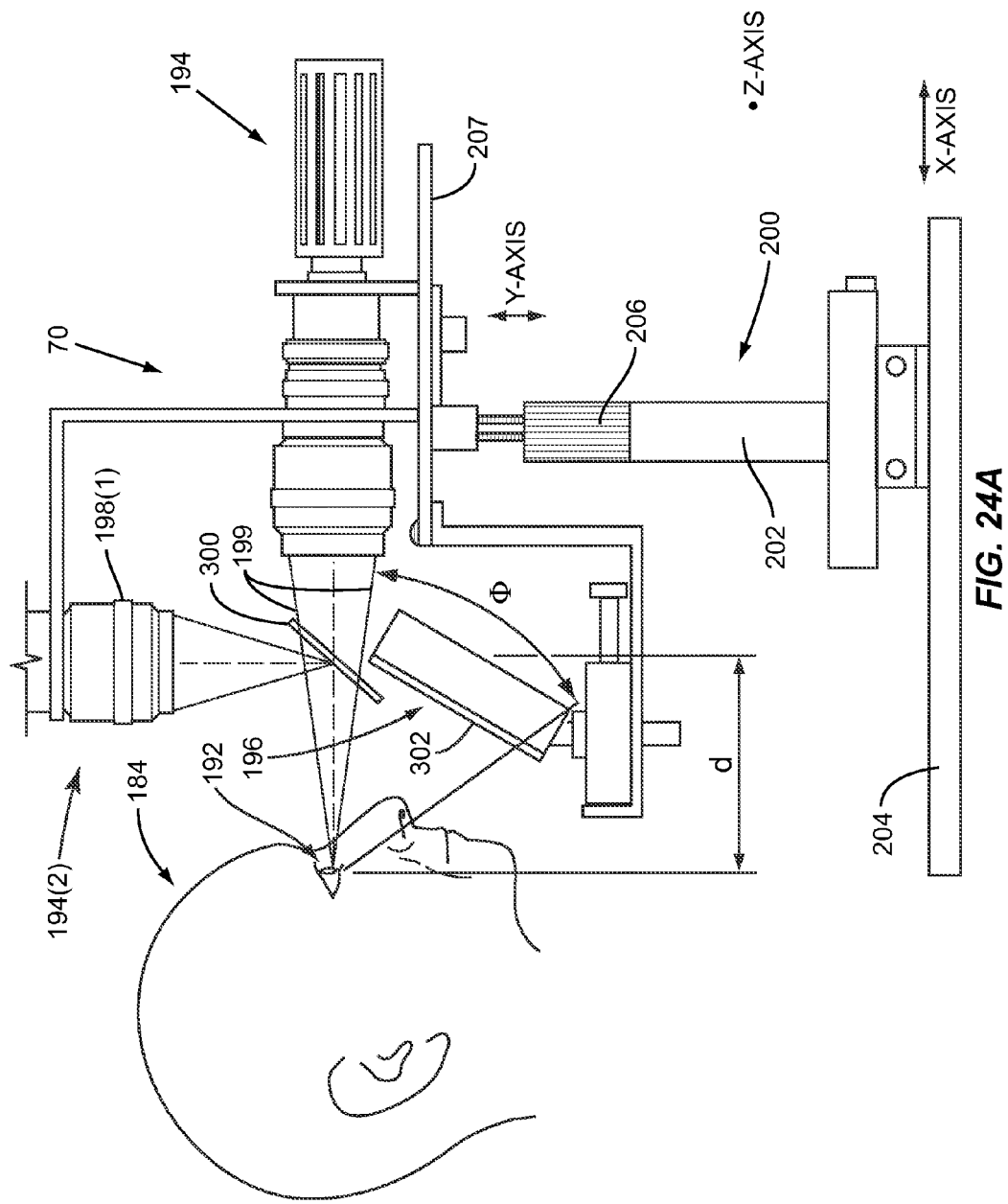

US 8,915,592 B2

APPARATUSES AND METHODS OF OCULAR SURFACE INTERFEROMETRY (OSI) EMPLOYING POLARIZATION AND SUBTRACTION FOR IMAGING, PROCESSING, AND/OR DISPLAYING AN OCULAR TEAR FILM

PRIORITY APPLICATIONS

The present application claims priority to U.S. Provisional Patent Application No. 61/638,231 entitled "APPARATUSES AND METHODS OF OCULAR SURFACE INTERFEROMETRY (OSI) EMPLOYING POLARIZATION AND SUBTRACTION FOR IMAGING, PROCESSING, AND/OR DISPLAYING AN OCULAR TEAR FILM," filed Apr. 25, 2012, which is incorporated herein by reference in its entirety.

The present application is also a continuation-in-part application of U.S. patent application Ser. No. 12/798,325 entitled "OCULAR SURFACE INTERFEROMETRY (OSI) METHODS FOR IMAGING, PROCESSING, AND/OR DISPLAYING AN OCULAR TEAR FILM," filed Apr. 1, 2010, which claims priority to U.S. Provisional Patent Application No. 61/211,596 entitled "OCULAR SURFACE INTERFEROMETRY (OSI) DEVICES, SYSTEMS, AND METHODS FOR MEASURING TEAR FILM LAYER THICKNESS(ES)," filed on Apr. 1, 2009, which are both incorporated herein by reference in their entireties.

RELATED APPLICATIONS

The present application is related to concurrently filed U.S. patent application Ser. No. 13/870,214 entitled "BACKGROUND REDUCTION APPARATUSES AND METHODS OF OCULAR SURFACE INTERFEROMETRY (OSI) EMPLOYING POLARIZATION FOR IMAGING, PROCESSING, AND/OR DISPLAYING AN OCULAR TEAR FILM", filed on Apr. 25, 2013, which claims priority to U.S. Provisional Patent Application No. 61/638,260 entitled "BACKGROUND REDUCTION APPARATUSES AND METHODS OF OCULAR SURFACE INTERFEROMETRY (OSI) EMPLOYING POLARIZATION FOR IMAGING, PROCESSING, AND/OR DISPLAYING AN OCULAR TEAR FILM," filed on Apr. 25, 2012, both of which are incorporated herein by reference in their entireties.

The present application is also related to U.S. patent application Ser. No. 11/820,664 entitled "TEAR FILM MEASUREMENT," filed on Jun. 20, 2007, issued as U.S. Pat. No. 7,758,190, which is incorporated herein by reference in its entirety.

The present application is also related to U.S. patent application Ser. No. 11/900,314 entitled "TEAR FILM MEASUREMENT," filed on Sep. 11, 2007, issued as U.S. Pat. No. 8,192,026, which is incorporated herein by reference in its entirety.

The present application is also related to U.S. patent application Ser. No. 12/798,275 entitled "OCULAR SURFACE INTERFEROMETRY (OSI) DEVICES AND SYSTEMS FOR IMAGING, PROCESSING, AND/OR DISPLAYING AN OCULAR TEAR FILM," filed on Apr. 1, 2010, which is incorporated herein by reference in its entirety.

The present application is also related to U.S. patent application Ser. No. 12/798,326 entitled "OCULAR SURFACE INTERFEROMETRY (OSI) METHODS FOR IMAGING AND MEASURING OCULAR TEAR FILM LAYER THICKNESS(ES)," filed on Apr. 1, 2010, issued as U.S. Pat. No. 8,092,023, which is incorporated herein by reference in its entirety.

The present application is also related to U.S. patent application Ser. No. 12/798,324 entitled "OCULAR SURFACE INTERFEROMETRY (OSI) DEVICES AND SYSTEMS FOR IMAGING AND MEASURING OCULAR TEAR FILM LAYER THICKNESS(ES)," filed on Apr. 1, 2010, issued as U.S. Pat. No. 8,215,774, which is incorporated herein by reference in its entirety.

The present application is being filed with three (3) sets of color versions of the drawings discussed and referenced in this disclosure. Color drawings more fully disclose the subject matter disclosed herein.

FIELD OF THE DISCLOSURE

The technology of the disclosure relates to imaging a mammalian ocular tear film. The technology of the disclosure also relates to measuring ocular tear film layer thickness(es), including lipid layer thickness (LLT) and/or aqueous layer thickness (ALT). Imaging the ocular tear film and measuring TFLT may be used to diagnose "dry eye," which may be due to any number of deficiencies, including lipid deficiency and aqueous deficiency.

BACKGROUND

In the human eye, the precorneal tear film covering ocular surfaces is composed of three primary layers: the mucin layer, the aqueous layer, and the lipid layer. Each layer plays a role in the protection and lubrication of the eye and thus affects dryness of the eye or lack thereof. Dryness of the eye is a recognized ocular disease, which is generally referred to as "dry eye," "dry eye syndrome" (DES), or "keratoconjunctivitis sicca" (KCS). Dry eye can cause symptoms, such as itchiness, burning, and irritation, which can result in discomfort. There is a correlation between the ocular tear film layer thicknesses and dry eye disease. The various different medical conditions and damage to the eye as well as the relationship of the aqueous and lipid layers to those conditions are reviewed in Surv Opthalmol 52:369-374, 2007 and additionally briefly discussed below.

As illustrated in FIG. 1, the precorneal tear film includes an innermost layer of the tear film in contact with a cornea 10 of an eye 11 known as the mucus layer 12. The mucus layer 12 is comprised of many mucins. The mucins serve to retain aqueous in the middle layer of the tear film known as the aqueous layer. Thus, the mucus layer 12 is important in that it assists in the retention of aqueous on the cornea 10 to provide a protective layer and lubrication, which prevents dryness of the eye 11.

A middle or aqueous layer 14 comprises the bulk of the tear film. The aqueous layer 14 is formed by secretion of aqueous by lacrimal glands 16 and accessory tear glands 17 surrounding the eye 11, as illustrated in FIG. 2. The aqueous, secreted by the lacrimal glands 16 and accessory tear glands 17, is also commonly referred to as "tears." One function of the aqueous layer 14 is to help flush out any dust, debris, or foreign objects that may get into the eye 11. Another important function of the aqueous layer 14 is to provide a protective layer and lubrication to the eye 11 to keep it moist and comfortable. Defects that cause a lack of sufficient aqueous in the aqueous layer 14, also known as "aqueous deficiency," are a common cause of dry eye. Contact lens wear can also contribute to dry eye. A contact lens can disrupt the natural tear film and can reduce corneal sensitivity over time, which can cause a reduction in tear production.

The outermost layer of the tear film, known as the "lipid layer" 18 and also illustrated in FIG. 1, also aids to prevent dryness of the eye. The lipid layer 18 is comprised of many lipids known as "meibum" or "sebum" that is produced by meibomian glands 20 in upper and lower eyelids 22, 24, as illustrated in FIG. 3. This outermost lipid layer is very thin, typically less than 250 nanometers (nm) in thickness. The lipid layer 18 provides a protective coating over the aqueous layer 14 to limit the rate at which the aqueous layer 14 evaporates. Blinking causes the upper eyelid 22 to mall up aqueous and lipids as a tear film, thus forming a protective coating over the eye 11. A higher rate of evaporation of the aqueous layer 14 can cause dryness of the eye. Thus, if the lipid layer 18 is not sufficient to limit the rate of evaporation of the aqueous layer 14, dryness of the eye may result.

Notwithstanding the foregoing, it has been a long standing and vexing problem for clinicians and scientists to quantify the lipid and aqueous layers and any deficiencies of same to diagnose evaporative tear loss and/or tear deficiency dry eye conditions. Further, many promising treatments for dry eye have failed to receive approval from the United States Food and Drug Administration due to the inability to demonstrate clinical effectiveness to the satisfaction of the agency. Many clinicians diagnose dry eye based on patient symptoms alone. Questionnaires have been used in this regard. Although it seems reasonable to diagnose dry eye based on symptoms alone, symptoms of ocular discomfort represent only one aspect of "dry eyes," as defined by the National Eye Institute workshop on dry eyes. In the absence of a demonstrable diagnosis of tear deficiency or a possibility of excessive tear evaporation and damage to the exposed surface of the eye, one cannot really satisfy the requirements of dry eye diagnosis.

SUMMARY OF THE DETAILED DESCRIPTION

Embodiments of the detailed description include ocular surface interferometry (OSI) devices, systems, and methods for imaging an ocular tear film and/or measuring a tear film layer thickness (TFLT) of a mammalian's ocular tear film. The OSI devices, systems, and methods can be used to measure the thickness of the lipid layer component (LLT) and/or the aqueous layer component (ALT) of the ocular tear film. "TFLT" as used herein includes LLT, ALT, or both LLT and ALT. "Measuring TFLT" as used herein includes measuring LLT, ALT, or both LLT and ALT. Imaging the ocular tear film and measuring TFLT can be used in the diagnosis of the tear film, including but not limited to lipid layer and aqueous layer deficiencies. These characteristics may be the cause or contributing factor to a patient experiencing dry eye syndrome (DES).

In this regard, embodiments disclosed herein include a multi-wavelength light source that is controlled to direct light in the visible region to an ocular tear film. The light source may be a Lambertian emitter that provides a uniform or substantially uniform intensity in all directions of emission. The light source is arranged such that light rays emitted from the light source are specularly reflected from the tear film and undergo constructive and destructive optical wave interference interactions (also referred to as "interference interactions") in the ocular tear film. An imaging device having a detection spectrum that includes the spectrum of the light source is focused on an area(s) of interest on the lipid layer of the tear film. The imaging device captures the interference interactions (i.e., modulation) of specularly reflected light rays from the illuminated tear film coming together by the focusing action of the imaging device in a first image. The imaging device then captures the optical wave interference signals (also referred to as "interference signals") representing the interference interactions of specularly reflected light from the tear film. The imaging device produces an output signal(s) representative of the interference signal in a first image. The first image may contain an interference signal for a given imaged pixel or pixels of the lipid layer by the imaging device.

The first image can be displayed to a technician or other user. The first image can also be processed and analyzed to measure a TFLT in the area or region of interest of the ocular tear film. In one embodiment, the first image also contains a background signal(s) that does not represent specularly reflected light from the tear film which is superimposed on the interference signal(s). The first image is processed to subtract or substantially subtract out the background signal(s) superimposed upon the interference signal to reduce error before being analyzed to measure TFLT. This is referred to as "background subtraction" in the present disclosure. The separate background signal(s) includes returned captured light that is not specularly reflected from the tear film and thus does not contain optical wave interference information (also referred to as "interference information"). For example, the background signal(s) may include stray, ambient light entering into the imaging device, scattered light from the patient's face and eye structures outside and within the tear film as a result of ambient light and diffuse illumination by the light source, and eye structure beneath the tear film, and particularly contribution from the extended area of the source itself. The background signal(s) adds a bias (i.e., offset) error to the interference signal(s) thereby reducing interference signal strength and contrast. This error can adversely influence measurement of TFLT. Further, if the background signal(s) has a color hue different from the light of the light source, a color shift can also occur to the captured optical wave interference (also referred to as "interference") of specularly reflected light thus introducing further error.

In this regard in one embodiment, an apparatus for imaging an ocular tear film is disclosed. The apparatus includes a control system configured to receive at least one first image containing optical wave interference of specularly reflecting light in a first polarization plane along with a background signal from a region of interest (ROI) of the ocular tear film captured by an imaging device while illuminated by the multi-wavelength light source. The control system is also configured to receive at least one second image containing the background signal in a second polarization plane perpendicular or substantially perpendicular to the first polarization plane from the ROI of the ocular tear film captured by an imaging device. In this manner, an imaging device captures background signal(s) in a second image that is representative of the signal which is superimposed on the interference of the specularly reflecting light from the tear film in the first image. The second image is subtracted from the first image to produce a resulting image having isolated interference signal components. The resulting image can then be displayed on a visual display to be analyzed by a technician and/or processed and analyzed to measure a TFLT. One non-limiting benefit of the apparatus is that it allows capturing the at least one second image containing the background signal in a second polarization plane perpendicular or substantially perpendicular to the first polarization plane from the ROI of the ocular tear film. As a result, the background signal is isolated from the interference of the specularly reflecting light from the tear film. Thus, a background offset captured in the at least one first image is removed or reduced from at least one resulting image generated by the subtraction of the at least one second image from the at least one first image.

In another embodiment, a method of imaging an ocular tear film is disclosed. The disclosed method involves illuminating the ROI of an ocular tear film with the multi-wavelength light source. The method includes capturing optical wave interference of specularly reflected light in a first polarization plane including a background signal from the ROI of the ocular tear film while illuminated by the multi-wavelength light source in at least one image by an imaging device. The method also includes capturing the background signal in a second polarizing plane perpendicular or substantially perpendicular to the first polarization plane from the ROI of the ocular tear film in at least one second image by an imaging device. The method also includes subtracting the at least one second image from the at least one first image to generate at least one resulting image containing the optical wave interference of specularly reflected light from the ROI of the ocular tear film with the background signal removed. Capturing the at least one second image containing the background signal in a second polarization plane perpendicular or substantially perpendicular to the first polarization plane from the ROI of the ocular tear film can isolate the background signal from the interference of the specularly reflecting light from the ocular tear film. In this manner, a background offset captured in the at least one first image is removed or reduced from at least one resulting image generated by the subtraction of the at least one second image from the at least one first image.

After the interference of the specularly reflected light is captured and a resulting image containing the interference signal is produced from any method or device disclosed in this disclosure, the resulting image can also be pre-processed before being processed and analyzed to measure TFLT. Pre-processing can involve performing a variety of methods to improve the quality of the resulting signal, including but not limited to detecting and removing eye blinks or other signals in the captured images that hinder or are not related to the tear film. After pre-processing, the interference signal or representations thereof can be processed to be compared against a tear film layer interference model to measure TFLT. The interference signal can be processed and converted by the imaging device into digital red-green-blue (RGB) component values which can be compared to RGB component values in a tear film interference model to measure TFLT on an image pixel-by-pixel basis. The tear film interference model is based on modeling the lipid layer of the tear film in various thicknesses and mathematically or empirically observing and recording resulting interference interactions of specularly reflected light from the tear film model when illuminated by the light source and detected by a camera (imaging device).

In a tear film interference model, the lipid layer is modeled of various LLTs to observe interference interactions resulting from the various LLTs. The aqueous layer may be modeled in the tear film interference model to be of an infinite, minimum, or varying thickness. If the aqueous layer is modeled to be of an infinite thickness, the tear film interference model assumes no specular reflections occur from the aqueous-to-mucin layer transition. If the aqueous layer is modeled to be of a certain minimum thickness (~>2 μm e.g.), the effect of specular reflection from the aqueous-to-mucin layer transition may be considered in the resulting interference. In either case, the tear film interference model is a 2-wave tear film interference model to represent the interference between specularly reflected light from the air-to lipid layer transition and the lipid-to-aqueous layer transition. Thus, a 2-wave tear film interference model will include one-dimension of data comprised of interference interactions corresponding to the various LLTs. In this case, to measure LLT the interference interactions in the interference signal representing specularly reflected light from the tear film produced by the imaging device are compared to the interference patterns in the tear film interference model. However, if the aqueous layer is also modeled to be of varying ALTs, the tear film interference model will be a 3-wave tear film interference model. The 3-wave tear film interference model will include interference between the air-to lipid layer, lipid-to-aqueous layer, and aqueous-to-mucus/cornea layer transitions. As a result, a 3-wave tear film interference model will include two-dimensions of data comprised of interference interactions corresponding to various LLT and ALT combinations. In this case, to measure LLT and/or ALT the interference interactions from the interference signal representing specularly reflected light from the tear film produced by the imaging device can be compared to interference interactions in the 3-wave tear film interference model.

The tear film interference model can be a theoretical tear film interference model where the light source and the tear film layers are modeled mathematically. The tear film layers may be mathematically modeled by modeling the tear film layers after certain biological materials. Interference interactions from the mathematically modeled light source illuminating the mathematically modeled tear film and received by the mathematically modeled camera are calculated and recorded for varying TFLTs. Alternatively, the tear film interference model can be based on a biological or phantom tear film model comprised of biological or phantom tear film layers. The actual light source is used to illuminate the biological or phantom tear film model and interference interactions representing interference of specularly reflected light are empirically observed and recorded for various TFLTs using the actual camera.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawing figures incorporated in and forming a part of this specification illustrate several aspects of the disclosure, and together with the description serve to explain the principles of the disclosure.

FIGS. 6A and 6B illustrate an exemplary light source and imaging device to facilitate discussion of illumination of the tear film and capture of interference interactions of specularly reflected light from the tear film;

FIG. 24A is a side view of an exemplary OSI device with the dual imager and polarizing beam splitter configuration that also includes a polarizer in the illumination path of the illuminator;

DETAILED DESCRIPTION

Figure 1:
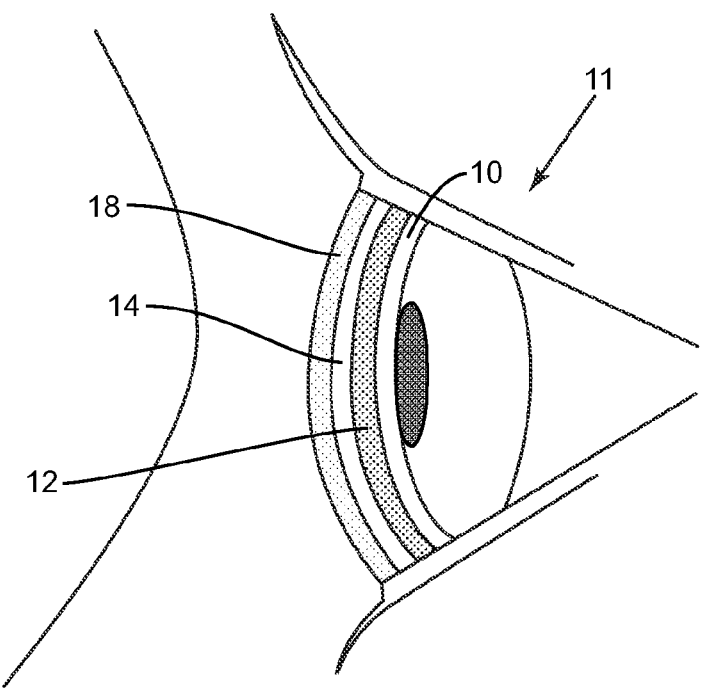
FIG. 1 is a side view of an exemplary eye showing the three layers of the tear film in exaggerated form.
Figure 2:
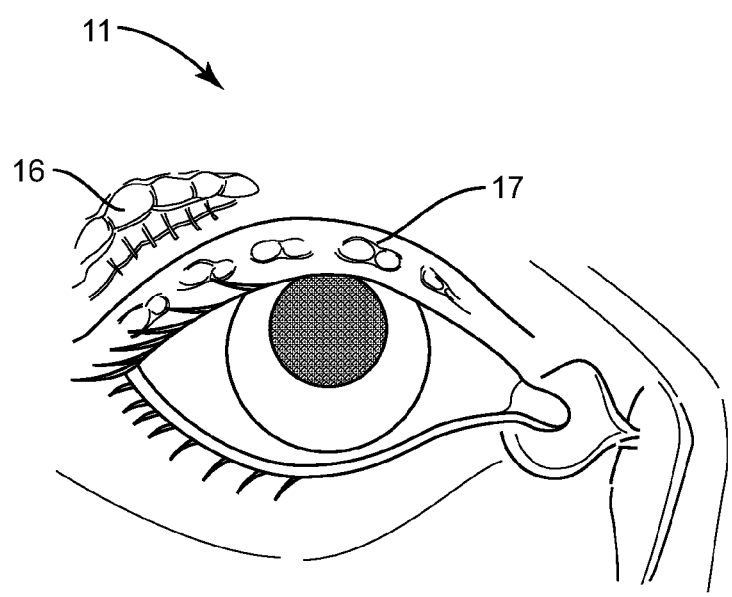
FIG. 2 is a front view of an exemplary eye showing the lacrimal and accessory tear glands that produce aqueous in the eye.
Figure 3:
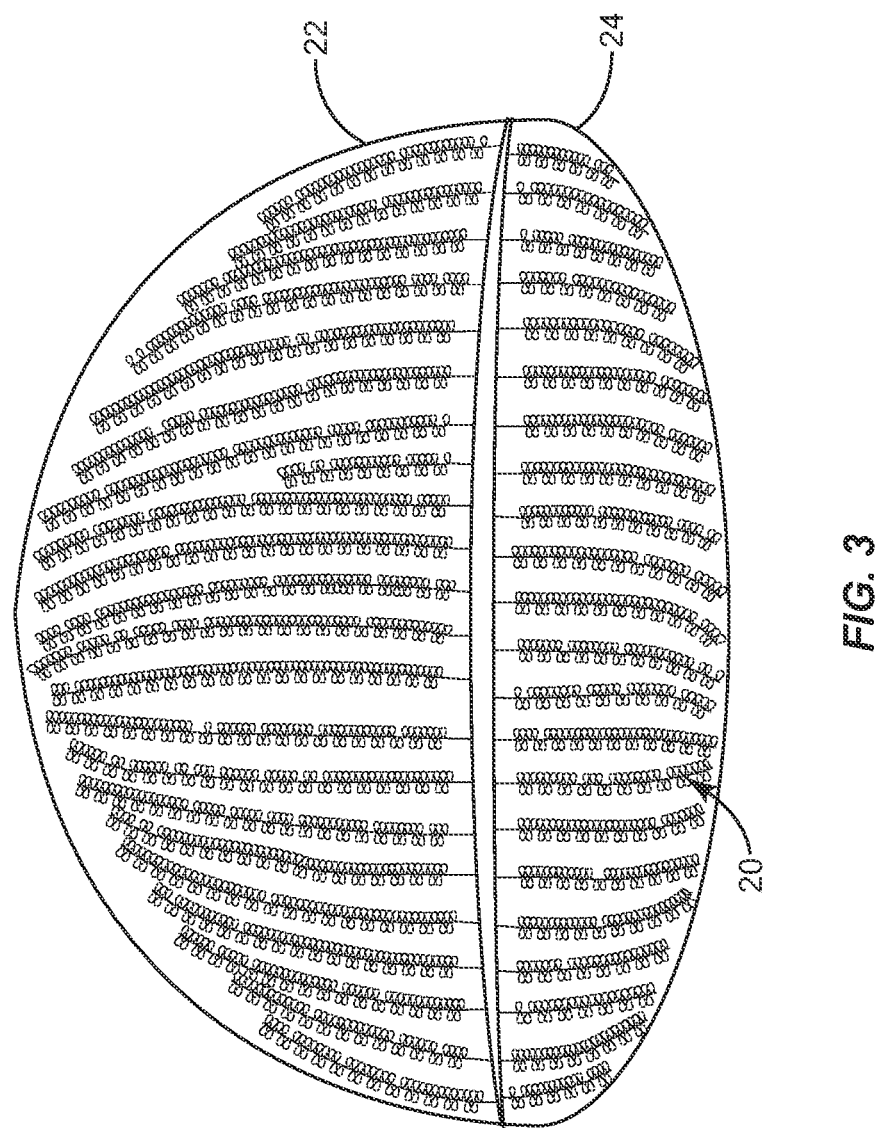
FIG. 3 illustrates exemplary upper and lower eyelids showing the meibomian glands contained therein.

The embodiments set forth below represent the necessary information to enable those skilled in the art to practice the disclosure and illustrate the best mode of practicing the disclosure. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

Embodiments of the detailed description include ocular surface interferometry (OSI) devices, systems, and methods for imaging an ocular tear film and/or measuring a tear film layer thickness (TFLT) of an ocular tear film. The OSI devices, systems, and methods can be used to measure the thickness of the lipid layer component (LLT) and/or the aqueous layer component (ALT) of the ocular tear film. "TFLT" as used herein includes LLT, ALT, or both LLT and ALT. "Measuring TFLT" as used herein includes measuring LLT, ALT, or both LLT and ALT. Imaging the ocular tear film and measuring TFLT can be used in the diagnosis of a patient's tear film, including but not limited to lipid layer and aqueous layer deficiencies. These characteristics may be the cause or contributing factor to a patient experiencing dry eye syndrome (DES).

In this regard, embodiments disclosed herein include a multi-wavelength light source that is controlled to direct light in the visible region to an ocular tear film. The light source may be a Lambertian emitter that provides a uniform or substantially uniform intensity in all directions of emission. The light source is arranged such that light rays emitted from the light source are specularly reflected from the tear film and undergo constructive and destructive optical wave interference interactions (also referred to as "interference interactions") in the ocular tear film. In some embodiments, the light source An imaging device having a detection spectrum that includes the spectrum of the light source is focused on an area(s) of interest on the lipid layer of the tear film. The imaging device captures the interference interactions (i.e., modulation) of specularly reflected light rays from the illuminated tear film coming together by the focusing action of the imaging device in a first image. The imaging device then captures the optical wave interference signals (also referred to as "interference signals") representing the interference interactions of specularly reflected light from the tear film. The imaging device produces an output signal(s) representative of the interference signal in a first image. The first image may contain an interference signal for a given imaged pixel or pixels of the lipid layer by the imaging device.

The first image can be displayed to a technician or other user. The first image can also be processed and analyzed to measure a TFLT in the area or region of interest of the ocular tear film. In one embodiment, the first image also contains a background signal(s) that does not represent specularly reflected light from the tear film which is superimposed on the interference signal(s). The first image is processed to subtract or substantially subtract out the background signal(s) superimposed upon the interference signal to reduce error before being analyzed to measure TFLT. This is referred to as "background subtraction" in the present disclosure. The separate background signal(s) includes returned captured light that is not specularly reflected from the tear film and thus does not contain optical wave interference information (also referred to as "interference information"). For example, the background signal(s) may include stray, ambient light entering into the imaging device, scattered light from the face and eye structures outside and within the tear film as a result of ambient light and diffuse illumination by the light source, and eye structure beneath the tear film, and particularly contribution from the extended area of the source itself. The background signal(s) adds a bias (i.e., offset) error to the interference signal(s) thereby reducing interference signal strength and contrast. This error can adversely influence measurement of TFLT. Further, if the background signal(s) has a color hue different from the light of the light source, a color shift can also occur to the captured optical wave interference (also referred to as "interference") of specularly reflected light thus introducing further error.

In this regard in one embodiment, an apparatus for imaging an ocular tear film is disclosed. The apparatus includes a control system configured to receive at least one first image containing optical wave interference of specularly reflecting light in a first polarization plane along with a background signal from a region of interest (ROI) of the ocular tear film captured by an imaging device while illuminated by the multi-wavelength light source. The control system is also configured to receive at least one second image containing the background signal in a second polarization plane perpendicular or substantially perpendicular to the first polarization plane from the ROI of the ocular tear film captured by an imaging device. In this manner, an imaging device captures background signal(s) in a second image that is representative of the signal which is superimposed on the interference of the specularly reflecting light from the tear film in the first image. The second image is subtracted from the first image to produce a resulting image having isolated interference signal components. The resulting image can then be displayed on a visual display to be analyzed by a technician and/or processed and analyzed to measure a TFLT. One non-limiting benefit of the apparatus is that it allows capturing the at least one second image containing the background signal in a second polarization plane perpendicular or substantially perpendicular to the first polarization plane from the ROI of the ocular tear film. As a result, the background signal is isolated from the interference of the specularly reflecting light from the tear film. Thus, a background offset captured in the at least one first image is removed or reduced from at least one resulting image generated by the subtraction of the at least one second image from the at least one first image.

In another embodiment, a method of imaging an ocular tear film is disclosed. The disclosed method involves illuminating the ROI of an ocular tear film with the multi-wavelength light source. The method include capturing optical wave interference of specularly reflected light in a first polarization plane including a background signal from the ROI of the ocular tear film while illuminated by the multi-wavelength light source in at least one image by an imaging device. The method also includes capturing the background signal in a second polarizing plane perpendicular or substantially perpendicular to the first polarization plane from the ROI of the ocular tear film in at least one second image by an imaging device. The method also includes subtracting the at least one second image from the at least one first image to generate at least one resulting image containing the optical wave interference of specularly reflected light from the ROI of the ocular tear film with the background signal removed. Capturing the at least one second image containing the background signal in a second polarization plane perpendicular or substantially perpendicular to the first polarization plane from the ROI of the ocular tear film can isolate the background signal from the interference of the specularly reflecting light from the ocular tear film. In this manner, a background offset captured in the at least one first image is removed or reduced from at least one resulting image generated by the subtraction of the at least one second image from the at least one first image.

Before discussing the particular embodiments of the present disclosure, a discussion of the electromagnetic nature of light waves is provided with regard to FIGS. 4A-4H. Light waves, like all electromagnetic waves, propagate with an oscillating electric field that generates an oscillating magnetic field that regenerates the oscillating electric field and so on. Moreover, light waves exhibit a property known as polarization. For example, when the orientation of the oscillating electric field is in a fixed plane in space, the light wave is a plane-polarized wave. When the plane of the electric field rotates as a light wave propagates spirally through space, the light wave is a circularly or elliptically polarized light wave. Furthermore, light made up of many light waves that are randomly polarized is referred to as unpolarized light, since there is no single polarization plane for unpolarized light.

Optical filters known as polarizers allow unimpeded transmission of light waves having a single polarization-plane. Any type of polarizer may be employed in the embodiments discussed below. For example, a linear polarizer may be employed to reduce the intensity of a background signal(s). An exemplary linear polarizer has a polarization axis that typically extends across the polarizer. Light waves that impinge upon the linear polarizer with a polarization-plane that is parallel to the polarization axis of the polarizer will pass through the polarizer unimpeded. In contrast, light waves that impinge upon the linear polarizer with polarization-planes that are not parallel to the polarization-plane of the polarizer will be impeded. As another non-limiting example, a circular polarizer or an elliptical polarizer can be employed in any of the embodiments below to reduce the intensity of a background signal(s). Circular polarizers and/or elliptical polarizers may also be usable to prevent unintentional secondary specular reflections in embodiments that use beam splitters. An exemplary circular polarizer may comprise two components. One component is a linear polarizer such as the exemplary polarizer described above that passes light waves in one polarization-plane. The other component is a quarter wave plate that transforms light waves passing through the linear polarizer in one polarization-plane into circularly polarized light waves. Exemplary elliptical polarizers may comprise the same components as circular polarizers. An elliptical polarizer is configured such that it transforms the light passing through the linear polarizer in one polarization-plane into elliptically polarized light. Elliptically polarized light has unequal electric field amplitudes.

The intensity of a light wave is related to its electric field amplitude. The degree to which the intensity of a light wave is reduced by a polarizer depends on the angle between the polarization plane of the light wave and the polarization axis of the polarizer. According to Malus' law, a light wave impinging on a polarizer will be reduced in amplitude in proportion to the cosine of the angle between the polarization plane of the light wave and the polarization axis of the polarizer. A light wave that has a polarization plane that is parallel with the polarization axis will have a 0° angle between its polarization plane and the polarization axis of the polarizer. Since the cosine of 0° is one, Malus' law ideally predicts no reduction of light intensity for a light wave that has a polarization plane that is parallel with the polarization axis. In contrast, Malus' law ideally predicts no transmission through a polarizer for a light wave that impinges on the polarizer with a polarization plane that is perpendicular to the polarization axis of the polarizer since the cosine of 90° is zero.

When unpolarized light impinges on a polarizer, the overall intensity of the light is reduced by at least 50% due to the summations of amplitude reductions due to Malus' law as applied to individual light waves having random polarization planes impinging on the polarizer. Light that is transmitted through the polarizer becomes polarized such that the light has a polarization plane that is parallel with the polarization axis of the polarizer.

Light intensity is proportional to the square of the amplitude. Therefore, the intensity of light transmitted through the polarizer from a non-polarized light source is ideally 25%. However, modern polarizers are not perfect, which results in additional losses of intensity for the transmitted light due to absorption, scattering and other intensity degrading effects.

Figure 4A:
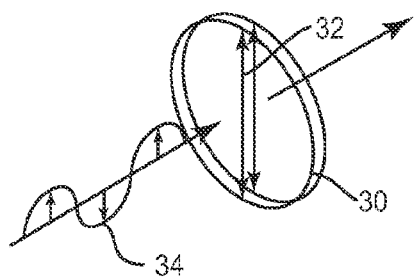
FIGS. 4A through 4H illustrate relationships between light waves, beam splitters, and polarizers.

In this regard, FIGS. 4A through 4H illustrate relationships between light waves, polarizers and beam splitters. Referring to FIG. 4A, a polarizer 30 has a polarization axis 32 that is oriented in a direction indicated by a polarization axis arrow. A light wave 34 impinging on the polarizer 30 is in a polarization plane that is parallel to the polarization axis 32 of the polarizer 30. As a result, the light wave 34 is transmitted unimpeded through the polarizer 30.

Figure 4B:
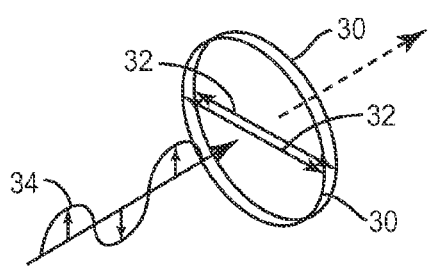
Figure 4C:
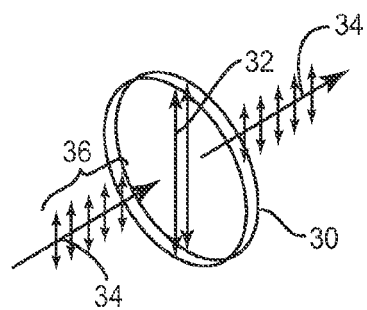
Figure 4D:
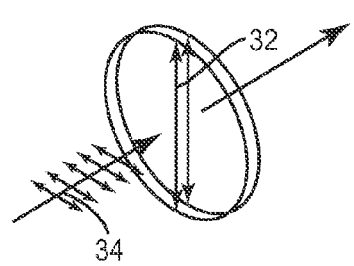

In contrast, FIG. 4B shows the polarizer 30 rotated such that the polarization axis 32 is perpendicular to the polarization plane of the light wave 34 as indicated by the polarization axis arrow. In this case, none of the light wave 34 will be transmitted through the polarizer 30. FIG. 4C and FIG. 4D represent the same conditions as FIG. 4A and FIG. 4B respectively. However, the polarization plane of light wave 34 is represented by double headed arrows 36 instead of the sine wave representation used to represent light wave 34 in FIGS. 4A and 4B.

Figure 4E:
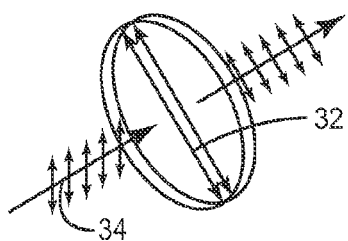

FIG. 4E illustrates a condition wherein the light wave 34 impinges upon the polarizer 30 when the difference in the angle between the polarization plane of the light wave 34 and the polarization axis 32 is intermediate of parallel and perpendicular. In this case, a portion of the light wave 34 is transmitted through the polarizer 30. The portion of light wave 34 that is transmitted through the polarizer 30 obtains a polarization plane that is parallel to the polarization axis 32 of the polarizer 30. The intensity of the transmitted portion of the light wave 34 is reduced relative to the intensity of the light wave 34 that is impinging on the polarizer 30. The relative intensity of the light wave 34 is represented by the relative difference in length of the double-headed arrows 36.

Figure 4F:
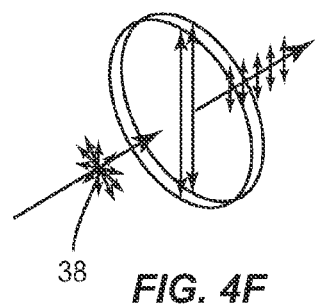

FIG. 4F illustrates a light beam 38 that is shown impinging on the polarizer 30. The light beam 38 is made up of a plurality of light waves that are in random polarization planes. In this example, the light beam 38 includes the light wave 34 having a polarization plane that aligns with the polarization axis 32 of the polarizer 30. As a result of the alignment, the light wave 34 is transmitted through the polarizer 30.

Figure 4G:
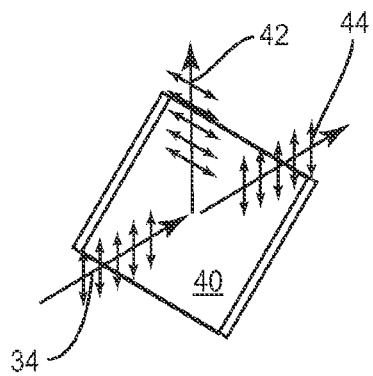

FIG. 4G illustrates a specular reflection and a refraction of the light wave 34 as the light wave 34 impinges on the minor-like surface of a polarizing beam splitter 40. In the example of FIG. 4G, the light wave 34 has a first polarization plane as it arrives at polarizing beam splitter 40. A first portion 42 of the light wave 34 specularly reflects from the polarizing beam splitter 40 in a second polarization plane that is perpendicular to the first polarization plane of the impinging light wave 34. A second portion 44 of the light wave 34 is refracted by the polarizing beam splitter 40. The second portion 44 of the light wave 34 maintains the first polarization plane of the impinging light wave 34.

Figure 4H:
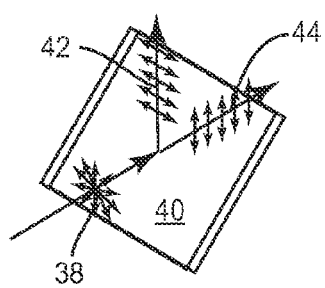

FIG. 4H illustrates a specular reflection and a refraction of the light wave 34 that is one of a plurality of light waves that make up the light beam 38 as it impinges upon the polarizing beam splitter 40. As in the previous case, the light wave 34 in the first polarization plane is split into the first portion 42 and the second portion 44. As before, the first portion 42 of the light wave 34 is specularly reflected from the polarizing beam splitter 40 in a polarization plane that is perpendicular to the first polarization plane of the impinging light wave 34. As before, the second portion 44 of the light wave 34 maintains the first polarization plane of the impinging light wave 34.

Figure 5:
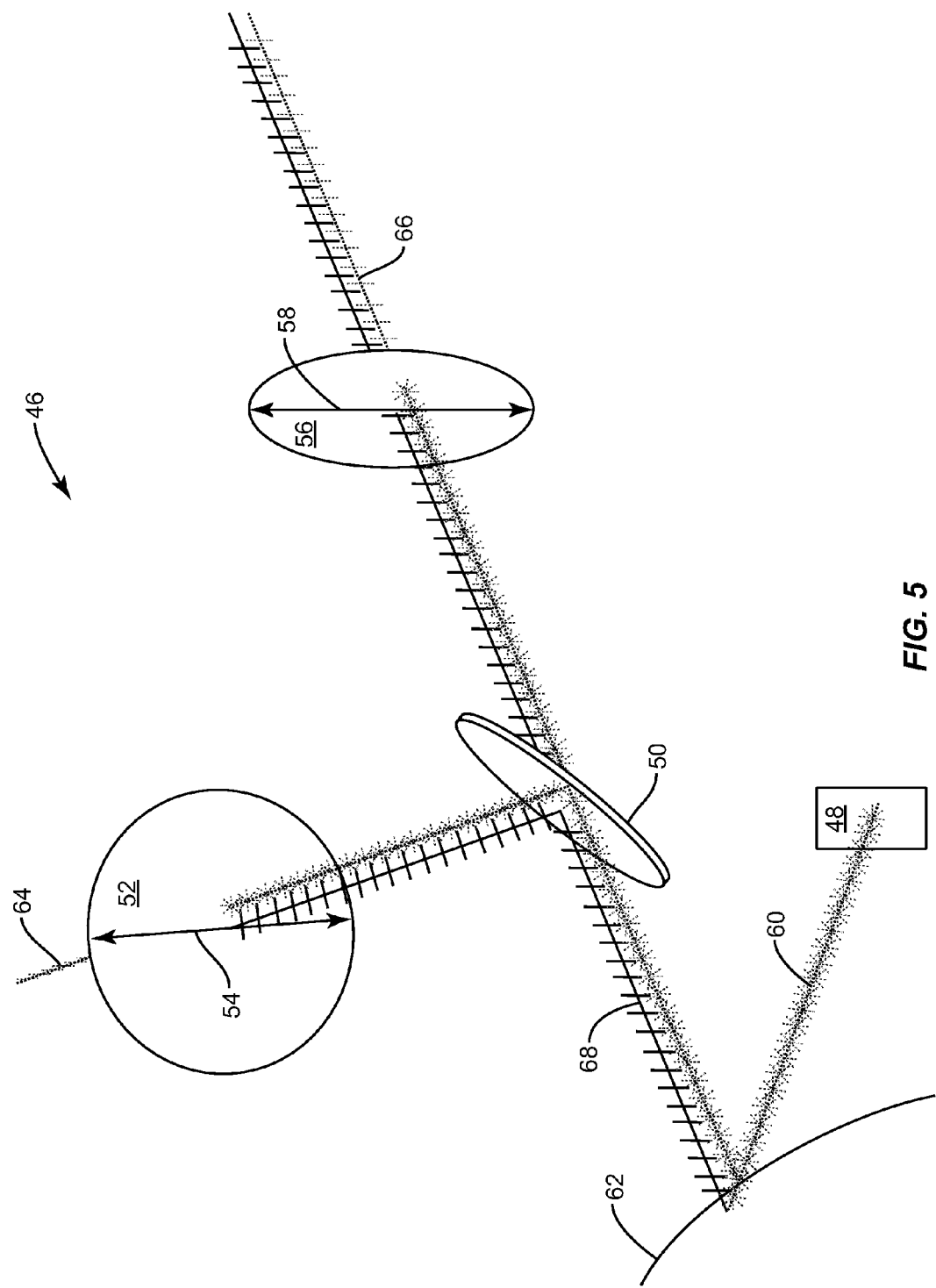
FIG. 5 illustrates a general principle of operation for embodiments of the present disclosure.

FIG. 5 illustrates exemplary devices that can be provided in an OSI device according to a first embodiment. An optical system 46 is made up of a light source 48, a non-polarizing beam splitter 50, a first polarizer 52 having a polarization axis 54 and a second polarizer 56 having a polarization axis 58. In the exemplary case of FIG. 5, light 60 emitted from the light source 48 is unpolarized. However, the exemplary case of FIG. 5 should not be viewed as limiting the present disclosure to unpolarized illumination, since at least one embodiment of the present disclosure utilizes a polarizer in the illumination path of a light source 48. The unpolarized light is directed from the light source 48 to a target 62, which in the case of the present disclosure is a tear film covering the human eye. The target 62 reflects the unpolarized light to the non-polarizing beam splitter 50. After reflecting from the target 62, the unpolarized light 60 comprises an undesirable background signal that will be eliminated or reduced from images captured by the imaging device by processing, techniques discussed later in the present disclosure.

A portion of the unpolarized light 60 reflects from the non-polarizing beam splitter 50 to the first polarizer 52. A portion of the unpolarized light 60 having a polarization plane that aligns with the polarization axis 54 passes through the first polarizer 52 unimpeded. A summation of other light waves making up the unpolarized light 60 having polarization planes that are not perpendicular to the polarization axis 54 are also transmitted through the first polarizer 52 with reduced intensity. Light waves 64 that are transmitted through the first polarizer 52 each have a polarization plane that is parallel to the polarization axis 54.

A refracted portion of the unpolarized light 60 is directed to the second polarizer 56. Similar to the light interaction with the first polarizer 52, a portion of the unpolarized light 60 having a polarization plane that aligns with the polarization axis 58 passes through the second polarizer 56 unimpeded. A summation of other light waves making up the unpolarized light 60 having polarization planes that are not perpendicular to the polarization axis 58 are also transmitted through the second polarizer 56 with reduced intensity. Light waves 66 that are transmitted through the second polarizer 56 each have a polarization plane that is parallel to the polarization axis 58.

Another portion of the unpolarized light 60 emitted from the light source 48 is specularly reflected from the target 62 such that a polarized light 68 is directed to the non-polarizing beam splitter 50. A first portion of the polarized light 68 is specularly reflected from the non-polarizing beam splitter 50 so that the polarized light is re-polarized in a polarization plane that is perpendicular to the polarization axis 54 of the first polarizer 52. In this way, the polarized light 68 that is specularly reflected from the target 62 is practically prevented from passing through the first polarizer 52. In contrast, a portion of the polarized light 68 that is refracted through the non-polarizing beam splitter 50 retains the polarization plane of the polarized light 68 as it specularly reflects from the target 62. The polarization axis 58 of the second polarizer 56 is aligned such that the portion of the specularly reflected light 84 passes through the second polarizer 56 unimpeded.

Against the discussion above, embodiments disclosed herein and discussed in more detail below include ocular surface interferometry (OSI) devices, systems, and methods for measuring a tear film layer thickness (TFLT) of the ocular tear film. The OSI devices, systems, and methods can be used to measure the thickness of the lipid layer component (LLT) and/or the aqueous layer component (ALT) of the ocular tear film. "TFLT" as used herein includes LLT, ALT, or both LLT and ALT. "Measuring TFLT" as used herein includes measuring LLT, ALT, or both LLT and ALT. Measuring TFLT can be used in the diagnosis of an ocular tear film, including but not limited to lipid layer and aqueous layer deficiencies. These characteristics may be the cause or contributing factor to a mammalian experiencing dry eye syndrome (DES).

In this regard, embodiments disclosed herein include a light source that is controlled to direct light in the visible region to an ocular tear film. For example, the light source may be a Lambertian emitter that provides a uniform or substantially uniform intensity in all directions of emission. The light source is arranged such that light rays emitted from the light source are specularly reflected toward an imaging device from the tear film and undergo constructive and destructive interference interactions in the ocular tear film. An imaging device having a detection spectrum that includes the spectrum of the light source is focused on an area(s) of interest on the lipid layer of the tear film. The imaging device captures a first image of the interference interactions (i.e., modulation) of specularly reflected light rays from the illuminated tear film coming together by the focusing action of the imaging device. The imaging device then captures the interference signals representing the interference interactions of specularly reflected light from the tear film. The imaging device produces an output signal(s) representative of the interference signal in a first image. The first image may contain an interference signal for a given imaged pixel or pixels of the lipid layer by the imaging device. The output signal(s) can be processed and analyzed to measure a TFLT in the area or region of interest of the ocular tear film.

OSI Device Employing Alternating Polarizers

Figure 6B:
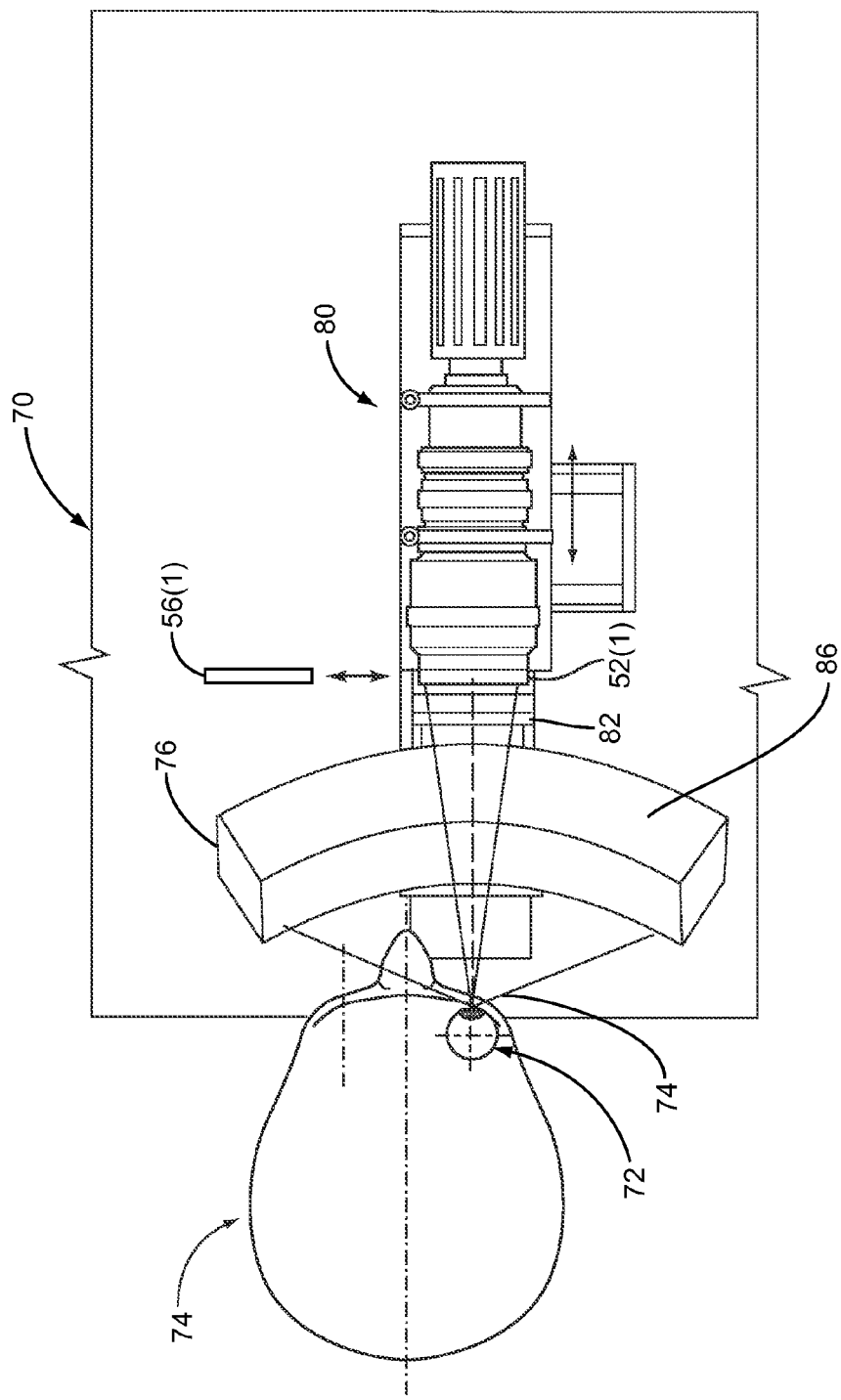

In this regard, FIGS. 6A and 6B illustrate a general embodiment of an ocular surface interferometry (OSI) device 70. Other embodiments will be described later in this application. In general, the OSI device 70 is configured to illuminate a patient's ocular tear film, capture images of interference interactions of specularly reflected light from the ocular tear film, and process and analyze the interference interactions to measure TFLT. As shown in FIG. 6A, the exemplary OSI device 70 positioned in front of one of the patient's eye 72 is shown from a side view. A top view of the patient 74 in front of the OSI device 70 is illustrated in FIG. 6B. The ocular tear film of a patient's eyes 72 is illuminated with a light source 76 (also referred to herein as "illuminator 76") and comprises a large area light source having a spectrum in the visible region adequate for TLFT measurement and correlation to dry eye. The illuminator 76 can be a white or multi-wavelength light source.

In this embodiment, the illuminator 76 is a Lambertian emitter and is adapted to be positioned in front of the eye 72 on a stand 78. As employed herein, the terms "Lambertian surface" and "Lambertian emitter" are defined to be a light emitter having equal or substantially equal (also referred to as "uniform" or substantially uniform) intensity in all directions. This allows the imaging of a uniformly or substantially uniformly bright tear film region for TFLT, as discussed in more detail in this disclosure. The illuminator 76 comprises a large surface area emitter, arranged such that rays emitted from the emitter are specularly reflected from the ocular tear film and undergo constructive and destructive interference in tear film layers therein. An image of the patient's 74 lipid layer is the backdrop over which the interference image is seen and it should be as spatially uniform as possible.

An imaging device 80 is included in the OSI device 70 and is employed to capture interference interactions of specularly reflected light from the patient's 74 ocular tear film when illuminated by the illuminator 76. The imaging device 80 may be a still or video camera, or other device that captures images and produces an output signal representing information in captured images. The output signal may be a digital representation of the captured images.

Optical filtering is used to improve isolation of interference interactions of specularly reflected light from the patient's 74 ocular tear film before images of the patient's 74 ocular tear film are captured. In this regard, a first polarizer 52(1) is selectively disposable in an imaging path of the imaging device 80 during the capture of at least one first image. A second polarizer 56(1) is selectively disposable in the imaging path of the imaging device 80 during the capture of at least one second image.

When the first polarizer 52(1) is in front of imaging lens 82, the specularly reflected light 84 from a region of interest (ROI) of the ocular tear film is allowed to pass or substantially pass to the imaging device 80. Simultaneously, the background signal is reduced before the background signal reaches the imaging device 80. In contrast, when the second polarizer 56(1) is in front of imaging lens 82, the specularly reflected light 84 from the ROI of the ocular tear film is reduced or eliminated before the specularly reflected light 84 reaches the imaging device 80 while passing a portion of the background signal. As a result, a first image captured with the first polarizer 52(1) in front of the imaging lens 82 will include a maximum amount of imagery resulting from the specularly reflected light 84 with a reduced amount of background signal. Moreover, a second image captured with the second polarizer 56(1) in front of the imaging lens 82 will have a minimum amount or none of the specularly reflected light along with a reduced background signal. Consequently, the second image can be subtracted from the first image to generate a resultant image that is predominately comprised of the ocular tear film.

As shown in FIGS. 6A and 6B, the first polarizer 52(1) and the second polarizer 56(1) are alternately translatable into the imaging path of the imaging device 80. In FIG. 6A the translation is shown occurring along the Y-AXIS, whereas in FIG. 6B the translation is shown occurring along the Z-AXIS. It is to be understood that translation of the first polarizer 52(1) and the second polarizer 56(1) along axes intermediate the Y-AXIS and the Z-AXIS may also be available depending on clearances and personal choice.

Figure 7:
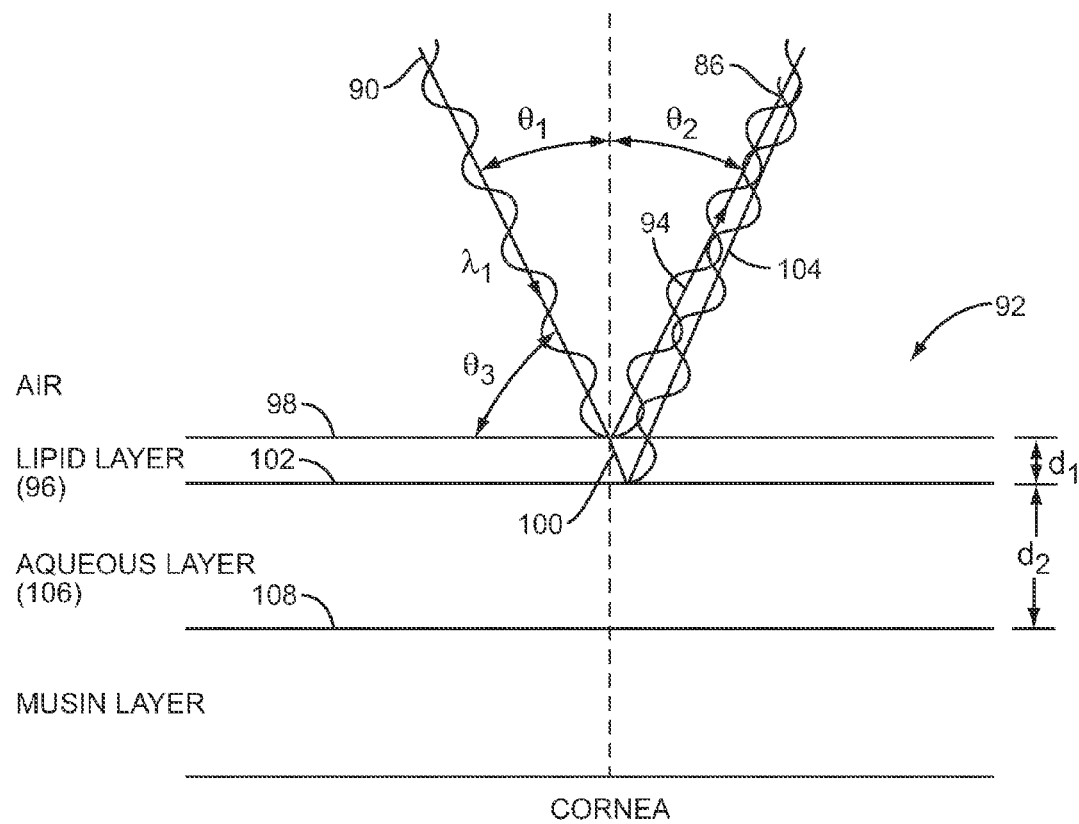
FIG. 7 illustrates (in a microscopic section view) exemplary tear film layers to illustrate how light rays can specularly reflect from various tear film layer transitions.

The geometry of the illuminator 76 can be understood by starting from an imaging lens 82 of the imaging device 80 and proceeding forward to the eye 72 and then to the illuminator 76. The fundamental equation for tracing ray lines is Snell's law, which provides:

$$n1 \sin \Theta_1 = n2 \sin \Theta_2,$$

where "n1" and "n2" are the indexes of refraction of two mediums containing the ray, and $\Theta_1$ and $\Theta_2$ is the angle of the ray relative to the normal from the transition surface. As illustrated in FIG. 7, light rays 90 are directed by the illuminator 76 (FIGS. 6A and 6B) to an ocular tear film 92. In the case of specularly reflected light 94 that does not enter a lipid layer 96 and instead reflects from an anterior surface 98 of the lipid layer 96, Snell's law reduces down to $\Theta_1=\Theta_2$, since the index of refraction does not change (i.e., air in both instances). Under these conditions, Snell's law reduces to the classical law of reflection such that the angle of incidence is equal and opposite to the angle of reflectance.

Some of the light rays 100 pass through the anterior surface 98 of the lipid layer 96 and enter into the lipid layer 96, as illustrated in FIG. 7. As a result, the angle of these light rays 100 (i.e., $\Theta_3$) normal to the anterior surface 98 of the lipid layer 96 will be different than the angle of the light rays 90 ($\Theta_1$) according to Snell's law. This is because the index of refraction of the lipid layer 96 is different than the index of refraction of air. Some of the light rays 100 passing through the lipid layer 96 will specularly reflect from the lipid layer-to-aqueous layer transition 102 thereby producing specularly reflected light rays 104. The specularly reflected light rays 94, 104 undergo constructive and destructive interference anterior of the lipid layer 96. The modulations of the interference of the specularly reflected light rays 94, 104 superimposed on the anterior surface 98 of the lipid layer 96 are collected by the imaging device 80 when focused on the anterior surface 98 of the lipid layer 96. Focusing the imaging device 80 on the anterior surface 98 of the lipid layer 96 allows capturing of the modulated interference information at the plane of the anterior surface 98. In this manner, the captured interference information and the resulting calculated TFLT from the interference information is spatially registered to a particular area of the tear film 92 since that the calculated TFLT can be associated with such particular area, if desired.

The thickness of the lipid layer 96 ('$d_1$') is a function of the interference interactions between specularly reflected light rays 94, 104. The thickness of the lipid layer 96 ('$d_1$') is on the scale of the temporal (or longitudinal) coherence of the light source 76. Therefore, thin lipid layer films on the scale of one wavelength of visible light emitted by the light source 76 offer detectable colors from the interference of specularly reflected light when viewed by a camera or human eye. The colors may be detectable as a result of calculations performed on the interference signal and represented as a digital values including but not limited to a red-green-blue (RGB) value in the RGB color space. Quantification of the interference of the specularly reflected light can be used to measure LLT. The thicknesses of an aqueous layer 106 ('$d_2$') can also be determined using the same principle. Some of the light rays 100 (not shown) passing through the lipid layer 96 can also pass through the lipid-to-aqueous layer transition 102 and enter into the aqueous layer 106 specularly reflecting from the aqueous-to-mucin/cornea layer transition 108. These specular reflections also undergo interference with the specularly reflected light rays 94, 104. The magnitude of the reflections from each interface depends on the refractive indices of the materials as well as the angle of incidence, according to Fresnel's equations, and so the depth of the modulation of the interference interactions is dependent on these parameters, thus so is the resulting color.

Turning back to FIGS. 6A and 6B, the illuminator 76 in this embodiment is a broad spectrum light source covering the visible region between about 400 nm to about 700 nm. The illuminator 76 contains an arced or curved housing 86 (see FIG. 6B) into which individual light emitters are mounted, subtending an arc of approximately 130 degrees from the optical axis of the eye 72 (see FIG. 6B). A curved surface may present better uniformity and be more efficient, as the geometry yields a smaller device to generating a given intensity of light. The total power radiated from the illuminator 76 should be kept to a minimum to prevent accelerated tear evaporation. Light entering the pupil can cause reflex tearing, squinting, and other visual discomforts, all of which affect TFLT measurement accuracy.

In order to prevent alteration of the proprioceptive senses and reduce heating of the tear film 92, incident power and intensity on the eye 72 may be minimized and thus, the step of collecting and focusing the specularly reflected light may carried out by the imaging device 80. The imaging device 80 may be a video camera, slit lamp microscope, or other observation apparatus mounted on the stand 78, as illustrated in FIGS. 6A and 6B. Detailed visualization of the image patterns of the tear film 92 involves collecting the specularly reflected light 84 and focusing the specularly reflected light at the lipid layer 96 such that the interference interactions of the specularly reflected light from the ocular tear film are observable.

In operation, the first polarizer 52(1) is translated in front of imaging lens 82 such that the polarization axis 54(1) is parallel or substantially parallel to the polarization plane of the specularly reflected light 84 from a region of interest (ROI) of the ocular tear film. In this manner, the specularly reflected light 84 is allowed to pass or substantially pass to the imaging device 80 while reducing the background signal before the background signal reaches the imaging device 80. Moreover, the second polarizer 56(1) is translated in front of imaging lens 82 such that the polarization axis 58(1) is perpendicular or substantially perpendicular to the polarization plane of the specularly reflected light 84 from the ROI of the ocular tear film. In this manner, the specularly reflected light 84 is reduced or eliminated before the specularly reflected light 84 reaches the imaging device 80 while passing a portion of the background signal.

Figure 8:
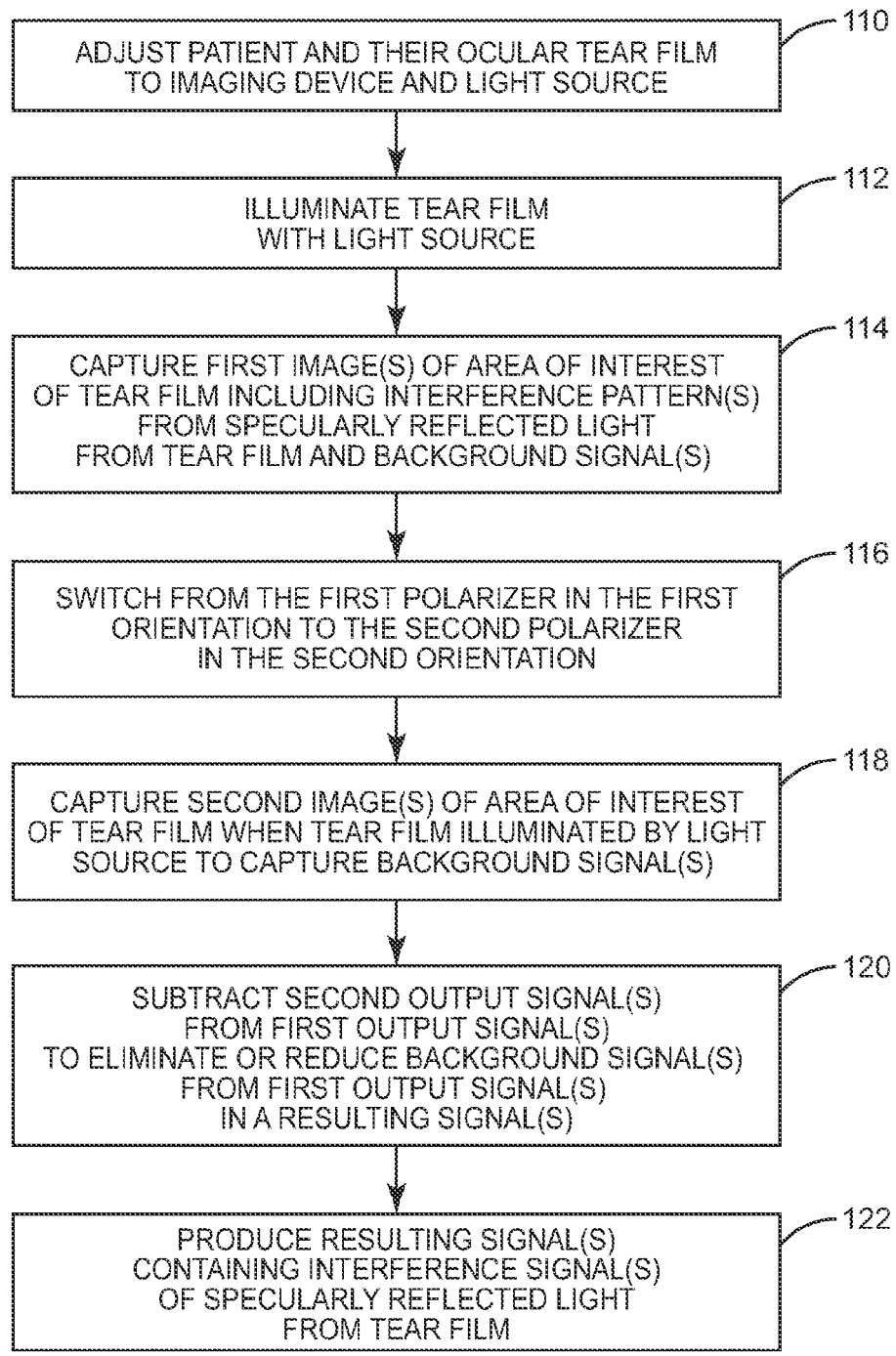
FIG. 8 is a flowchart of an exemplary process that incorporates alternating polarizers for obtaining one or more interference signals from images of a tear film representing specularly reflected light from the tear film with background signal subtracted or substantially subtracted.

Against the backdrop of the OSI device 70 in FIGS. 6A and 6B, FIG. 8 illustrates a flowchart discussing how the OSI device 70 can be used to obtain interference interactions of specularly reflected light from the tear film 92, which can be used to measure TFLT. Interference interactions of specularly reflected light from the tear film 92 are first obtained and discussed before measurement of TFLT is discussed. In this embodiment as illustrated in FIG. 8, the process starts by adjusting the patient 74 with regard to an illuminator 76 and an imaging device 80 (block 110). The illuminator 76 is controlled to illuminate the patient's 74 tear film 92. The imaging device 80 is controlled to be focused on the anterior surface 98 of the lipid layer 96 such that the interference interactions of specularly reflected light from the tear film 92 are collected and are observable. Thereafter, the patient's 74 tear film 92 is illuminated by the illuminator 76 (block 112).

Figure 9:
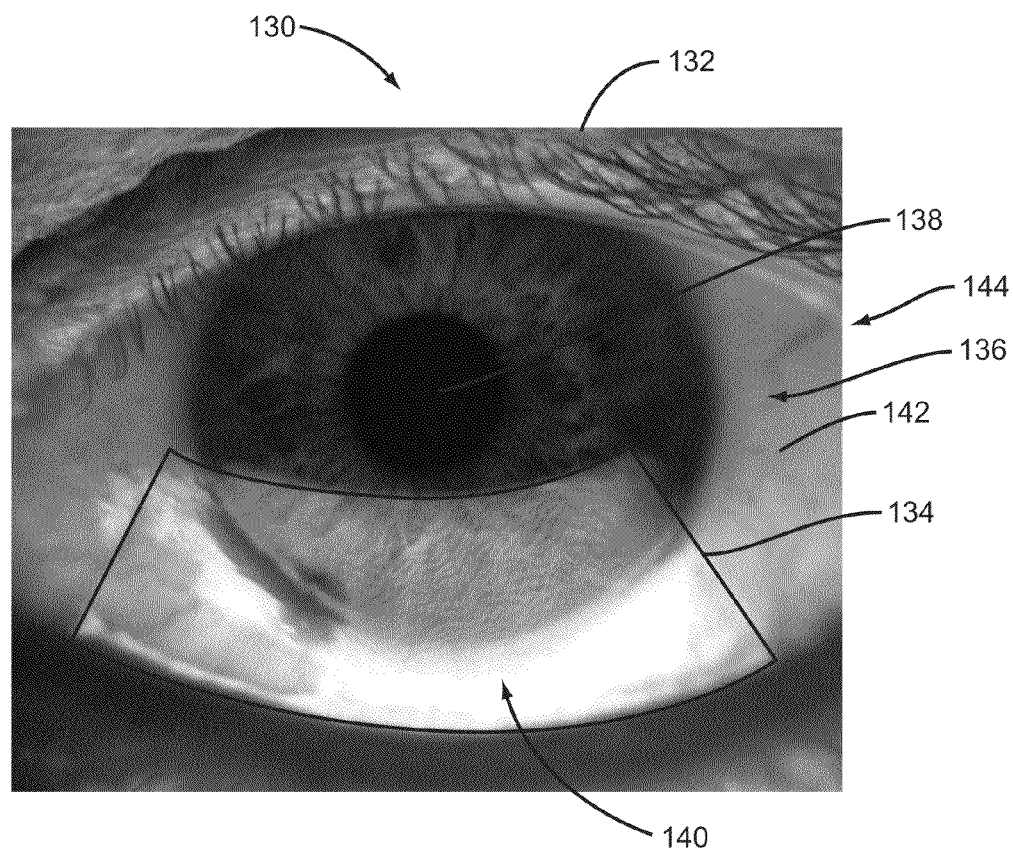
FIG. 9 illustrates an exemplary first image focused on a lipid layer of a tear film and capturing interference interactions of specularly reflected light from an area or region of interest of the tear film.

The imaging device 80 is then controlled and focused on the lipid layer 96 to collect specularly reflected light from an area or ROI on a tear film as a result of illuminating the tear film with the illuminator 76 in a first image (block 114, FIG. 8). An example of the first image by the illuminator 76 is provided in FIG. 9. As illustrated therein, a first image 130 of a patient's eye 132 is shown that has been illuminated with the illuminator 76. The illuminator 76 and the imaging device 80 may be controlled to illuminate an area or region of interest 134 on a tear film 136 that does not include a pupil 138 of the eye 132 so as to reduce reflex tearing. Reflex tearing will temporarily lead to thicker aqueous and lipid layers, thus temporarily altering the interference signals of specularly reflected light from the tear film 136. As shown in FIG. 9, when the imaging device 80 is focused on an anterior surface 142 of the lipid layer 144 of the tear film 136, interference interactions 140 of the interference signal of the specularly reflected light from the tear film 136 as a result of illumination by the illuminator 76 are captured in the area or region of interest 134 in the first image 130. The interference interactions 140 appear to a human observer as colored patterns as a result of the wavelengths present in the interference of the specularly reflected light from the tear film 136.

However, even though the background signal is reduced by the first polarizer 52(1), a portion of the background signal is also captured in the first image 130. The background signal is added to the specularly reflected light in the area or region of interest 134 and included outside the area or region of interest 134 as well. Background signal is light that is not specularly reflected from the tear film 136 and thus contains no interference information. Background signal can include stray and ambient light entering into the imaging device 80, scattered light from the patient's 74 face, eyelids, and/or eye 132 structures outside and beneath the tear film 136 as a result of stray light, ambient light and diffuse illumination by the illuminator 76, and images of structures beneath the tear film 136. For example, the first image 130 includes the iris of the eye 132 beneath the tear film 136. Background signal adds a bias (i.e., offset) error to the captured interference of specularly reflected light from the tear film 136 thereby reducing its signal strength and contrast. Further, if the background signal has a color hue different from the light of the light source, a color shift can also occur to the interference of specularly reflected light from the tear film 136 in the first image 130. The imaging device 80 produces a first output signal that represents the light rays captured in the first image 130. Because the first image 130 contains light rays from specularly reflected light as well as the background signal, the first output signal produced by the imaging device 80 from the first image 130 will contain an interference signal representing the captured interference of the specularly reflected light from the tear film 136 with a bias (i.e., offset) error caused by the background signal. As a result, the first output signal analyzed to measure TFLT may contain error as a result of the background signal bias (i.e., offset) error.

Thus, in this embodiment, the first output signal generated by the imaging device 80 as a result of the first image 130 is processed to subtract or substantially subtract the background signal from the interference signal to reduce error before being analyzed to measure TFLT. This is also referred to as "background subtraction." Background subtraction is the process of removing unwanted reflections from images. In this regard, the imaging device 80 is controlled to capture a second image 146 of the tear film 136 as illustrated by example in FIG. 10. However, before the second image 146 is captured, a switch from the first polarizer 52(1) in the first orientation to the second polarizer 56(1) in the second orientation is made (block 116 in FIG. 8). In this way, the second image 146 will contain mostly background signal and when the second image 146 is subtracted from the first image 130 the captured interference of specularly reflected light from the tear film 136 will not be reduced or at least not significantly reduced.

Figure 11:
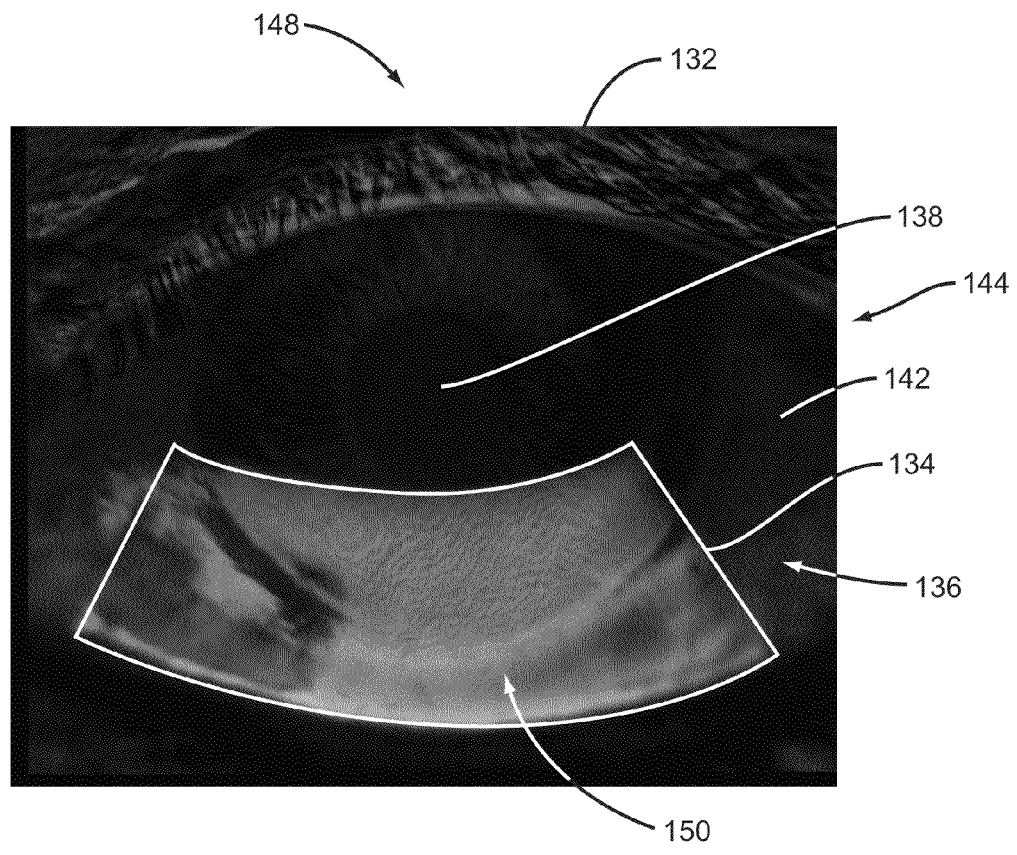
FIG. 11 illustrates an exemplary image of the tear film when background signal captured in the second image of FIG. 10 is subtracted from the first image of FIG. 9.

The second image 146 should be captured using the same imaging device 80 settings and focal point as when capturing the first image 130 so that the first image 130 and second images 146 forms corresponding image pairs captured within a short time of each other. The imaging device 80 produces a second output signal containing background signal present in the first image 130 (block 118 in FIG. 8). To eliminate or reduce this background signal from the first output signal, the second output signal is subtracted from the first output signal to produce a resulting signal (block 120 in FIG. 8). The image representing the resulting signal in this example is illustrated in FIG. 11 as resulting image 148. Thus, in this example, background subtraction involves two images 130, 146 to provide a frame pair where the two images 130, 146 are subtracted from each other, whereby specular reflection from the tear film 136 is retained, and while diffuse reflections from the iris and other areas are removed in whole or part.

As illustrated in FIG. 11, the resulting image 148 contains an image of the isolated interference 150 of the specularly reflected light from the tear film 136 with the background signal eliminated or reduced (block 122 in FIG. 8). In this manner, the resulting signal (representing the resulting image 148 in FIG. 11) includes an interference signal having signal improved purity and contrast in the area or region of interest 134 on the tear film 136. As will be discussed later in this application, the resulting signal provides for accurate analysis of interference interactions from the interference signal of specular reflections from the tear film 136 to in turn accurately measure TFLT. Any method or device to obtain the first and second images of the tear film 136 and perform the subtraction of background signal in the second image 146 from the first image 130 may be employed. Other specific examples are discussed throughout the remainder of this application.

An optional registration function may be performed between the first image(s) 130 and the second image(s) 146 before subtraction is performed to ensure that an area or point in the second image(s) 146 to be subtracted from the first image(s) 130 is for an equivalent or corresponding area or point on the first image(s) 130. For example, a set of homologous points may be taken from the first and second images 130, 146 to calculate a rigid transformation matrix between the two images. The transformation matrix allows one point on one image (e.g., x1, y1) to be transformed to an equivalent two-dimensional (2D) image on the other image (e.g., x2, y2). For example, the Matlab® function "cp2tform" can be employed in this regard. Once the transformation matrix is determined, the transformation matrix can be applied to every point in the first and second images, and then each re-interpolated at the original points. For example, the Matlab® function "imtransform" can be employed in this regard. This allows a point from the second image (e.g., x2, y2) to be subtracted from the correct, equivalent point (e.g., x1, y1) on the first image(s) 130, in the event there is any movement in orientation or the patient's eye between the capture of the first and second images 130, 146. The first and second images 130, 146 should be captured close in time. A similar registration technique is explained in greater detail later on in this disclosure.

Note that while this example discusses a first image and a second image captured by the imaging device 80 and a resulting first output signal and second output signal, the first image and the second image may comprise a plurality of images taken in a time-sequenced fashion. If the imaging device 80 is a video camera, the first and second images may contain a number of sequentially-timed frames governed by the frame rate of the imaging device 80. The imaging device 80 produces a series of first output signals and second output signals. If more than one image is captured, the subtraction performed in a first image should ideally be from a second image taken immediately after the first image so that the same or substantially the same lighting conditions exist between the images so the background signal in the second image is present in the first image.

The subtraction of the second output signal from the first output signal can be performed in real time. Alternatively, the first and second output signals can be recorded and processed at a later time. The illuminator 76 may be controlled to oscillate off and on quickly so that first and second images can be taken and the second output signal subtraction from the first output signal be performed in less than one second. For example, if the illuminator 76 oscillates between on and off at 30 Hz, the imaging device 80 can be synchronized to capture images of the tear film 92 at 106 frames per second (fps). In this regard, thirty (30) first images and thirty (30) second images can be obtained in one second, with each pair of first and second images taken sequentially.

After the interference of the specularly reflected light is captured and a resulting signal containing the interference signal is produced and processed, the interference signal or representations thereof can be compared against a tear film layer interference model to measure TFLT. The interference signal can be processed and converted by the imaging device into digital red-green-blue (RGB) component values which can be compared to RGB component values in a tear film interference model to measure tear film TFLT. The tear film interference model is based on modeling the lipid layer of the tear film in various LLTs and representing resulting interference interactions in the interference signal of specularly reflected light from the tear film model when illuminated by the light source. The tear film interference model can be a theoretical tear film interference model where the particular light source, the particular imaging device, and the tear film layers are modeled mathematically, and the resulting interference signals for the various LLTs recorded when the modeled light source illuminates the modeled tear film layers recorded using the modeled imaging device. The settings for the mathematically modeled light source and imaging device should be replicated in the illuminator 76 and imaging device 80 used in the OSI device 70. Alternatively, the tear film interference model can be based on a phantom tear film model, comprised of physical phantom tear film layers wherein the actual light source is used to illuminate the phantom tear film model and interference interactions in the interference signal representing interference of specularly reflected light are empirically observed and recorded using the actual imaging device.

The aqueous layer may be modeled in the tear film interference model to be of an infinite, minimum, or varying thickness. If the aqueous layer is modeled to be of an infinite thickness, the tear film interference model assumes no specular reflections occur from the aqueous-to-mucin layer transition 108 (see FIG. 7). If the aqueous layer 106 is modeled to be of a certain minimum thickness (e.g., ≥2 µm), the specular reflection from the aqueous-to-mucin layer transition 108 may be considered negligible on the effect of the convolved RGB signals produced by the interference signal. In either case, the tear film interference model will only assume and include specular reflections from the lipid-to-aqueous layer transition 102. Thus, these tear film interference model embodiments allow measurement of LLT regardless of ALT. The interference interactions in the interference signal are compared to the interference interactions in the tear film interference model to measure LLT.

Alternatively, if the aqueous layer 106 is modeled to be of varying thicknesses, the tear film interference model additionally includes specular reflections from the aqueous-to-mucin layer transition 108 in the interference interactions. As a result, the tear film interference model will include two-dimensions of data comprised of interference interactions corresponding to various LLT and ALT combinations. The interference interactions from the interference signal can be compared to interference interactions in the tear film interference model to measure both LLT and ALT. More information regarding specific tear film interference models will be described later in this application.

In the above described embodiment in FIGS. 8-11, the second image 146 of the tear film 136 contains a background signal. Only ambient light illuminates the tear film 136 and eye 132 structures beneath. Thus, the second image 146 and the resulting second output signal produced by the imaging device 80 from the second image 146 does not include background signal resulting from scattered light from the patient's face and eye structures as a result of diffuse illumination by the illuminator 76. Only scattered light resulting from ambient light is included in the second image 146. However, scattered light resulting from diffuse illumination by the illuminator 76 is included in background signal in the first image 130 containing the interference interactions of specularly reflected light from the tear film 136.

Further, because the first image 130 is captured when the illuminator 76 is illuminating the tear film, the intensity of the eye structures beneath the tear film 136 captured in the first image 130, including the iris, are brighter than captured in the second image 146. Thus, in other embodiments described herein, the imaging device 80 is controlled to capture a second image of the tear film 136 when obliquely illuminated by the illuminator 76. As a result, the captured second image additionally includes background signal from scattered light as a result of diffuse illumination by the illuminator 76 as well as a higher intensity signal of the eye directly illuminated structures beneath the tear film 136. Thus, when the second output signal is subtracted from the first output signal, the higher intensity eye structure background and the component of background signal representing scattered light as a result of diffuse illumination by the illuminator 76, as well as ambient and stray light, are subtracted or substantially subtracted from the resulting signal thereby further increasing the interference signal purity and contrast in the resulting signal. The resulting signal can then be processed and analyzed to measure TFLT, as will be described in detail later in this application.

Exemplary OSI Devices

The above discussed illustrations provide examples of illuminating and imaging a patient's TFLT. These principles are described in more detail with respect to a specific example of an OSI device 170 illustrated in FIGS. 12-55F and described below throughout the remainder of this application. The OSI device 170 can illuminate a patient's tear film, capture interference information from the patient's tear film, and process and analyze the interference information to measure TFLT. Further, the OSI device 170 includes a number of optional pre-processing features that may be employed to process the interference signal in the resulting signal to enhance TFLT measurement. The OSI device 170 may include a display and user interface to allow a physician or technician to control the OSI device 170 to image a patient's eye and tear film and measure the patient's TFLT.

Illumination and Imaging

Figure 12:
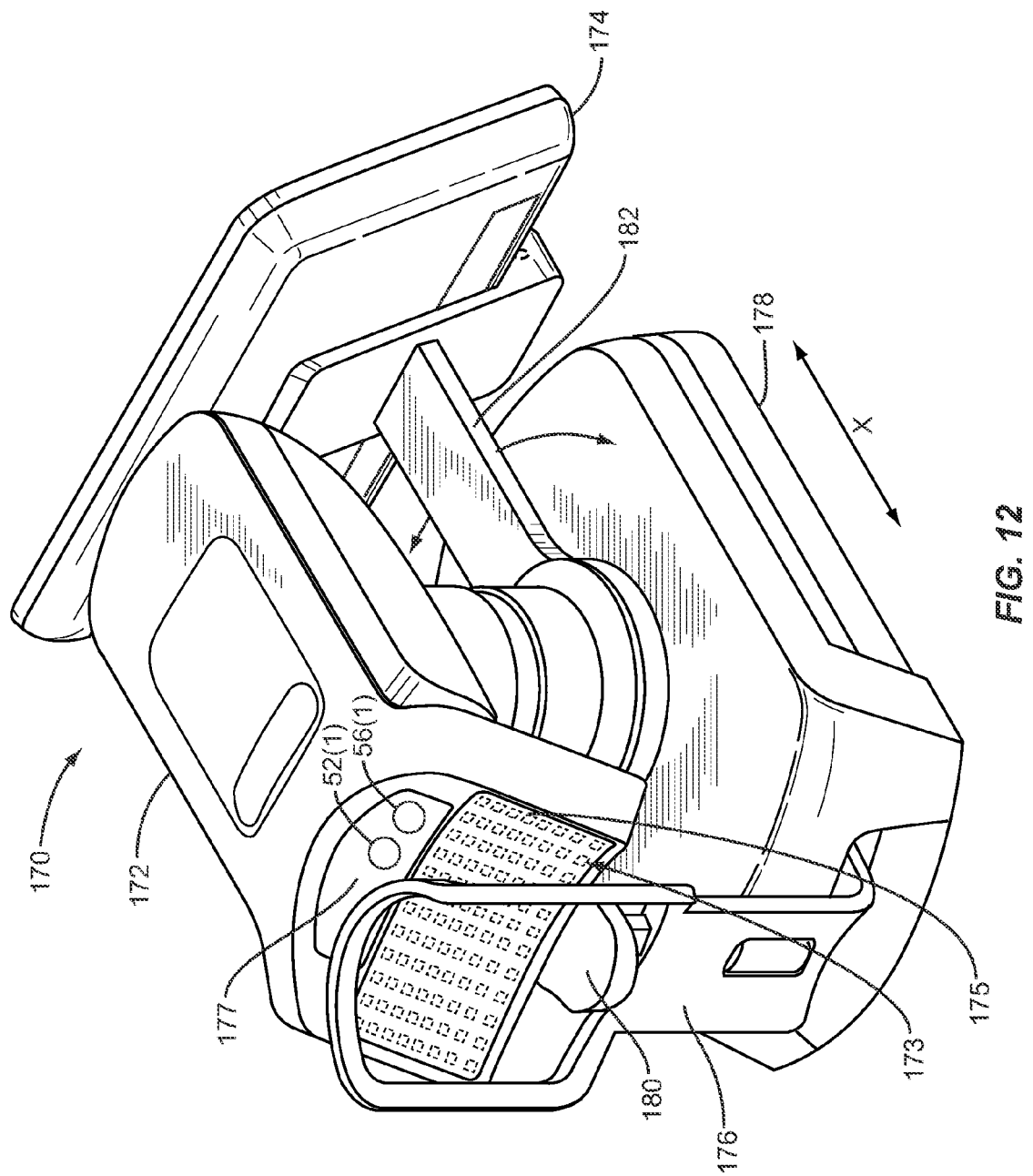
FIG. 12 is a perspective view of an exemplary ocular surface interferometry (OSI) device for illuminating and imaging a patient's tear film, displaying images, analyzing the patient's tear film, and generating results from the analysis of the patient's tear film.

In this regard, FIG. 12 illustrates a perspective view of the OSI device 170. The OSI device 170 is designed to facilitate imaging of the patient's ocular tear film and processing and analyzing the images to determine characteristics regarding a patient's tear film. The OSI device 170 includes an imaging device and light source in this regard, as will be described in more detail below. As illustrated in FIG. 12, the OSI device 170 is comprised generally of a housing 172, a display monitor ("display") 174, and a patient head support 176. The housing 172 may be designed for table top placement. The housing 172 rests on a base 178 in a fixed relationship. As will be discussed in more detail below, the housing 172 houses an imaging device and other electronics, hardware, and software to allow a clinician to image a patient's ocular tear film. A light source 173 (also referred to herein as "illuminator 173")

is also provided in the housing 172 and provided behind a diffusing translucent window 175. The translucent window 175 may be a flexible, white, translucent acrylic plastic sheet.

To image a patient's ocular tear film, the patient places his or her head in the patient head support 176 and rests his or her chin on a chin rest 180. The chin rest 180 can be adjusted to align the patient's eye and tear film with the imaging device inside the housing 172, as will be discussed in more detail below. The chin rest 180 may be designed to support up to two (2) pounds of weight, but such is not a limiting factor. A transparent window 177 allows the imaging device inside the housing 172 to have a clear line of sight to a patient's eye and tear film when the patient's head is placed in the patient head support 176. The first polarizer 52(1) shown in dashed line is behind the transparent window 177 and within the imaging path of the imaging device (not visible). The second polarizer 56(1) is also shown in dashed line. However, in this example the second polarizer 56(1) is shown translated away from the imaging path of the imaging device. The OSI device 170 is designed to image one eye at a time, but can be configured to image both eyes of a patient, if desired.

In general, the display 174 provides input and output from the OSI device 170. For example, a user interface can be provided on the display 174 for the clinician to operate the OSI device 170 and to interact with a control system provided in the housing 172 that controls the operation of the OSI device 170, including an imaging device, an imaging device positioning system, a light source, other supporting hardware and software, and other components. For example, the user interface can allow control of imaging positioning, focus of the imaging device, and other settings of the imaging device for capturing images of a patient's ocular tear film. The control system may include a general purpose microprocessor or computer with memory for storage of data, including images of the patient's eye and tear film. The microprocessor should be selected to provide sufficient processing speed to process images of the patient's tear film and generate output characteristic information about the tear film (e.g., one minute per twenty second image acquisition). The control system may control synchronization of activation of the light source and the imaging device to capture images of areas of interest on the patient's ocular tear film when properly illuminated. Various input and output ports and other devices can be provided, including but not limited to a joystick for control of the imaging device, USB ports, wired and wireless communication including Ethernet communication, a keyboard, a mouse, speaker(s), etc. A power supply is provided inside the housing 172 to provide power to the components therein requiring power. A cooling system, such as a fan, may also be provided to cool the OSI device 170 from heat generating components therein.

The display 174 is driven by the control system to provide information regarding a patient's imaged tear film, including TFLT. The display 174 also provides a graphical user interface (GUI) to allow a clinician or other user to control the OSI device 170. To allow for human diagnosis of the patient's tear film, images of the patient's ocular tear film taken by the imaging device in the housing 172 can also be displayed on the display 174 for review by a clinician, as will be illustrated and described in more detail below. The images displayed on the display 174 may be real-time images being taken by the imaging device, or may be previously recorded images stored in memory. To allow for different orientations of the OSI device 170 to provide a universal configuration for manufacturing, the display 174 can be rotated about the base 178. The display 174 is attached to a monitor arm 182 that is rotatable about the base 178, as illustrated. The display 174 can be placed opposite of the patient head support 176, as illustrated in FIG. 12, if the clinician desires to sit directly across from the patient. Alternatively, display 174 can be rotated either left or right about the X-axis to be placed adjacent to the patient head support 176. The display 174 may be a touch screen monitor to allow a clinician or other user to provide input and control to the control system inside the housing 172 directly via touch of the display 174 for control of the OSI device 170. The display 174 illustrated in FIG. 12 is a fifteen inch (15") flat panel liquid crystal display (LCD). However, the display 174 may be provided of any type or size, including but not limited to a cathode ray tube (CRT), plasma, LED, OLED, projection system, etc.

Figure 13:
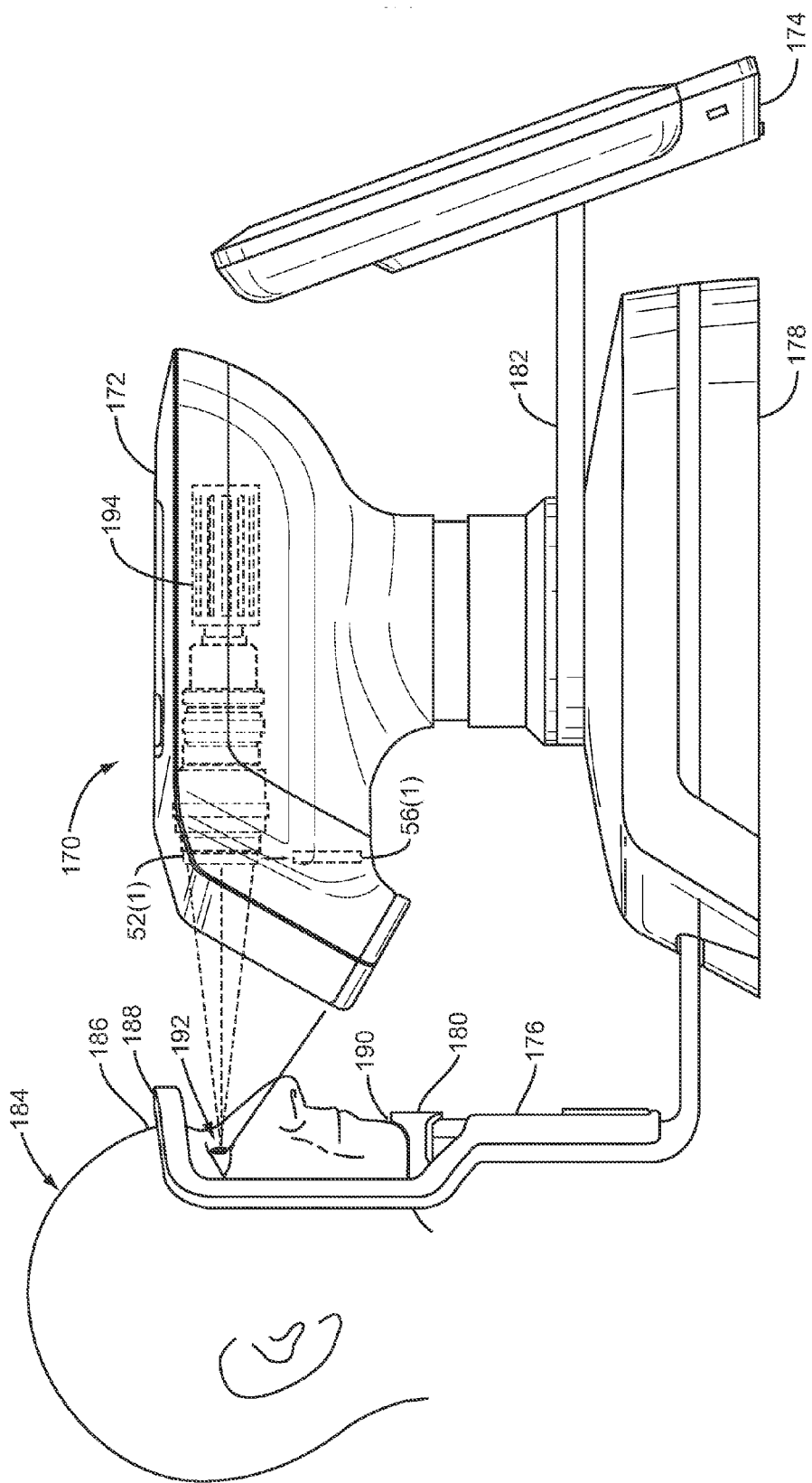
FIG. 13 is a side view of the OSI device of FIG. 12 illuminating and imaging the eye and tear film.

FIG. 13 illustrates a side view of the OSI device 170 of FIG. 12 to further illustrate imaging of a patient's eye and ocular tear film. As illustrated therein, a patient places their head 184 in the patient head support 176. More particularly, the patient places their forehead 186 against a headrest 188 provided as part of the patient head support 176. The patient places their chin 190 in the chin rest 180. The patient head support 176 is designed to facilitate alignment of a patient's eye 192 with the OSI device 170, and in particular, an imaging device 194 (and illuminator) shown as being provided inside the housing 172. The chin rest 180 can be adjusted higher or lower to move the patient's eye 192 with respect to the OSI device 170. The first polarizer 52(1) shown in dashed line is within the imaging path of the imaging device 194. The second polarizer 56(1) is also shown in dashed line. However, in this example the second polarizer 56(1) is shown translated below the first polarizer 52(1) and away from the imaging path of the imaging device.

OSI Device Employing Rotatable Polarizer

Figure 14A:
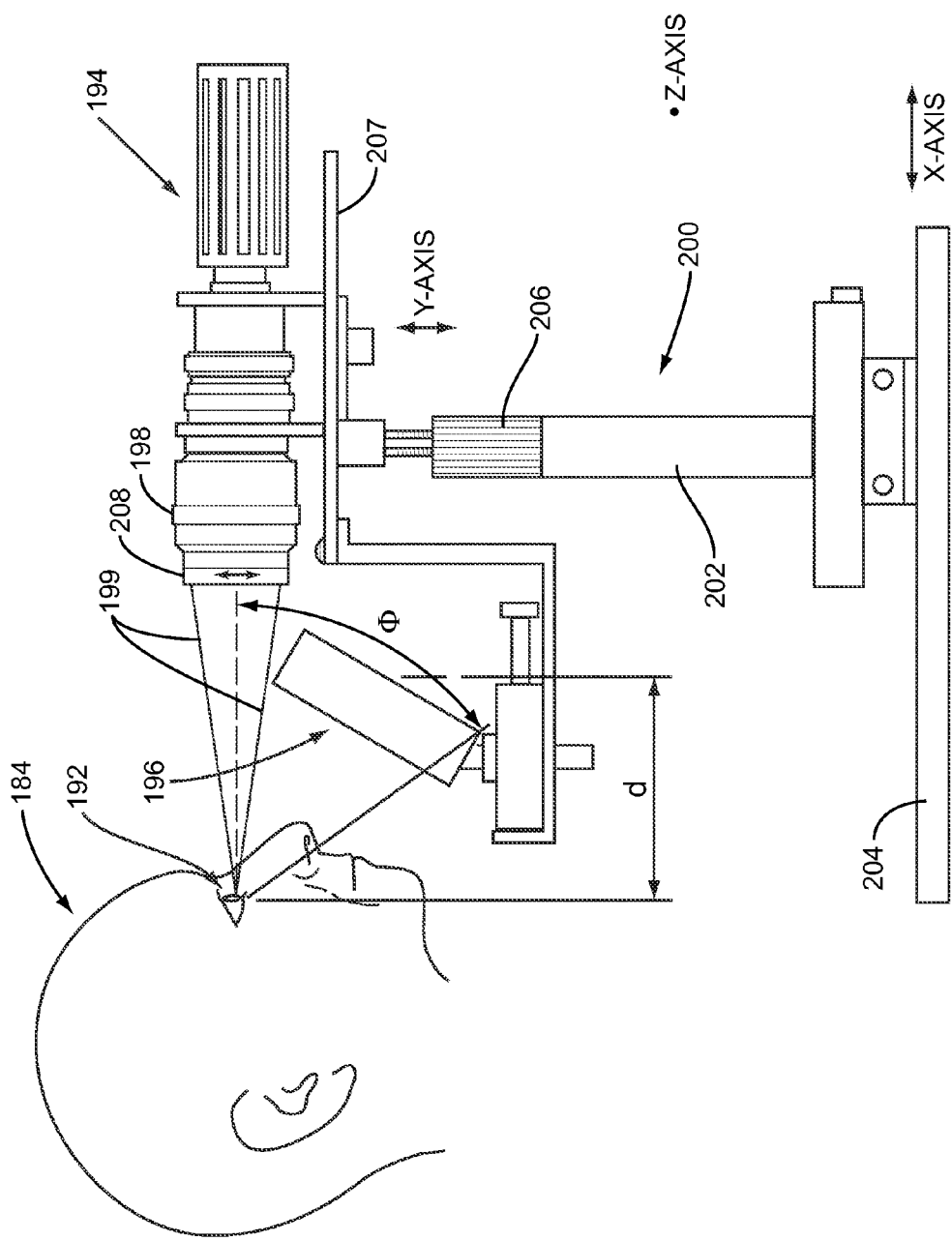
FIG. 14A is a side view of an exemplary video camera and illuminator with a rotatable polarizer.
Figure 14B:
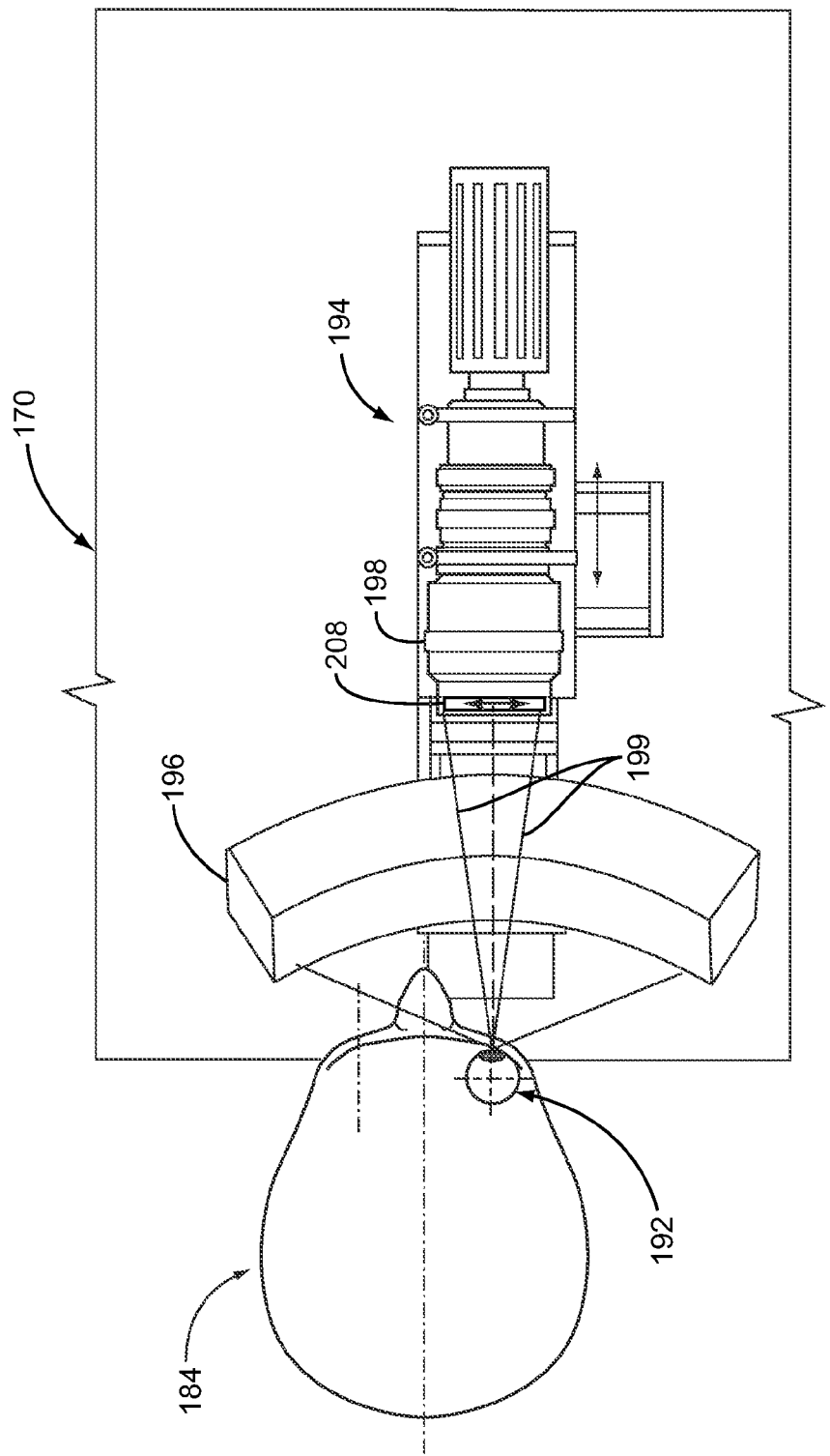
FIG. 14B is a top view of the video camera and illuminator in FIG. 14A with the rotatable polarizer.

As shown in FIGS. 14A and 14B, the imaging device 194 can be used to image the patient's ocular tear film to determine characteristics of the patient's tear film. In particular, the imaging device 194 is used to capture interference interactions of the specularly reflected light from the patient's tear film when illuminated by the light source 196 (also referred to herein as "illuminator 196") as well as background signal. In the OSI device 170, the imaging device 194 is the "The Imaging Source" model DFK21BU04 charge coupling device (CCD) digital video camera 198, but many types of metrological grade cameras or imaging devices can be provided. A CCD camera enjoys characteristics of efficient light gathering, linear behavior, cooled operation, and immediate image availability. A linear imaging device is one that provides an output signal representing a captured image which is precisely proportional to the input signal from the captured image. Thus, use of a linear imaging device (e.g., gamma correction set to 1.0, or no gamma correction) provides undistorted interference data which can then be analyzed using linear analysis models. In this manner, the resulting images of the tear film do not have to be linearized before analysis, thus saving processing time. Gamma correction can then be added to the captured linear images for human-perceptible display on the non-linear display 174 in the OSI device 170 (FIGS. 12 and 13). Alternatively, the opposite scenario could be employed. That is, a non-linear imaging device or non-linear setting would be provided to capture tear film images, wherein the non-linear data representing the interference interactions of the interference signal can be provided to a non-linear display monitor without manipulation to display the tear film images to a clinician. The non-linear data would be linearized for tear film processing and analysis to estimate tear film layer thickness.

The video camera 198 is capable of producing lossless full motion video images of the patient's eye. As illustrated in FIGS. 14A and 14B, the video camera 198 has a depth of field defined by the angle between rays 199 and the lens focal length that allows the patient's entire tear film to be in focus simultaneously. The video camera 198 has an external trigger support so that the video camera 198 can be controlled by a control system to image the patient's eye. The video camera 198 includes a lens and a rotatable polarizer 208 that can fit within the housing 172 (FIG. 13) that is usable in place of both the first and second polarizers 52(1) and 56(1).

Employing the rotatable polarizer 208 is less mechanically complex than alternating the first and second polarizers 52(1) and 56(1) into the imaging path of the video camera 198. For example, the rotatable polarizer 208 is always in the imaging path of the video camera 198. Therefore, the rotatable polarizer 208 only needs to be rotated from one polarization orientation to another between a first and second image capture. Moreover, due to its relatively low mechanical complexity, the rotatable polarizer 208 can offer a relatively fast response when rotating from one polarization orientation to another. This relatively fast response allows the rotatable polarizer 208 to be more easily synchronized with the video camera 198.

The rotatable polarizer 208 is disposed in an imaging path of the imaging device 194, which in this case is the video camera 198. The rotatable polarizer 208 has a center axis shown in dashed line extending to the eye 192. The rotatable polarizer 208 is selectively rotatable about the center axis to provide a first polarization axis relative to the polarization plane of the specularly reflected light from the ROI of the ocular tear film on the eye 192 during a capture of at least one first image. The rotatable polarizer 208 is also selectively rotatable to provide a second polarization axis that is perpendicular or substantially perpendicular relative to the first polarization axis during the capture of at least one second image. An actuator such as a motor could be coupled to the rotatable polarizer 208 to rotate the from one polarization orientation to another in synchronization with the video camera 198.

The video camera 198 in this embodiment has a resolution of 640×480 pixels and is capable of frame rates up to sixty (60) frames per second (fps). The lens system employed in the video camera 198 images a 16×12 mm dimension in a sample plane onto an active area of a CCD detector within the video camera 198. As an example, the video camera 198 may be the DBK21AU04 Bayer VGA (640×480) video camera using a Pentax VS-LD25 Daitron 25-mm fixed focal length lens. Other camera models with alternate pixel size and number, alternate lenses, (etc) may also be employed.

Although a video camera 198 is provided in the OSI device 170, a still camera could also be used if the frame rate is sufficiently fast enough to produce high quality images of the patient's eye. High frame rate in frames per second (fps) facilitate high quality subtraction of background signal from a captured interference signal representing specularly reflected light from a patient's tear film, and may provide less temporal (i.e., motion) artifacts (e.g., motion blurring) in captured images, resulting in high quality captured images. This is especially the case since the patient's eye may move irregularly as well as blinking, obscuring the tear film from the imaging device during examination.

A camera positioning system 200 is also provided in the housing 172 of the OSI device 170 to position the video camera 198 for imaging of the patient's tear film. The camera positioning system 200 is under the control of a control system. In this manner, a clinician can manipulate the position of the video camera 198 to prepare the OSI device 170 to image the patient's tear film. The camera positioning system 200 allows a clinician and/or control system to move the video camera 198 between different patients' eyes 192, but can also be designed to limit the range of motion within designed tolerances. The camera positioning system 200 also allows for fine tuning of the video camera 198 position. The camera positioning system 200 includes a stand 202 attached to a base 204. A linear servo or actuator 206 is provided in the camera positioning system 200 and connected between the stand 202 and a camera platform 207 supporting the video camera 198 to allow the video camera 198 to be moved in the vertical (i.e., Y-axis) direction.

In this embodiment of the OSI device 170, the camera positioning system 200 may not allow the video camera 198 to be moved in the X-axis or the Z-axis (in and out of FIG. 14A), but other embodiments of the disclosure are not so limited. The illuminator 196 is also attached to the camera platform 207 such that the illuminator 196 maintains a fixed geometric relationship to the video camera 198. Thus, when the video camera 198 is adjusted to the patient's eye 192, the illuminator 196 is automatically adjusted to the patient's eye 192 in the same regard as well. This may be important to enforce a desired distance (d) and angle of illumination (Φ) of the patient's eye 192, as illustrated in FIG. 14A, to properly capture the interference interactions of the specularly reflected light from the patient's tear film at the proper angle of incidence according to Snell's law, since the OSI device 170 is programmed to assume a certain distance and certain angles of incidence. In the OSI device 170 in FIG. 14A, the angle of illumination (Φ) of the patient's eye 192 relative to the video camera 198 axis is approximately 30 degrees at the center of the illuminator 196 and includes a relatively large range of angles from about 5 to 60 degrees, but any angle may be provided.

Figure 15:
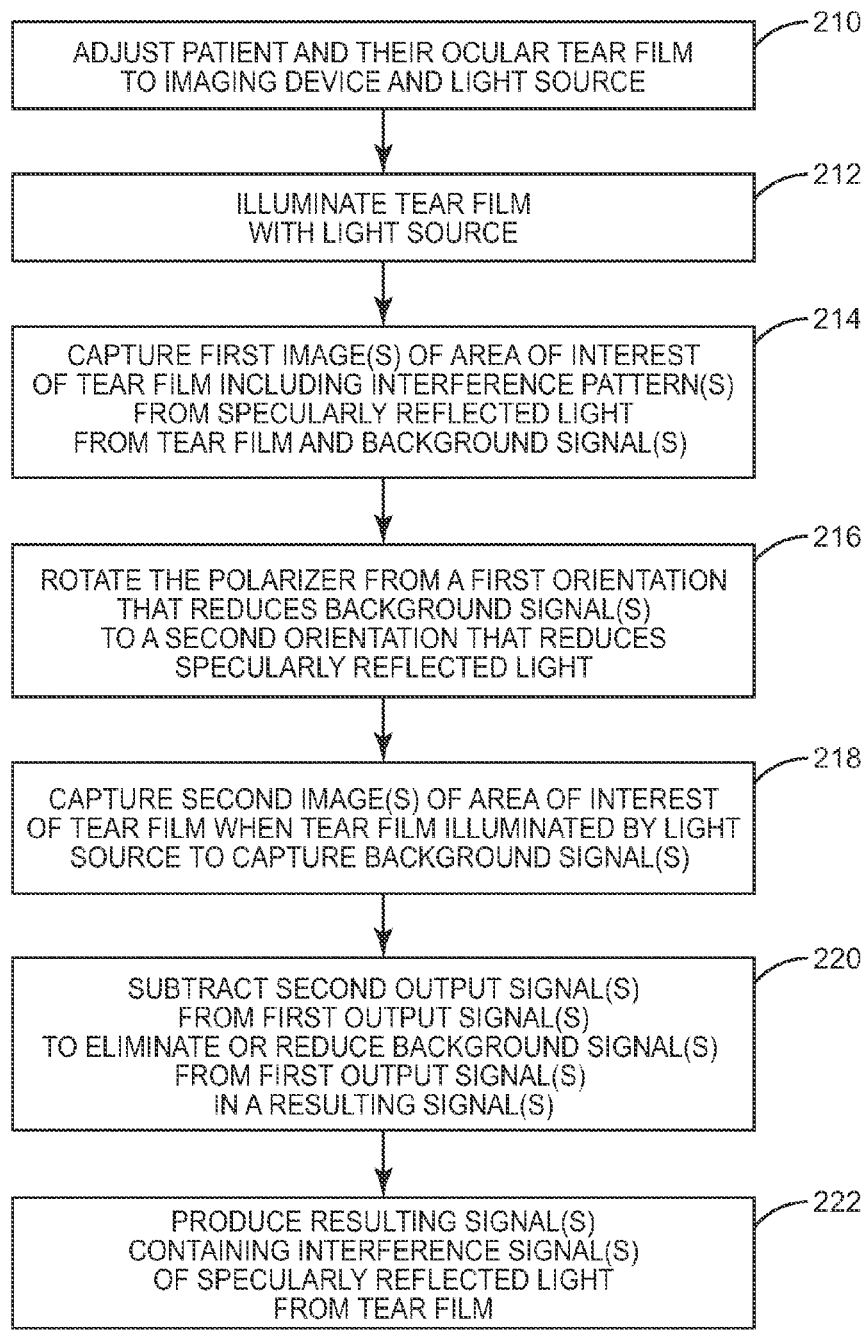
FIG. 15 is a flowchart of an exemplary process that employs a rotatable polarizer for obtaining one or more interference signals from images of a tear film representing specularly reflected light from the tear film with background signal subtracted or substantially subtracted.

FIG. 15 is a flowchart of an exemplary process for OSI device 170 that incorporates the rotatable polarizer 208 for obtaining one or more interference signals from images of a tear film representing specularly reflected light from the tear film with background signal subtracted or substantially subtracted. Against the backdrop of the OSI device 170 in FIGS. 14A and 14B, FIG. 15 illustrates a flowchart discussing how the OSI device 170 can be used to obtain interference interactions of specularly reflected light from the tear film 92, which can be used to measure TFLT. Interference interactions of specularly reflected light from the tear film 92 are first obtained and discussed before measurement of TFLT is discussed. In this embodiment as illustrated in FIG. 15, the process starts by adjusting the patient 184 with regard to the illuminator 196 and the imaging device 194 (block 210). The illuminator 196 is then controlled to illuminate the patient's 184 tear film 92(block 212).

Next, the imaging device 194 is controlled to be focused on the anterior surface 98 of the lipid layer 96 such that the interference interactions of specularly reflected light from the tear film 92 are captured in first image(s) (block 214). An example of the first image(s) captured by the imaging device is provided in FIG. 9. As illustrated therein, a first image 130 of a patient's eye 192 is shown that has been illuminated with the illuminator 196. The illuminator 196 and the imaging device 194 may be controlled to illuminate an area or region of interest 134 on a tear film 136 that does not include a pupil 138 of the eye 132 so as to reduce reflex tearing. Reflex tearing will temporarily lead to thicker aqueous and lipid layers, thus temporarily altering the interference signals of specularly reflected light from the tear film 136. As shown in FIG. 9, when the imaging device 194 is focused on an anterior surface 142 of the lipid layer 144 of the tear film 136, interference interactions 140 of the interference signal of the specularly reflected light from the tear film 136 as a result of illumination by the illuminator 76 are captured in the area or region of interest 134 in the first image 130. The interference interactions 140 appear to a human observer as colored patterns as a result of the wavelengths present in the interference of the specularly reflected light from the tear film 136.

However, even though the background signal is reduced by the rotatable polarizer 208, a portion of the background signal is also captured in the first image 130. The background signal is added to the specularly reflected light in the area or region of interest 134 and included outside the area or region of interest 134 as well. Background signal is light that is not specularly reflected from the tear film 136 and thus contains no interference information. Background signal can include stray and ambient light entering into the imaging device 194, scattered light from the patient's 184 face, eyelids, and/or eye 192 structures outside and beneath the tear film 136 as a result of stray light, ambient light and diffuse illumination by the illuminator 196, and images of structures beneath the tear film 136. For example, the first image 130 includes the iris of the eye 132 beneath the tear film 136. Background signal adds a bias (i.e., offset) error to the captured interference of specularly reflected light from the tear film 136 thereby reducing its signal strength and contrast. Further, if the background signal has a color hue different from the light of the light source, a color shift can also occur due to the interference of specularly reflected light from the tear film 136 in the first image 130.

The imaging device 194 produces a first output signal that represents the light rays captured in the first image 130. Because the first image 130 contains light rays from specularly reflected light as well as the background signal, the first output signal produced by the imaging device 194 from the first image 130 will contain an interference signal representing the captured interference of the specularly reflected light from the tear film 136 with a bias (i.e., offset) error caused by the background signal. As a result, the first output signal analyzed to measure TFLT may contain error as a result of the background signal bias (i.e., offset) error.

Thus, in this embodiment, the first output signal generated by the imaging device 194 as a result of the first image 130 is processed to subtract or substantially subtract the background signal from the interference signal to reduce error before being analyzed to measure TFLT. This is also referred to as "background subtraction." Background subtraction is the process of removing unwanted reflections from images. In this regard, the imaging device 194 is controlled to capture a second image 146 of the tear film 136. However, before the second image 146 is captured, the rotatable polarizer 208 is rotated from a first orientation that reduces background signal to a second orientation that reduces specularly reflected light (block 216 in FIG. 15). In this way, the second image 146 will contain mostly background signal and when the second image 146 is subtracted from the first image 130 the captured interference of specularly reflected light from the tear film 136 will not be reduced or at least not significantly reduced.

The second image 146 should be captured using the same imaging device 194 settings and focal point as when capturing the first image 130 so that the first image 130 and second image 146 form corresponding image pairs captured within a short time of each other. The imaging device 194 produces a second output signal containing background signal present in the first image 130 (block 218 in FIG. 15). To eliminate or reduce this background signal from the first output signal, the second output signal is subtracted from the first output signal to produce a resulting signal (block 220 in FIG. 15). The image(s) representing the resulting signal(s) containing interference signal(s) of specularly reflected light from the tear film is produced (block 222 in FIG. 15). In this example the resulting image 148 is illustrated in FIG. 11. Thus, in this example, background subtraction involves two images 130, 146 to provide a frame pair where the two images 130, 146 are subtracted from each other, whereby specular reflection from the tear film 136 is retained, and while diffuse reflections from the iris and other areas are removed in whole or part.

Illuminator Details

Figure 16:
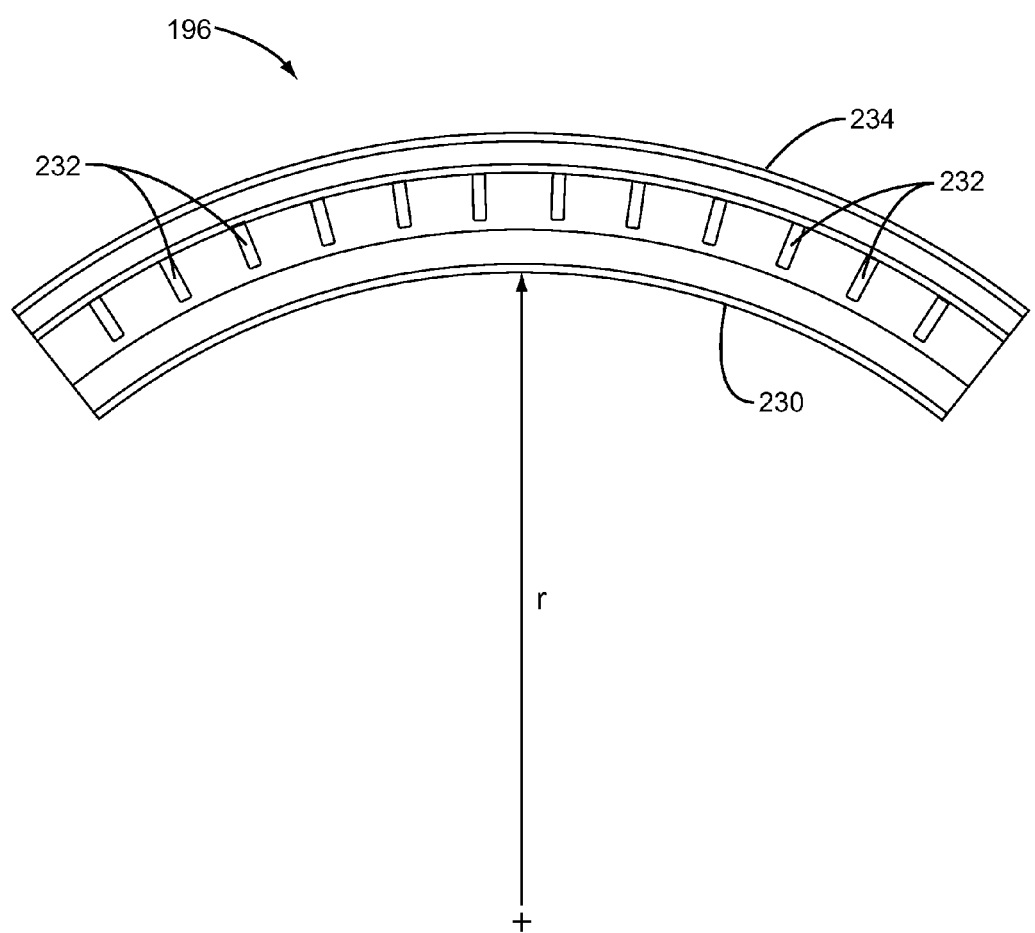
FIG. 16 is a top view of the illumination device provided in the OSI device of FIGS. 14A and 14B illuminating the tear film with the video camera capturing images of the patient's tear film.
Figure 17:
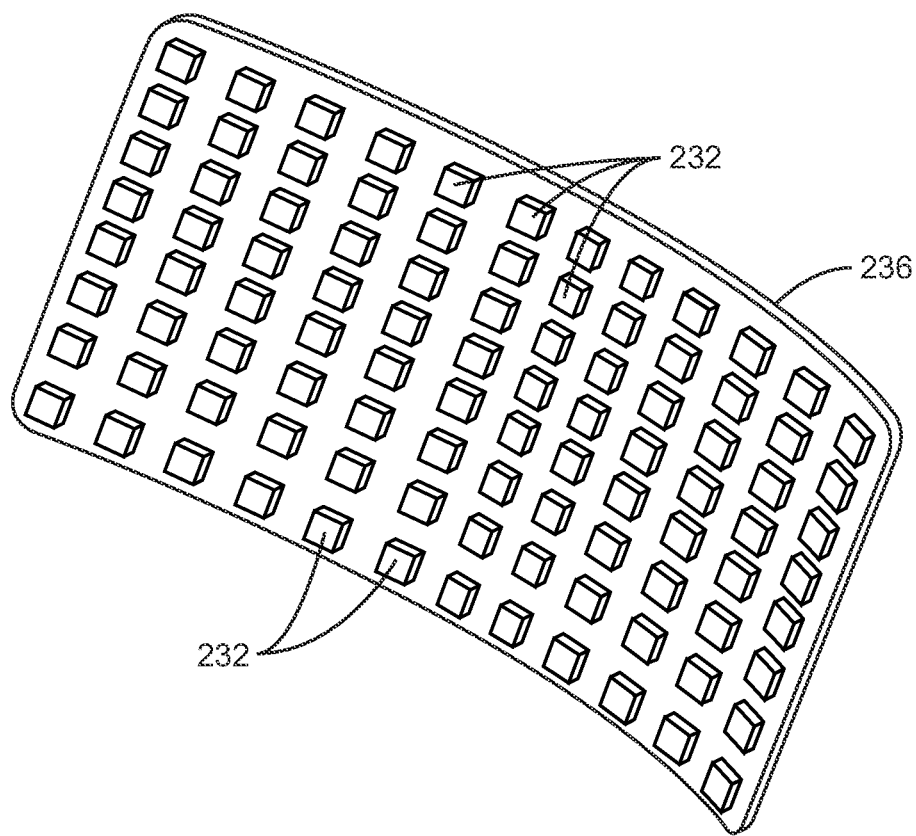
FIG. 17 is a perspective view of an exemplary printed circuit board (PCB) with a plurality of light emitting diodes (LED) provided in the illumination device of the OSI device in FIGS. 14A and 14B to illuminate the tear film.
Figure 18:
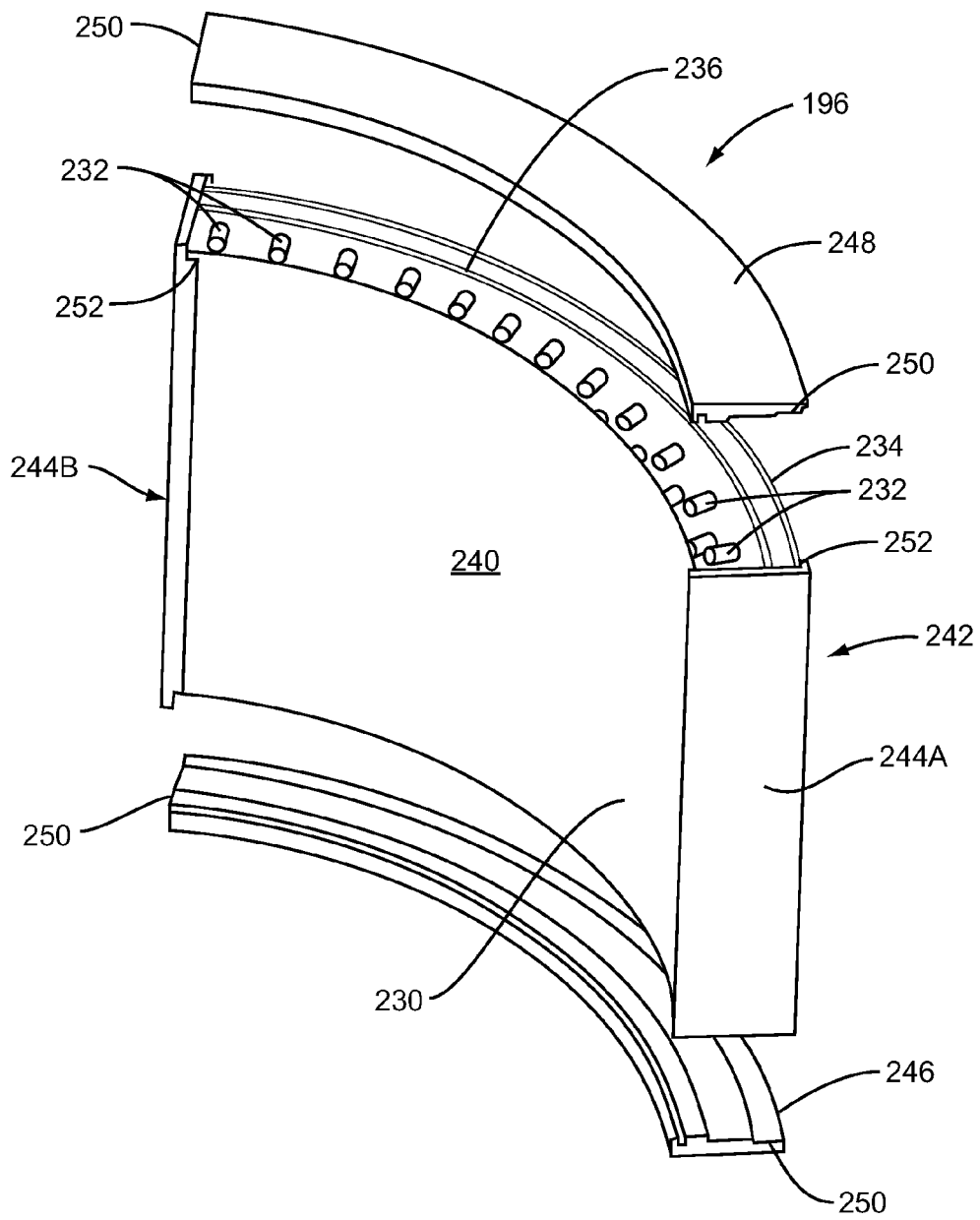
FIG. 18 is a perspective view of the illumination device and housing in the OSI device of FIGS. 14A and 14B.

FIGS. 16-18 provide more detail on the illuminator 196. As illustrated in FIG. 16, the exemplary illuminator 196 is provided on an arced surface 230 (see also, FIGS. 17-18) of approximately 75 degrees to provide a large area, broad spectrum light source covering the visible regions of approximately 400 nanometers (nm) to 700 nm. In this embodiment, the arced surface 230 has a radius to an imaginary center of approximately 190 mm ("r" in FIG. 16) and has a face 250 mm high by 100 mm wide. The arced surface 230 could be provided as a flat surface, but an arced surface may allow for: better illumination uniformity, and, a smaller sized illuminator 196 for packaging constraints, while providing the same effective illumination area capability. In this example, the illuminator 196 is a Lambertian emitter wherein the light emitter has approximately the same intensity in all directions; however, other embodiments of the present disclosure are not so limited. The illuminator 196 is arranged so that, from the perspective of the video camera 198, emitted light rays are specularly reflected from the tear film of the patient's eye 192 and undergo constructive and destructive interference in the lipid layer and layers beneath the lipid layer. In this embodiment, the illuminator 196 is comprised of high efficiency, white light emitting diodes (LEDs) 232 (see FIGS. 17 and 18) mounted on a printed circuit board (PCB) 236 (FIG. 17). Supporting circuitry (not shown) may be included to control operation of the LEDs 232, and to automatically shut off the LEDs 232 when the OSI device 170 is not in use. Each LED 232 has a 120 degree ("Lambertian") forward projection angle, a 1350 mcd maximum intensity, manufactured by LEDtronics. Other light sources other than LEDs are also possible, including but not limited to lasers, incandescent light, and organic LEDs (OLEDs), as examples. Further, the light source is not required to be a Lambertian emitter. For example, the light emitted from the light source may be collimated.

As illustrated in FIG. 18, the PCB 236 is placed inside an illuminator housing 242. The illuminator housing 242 is comprised of two side panels 244A, 244B that are disposed on opposite sides of the arced surfaced 230 when held by base panel 246 and top panel 248, and also includes a rear panel 234. The arced surface 230 is comprised of a diffuser 240 to diffuse the light emitted by the LEDs 232. The diffuser 240 can be selected to minimize intensity reduction, while providing sufficient scattering to make the illumination uniform light wave fall off on the light emitted by the outside LEDs 232. The diffuser 240, PCB 236, and rear panel 234 are flexible and fit within grooves 250 located in the top panel 248 and base panel 246, and grooves 252 located in the side panels 244A, 244B. The illuminator housing 242 is snapped together and the side panels 244A, 244B are then screwed to the top panel 248 and base panel 246.

The diffuser 240 may also be comprised of more than one diffuser panel to improve uniformity in the light emitted from the illuminator 196. The side panels 244A, 244B and the base panel 246 and top panel 248 form baffles around the PCB 236 and the LEDs 232. The inside of these surfaces may contain a reflective film (e.g., 3M ESR film) to assist in the uniformity of light emitted by the LEDs 232. The reflective film may assist in providing a uniform light intensity over an entire area or region of interest on a patient's tear film. This may be particularly an issue on the outer edges of the illumination pattern. The diffuser 240 should also be sufficiently tightly held to the edges in the illuminator housing 242 to prevent or reduce shadows on in the illumination pattern.

OSI Device Employing Polarizer Wheel

Figure 19A:
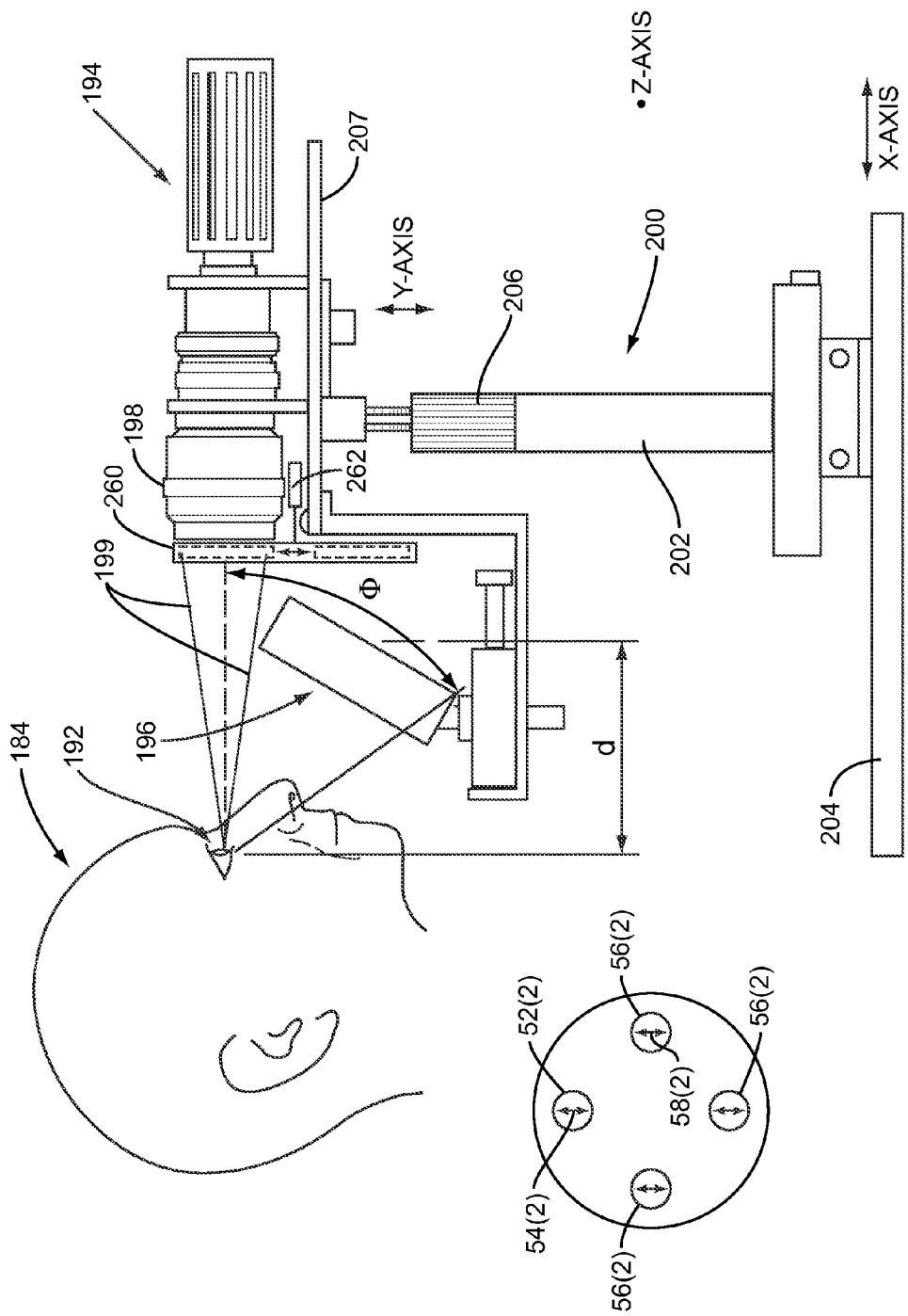
FIG. 19A is a side view of an exemplary OSI device with a polarizer wheel having a plurality of polarizers.
Figure 19B:
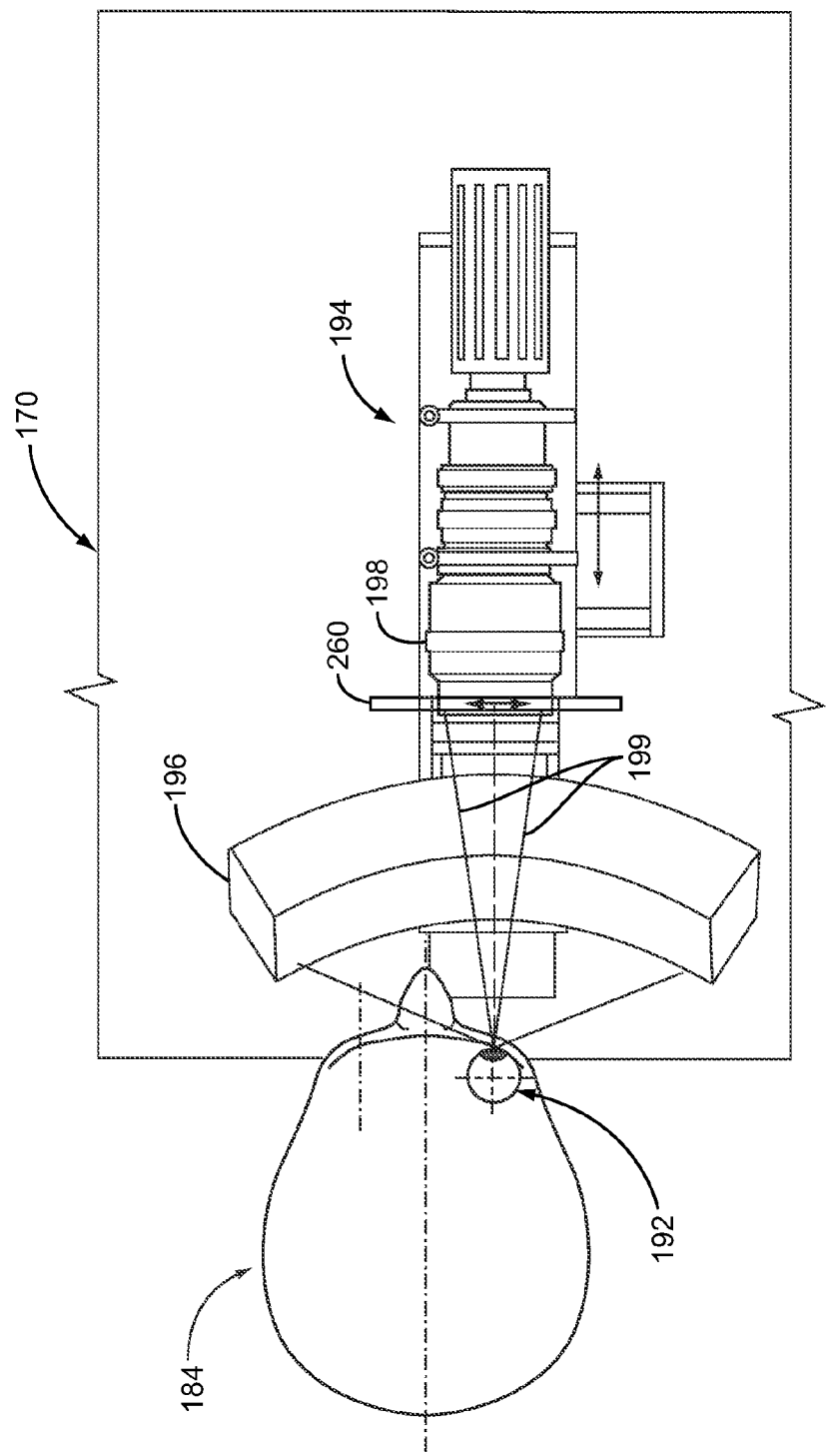
FIG. 19B is a top view of the OSI device in FIG. 19A with the polarizer wheel having a plurality of polarizers.

FIG. 19A is a side view of the imaging device 194 and illuminator 196 configured with a polarizer wheel 260 having a plurality of polarizers. FIG. 19B is a top view of the imaging device 194 and illuminator 196 with the polarizer wheel 260. In particular, the polarizer wheel 260 includes a plurality of polarizers made up of a first polarizer 52(2) and a second polarizer 56(2). The polarizer wheel 260 is selectively rotatable such that the first polarizer 52(2) is disposed in an imaging path of the imaging device 194 during the capture of the at least one first image, and wherein the second polarizer 56(2) is alternately disposed in the imaging path of the imaging device 194 during the capture of the at least one second image. In this manner, the first polarizer 52(2) and the second polarizer 56(2) are alternately rotatable into the imaging path of the imaging device 194 that includes rays 199 and is centered on the dashed line that extends from eye 192. A motor 262 coupled to polarizer wheel 260 is controllable to selectively synchronize the rotation of the polarizer wheel 260 with the image capturing by the imaging device 194.

The first polarizer 52(2) has a polarization axis 54(2) that is parallel or substantially parallel to the polarization plane of the specularly reflected light from the ROI of the ocular tear film 92 (FIG. 7) to pass or substantially pass the specularly reflected light to the imaging device 194 while reducing the background signal. Furthermore, the second polarizer 56(2) has a polarization axis 58(2) that is perpendicular or substantially perpendicular to the polarization plane of the specularly reflected light from the ROI of the ocular tear film 92 (FIG. 7) to eliminate or substantially eliminate the specularly reflected light while passing a portion of background signal to the imaging device 194.

Figure 20:
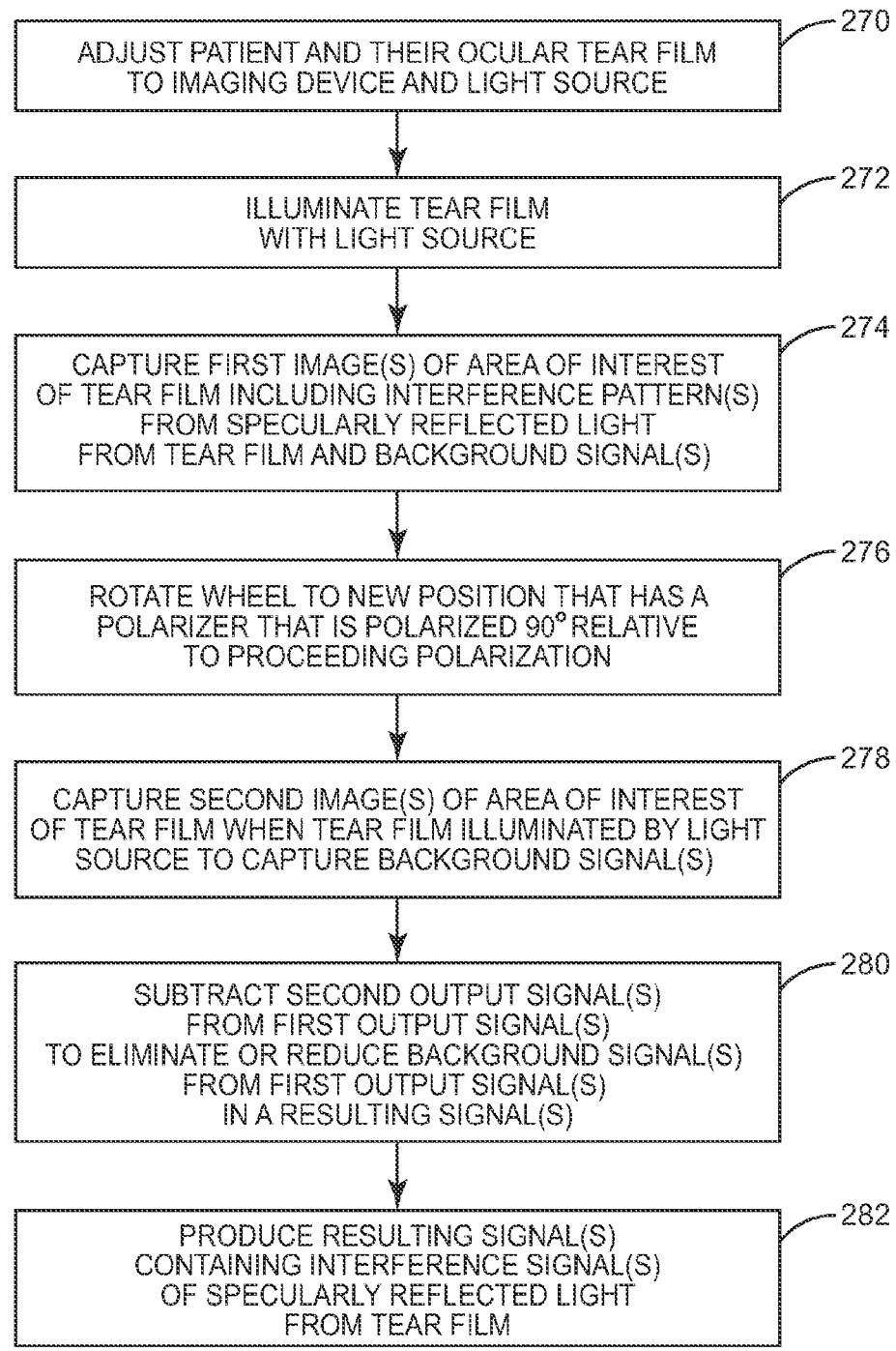
FIG. 20 is a flowchart of an exemplary process that employs the polarizer wheel in FIGS. 19A and 19B for obtaining one or more interference signals from images of a tear film representing specularly reflected light from the tear film with background signal subtracted or substantially subtracted.

FIG. 20 is a flowchart of an exemplary process for the OSI device 170 that incorporates the polarizer wheel 260 for obtaining one or more interference signals from images of a tear film 92 representing specularly reflected light from the tear film 92 with background signal subtracted or substantially subtracted. Against the backdrop of the OSI device 170 in FIGS. 19A and 19B, FIG. 20 illustrates a flowchart discussing how the OSI device 170 can be used to obtain interference interactions of specularly reflected light from the tear film 92, which can be used to measure TFLT. Interference interactions of specularly reflected light from the tear film 92 are first obtained and discussed before measurement of TFLT is discussed. In this embodiment as illustrated in FIG. 20, the process starts by adjusting the patient 184 with regard to the illuminator 196 and the imaging device 194 (block 270). The illuminator 196 is controlled to illuminate the patient's 184 tear film 92. The imaging device 194 is controlled to be focused on the anterior surface 98 of the lipid layer 96 such that the interference interactions of specularly reflected light from the tear film 92 are collected and are observable. Thereafter, the patient's 184 tear film 92 is illuminated by the illuminator 196 (block 272).

The imaging device 194 is then controlled and focused on the lipid layer 96 to collect specularly reflected light from an area or ROI 134 on a tear film 92 as a result of illuminating the tear film 92 with the illuminator 196 in a first image (block 274, FIG. 20). An example of the first image by the illuminator 196 is provided in FIG. 9. As illustrated therein, a first image 130 of a patient's eye 132 is shown that has been illuminated with the illuminator 196. The illuminator 196 and the imaging device 194 may be controlled to illuminate an area or ROI 134 on a tear film 136 that does not include a pupil 138 of the eye 132 so as to reduce reflex tearing. Reflex tearing will temporarily lead to thicker aqueous and lipid layers, thus temporarily altering the interference signals of specularly reflected light from the tear film 136. As shown in FIG. 9, when the imaging device 194 is focused on an anterior surface 142 of the lipid layer 144 of the tear film 136, interference interactions 140 of the interference signal of the specularly reflected light from the tear film 136 as a result of illumination by the illuminator 196 are captured in the area or ROI 134 in the first image 130. The interference interactions 140 appear to a human observer as colored patterns as a result of the wavelengths present in the interference of the specularly reflected light from the tear film 136.

However, even though the background signal is reduced by the first polarizer 52(2), a portion of the background signal is also captured in the first image 130. The background signal is added to the specularly reflected light in the area or ROI 134 and included outside the area or ROI 134 as well. Background signal is light that is not specularly reflected from the tear film 136 and thus contains no interference information. Background signal can include stray and ambient light entering into the imaging device 194, scattered light from the patient's 184 face, eyelids, and/or eye 132 structures outside and beneath the tear film 136 as a result of stray light, ambient light and diffuse illumination by the illuminator 196, and images of structures beneath the tear film 136. For example, the first image 130 includes the iris of the eye 132 beneath the tear film 136. Background signal adds a bias (i.e., offset) error to the captured interference of specularly reflected light from the tear film 136 thereby reducing its signal strength and contrast. Further, if the background signal has a color hue different from the light of the light source, a color shift can also occur due to the interference of specularly reflected light from the tear film 136 in the first image 130. The imaging device 194 produces a first output signal that represents the light rays captured in the first image 130. Because the first image 130 contains light rays from specularly reflected light as well as the background signal, the first output signal produced by the imaging device 194 from the first image 130 will contain an interference signal representing the captured interference of the specularly reflected light from the tear film 136 with a bias (i.e., offset) error caused by the background signal. As a result, the first output signal analyzed to measure TFLT may contain error as a result of the background signal bias (i.e., offset) error.

Thus, in this embodiment, the first output signal generated by the imaging device 194 as a result of the first image 130 is processed to subtract or substantially subtract the background signal from the interference signal to reduce error before being analyzed to measure TFLT. This is also referred to as "background subtraction." Background subtraction is the process of removing unwanted reflections from images. In this regard, the imaging device 194 is controlled to capture a second image 146 of the tear film 136. However, before the second image 146 is captured, the polarizer wheel 260 is rotated such that the second polarizer 56(2) is disposed in the imaging path of the imaging device 194 in a second orientation that is polarized 90° relative to the first polarization orientation (block 276 in FIG. 20). In this way, the second image 146 will contain mostly background signal and when the second image 146 is subtracted from the first image 130 the captured interference of specularly reflected light from the tear film 136 will not be reduced or at least not significantly reduced.

The second image 146 should be captured using the same imaging device 194 settings and focal point as when capturing the first image 130 so that the first image 130 and second image 146 form corresponding image pairs captured within a short time of each other. The imaging device 194 produces a second output signal containing background signal present in the first image 130 (block 278 in FIG. 20). To eliminate or reduce this background signal from the first output signal, the second output signal is subtracted from the first output signal to produce a resulting signal (block 280 in FIG. 20). The image representing the resulting signal in this example is illustrated in FIG. 11 as resulting image 148 (block 282 in FIG. 20). Thus, in this example, background subtraction involves two images 130, 146 to provide a frame pair where the two images 130, 146 are subtracted from each other, whereby specular reflection from the tear film 136 is retained, and while diffuse reflections from the iris and other areas are removed in whole or part.

OSI Device Employing Two Imaging Devices/Non-Polarizing Beam Splitter

Figure 21A:
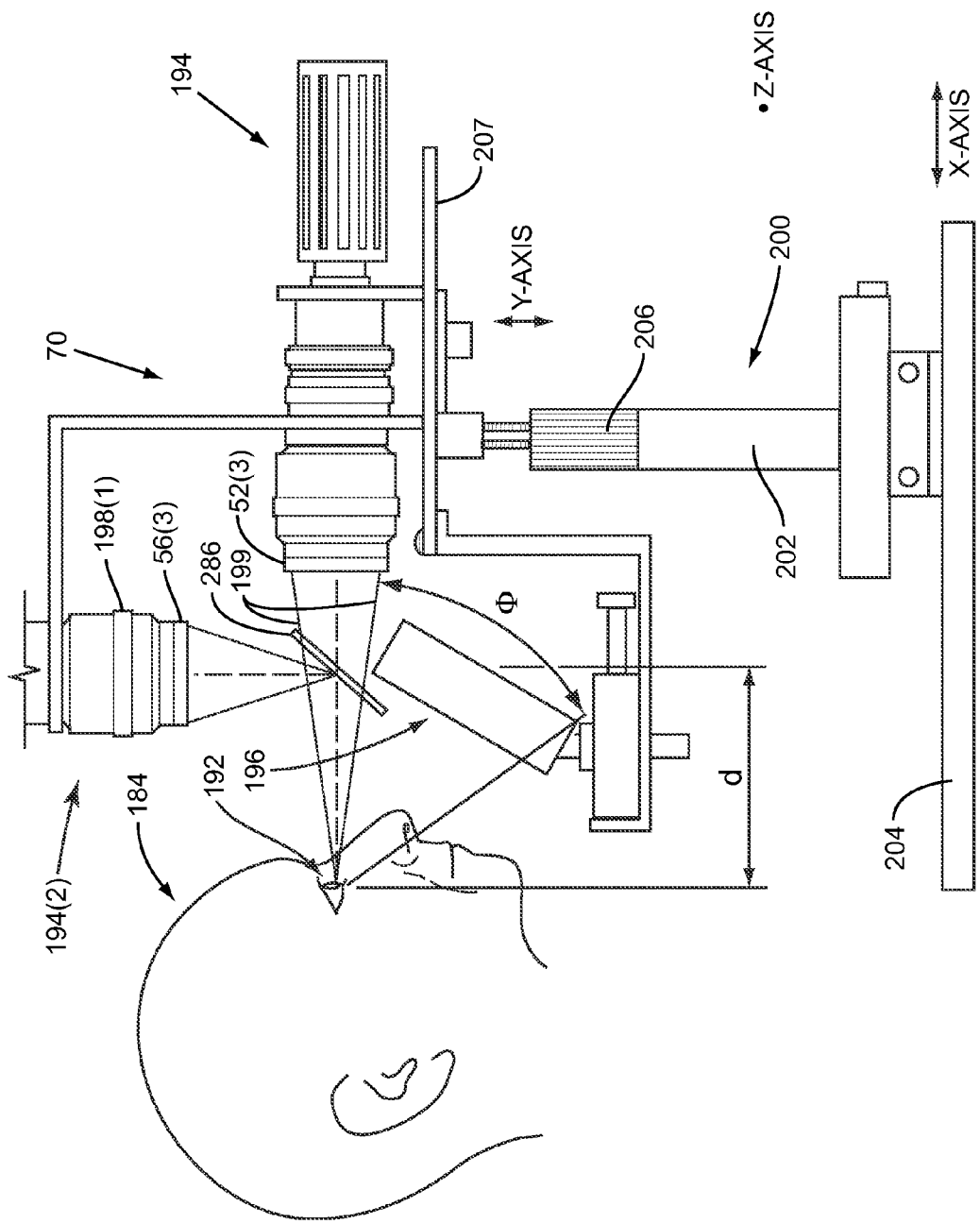
FIG. 21A is a side view of an exemplary OSI device employing a dual imager, beam splitter, and individual fixed polarizers configuration.
Figure 21B:
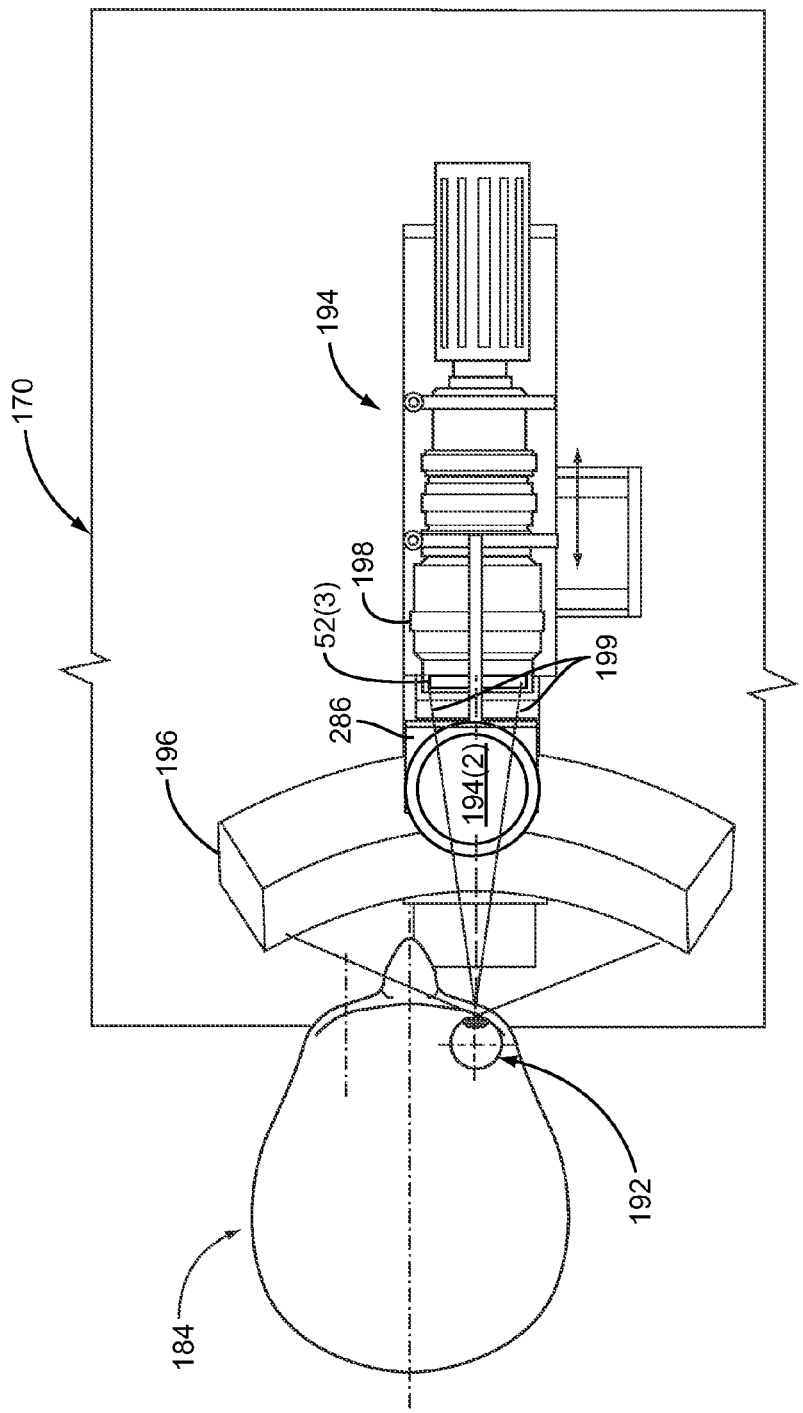
FIG. 21B is a top view of the OSI device in FIG. 21A in the dual imager, beam splitter, and individual fixed polarizers configuration.

FIG. 21A is a side view and FIG. 21B is a top view of the OSI device 170 with a dual imaging device configuration. The first imaging device 194 is configured to capture the at least one first image, and a second imaging device 194(2) is configured to capture the at least one second image. A non-polarizing beam splitter 286 is configured to direct a first portion of the specularly reflected light including the background signal to the first imaging device 194 while simultaneously directing a second portion of the specularly reflected light including the background signal to the second imaging device 194(2).

A first polarizer 52(3) is disposed in an imaging path of the first imaging device 194. The first polarizer 52(3) has a polarization axis that is parallel or substantially parallel to the polarization plane of the specularly reflected light from the ROI 134 of the ocular tear film to pass or substantially pass the specularly reflected light to the first imaging device 194 while reducing the background signal. A second polarizer 56(3) is disposed in an imaging path of a second imaging device 194(2). The second polarizer 56(3) has a polarization axis that is perpendicular or substantially perpendicular to the polarization plane of the specularly reflected light from the ROI 134 of the ocular tear film 92 to reduce or eliminate the specularly reflected light while passing a portion of background signal to the second imaging device 194(2). In this exemplary case, the second imaging device 194(2) is a video camera 198(1), which is the same type and model as the video camera 198.

Figure 22:
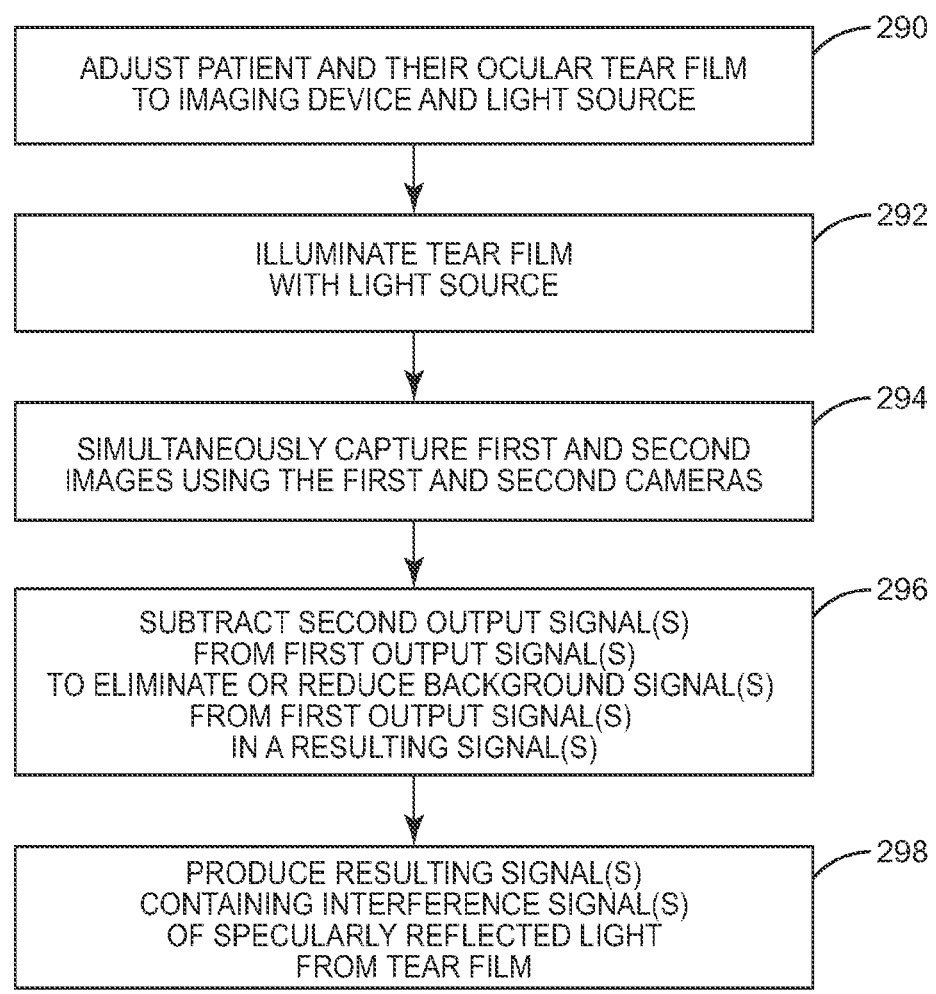
FIG. 22 is a flow chart of an exemplary process for the OSI device that incorporates the dual imager, beam splitter and individual fixed polarizers configuration in FIGS. 21A and 21B.

FIG. 22 is a flowchart of an exemplary process for the dual camera configuration of FIGS. 21A-21B, FIGS. 23A-23B, and FIGS. 24A-24B for obtaining one or more interference signals from images of a tear film 92 representing specularly reflected light from the tear film 92 with background signal subtracted or substantially subtracted. Against the backdrop of the OSI device 170 in FIGS. 21A-21B, FIGS. 23A-23B, and FIGS. 24A-24B, FIG. 22 illustrates a flowchart discussing how the OSI device 170 can be used to obtain interference interactions of specularly reflected light from the tear film 92, which can be used to measure TFLT. Interference interactions of specularly reflected light from the tear film 92 are first obtained and discussed before measurement of TFLT is discussed. In this embodiment as illustrated in FIG. 22, the process starts by adjusting the patient 184 with regard to an illuminator 196 and an imaging device 194 (block 290). The illuminator 196 is controlled to illuminate the patient's 184 tear film 92. The imaging device 194 is controlled to be focused on the anterior surface 98 of the lipid layer 96 such that the interference interactions of specularly reflected light from the tear film 92 are collected and are observable. Thereafter, the patient's 184 tear film 92 is illuminated by the illuminator 196 (block 292).

The imaging device 194 is then controlled and focused on the lipid layer 96 to collect specularly reflected light from an area or ROI 134 on a tear film 92 as a result of illuminating the tear film 92 with the illuminator 196 in a first image (block 294, FIG. 22). An example of the first image by the illuminator 196 is provided in FIG. 9. As illustrated therein, a first image 130 of a patient's eye 132 is shown that has been illuminated with the illuminator 196. The illuminator 196 and the imaging device 194 may be controlled to illuminate an area or ROI 134 on a tear film 136 that does not include a pupil 138 of the eye 132 so as to reduce reflex tearing. Reflex tearing will temporarily lead to thicker aqueous and lipid layers, thus temporarily altering the interference signals of specularly reflected light from the tear film 136. As shown in FIG. 9, when the imaging device 194 is focused on an anterior surface 142 of the lipid layer 144 of the tear film 136, interference interactions 140 of the interference signal of the specularly reflected light from the tear film 136 as a result of illumination by the illuminator 196 are captured in the area or ROI 134 in the first image 130. The interference interactions 140 appear to a human observer as colored patterns as a result of the wavelengths present in the interference of the specularly reflected light from the tear film 136.

However, even though the background signal is reduced by the first polarizer 52(3), a portion of the background signal is also captured in the first image 130. The background signal is added to the specularly reflected light in the area or ROI 134 and included outside the area or ROI 134 as well. Background signal is light that is not specularly reflected from the tear film 136 and thus contains no interference information. Background signal can include stray and ambient light entering into the imaging device 194, scattered light from the patient's 184 face, eyelids, and/or eye 132 structures outside and beneath the tear film 136 as a result of stray light, ambient light and diffuse illumination by the illuminator 196, and images of structures beneath the tear film 136. For example, the first image 130 includes the iris of the eye 132 beneath the tear film 136. Background signal adds a bias (i.e., offset) error to the captured interference of specularly reflected light from the tear film 136 thereby reducing its signal strength and contrast. Further, if the background signal has a color hue different from the light of the light source, a color shift can also occur due to the interference of specularly reflected light from the tear film 136 in the first image 130. The imaging device 194 produces a first output signal that represents the light rays captured in the first image 130. Because the first image 130 contains light rays from specularly reflected light as well as the background signal, the first output signal produced by the imaging device 194 from the first image 130 will contain an interference signal representing the captured interference of the specularly reflected light from the tear film 136 with a bias (i.e., offset) error caused by the background signal. As a result, the first output signal analyzed to measure TFLT may contain error as a result of the background signal bias (i.e., offset) error.

Thus, in this embodiment, the first output signal generated by the imaging device 194 as a result of the first image 130 is processed to subtract or substantially subtract the background signal from the interference signal to reduce error before being analyzed to measure TFLT. This is also referred to as "background subtraction." Background subtraction is the process of removing unwanted reflections from images. In this regard, the second imaging device 194(2) is controlled simultaneously with the first imaging device 194 to capture a second image 146 of the tear film 136. In this way, the second image 146 will contain mostly background signal and when the second image 146 is subtracted from the first image 130 the captured interference of specularly reflected light from the tear film 136 will not be reduced or at least not significantly reduced.

The second imaging device 194(2) produces a second output signal containing background signal present in the first image 130 (block 294 in FIG. 22). To eliminate or reduce this background signal from the first output signal, the second output signal is subtracted from the first output signal to produce a resulting signal (block 296 in FIG. 22). The image(s) representing the resulting signal(s) containing interference signal(s) of specularly reflected light from the tear film is produced (block 298 in FIG. 22). In this example the resulting image 148 is illustrated in FIG. 11. Thus, in this example, background subtraction involves two images 130, 146 to provide a frame pair where the two images 130, 146 are subtracted from each other, whereby specular reflection from the tear film 136 is retained, and while diffuse reflections from the iris and other areas are removed in whole or part.

OSI Device Employing Two Imaging Devices/Polarizing Beam Splitter

Figure 23A:
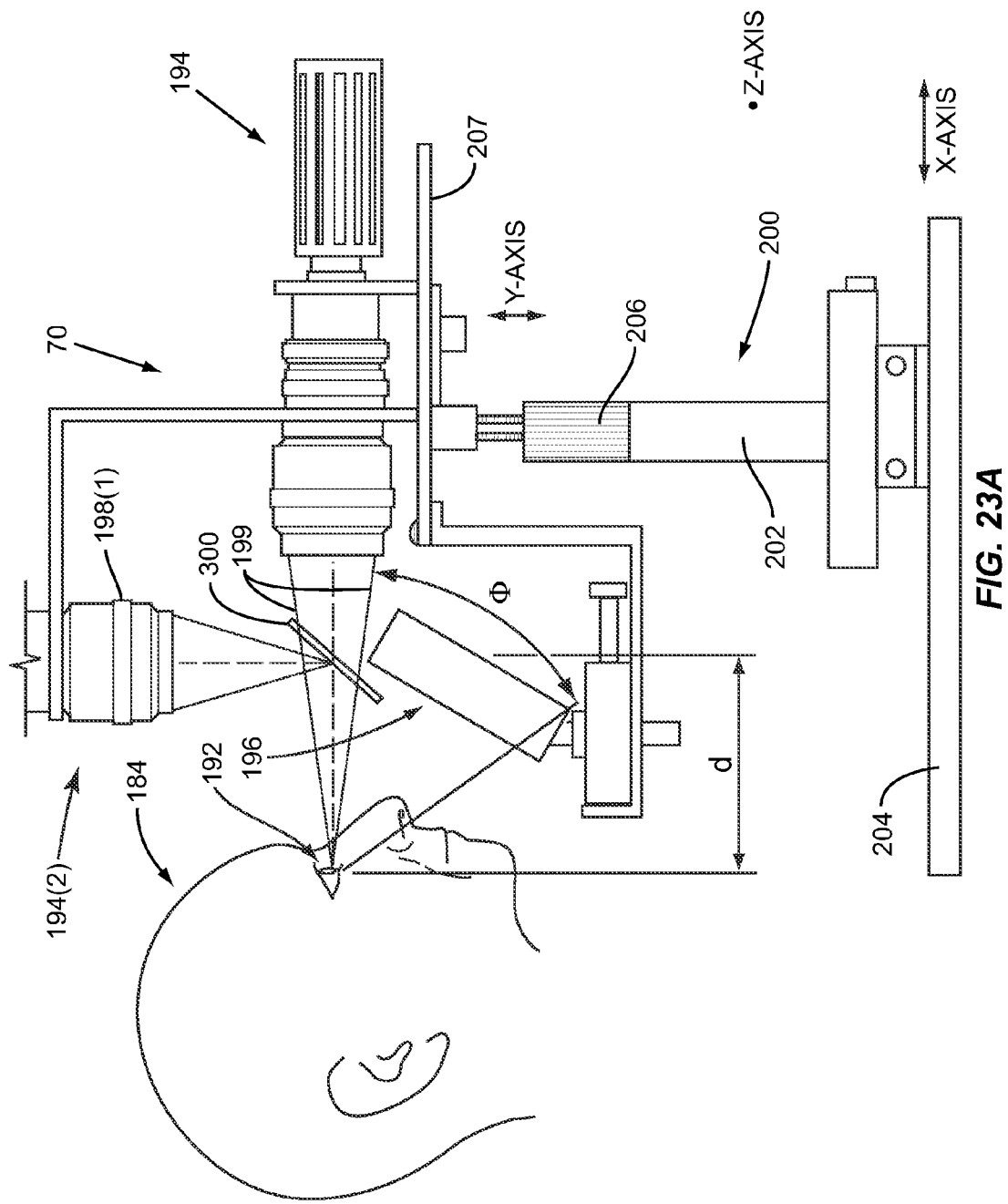
FIG. 23A is a side view of an exemplary OSI device employing a dual imager and polarizing beam splitter configuration.
Figure 23B:
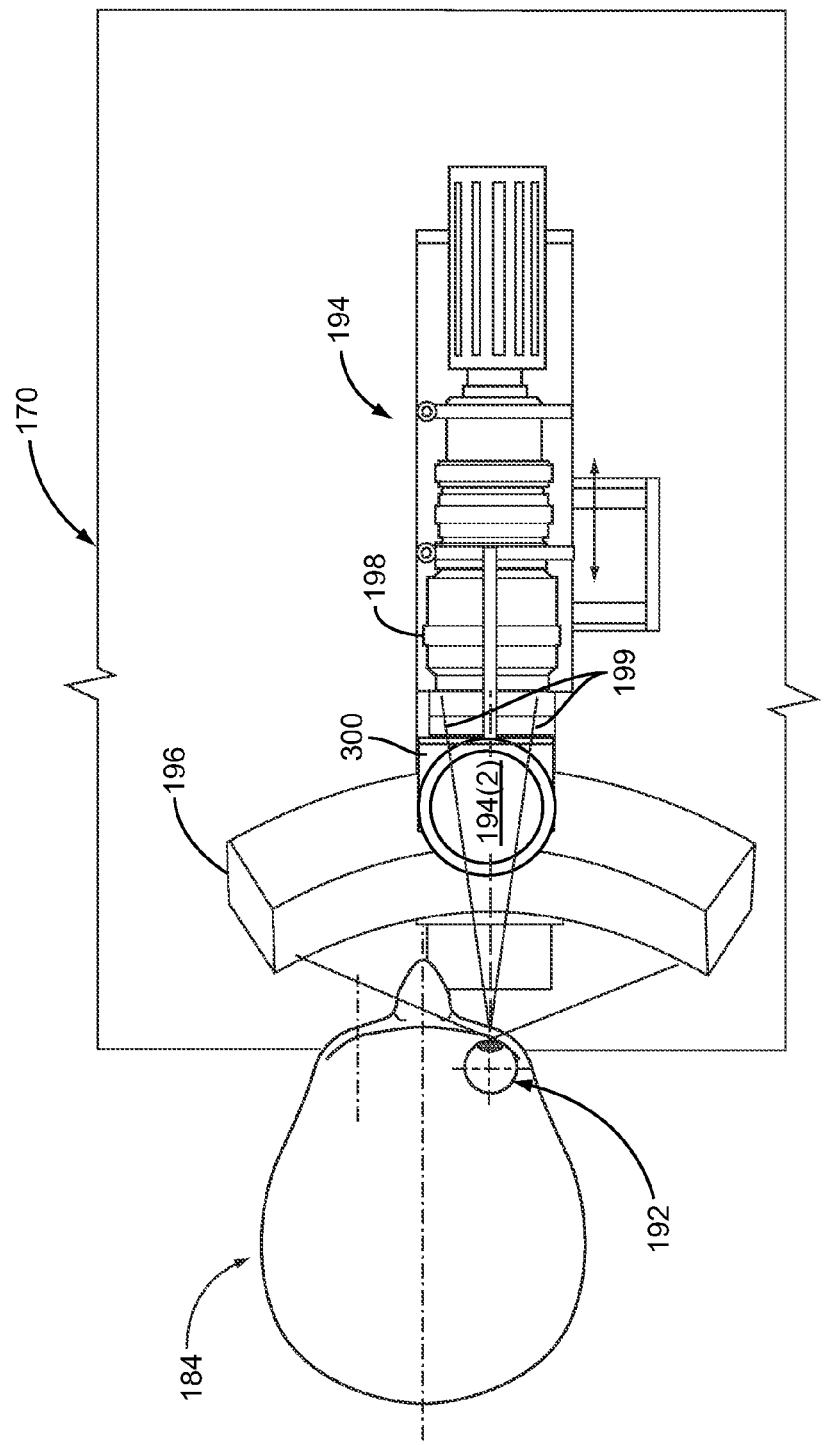
FIG. 23B is a top view of the OSI device in FIG. 23A employing the dual imager and polarizing beam splitter configuration.

FIG. 23A is a side view and FIG. 23B is a top view of the OSI device with yet another dual imaging device configuration. In this embodiment, the first polarizer 52(3) and the second polarizer 56(3) of FIGS. 21A and 21B are replaced by a polarizing beam splitter 300. However, the operation of the embodiment is operated as described by the flowchart of FIG. 22.

In this embodiment, specularly reflected light from the tear film 136 passes largely unimpeded through the polarizing beam splitter 300 and onward to the first imaging device 194. A portion of background signal is also transmitted through the polarizing beam splitter 300 to the first imaging device 194. In contrast, specularly reflected light from the tear film 136 is practically blocked from reflecting to the second imaging device 194(1), while a portion of the background signal is directed to the second imaging device 194(1).

OSI Device Employing Illuminator Polarizer

Figure 24B:
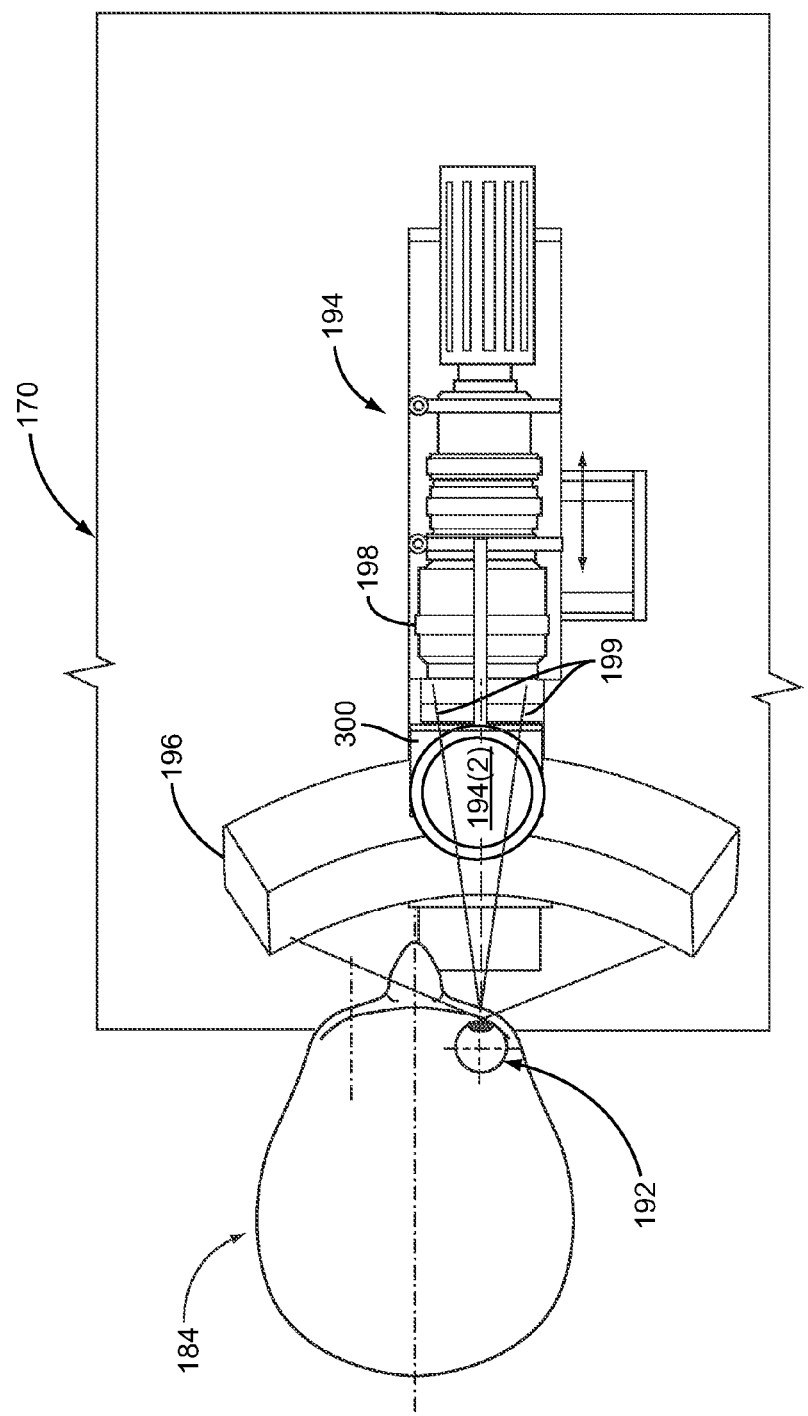
FIG. 24B is a top view of the OSI device in FIG. 24A employing the dual imager and polarizing beam splitter that also includes a polarizer in the illumination path of the illuminator.

FIG. 24A is a side view and FIG. 24B is a top view of the OSI device of FIG. 23A and FIG. 23B that further includes a polarizer 302. The polarizer 302 is disposed in the illumination path of the illuminator 196 to polarize multi-wavelength light emitted from the illuminator 196 that is illuminating the ROI 134 of the ocular tear film 136. The polarizer 302 helps further isolate by reducing the amount of unpolarized light that makes up the background signal. The polarizer 302 can be either a linear polarizer or a circular polarizer.

System Level

Figure 25A:
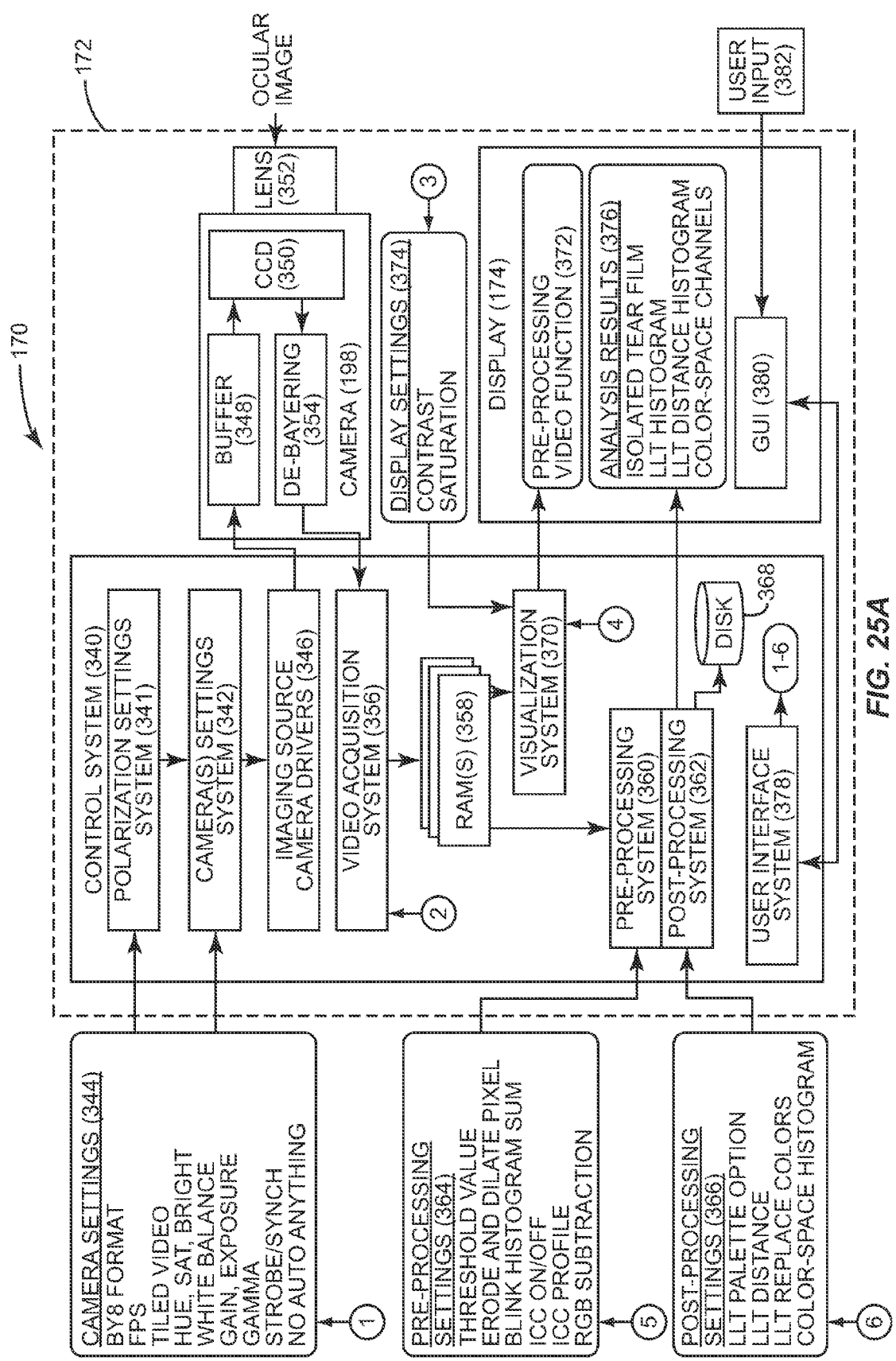
FIG. 25A illustrates an exemplary system diagram of a control system and supporting components that can include the exemplary OSI devices of FIGS. 6A, 6B, 12, 13, 14A, 14B, 19A, 19B, 21A, 21B, 23A, 23B, 24A, and 24B.

Now that the imaging and illumination functions of the OSI device 170 have been described, FIG. 25A illustrates a system level diagram illustrating more detail regarding the control system and other internal components of the OSI device 170 provided inside the housing 172 according to one embodiment to capture images of a patient's tear film and process those images. As illustrated therein, a control system 340 is provided that provides the overall control of the OSI device 170. The control system 340 may be provided by any microprocessor-based or computer system. The control system 340 illustrated in FIG. 25A is provided in a system-level diagram and does not necessarily imply a specific hardware organization and/or structure. As illustrated therein, the control system 340 contains several systems. A polarization settings system 341 may be provided that accepts input from a clinician user. The polarization settings may include but are not limited to synchronization values that adjust video camera and polarizer synchronization. A camera settings system 342 may be provided that accepts camera settings from a clinician user. Exemplary camera settings 344 are illustrated, but may be any type according to the type and model of camera provided in the OSI device 170 as is well understood by one of ordinary skill in the art.

The camera settings 344 may be provided to (The Imaging Source) camera drivers 346, which may then be loaded into the video camera 198 upon initialization of the OSI device 170 for controlling the settings of the video camera 198. The settings and drivers may be provided to a buffer 348 located inside the video camera 198 to store the settings for controlling a CCD 350 for capturing ocular image information from a lens 352. Ocular images captured by the lens 352 and the CCD 350 are provided to a de-Bayering function 354 which contains an algorithm for post-processing of raw data from the CCD 350 as is well known. The ocular images are then provided to a video acquisition system 356 in the control system 340 and stored in memory, such as random access memory(s) (RAM(s)) 358. The stored ocular images or signal representations can then be provided to a pre-processing system 360 and a post-processing system 362 to manipulate the ocular images to obtain the interference interactions of the specularly reflected light from the tear film and analyze the information to determine characteristics of the tear film. Pre-processing settings 364 and post-processing settings 366 can be provided to the pre-processing system 360 and post-processing system 362, respectively, to control these functions. The pre-processing settings 364 and the post-processing settings 366 will be described in more detail below. The post-processed ocular images and information may also be stored in mass storage, such as disk memory 368, for later retrieval and viewing on the display 174.

The control system 340 may also contain a visualization system 370 that provides the ocular images to the display 174 to be displayed in human-perceptible form on the display 174. Before being displayed, the ocular images may have to be pre-processed in a pre-processing video function 372. For example, if the ocular images are provided by a linear camera, non-linearity (i.e. gamma correction) may have to be added in order for the ocular images to be properly displayed on the display 174. Further, contrast and saturation display settings 374, which may be controlled via the display 174 or a device communicating to the display 174, may be provided by a clinician user to control the visualization of ocular images displayed on the display 174. The display 174 is also adapted to display analysis result information 376 regarding the patient's tear film, as will be described in more detail below. The control system 340 may also contain a user interface system 378 that drives a graphical user interface (GUI) utility 380 on the display 174 to receive user input 382. The user input 382 can include any of the settings for the OSI device 170, including the camera settings 344, the pre-processing settings 364, the post-processing settings 366, the display settings 374, the visualization system 370 enablement, and video acquisition system 356 enablement, labeled 1-6. The GUI utility 380 may only be accessible by authorized personnel and used for calibration or settings that would normally not be changed during normal operation of the OSI device 170 once configured and calibrated.

Overall Process Flow

Figure 25B:
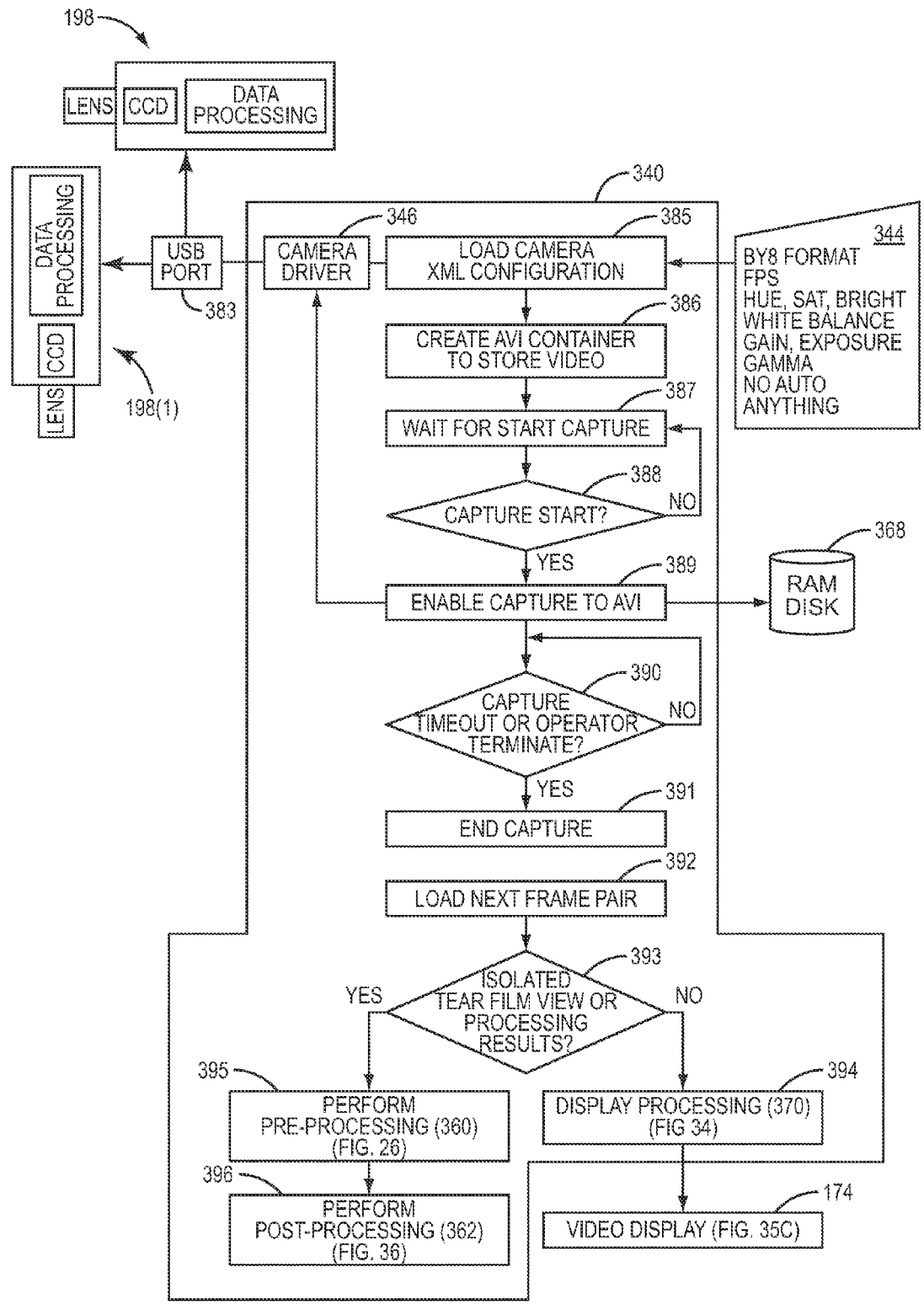
FIG. 25B is a flowchart illustrating an exemplary overall processing that can be employed by the OSI devices of FIGS. 6A, 6B, 12, 13, 14A, 14B, 19A, 19B, 21A, 21B, 23A, 23B, 24A, and 24B having systems components according to the exemplary system diagram of the OSI device in FIG. 25A.

FIG. 25B illustrates an exemplary overall flow process performed by the OSI device 170 for capturing tear film images from a patent and analysis for TFLT measurement. As illustrated in FIG. 25B, the first video camera 198 and an optional second video camera 198(1) are connected via a USB port(s) 383 to the control system 340 (see FIG. 25A) for control of the first video camera 198 and the second video camera 198(1) and for transferring images of a patient's tear film taken by the video camera 198 back to the control system 340. The control system 340 includes a compatible camera driver 346 to provide a transfer interface between the control system 340 and the video camera 198. Prior to tear film image capture, the configuration or camera settings 344 are loaded into the video camera 198 over the USB port 383 to prepare the video camera 198 for tear film image capture (block 385). Further, an audio video interleaved (AVI) container is created by the control system 340 to store video of tear film images to be captured by the video camera 198 (block 386). At this point, the video camera 198 and control system 340 are ready to capture images of a patient's tear film. The control system 340 waits for a user command to initiate capture of a patient's tear film (blocks 387, 388).

Once image capture is initiated (block 388), the control system enables image capture to the AVI container previously setup (block 386) for storage of images captured by the video camera 198 (block 389). The control system 340 controls the video camera 198 to capture images of the patient's tear film (block 389) until timeout or the user terminates image capture (block 390) and image capture halts or ends (block 391). Images captured by the video camera 198 and provided to the control system 340 over the USB port 383 are stored by the control system 340 in RAM(S) 358.

The captured images of the patient's ocular tear film can subsequently be processed and analyzed to perform TFLT measurement, as described in more detail below and throughout the remainder of this disclosure. The process in this embodiment involves processing tear film image pairs to perform background subtraction, as previously discussed. The processing can include simply displaying the patient's tear film or performing TFLT measurement (block 393). If the display option is selected to allow a technician to visually view the patient's tear film, display processing is performed (block 394) which can be the display processing 370 described in more detail below with regard to FIG. 34. For example, the control system 340 can provide a combination of images of the patient's tear film that show the entire region of interest of the tear film on the display 174. The displayed image may include the background signal or may have the background signal subtracted. If TFLT measurement is desired, the control system 340 performs pre-processing of the tear film images for TFLT measurement (block 395), which can be the pre-processing system 360 described in more detail below with regard to FIG. 26. The control system 340 also performs post-processing of the tear film images for TFLT measurement (block 396), which can be the post-processing system 362 described in more detail below with regard to FIG. 36.

Pre-Processing

Figure 26:
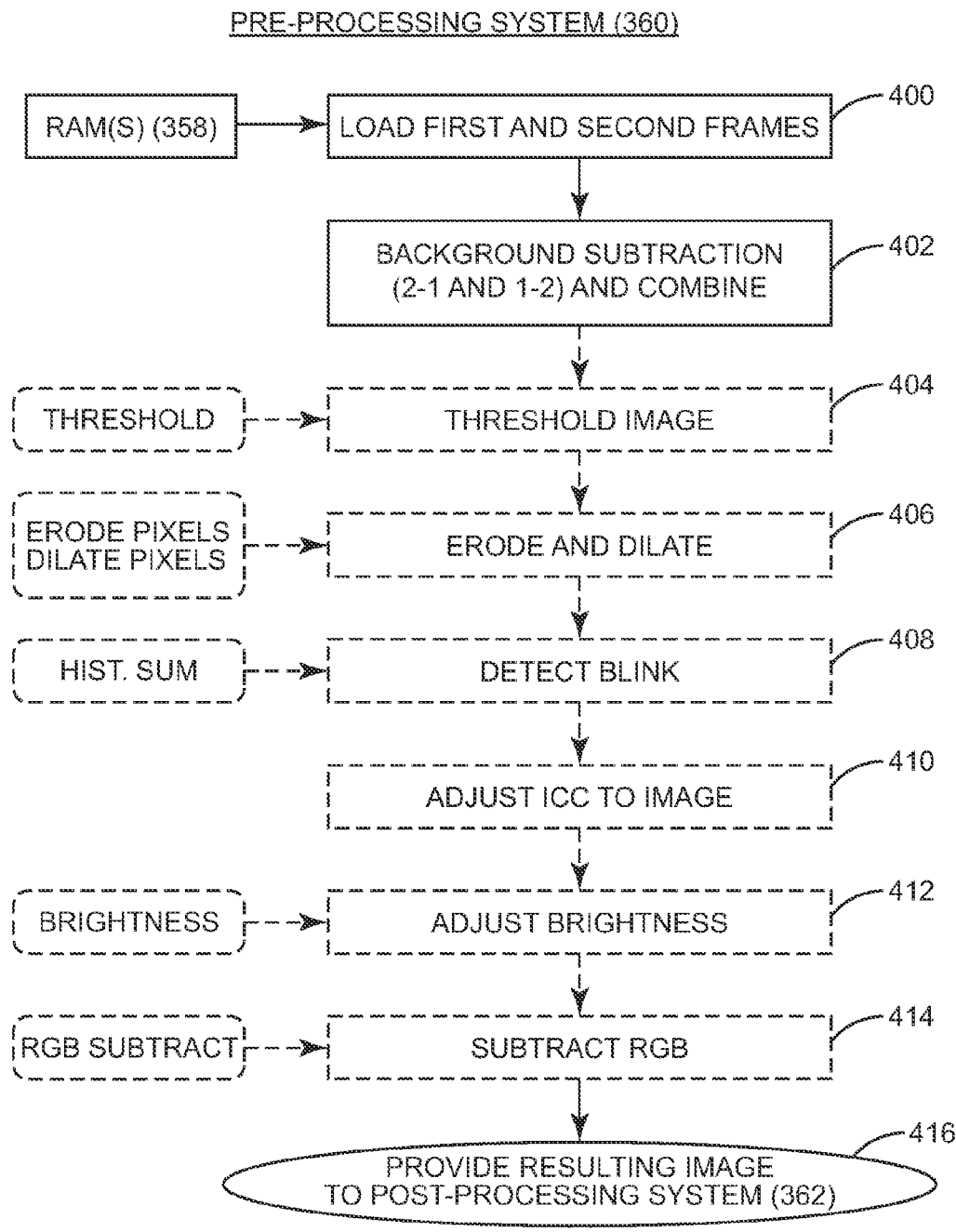
FIG. 26 is a flowchart illustrating exemplary pre-processing steps performed on the combined first and second images of a patient's tear film before measuring tear film layer thickness (TFLT)
Figure 27:
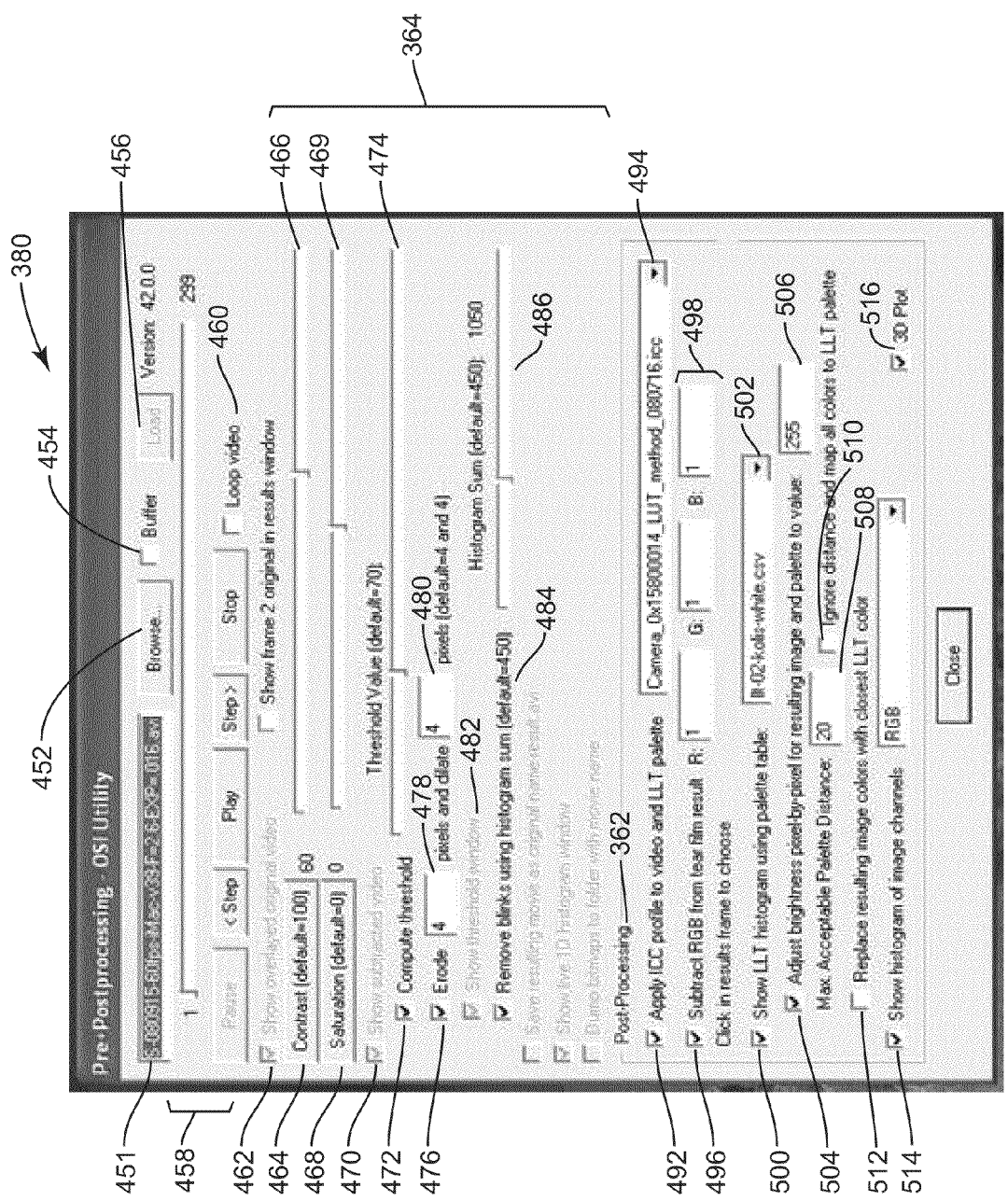
FIG. 27 is an exemplary graphical user interface (GUI) for controlling imaging, pre-processing, and post-processing settings that can be employed by the OSI devices of FIGS. 6A, 6B, 12, 13, 14A, 14B, 19A, 19B, 21A, 21B, 23A, 23B, 24A, and 24B.
Figure 28:
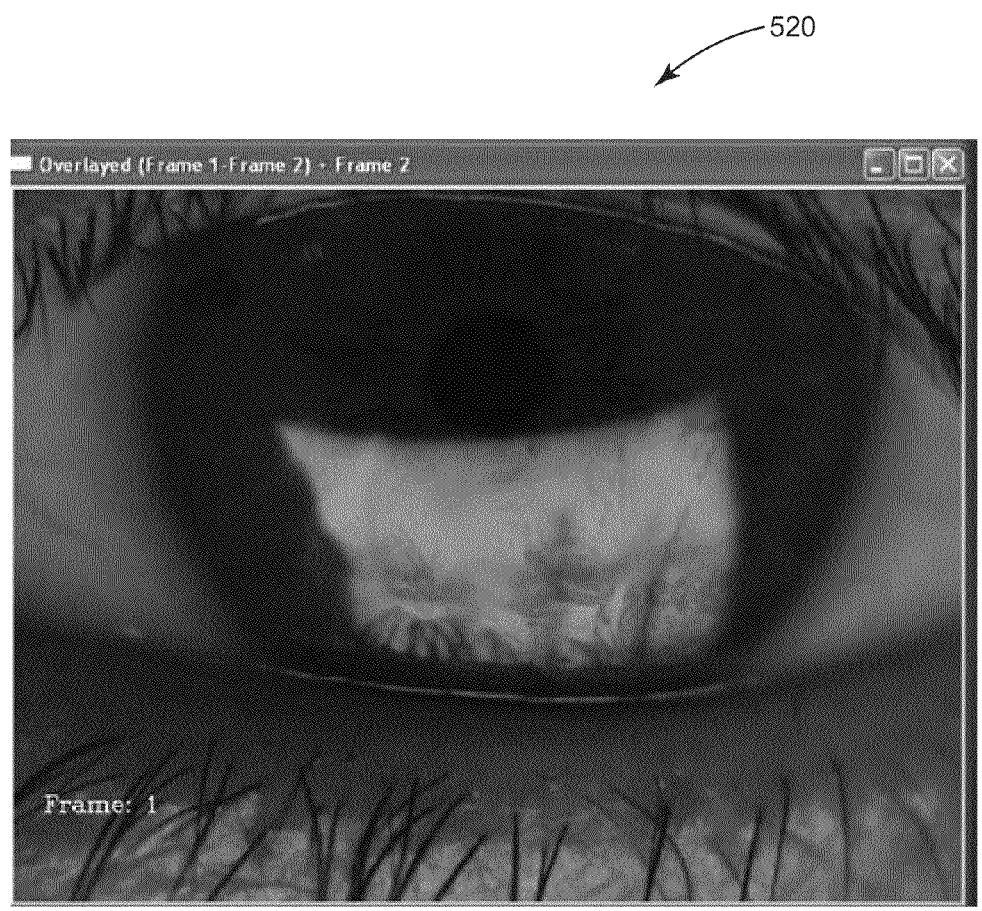
FIG. 28 illustrates an example of a subtracted image in an area or region of interest of a tear film containing specularly reflected light from the tear film overlaid on top of a background image of the tear film.

FIG. 26 illustrates an exemplary pre-processing system 360 for pre-processing ocular tear film images captured by the OSI device 170 for eventual analysis and TFLT measurement. In this system, the video camera 198 has already taken the first and second images of a patient's ocular tear film, as previously illustrated in FIGS. 9 and 10, and provided the images to the video acquisition system 356. The frames of the first and second images were then loaded into RAM(s) 358 by the video acquisition system 356. Thereafter, as illustrated in FIG. 26, the control system 340 commands the pre-processing system 360 to pre-process the first and second images. An exemplary GUI utility 380 is illustrated in FIG. 27 that may be employed by the control system 340 to allow a clinician to operate the OSI device 170 and control pre-processing settings 364 and post-processing settings 366, which will be described later in this application. In this regard, the pre-processing system 360 loads the first and second image frames of the ocular tear film from RAM(s) 358 (block 400). The exemplary GUI utility 380 in FIG. 27 allows for a stored image file of previously stored video sequence of first and second image frames captured by the video camera 198 by entering a file name in the file name field 451. A browse button 452 also allows searches of the memory for different video files, which can either be buffered by selecting a buffered box 454 or loaded for pre-processing by selecting the load button 456.

If the loaded first and second image frames of the tear film are buffered, they can be played using display selection buttons 458, which will in turn display the images on the display 174. The images can be played on the display 174 in a looping fashion, if desired, by selecting the loop video selection box 460. A show subtracted video selection box 470 in the GUI utility 380 allows a clinician to show the resulting, subtracted video images of the tear film on the display 174 representative of the resulting signal comprised of the second output signal combined or subtracted from the first output signal, or vice versa. Also, by loading the first and second image frames, the previously described subtraction technique can be used to remove background image from the interference signal representing interference of the specularly reflected light from the tear film, as previously described above and illustrated in FIG. 11 as an example. The first image is subtracted from the second image to subtract or remove the background signal in the portions producing specularly reflected light in the second image, and vice versa, and then combined to produce an interference interaction of the specularly reflected light of the entire area or region of interest of the tear film, as previously illustrated in FIG. 11 (block 402 in FIG. 26). For example, this processing could be performed using the Matlab® function "cvAbsDiff."

The subtracted image containing the specularly reflected light from the tear film can also be overlaid on top of the original image capture of the tear film to display an image of the entire eye and the subtracted image in the display 174 by selecting the show overlaid original video selection box 462 in the GUI utility 380 of FIG. 27. An example of an overlaid original video to the subtracted image of specularly reflected light from the tear film is illustrated in the image 520 of FIG. 28. This overlay is provided so that flashing images of specularly reflected light from the tear film are not displayed, which may be unpleasant to visualize. The image 520 of the tear film illustrated in FIG. 28 was obtained with a DBK 21AU04 Bayer VGA (640×480) video camera having a Pentax VS-LD25 Daitron 25-mm fixed focal length lens with maximum aperture at a working distance of 120 mm and having the following settings, as an example:

Gamma=100 (to provide linearity with exposure value)
Exposure=$\frac{1}{16}$ second
Frame rate=60 fps
Data Format=BY8
Video Format=-uncompressed, RGB 24-bit AVI
Hue=180 (neutral, no manipulation)
Saturation=128(neutral, no manipulation)
Brightness=0 (neutral, no manipulation)
Gain=260 (minimum available setting in this camera driver)
White balance=B=78; R=20.

Thresholding

Any number of optional pre-processing steps and functions can next be performed on the resulting combined tear film image(s), which will now be described. For example, an optional threshold pre-processing function may be applied to the resulting image or each image in a video of images of the tear film (e.g., FIG. 11) to eliminate pixels that have a subtraction difference signal below a threshold level (block 404 in FIG. 26). Image threshold provides a black and white mask (on/off) that is applied to the tear film image being processed to assist in removing residual information that may not be significant enough to be analyzed and/or may contribute to inaccuracies in analysis of the tear film. The threshold value used may be provided as part of a threshold value setting provided by a clinician as part of the pre-processing settings 364, as illustrated in the system diagram of FIG. 25A. For example, the GUI utility 380 in FIG. 27 includes a compute threshold selection box 472 that may be selected to perform thresholding, where the threshold brightness level can be selected via the threshold value slide 474. The combined tear film image of FIG. 12 is copied and converted to grayscale. The grayscale image has a threshold applied according to the threshold setting to obtain a binary (black/white) image that will be used to mask the combined tear film image of FIG. 11. After the mask is applied to the combined tear film image of FIG. 11, the new combined tear film image is stored in RAM(s) 358. The areas of the tear film image that do not meet the threshold brightness level are converted to black as a result of the threshold mask.

Figure 29A:
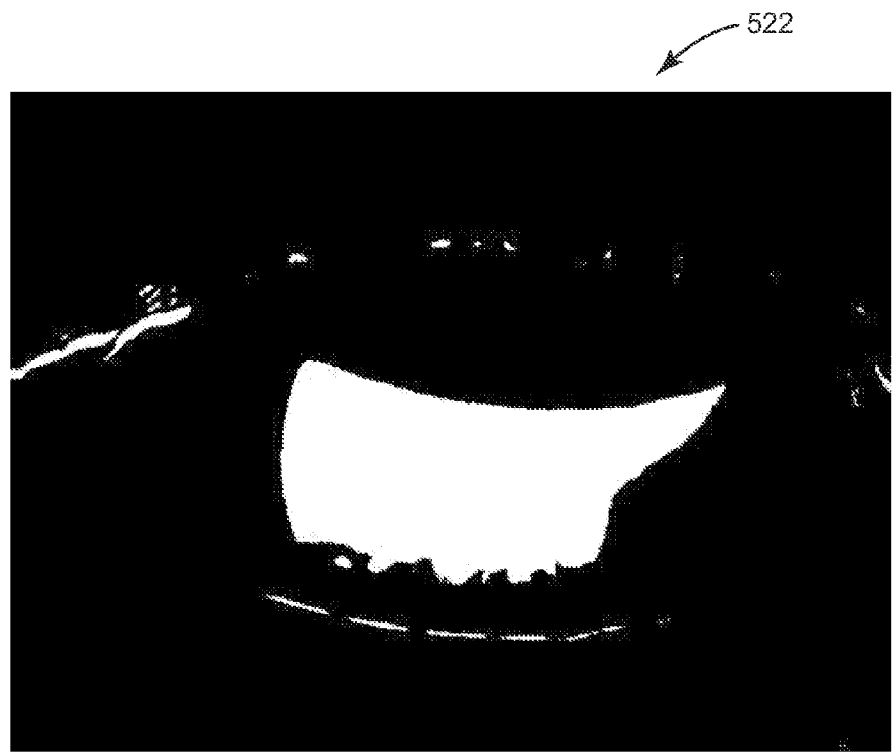
FIGS. 29A and 29B illustrate exemplary threshold masks that may be used to provide a threshold function during pre-processing of a resulting image containing specularly reflected light from a patient's tear film.
Figure 29B:
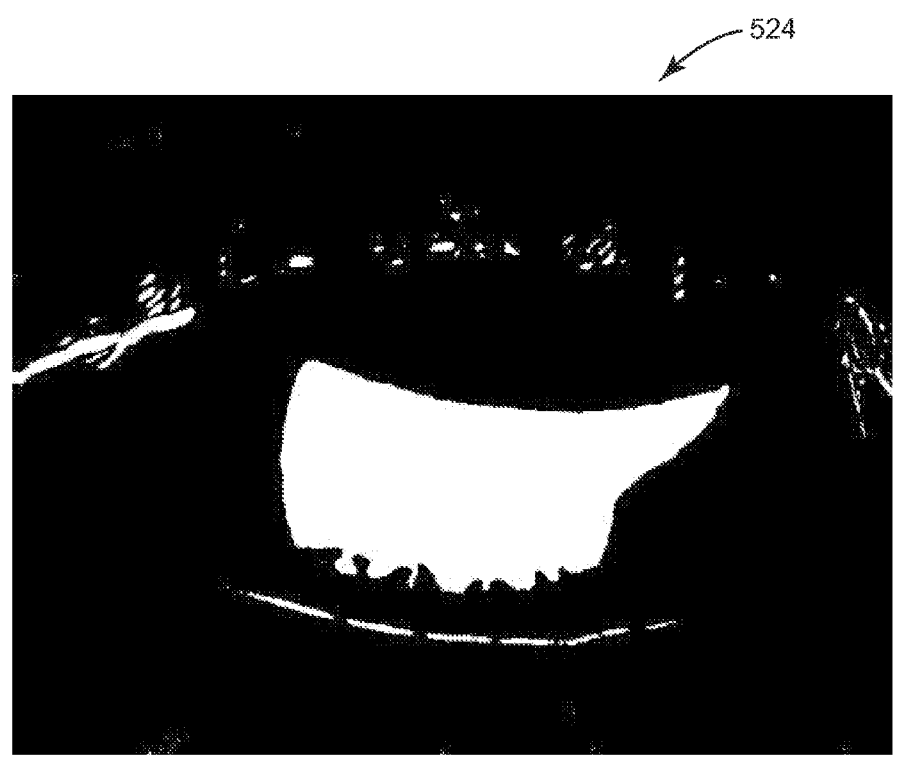
Figure 30:
FIG. 30 illustrates an exemplary image of FIG. 28 after a threshold pre-processing function has been performed leaving interference of the specularly reflected light from the patient's tear film.

FIGS. 29A and 29B illustrate examples of threshold masks for the combined tear film provided in FIG. 11. FIG. 29A illustrates a threshold mask 522 for a threshold setting of 70 counts out of a full scale level of 255 counts. FIG. 29B illustrates a threshold mask 524 for a threshold setting of 50. Note that the threshold mask 522 in FIG. 29A contains less portions of the combined tear film image, because the threshold setting is higher than for the threshold mask 524 of FIG. 29B. When the threshold mask according to a threshold setting of 70 is applied to the exemplary combined tear film image of FIG. 11, the resulting tear film image is illustrated FIG. 30. Much of the residual subtracted background image that surrounds the area or region of interest has been masked away.

Erode and Dilate

Figure 31:
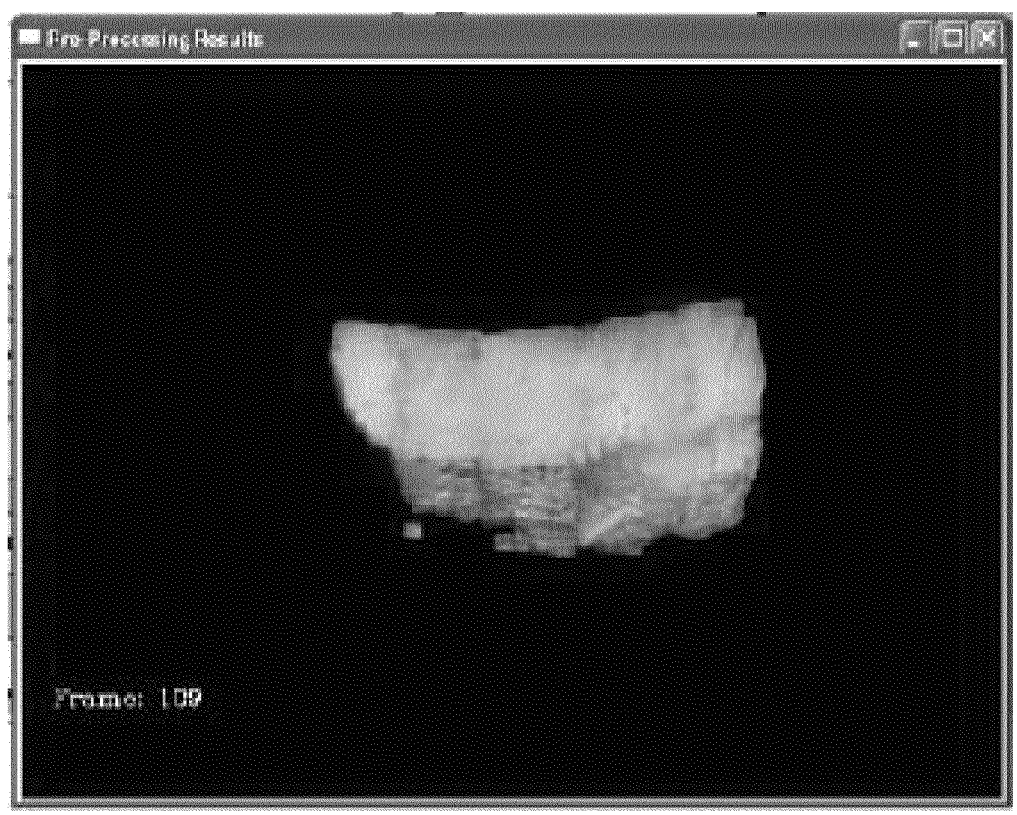
FIG. 31 illustrates an exemplary image of the image of FIG. 30 after erode and dilate pre-processing functions have been performed on the image.

Another optional pre-processing function that may be applied to the resulting image or each image in a video of images of the tear film to correct anomalies in the combined tear film image(s) is the erode and dilate functions (block 406 in FIG. 26). The erode function generally removes small anomaly artifacts by subtracting objects with a radius smaller than an erode setting (which is typically in number of pixels) removing perimeter pixels where interference information may not be as distinct or accurate. The erode function may be selected by a clinician in the GUI utility 380 (see FIG. 27) by selecting the erode selection box 476. If selected, the number of pixels for erode can be provided in an erode pixels text box 478. Dilating generally connects areas that are separated by spaces smaller than a minimum dilate size setting by adding pixels of the eroded pixel data values to the perimeter of each image object remaining after the erode function is applied. The dilate function may be selected by a clinician in the GUI utility 380 (see FIG. 27) by providing the number of pixels for dilating in a dilate pixels text box 480. Erode and dilate can be used to remove small region anomalies in the resulting tear film image prior to analyzing the interference interactions to reduce or avoid inaccuracies. The inaccuracies may include those caused by bad pixels of the video camera 198 or from dust that may get onto a scanned image, or more commonly, spurious specular reflections such as: tear film meniscus at the juncture of the eyelids, glossy eyelash glints, wet skin tissue, etc. FIG. 31 illustrates the resulting tear film image of FIG. 30 after erode and dilate functions have been applied and the resulting tear film image is stored in RAM(s) 358. As illustrated therein, pixels previously included in the tear film image that was not in the tear film area or region of interest are removed. This prevents data in the image outside the area or region of interest from affecting the analysis of the resulting tear film image(s).

Removing Blinks/Other Anomalies

Another optional pre-processing function that may be applied to the resulting image or each image in a video of images of the tear film to correct anomalies in the resulting tear film image is to remove frames from the resulting tear film image that include patient blinks or significant eye movements (block 408 in FIG. 26). As illustrated in FIG. 26, blink detection is shown as being performed after a threshold and erode and dilate functions are performed on the tear film image or video of images. Alternatively, the blink detection could be performed immediately after background subtraction, such that if a blink is detected in a given frame or frames, the image in such frame or frames can be discarded and not pre-processed. Not pre-processing images where blinks are detected may increase the overall speed of pre-processing. The remove blinks or movement pre-processing may be selectable. For example, the GUI utility 380 in FIG. 27 includes a remove blinks selection box 484 to allow a user to control whether blinks and/or eye movements are removed from a resulting image or frames of the patient's tear film prior to analysis. Blinking of the eyelids covers the ocular tear film, and thus does not produce interference signals representing specularly reflected light from the tear film. If frames containing whole or partial blinks obscuring the area or region of interest in the patient's tear film are not removed, it would introduce errors in the analysis of the interference signals to determine characteristics of the TFLT of the patient's ocular tear film. Further, frames or data with significant eye movement between sequential images or frames can be removed during the detect blink pre-processing function. Large eye movements could cause inaccuracy in analysis of a patient's tear film when employing subtraction techniques to remove background signal, because subtraction involves subtracting frame-pairs in an image that closely match spatially. Thus, if there is significant eye movement between first and second images that are to be subtracted, frame pairs may not be closely matched spatially thus inaccurately removing background signal, and possibly removing a portion of the interference image of specularly reflected light from the tear film.

Different techniques can be used to determine blinks in an ocular tear film image and remove the frames as a result. For example, in one embodiment, the control system 340 directs the pre-processing system 360 to review the stored frames of the resulting images of the tear film to monitor for the presence of an eye pupil using pattern recognition. A Hough Circle Transform may be used to detect the presence of the eye pupil in a given image or frame. If the eye pupil is not detected, it is assembled such that the image or frame contains an eye blink and thus should be removed or ignored during pre-processing from the resulting image or video of images of the tear film. The resulting image or video of images can be stored in RAM(s) 358 for subsequent processing and/or analyzation.

Figure 32:
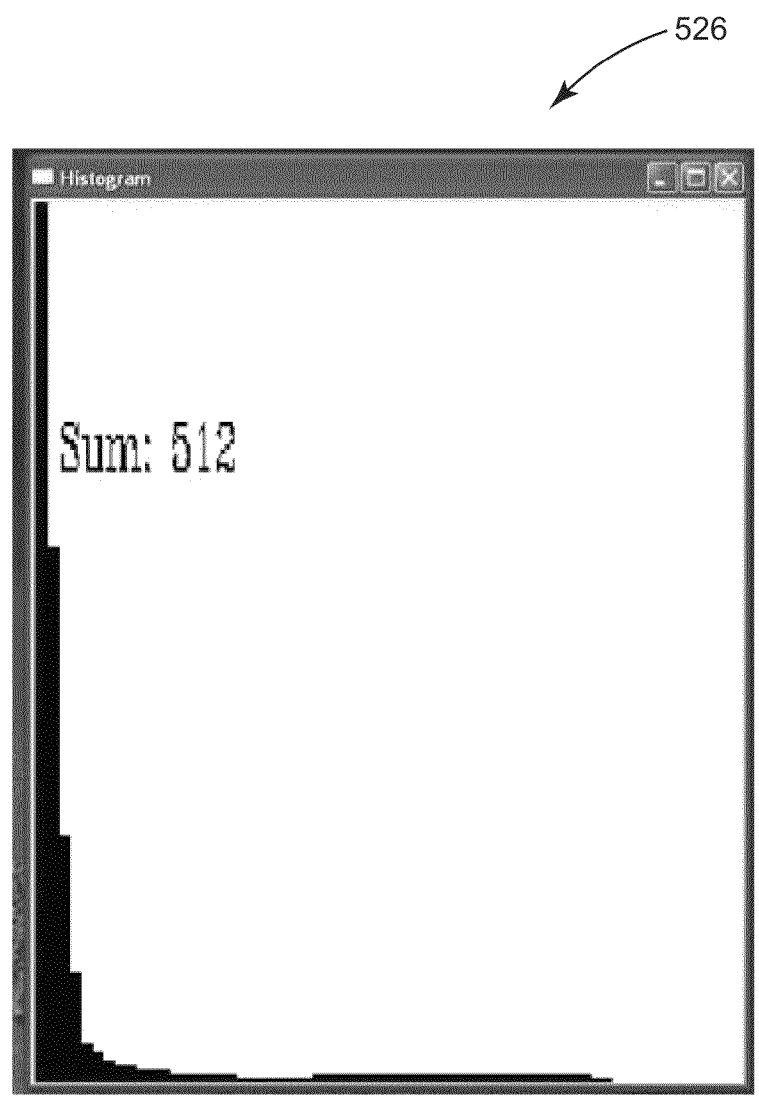
FIG. 32 illustrates an exemplary histogram used to detect eye blinks and/or eye movements in captured images or frames of a tear film.

In another embodiment, blinks and significant eye movements are detected using a histogram sum of the intensity of pixels in a resulting subtracted image or frame of a first and second image of the tear film. An example of such a histogram 526 is illustrated in FIG. 32. The resulting or subtracted image can be converted to grayscale (i.e., 255 levels) and a histogram generated with the gray levels of the pixels. In the histogram 526 of FIG. 32, the x-axis contains gray level ranges, and the number of pixels falling within each gray level is contained in the y-axis. The total of all the histogram 526 bins are summed. In the case of two identical frames that are subtracted, the histogram sum would be zero. However, even without an eye blink or significant eye movement, two sequentially captured frames of the patient's eye and the interference signals representing the specularly reflected light from the tear film are not identical. However, frame pairs with little movement will have a low histogram sum, while frame pairs with greater movement will yield a larger histogram sum. If the histogram sum is beyond a pre-determined threshold, an eye blink or large eye movement can be assumed and the image or frame removed. For example, the GUI utility 380 illustrated in FIG. 27 includes a histogram sum slide bar 486 that allows a user to set the threshold histogram sum. The threshold histogram sum for determining whether a blink or large eye movement should be assumed and thus the image removes from analysis of the patient's tear film can be determined experimentally, or adaptively over the course of a frame playback, assuming that blinks occur at regular intervals.

An advantage of a histogram sum of intensity method to detect eye blinks or significant eye movements is that the calculations are highly optimized as opposed to pixel-by-pixel analysis, thus assisting with real-time processing capability. Further, there is no need to understand the image structure of the patient's eye, such as the pupil or the iris details. Further, the method can detect both blinks and eye movements.

Another alternate technique to detect blinks in the tear film image or video of images for possible removal is to calculate a simple average gray level in an image or video of images. Because the subtracted, resulting images of the tear film subtract background signal, and have been processed using a threshold mask, and erode and dilate functions performed in this example, the resulting images will have a lower average gray level due to black areas present than if a blink is present. A blink contains skin color, which will increase the average gray level of an image containing a blink. A threshold average gray level setting can be provided. If the average gray level of a particular frame is below the threshold, the frame is ignored from further analysis or removed from the resulting video of frames of the tear film.

Another alternate technique to detect blinks in an image or video of images for removal is to calculate the average number of pixels in a given frame that have a gray level value below a threshold gray level value. If the percentage of pixels in a given frame is below a defined threshold percentage, this can be an indication that a blink has occurred in the frame, or that the frame is otherwise unworthy of consideration when analyzing the tear film. Alternatively, a spatial frequency calculation can be performed on a frame to determine the amount of fine detail in a given frame. If the detail present is below a threshold detail level, this may be an indication of a blink or other obscurity of the tear film, since skin from the eyelid coming down and being captured in a frame will have less detail than the subtracted image of the tear film. A histogram can be used to record any of the above-referenced calculations to use in analyzing whether a given frame should be removed from the final pre-processed resulting image or images of the tear film for analyzation.

ICC Profiling

Figure 33:
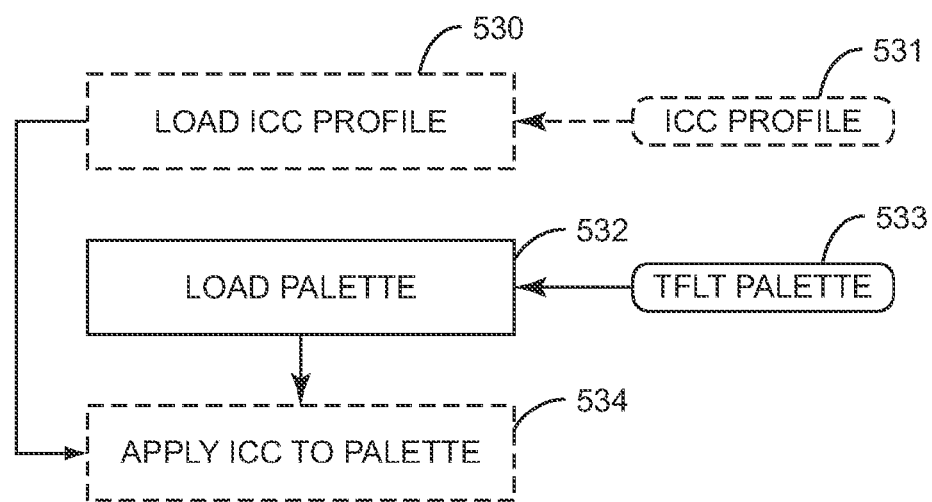
FIG. 33 illustrates an exemplary process for loading an International Colour Consortium (ICC) profile and tear film interference model into the OSI devices of FIGS. 6A, 6B, 12, 13, 14A, 14B, 19A, 19B, 21A, 21B, 23A, 23B, 24A, and 24B.

Pre-processing of the resulting tear film image(s) may also optionally include applying an International Colour Consortium (ICC) profile to the pre-processed interference images of the tear film (block 410, FIG. 26). FIG. 33 illustrates an optional process of loading an ICC profile into an ICC profile 531 in the control system 340 (block 530). In this regard, the GUI utility 380 illustrated in FIG. 27 also includes an apply ICC box 492 that can be selected by a clinician to load the ICC profile 531. The ICC profile 531 may be stored in memory in the control system 340, including in RAM(s) 358. In this manner, the GUI utility 380 in FIG. 27 also allows for a particular ICC profile 531 to be selected for application in the ICC profile file text box 494. The ICC profile 531 can be used to adjust color reproduction from scanned images from cameras or other devices into a standard red-green-blue (RGB) color space (among other selectable standard color spaces) defined by the ICC and based on a measurement system defined internationally by the Commission Internationale de l'Eclairage (CIE). Adjusting the pre-processed resulting tear film interference images corrects for variations in the camera color response and the light source spectrum and allows the images to be compatibly compared with a tear film layer interference model to measure the thickness of a TFLT, as will be described later in this application. The tear film layers represented in the tear film layer interference model can be LLTs, ALTs, or both, as will be described in more detail below.

In this regard, the ICC profile 531 may have been previously loaded to the OSI device 170 before imaging of a patient's tear film and also applied to a tear film layer interference model when loaded into the OSI device 170 independent of imaging operations and flow. As will be discussed in more detail below, a tear film layer interference model in the form of a TFLT palette 533 containing color values representing interference interactions from specularly reflected light from a tear film for various LLTs and ALTs can also be loaded into the OSI device 170 (block 532 in FIG. 36). The TFLT palette 533 contains a series of color values that are assigned LLTs and/or ALTs based on a theoretical tear film layer interference model to be compared against the color value representations of interference interactions in the resulting image(s) of the patient's tear film. When applying the optional ICC profile 531 to the TFLT palette 533 (block 534 in FIG. 33), the color values in both the tear film layer interference model and the color values representing interference interactions in the resulting image of the tear film are adjusted for a more accurate comparison between the two to measure LLT and/or ALT.

Brightness

Also as an optional pre-processing step, brightness and red-green-blue (RGB) subtract functions may be applied to the resulting interference signals of the patient's tear film before post-processing for analysis and measuring TFLT is performed (blocks 412 and 414 in FIG. 26). The brightness may be adjusted pixel-by-pixel by selecting the adjust brightness selection box 504 according to a corresponding brightness level value provided in a brightness value box 506, as illustrated in the GUI utility 380 of FIG. 27. When the brightness value box 506 is selected, the brightness of each palette value of the TFLT palette 533 is also adjusted accordingly.

RGB Subtraction (Normalization)

The RGB subtract function subtracts a DC offset from the interference signal in the resulting image(s) of the tear film representing the interference interactions in the interference signal. An RGB subtract setting may be provided from the pre-processing settings 364 to apply to the interference signal in the resulting image of the tear film to normalize against. As an example, the GUI utility 380 in FIG. 27 allows an RGB offset to be supplied by a clinician or other technician for use in the RGB subtract function. As illustrated therein, the subtract RGB function can be activated by selecting the RGB subtract selection box 496. If selected, the individual RGB offsets can be provided in offset value input boxes 498. After pre-processing is performed, if any, on the resulting image, the resulting image can be provided to a post-processing system to measure TLFT (block 416), as discussed later below in this application.

Displaying Images

The resulting images of the tear film may also be displayed on the display 174 of the OSI device 170 for human diagnosis of the patient's ocular tear film. The OSI device 170 is configured so that a clinician can display and see the raw captured image of the patient's eye 192 by the video camera 198, the resulting images of the tear film before pre-processing, or the resulting images of the tear film after pre-processing. Displaying images of the tear film on the display 174 may entail different settings and steps. For example, if the video camera 198 provides linear images of the patient's tear film, the linear images must be converted into a non-linear format to be properly displayed on the display 174. In this regard, a process that is performed by the visualization system 370 according to one embodiment is illustrated in FIG. 34.

Figure 10:
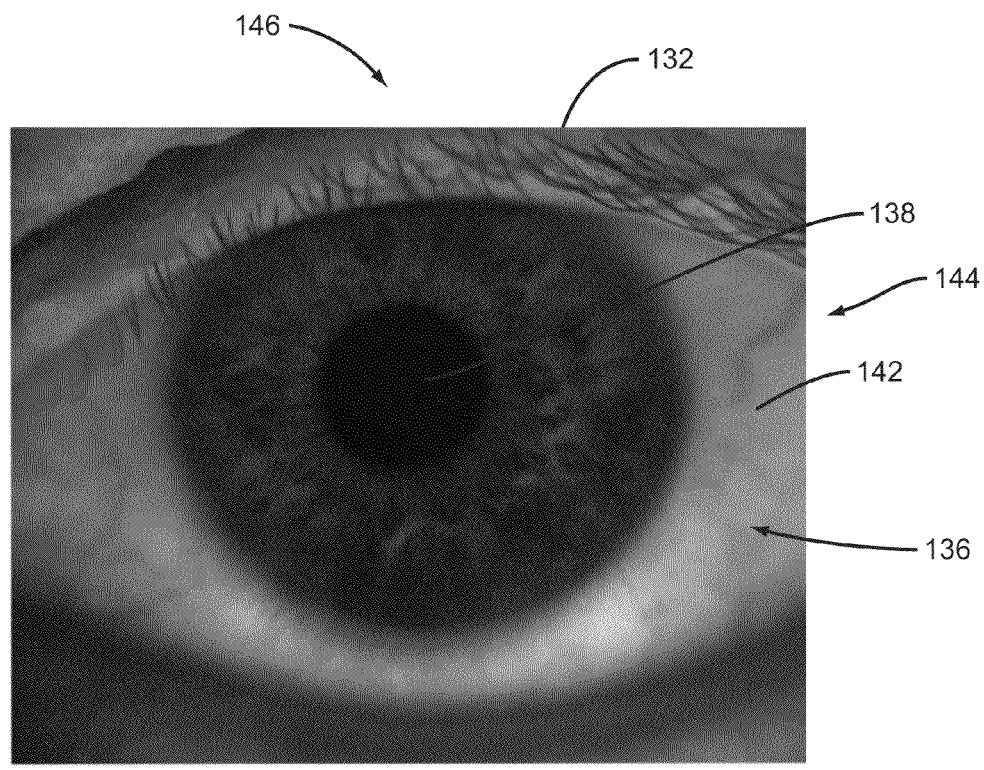
FIG. 10 illustrates an exemplary second image focused on the lipid layer of the tear film in FIG. 9 and capturing background signal when illuminated by the light source.
Figure 34:
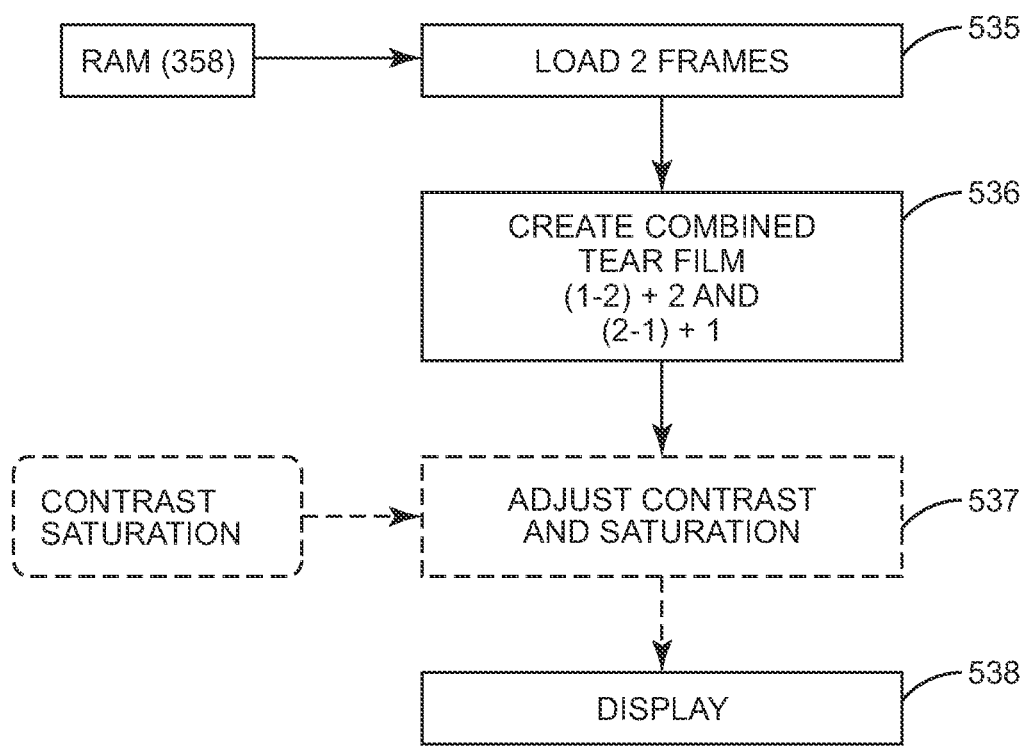
FIG. 34 illustrates a flowchart providing an exemplary visualization system process for displaying images of a patient's tear film on a display in the OSI devices of FIGS. 6A, 6B, 12, 13, 14A, 14B, 19A, 19B, 21A, 21B, 23A, 23B, 24A, and 24B.

As illustrated in FIG. 34, the video camera 198 has already taken the first and second images of a patient's ocular tear film as previously illustrated in FIGS. 9 and 10, and provided the images to the video acquisition system 356. The frames of the first and second images were then loaded into RAM(s) 358 by the video acquisition system 356. Thereafter, as illustrated in FIG. 34, the control system 340 commands the visualization system 370 to process the first and second images to prepare them for being displayed on the display 174, 538. In this regard, the visualization system 370 loads the first and second image frames of the ocular tear film from RAM(s) 358 (block 535). The previously described subtraction technique is used to remove background signal from the interference interactions of the specularly reflected light from the tear film, as previously described above and illustrated in FIG. 11. The first image(s) is subtracted from the second image(s) to remove background signal in the illuminated portions of the first image(s), and vice versa, and the subtracted images are then combined to produce an interference interaction of the specularly reflected light of the entire area or region of interest of the tear film, as previously discussed and illustrated in FIG. 11 (block 536 in FIG. 34).

Again, for example, this processing could be performed using the Matlab® function "cvAbsDiff." Before being displayed, the contrast and saturation levels for the resulting images can be adjusted according to contrast and saturation settings provided by a clinician via the user interface system 378 and/or programmed into the visualization system 370 (block 537). For example, the GUI utility 380 in FIG. 27 provides an apply contrast button 464 and a contrast setting slide 466 to allow the clinician to set the contrast setting in the display settings 374 for display of images on the display 174. The GUI utility 380 also provides an apply saturation button 468 and a saturation setting slide 469 to allow a clinician to set the saturation setting in the display settings 374 for the display of images on the display 174. The images can then be provided by the visualization system 370 to the display 174 for displaying (block 538 in FIG. 34). Also, any of the resulting images after pre-processing steps in the pre-processing system 360 can be provided to the display 174 for processing.

Figure 35A:
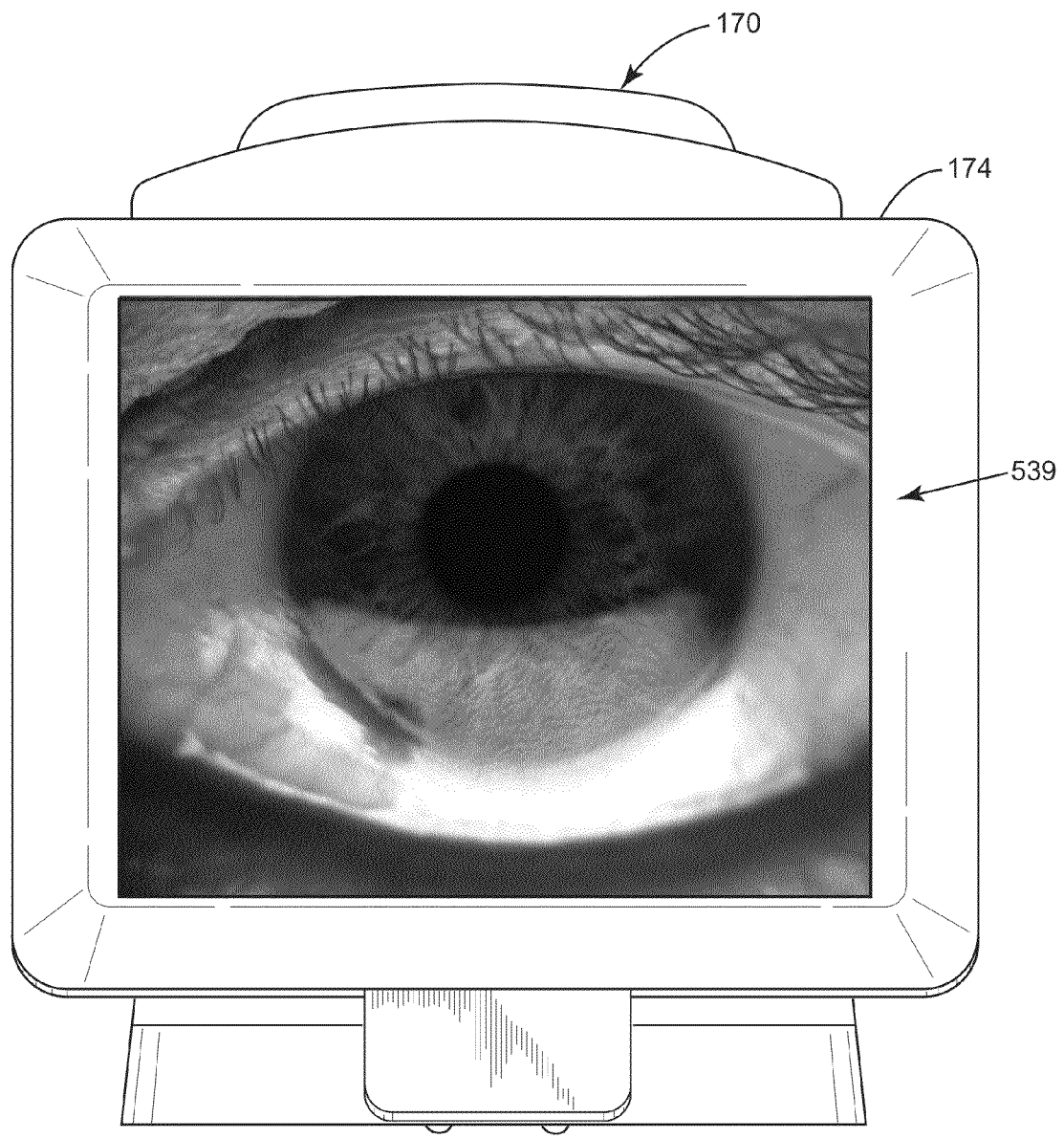
FIGS. 35A-35C illustrate exemplary images of a tear film with a pattern of interference interactions from specularly reflected light from the tear film displayed on a display.
Figure 35B:
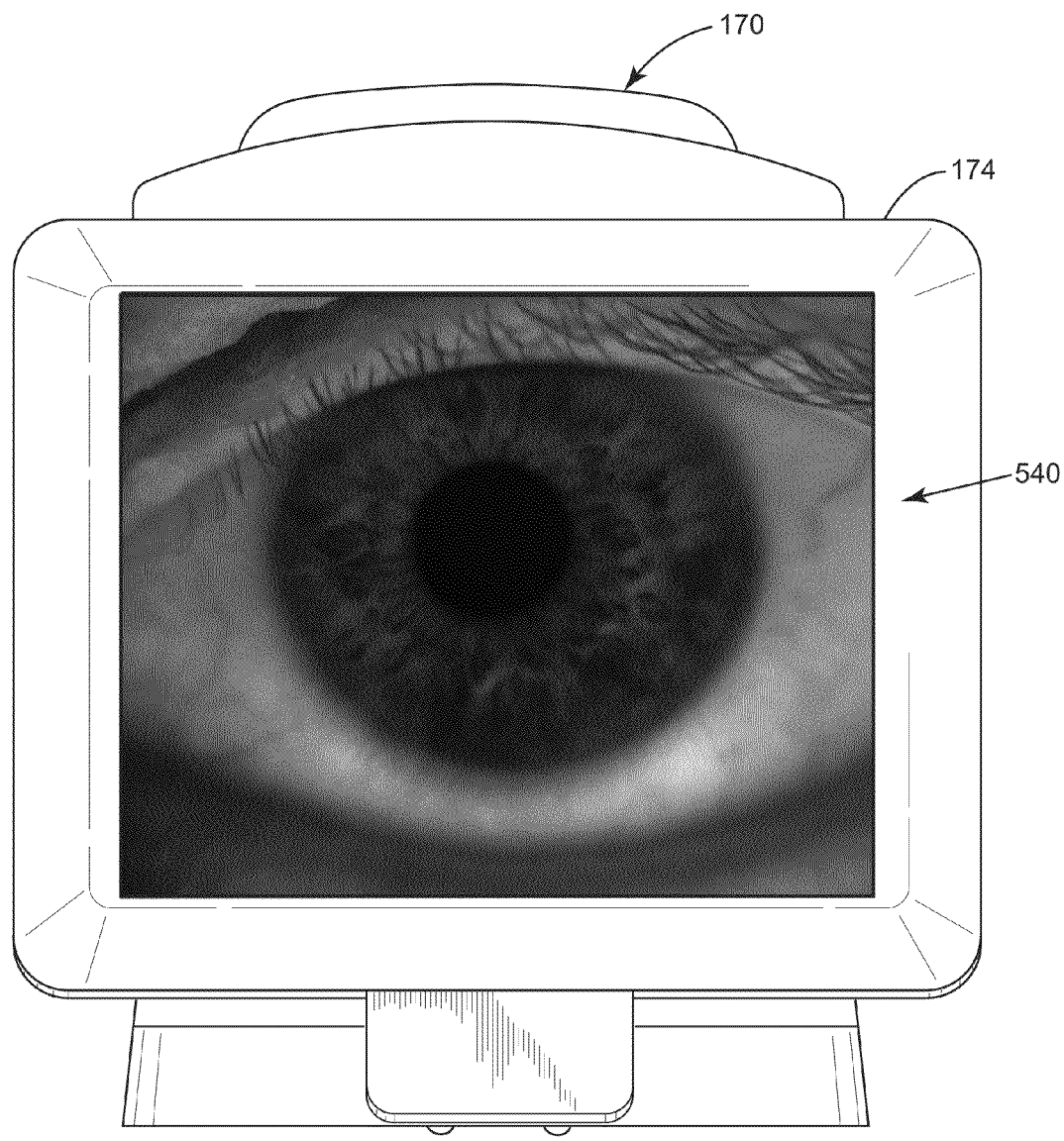
Figure 35C:
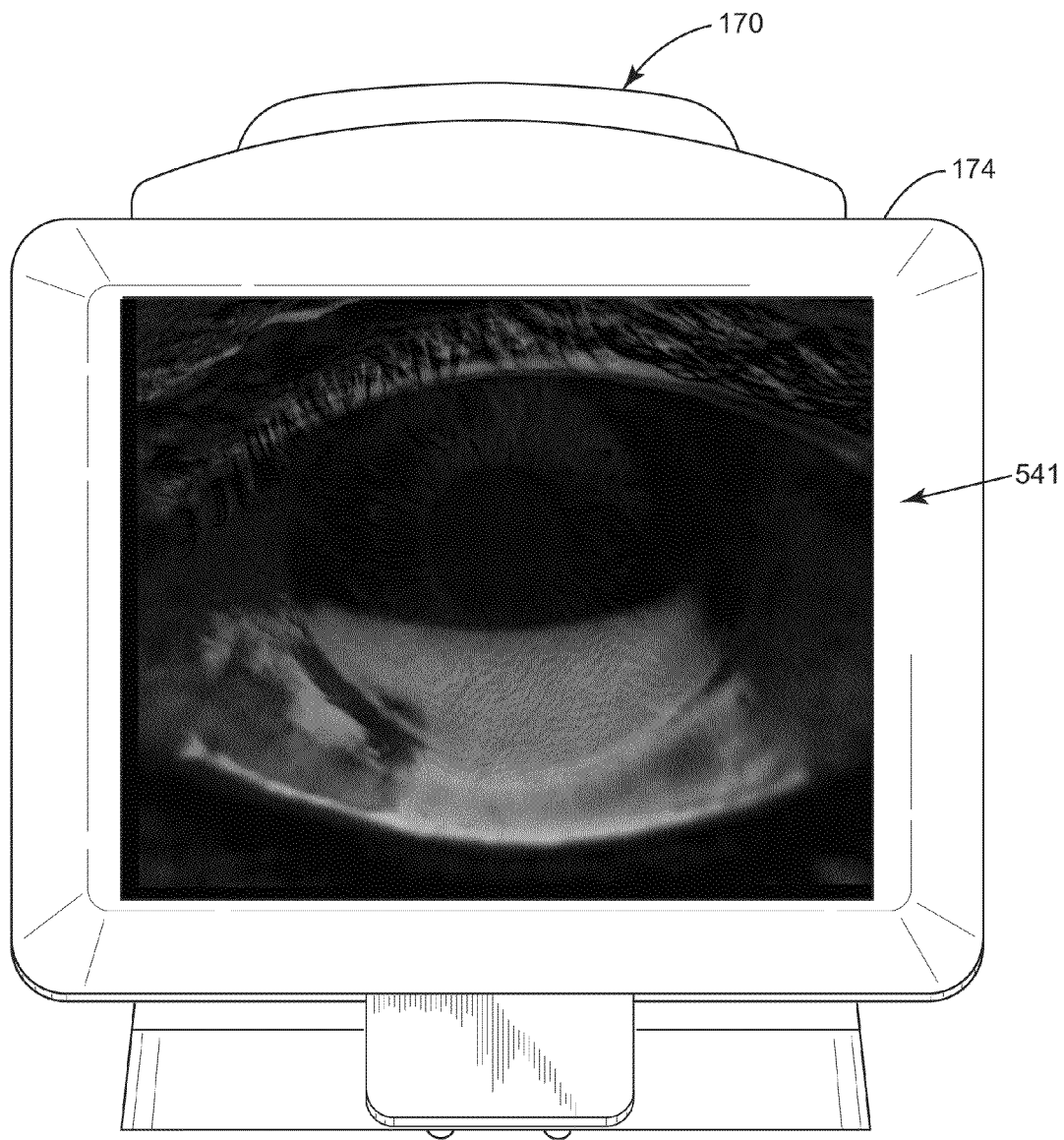

FIGS. 35A-35C illustrate examples of different tear film images that are displayed on the display 174 of the OSI device 170. FIG. 35A illustrates a first image 539 of the patient's tear film showing the pattern captured by the video camera 198. This image is the same image as illustrated in FIG. 9 and previously described above, but processed from a linear output from the video camera 198 to be properly displayed on the display 174. FIG. 35B illustrates a second image 540 of the patient's tear film illustrated in FIG. 10 and previously described above. FIG. 35C illustrates a resulting "overlaid" image 341 of the first and second images 539, 540 of the patient's tear film and to provide interference interactions of the specularly reflected light from the tear film over the entire area or region of interest. This is the same image as illustrated in FIG. 11 and previously described above.

In this example, the original number of frames of the patient's tear film captured can be reduced if frames in the subtracted image frames capture blinks or erratic movements, and these frames are eliminated in pre-processing, a further reduction in frames will occur during pre-processing from the number of images raw captured in images of the patient's tear film. Although these frames are eliminated from being further processed, they can be retained for visualization rendering a realistic and natural video playback. Further, by applying a thresholding function and erode and dilating functions, the number of non-black pixels which contain TLFT interference information is substantially reduced as well. Thus, the amount of pixel information that is processed by the post-processing system 362 is reduced, and may be on the order of 70% less information to process than the raw image capture information, thereby pre-filtering for the desired interference ROI and reducing or elimination potentially erroneous information as well as allowing for faster analysis due to the reduction in information.

At this point, the resulting images of the tear film have been pre-processed by the pre-processing system 360 according to whatever pre-processing settings 364 and pre-processing steps have been selected or implemented by the control system 340. The resulting images of the tear film are ready to be processed for analyzing and determining TFLT. In this example, this is performed by the post-processing system 362 in FIG. 25A and is based on the post-processing settings 366 also illustrated therein. An embodiment of the post-processing performed by the post-processing system 362 is illustrated in the flowchart of FIG. 36.

Tear Film Interference Models

Figure 36:
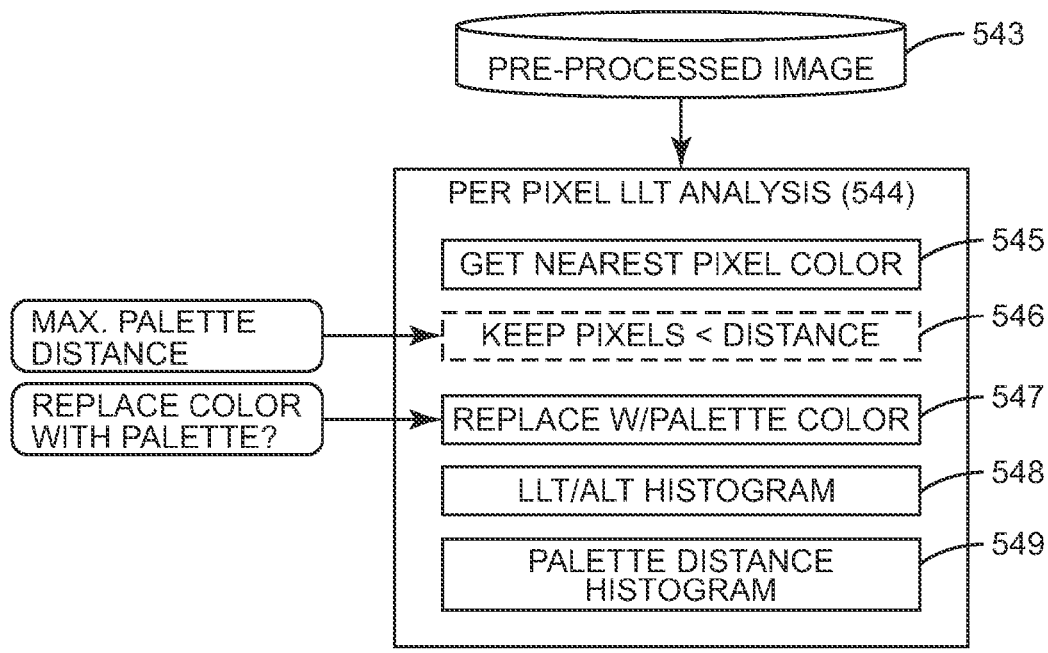
FIG. 36 illustrates an exemplary post-processing system that may be provided in the OSI devices of FIGS. 6A, 6B, 12, 13, 14A, 14B, 19A, 19B, 21A, 21B, 23A, 23B, 24A, and 24B.

As illustrated in FIG. 36, pre-processed images 543 of the resulting images of the tear film are retrieved from RAM(s) 358 where they were previously stored by the pre-processing system 360. Before discussing the particular embodiment of the post-processing system 362 in FIG. 36, in general, to measure TFLT, the RGB color values of the pixels in the resulting images of the tear film are compared against color values stored in a tear film interference model that has been previously loaded into the OSI device 170 (see FIG. 33. The tear film interference model may be stored as a TFLT palette 533 containing RGB values representing interference colors for given LLTs and/or ALTs. The TFLT palette contains interference color values that represent TFLTs based on a theoretical tear film interference model in this embodiment. Depending on the TFLT palette provided, the interference color values represented therein may represent LLTs, ALTs, or both. An estimation of TFLT for each ROI pixel is based on this comparison. This estimate of TFLT is then provided to the clinician via the display 174 and/or recorded in memory to assist in diagnosing DES.

Before discussing embodiments of how the TFLTs are estimated from the pre-processed resulting image colored interference interactions resulting from specularly reflected light from the tear film, tear film interference modeling is first discussed. Tear film interference modeling can be used to determine an interference color value for a given TFLT to measure TFLT, which can include both LLT and/or ALT.

Although the interference signals representing specularly reflected light from the tear film are influenced by all layers in the tear film, the analysis of interference interactions due to the specularly reflected light can be analyzed under a 2-wave tear film model (i.e., two reflections) to measure LLT. A 2-wave tear film model is based on a first light wave(s) specularly reflecting from the air-to-lipid layer transition of a tear film and a second light wave specularly reflecting from the lipid layer-to-aqueous layer transition of the tear film. In the 2-wave model, the aqueous layer is effective ignored and treated to be of infinite thickness. To measure LLT using a 2-wave model, a 2-wave tear film model was developed wherein the light source and lipid layers of varying thicknesses were modeled mathematically. To model the tear-film interference portion, commercially available software, such as that available by FilmStar and Zemax as examples, allows image simulation of thin films for modeling. Relevant effects that can be considered in the simulation include refraction, reflection, phase difference, polarization, angle of incidence, and refractive index wavelength dispersion. For example, a lipid layer could be modeled as having an index of refraction of 1.48, or as a BK7 fused silica having an index of refraction of 1.52, or $SiO_2$ fused silica substrate having a 1.46 index of refraction, as non-limiting examples. A back material, such as Magnesium Oxide (MgO) having an index of refraction of 1.74, or Magnesium Flouride ($MgF_2$) having an index of refraction of 1.38, may be used to provide a 2-wave model of air/(BK7 fused silica or $SiO_2$)/(BK7, MgO or $MgF_2$) (e.g., I/O/1.52/1.74 for air/BK7/MgO or 1.0/1.46/1.38 for air/$SiO_2$/$MgF_2$). To obtain the most accurate modeling results, the model can include the refractive index and wavelength dispersion values of biological lipid material and biological aqueous material, found from the literature, thus to provide a precise two-wave model of air/lipid/aqueous layers. Thus, a 2-wave tear film interference model allows measurement of LLT regardless of ALT.

Simulations can be mathematically performed by varying the LLT between 10 to 300 nm. As a second step, the RGB color values of the resulting interference signals from the modeled light source causing the modeled lipid layer to specularly reflected light and received by the modeled camera were determined for each of the modeled LLT. These RGB color values representing interference interactions in specularly reflected light from the modeled tear film were used to form a 2-wave model LLT palette, wherein each RGB color value is assigned a different LLT. The resulting subtracted image of the first and second images from the patient's tear film containing interference signals representing specularly reflected light are compared to the RGB color values in the 2-wave model LLT palette to measure LLT.

In another embodiment, a 3-wave tear film interference model may be employed to estimate LLT. A 3-wave tear film interference model does not assume that the aqueous layer is infinite in thickness. In an actual patient's tear film, the aqueous layer is not infinite. The 3-wave tear film interference model is based on both the first and second reflected light waves of the 2-wave model and additionally light wave(s) specularly reflecting from the aqueous-to-mucin layer and/or cornea transitions. Thus, a 3-wave tear film interference model recognizes the contribution of specularly reflected light from the aqueous-to-mucin layer and/or cornea transition that the 2-wave tear film interference model does not. To estimate LLT using a 3-wave tear film interference model, a 3-wave tear film model was previously constructed wherein the light source and a tear film of varying lipid and aqueous layer thicknesses were mathematically modeled. For example, a lipid layer could be mathematically modeled as a material having an index of refraction of 1.48 or as fused silica substrate ($SiO_2$), which has a 1.46 index of refraction, or as BK7 fused silica having an index of refraction of 1.52. Different thicknesses of the lipid layer can be simulated. A fixed thickness aqueous layer (e.g., $>=2$ μm) could be mathematically modeled as Magnesium Flouride ($MgF_2$) having an index of refraction of 1.38 or Magnesium Oxide (MgO) having an index of refraction of 1.74. A biological cornea could be mathematically modeled as fused silica with no dispersion, thereby resulting in a 3-wave model of air/$SiO_2$/$MgF_2$/$SiO_2$ (i.e., 1.0/1.46/1.38/1.46 with no dispersion) or air/BK7/MgO/BK7 (i.e., 1.0/1.52/1.74/1.52), as non-limiting examples. As before, accurate results are obtained if the model can include the refractive index and wavelength dispersion values of biological lipid material, biological aqueous material, and cornea tissue, found from the literature, thus to provide a precise two-wave model of air/lipid/aqueous/cornea layers. The resulting interference interactions of specularly reflected light from the various LLT values and with a fixed ALT value are recorded in the model and, when combined with modeling of the light source and the camera, will be used to compare against interference from specularly reflected light from an actual tear film to measure LLT and/or ALT.

In another embodiment of the OSI device 170 and the post-processing system 362 in particular, a 3-wave tear film interference model is employed to estimate both LLT and ALT. In this regard, instead of providing either a 2-wave theoretical tear film interference model that assumes an infinite aqueous layer thickness or a 3-wave model that assumes a fixed or minimum aqueous layer thickness (e.g., ≥2 μm), a 3-wave theoretical tear film interference model is developed that provides variances in both LLT and ALT in the mathematical model of the tear film. Again, the lipid layer in the tear film model could be modeled mathematically as a material having an index of refraction of 1.48, as fused silica substrate ($SiO_2$) having a 1.46 index of refraction, or as BK7 fused silica having an index of refraction of 1.52 as non-limiting examples. The aqueous layer could be modeled mathematically as Magnesium Flouride ($MgF_2$) having an index of refraction of 1.38 or Magnesium Oxide (MgO) having an index of refraction of 1.74. A biological cornea could be modeled as fused silica with no dispersion, thereby resulting in a 3-wave model of air/$SiO_2$/$MgF_2$/$SiO_2$ (no dispersion) or air/BK7/MgO/BK7, as non-limiting examples. Once again, the most accurate results are obtained if the model can include the refractive index and wavelength dispersion values of biological lipid material, biological aqueous material, and cornea tissue, found from the literature, thus to provide a precise two-wave model of air/lipid/aqueous/cornea layers. Thus, a two-dimensional (2D) TFLT palette 560 (FIG. 37A) is produced for analysis of interference interactions from specularly reflected light from the tear film. One dimension of the TFLT palette 560 represents a range of RGB color values each representing a given theoretical LLT calculated by mathematically modeling the light source and the camera and calculating the interference interactions from specularly reflected light from the tear film model for each variation in LLT 564 in the tear film interference model. A second dimension of the TFLT palette 560 represents ALT also calculated by mathematically modeling the light source and the camera and calculating the interference interactions from specularly reflected light from the tear film interference model for each variation in ALT 562 at each LLT value 564 in the tear film interference model.

Post-Processing/TFLT Measurement

Figure 37A:
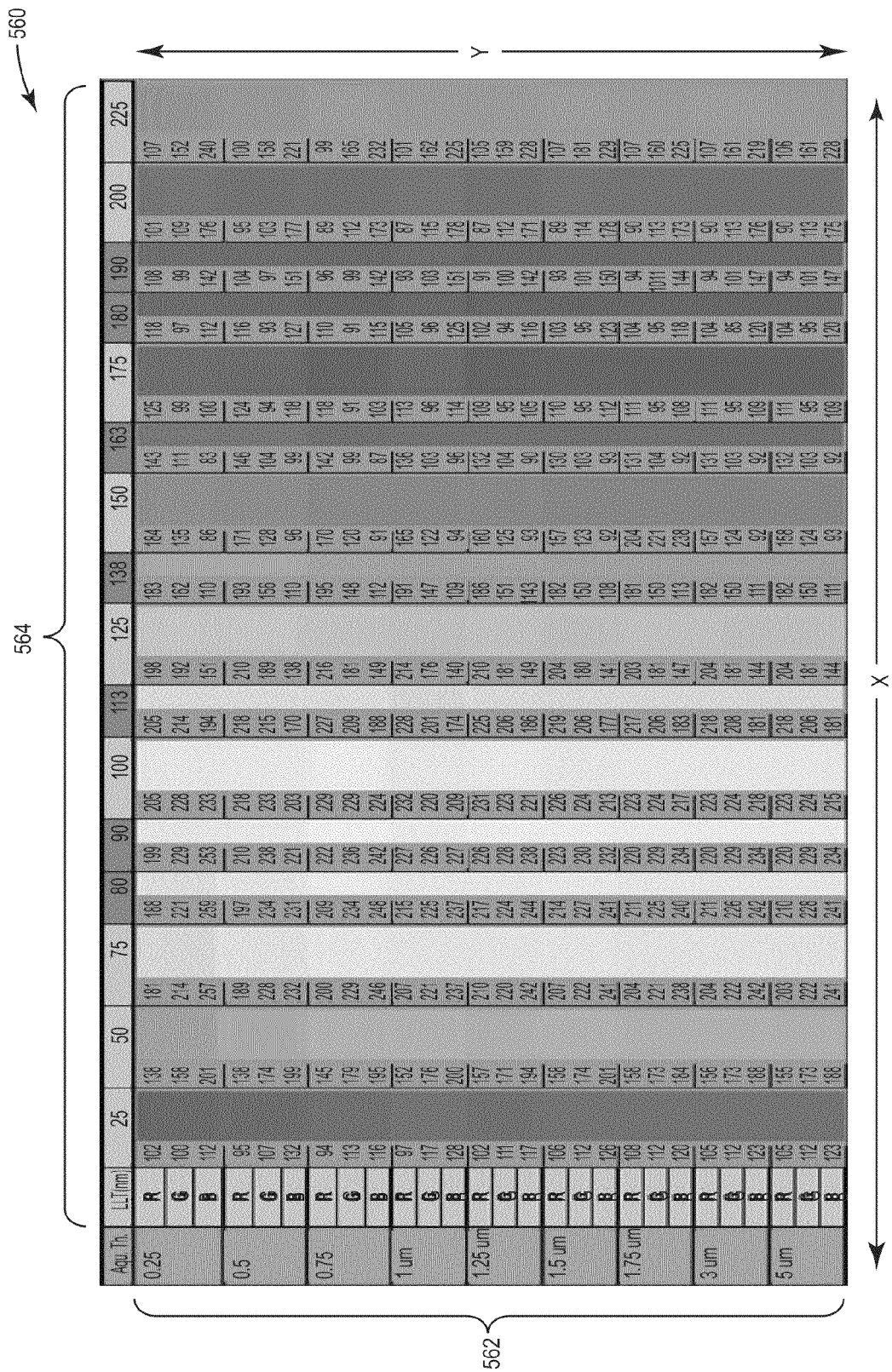
FIG. 37A illustrates an exemplary 3-wave tear film interference model based on a 3-wave theoretical tear film model to correlate different observed interference color with different lipid layer thicknesses (LLTs) and aqueous layer thicknesses (ALTs)
Figure 37B:
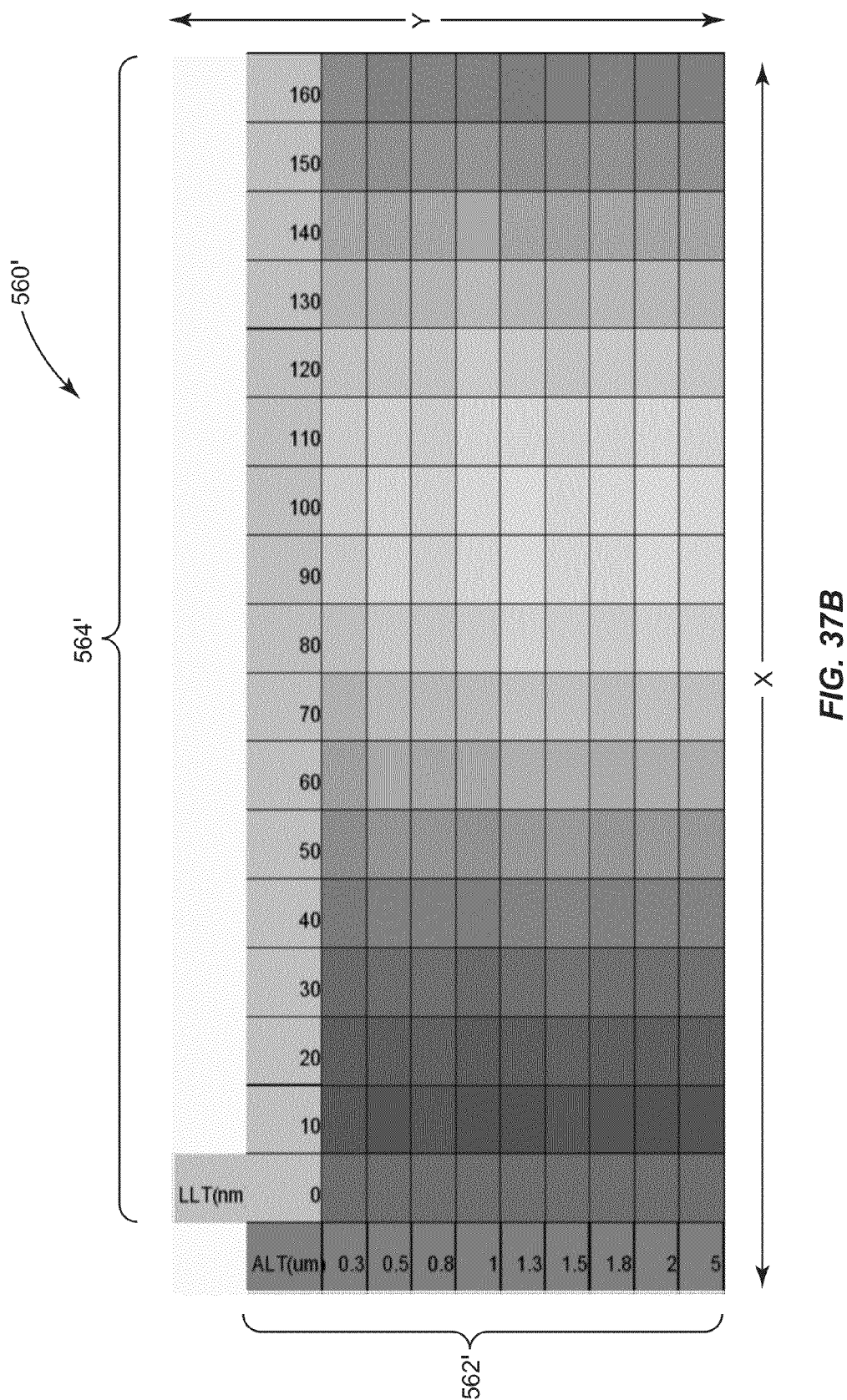
FIG. 37B illustrates another exemplary 3-wave tear film interference model based on a 3-wave theoretical tear film model to correlate different observed interference color with different lipid layer thicknesses (LLTs) and aqueous layer thicknesses (ALTs)

To measure TFLT, a spectral analysis of the resulting interference signal or image is performed during post-processing to calculate a TFLT. In one embodiment, the spectral analysis is performed by performing a look-up in a tear film interference model to compare one or more interference interactions present in the resulting interference signal representing specularly reflected light from the tear film to the RGB color values in the tear film interference model. In this regard, FIGS. 37A and 37B illustrate two examples of palette models for use in post-processing of the resulting image having interference interactions from specularly reflected light from the tear film using a 3-wave theoretical tear film interference model developed using a 3-wave theoretical tear film model. In general, an RGB numerical value color scheme is employed in this embodiment, wherein the RGB value of a given pixel from a resulting pre-processed tear film image of a patient is compared to RGB values in the 3-wave tear film interference model representing color values for various LLTs and ALTs in a 3-wave modeled theoretical tear film. The closest matching RGB color is used to determine the LLT and/or ALT for each pixel in the resulting signal or image. All pixels for a given resulting frame containing the resulting interference signal are analyzed in the same manner on a pixel-by-pixel basis. A histogram of the LLT and ALT occurrences is then developed for all pixels for all frames and the average LLT and ALT determined from the histogram (block 548 in FIG. 36).

FIG. 37A illustrates an exemplary TFLT palette 560 in the form of colors representing the included RGB color values representing interference of specularly reflected light from a 3-wave theoretical tear film model used to compared colors from the resulting image of the patient's tear film to estimate LLT and ALT. FIG. 37B illustrates an alternative example of a TFLT palette 560' in the form of colors representing the included RGB color values representing interference of specularly reflected light from a 3-wave theoretical tear film model used to compare colors from the resulting image of the patient's tear film to estimate LLT and ALT. As illustrated in FIG. 37A, the TFLT palette 560 contains a plurality of hue colors arranged in a series of rows 562 and columns 564. In this example, there are 144 color hue entries in the TFLT palette 560, with nine (9) different ALTs and sixteen (16) different LLTs in the illustrated TFLT palette 560, although another embodiment includes thirty (30) different LLTs. Providing any number of LLT and TFLT increments is theoretically possible. The columns 564 in the TFLT palette 560 contain a series of LLTs in ascending order of thickness from left to right. The rows 562 in the TFLT palette 560 contain a series of ALTs in ascending order of thickness from top to bottom. The sixteen (16) LLT increments provided in the columns 564 in the TFLT palette 560 are 25, 50, 75, 80, 90, 100, 113, 125, 138, 150, 163, 175, 180, 190, 200, and 225 nanometers (nm). The nine (9) ALT increments provided in the rows 562 in the TFLT palette 560 are 0.25, 0.5, 0.75, 1.0, 1.25, 1.5, 1.75, 3.0 and 6.0 µm. As another example, as illustrated in FIG. 37B, the LLTs in the columns 564' in the TFLT palette 560' are provided in increments of 10 nm between 0 nm and 160 nm. The nine (9) ALT increments provided in the rows 562' in the TFLT palette 560 are 0.3, 0.5, 0.8, 1.0, 1.3, 1.5, 1.8, 2.0 and 5.0 µm.

Figure 38:
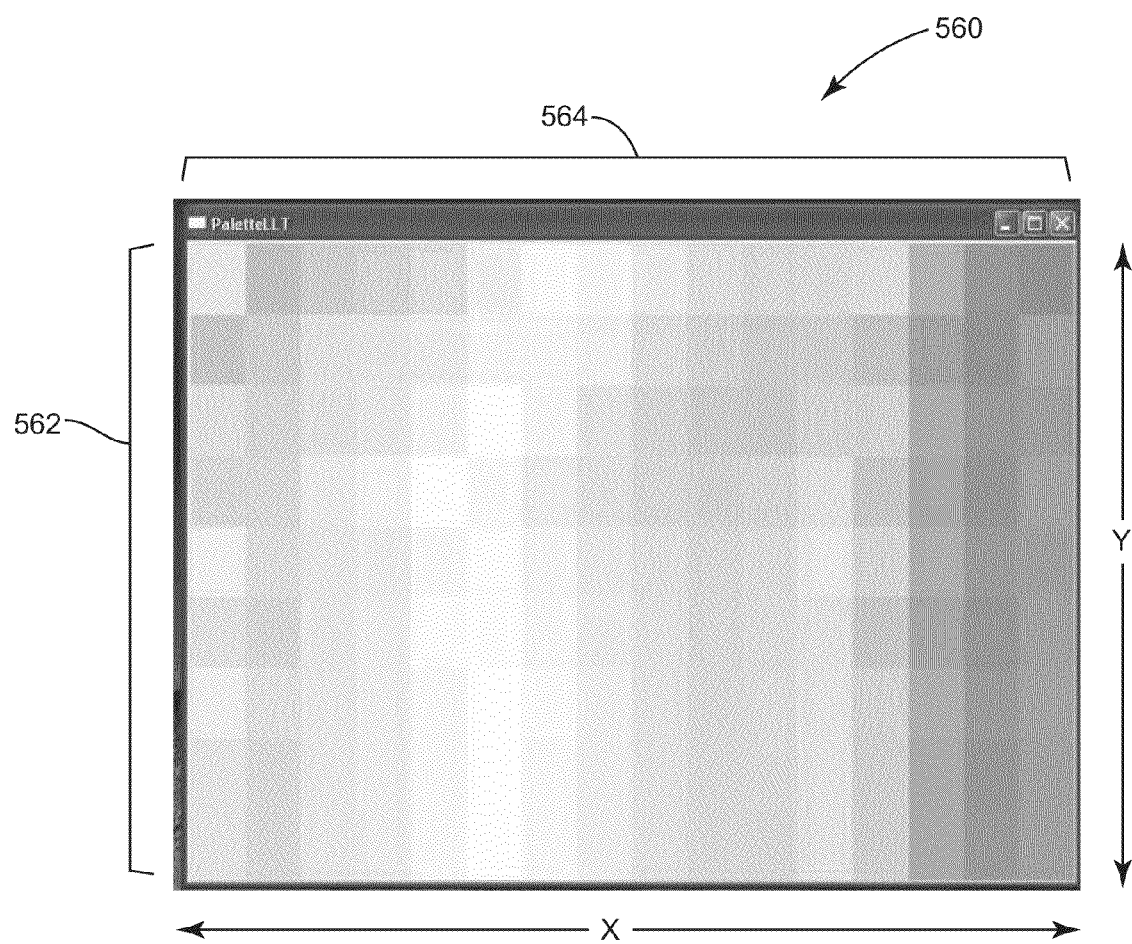
FIG. 38 is another representation of the 3-wave tear film interference model of FIG. 37 with normalization applied to each red-green-blue (RGB) color value individually.

As part of a per pixel LLT analysis 544 provided in the post-processing system 362 in FIG. 36, for each pixel in each of the pre-processed resulting images of the area or region of interest in the tear film, a closest match determination is made between the RGB color of the pixel to the nearest RGB color in the TFLT palette 560 (block 545 in FIG. 36). The ALTs and LLTs for that pixel are determined by the corresponding ALT thickness in the y-axis of the TFLT palette 560, and the corresponding LLT thickness in the x-axis of the TFLT palette 560. As illustrated in FIG. 37, the TFLT palette 560 colors are actually represented by RGB values. The pixels in each of the pre-processed resulting images of the tear film are also converted and stored as RGB values, although any other color representation can be used as desired, as long as the palette and the image pixel data use the same representational color space. FIG. 38 illustrates the TFLT palette 560 in color pattern form with normalization applied to each red-green-blue (RGB) color value individually. Normalizing a TFLT palette is optional. The TFLT palette 560 in FIG. 38 is displayed using brightness control (i.e., normalization, as previously described) and without the RGB values included, which may be more visually pleasing to a clinician if displayed on the display 174. The GUI utility 380 allows selection of different palettes by selecting a file in the palette file drop down 502, as illustrated in FIG. 27, each palette being specific to the choice of 2-wave vs. 3-wave mode, the chosen source's spectrum, and the chosen camera's RGB spectral responses. To determine the closest pixel color in the TFLT palette 560, a Euclidean distance color difference equation is employed to calculate the distance in color between the RGB value of a pixel from the pre-processed resulting image of the patient's tear film and RGB values in the TFLT palette 560 as follows below, although other embodiments of the present disclosure are not so limited:

$$\text{Diff.} = \sqrt{((R\text{pixel} - R\text{palette})^2 + (G\text{pixel} - G\text{palette})^2 + (B\text{pixel} - B\text{palette})^2)}$$

Thus, the color difference is calculated for all palette entries in the TFLT palette 560. The corresponding LLT and ALT values are determined from the color hue in the TFLT palette 560 having the least difference from each pixel in each frame of the pre-processed resulting images of the tear film. The results can be stored in RAM(s) 358 or any other convenient storage medium. To prevent pixels without a close match to a color in the TFLT palette 560 from being included in a processed result of LLT and ALT, a setting can be made to discard pixels from the results if the distance between the color of a given pixel is not within the entered acceptable distance of a color value in the TFLT palette 560 (block 546 in FIG. 36). The GUI utility 380 in FIG. 27 illustrates this setting such as would be the case if made available to a technician or clinician. A distance range input box 508 is provided to allow the maximum distance value to be provided for a pixel in a tear film image to be included in LLT and ALT results. Alternatively, all pixels can be included in the LLT and ALT results by selecting the ignore distance selection box 510 in the GUI utility 380 of FIG. 27.

Figure 39:
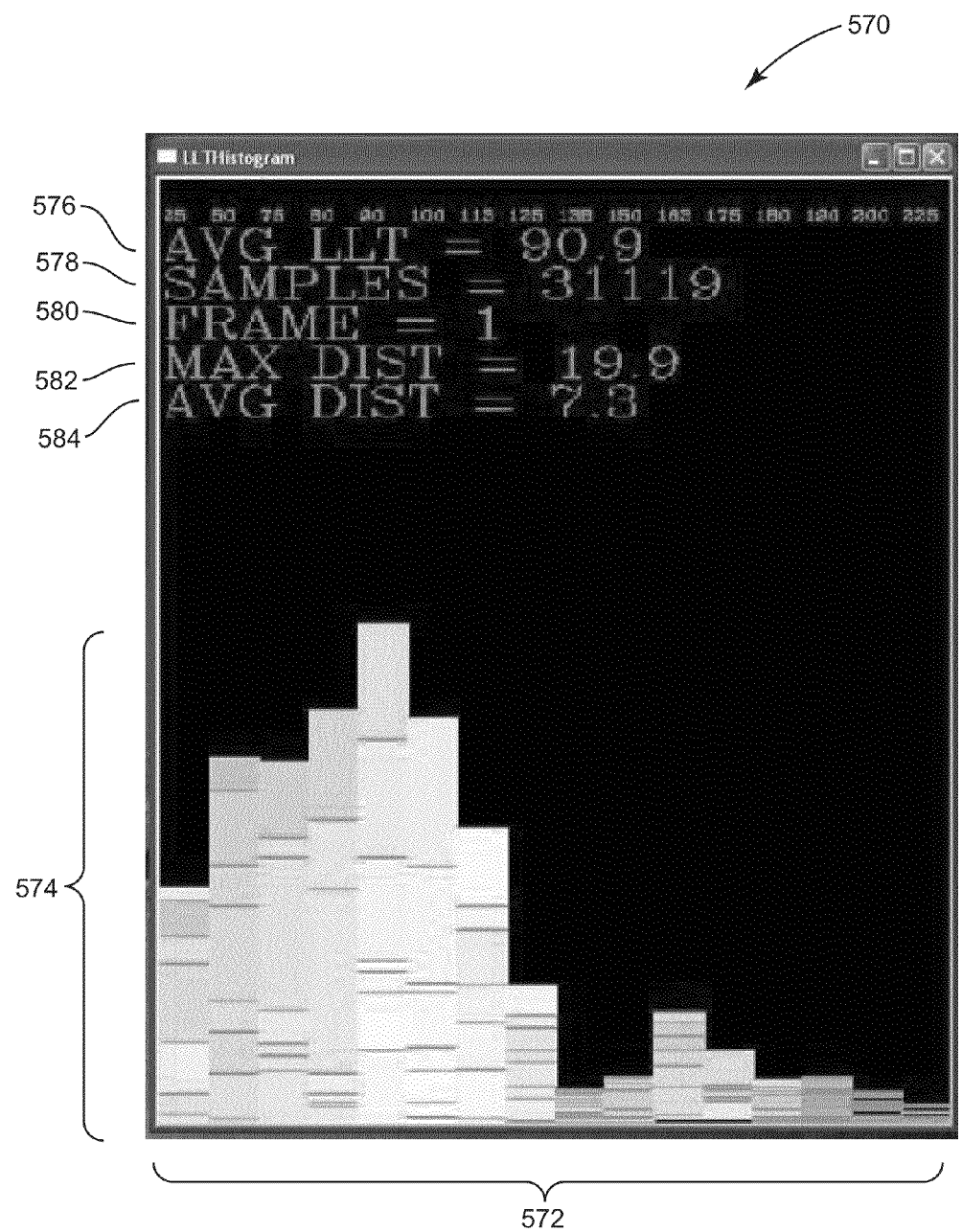
FIG. 39 is an exemplary histogram illustrating results of a comparison of interference interactions from the interference signal of specularly reflected light from a patient's tear film to the 3-wave tear film interference model of FIGS. 37 and 38 for measuring TFLT of a patient's tear film.

Each LLT and ALT determined for each pixel from a comparison in the TFLT palette 560 via the closest matching color that is within a given distance (if that post-processing setting 366 is set) or for all LLT and ALT determined values are then used to build a TFLT histogram. The TFLT histogram is used to determine a weighted average of the LLT and ALT values for each pixel in the resulting image(s) of the patient's tear film to provide an overall estimate of the patient's LLT and ALT. FIG. 39 illustrates an example of such a TFLT histogram 460. This TFLT histogram 570 may be displayed as a result of the shown LLT histogram selection box 500 being selected in the GUI utility 380 of FIG. 27. As illustrated therein, for each pixel within an acceptable distance, the TFLT histogram 570 is built in a stacked fashion with determined ALT values 574 stacked for each determined LLT value 572 (block 549 in FIG. 36). Thus, the TFLT histogram 570 represents LLT and ALT values for each pixel. A horizontal line separates each stacked ALT value 574 within each LLT bar.

Figure 40:
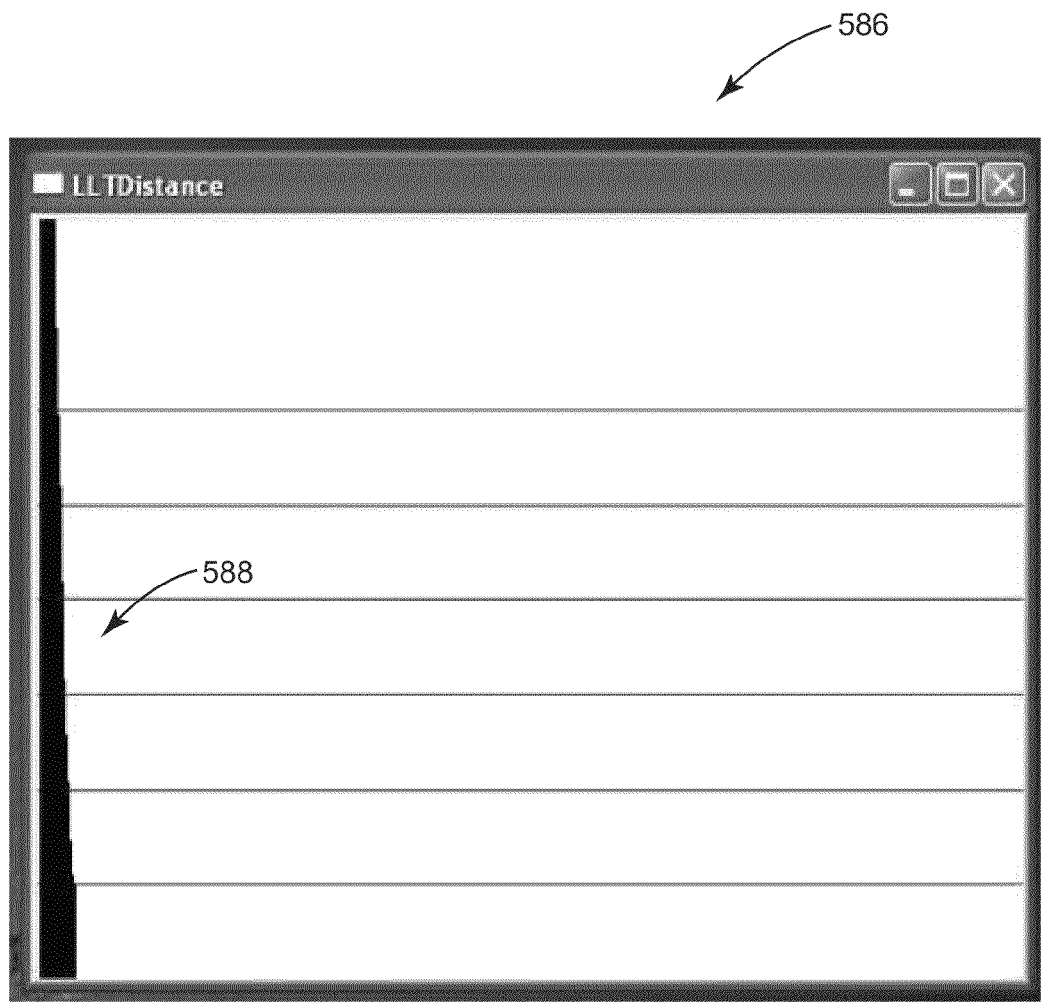
FIG. 40 is an exemplary histogram plot of distances in pixels between RGB color value representation of interference interactions from the interference signal of specularly reflected light from a patient's tear film and the nearest distance RGB color value in the 3-wave tear film interference model of FIGS. 37 and 38.

One convenient way to determine the final LLT and ALT estimates is with a simple weighted average of the LLT and ALT values 572, 574 in the TFLT histogram 570. In the example of the TFLT histogram 570 in FIG. 39, the average LLT value 576 was determined to be 90.9 nm. The number of samples 578 (i.e., pixels) included in the TFLT histogram 570 was 31,119. The frame number 580 indicates which frame of the resulting video image is being processed, since the TFLT histogram 570 represents a single frame result, or the first of a frame pair in the case of background subtraction. The maximum distance 582 between the color of any given pixel among the 31,119 pixels and a color in the TFLT palette 560 was 19.9, 20 may have been the set limit (Maximum Acceptable Palette Distance) for inclusion of any matches. The average distance 584 between the color of each of the 31,119 pixels and its matching color in the TFLT palette 560 was 7.8. The maximum distance 582 and average distance 584 values provide an indication of how well the color values of the pixels in the interference signal of the specularly reflected light from the patient's tear film match the color values in the TFLT palette 560. The smaller the distance, the closer the matches. The TFLT histogram 570 can be displayed on the display 174 to allow a clinician to review this information graphically as well as numerically. If either the maximum distance 582 or average distance 584 values are too high, this may be an indication that the measured LLT and ALT values may be inaccurate, or that the image normalization is not of the correct value. Further imaging of the patient's eye and tear film, or system recalibration can be performed to attempt to improve the results. Also, a histogram 586 of the LLT distances 588 between the pixels and the colors in the TFLT palette 560 can be displayed as illustrated in FIG. 40 to show the distribution of the distance differences to further assist a clinician in judgment of the results.

Figure 41:
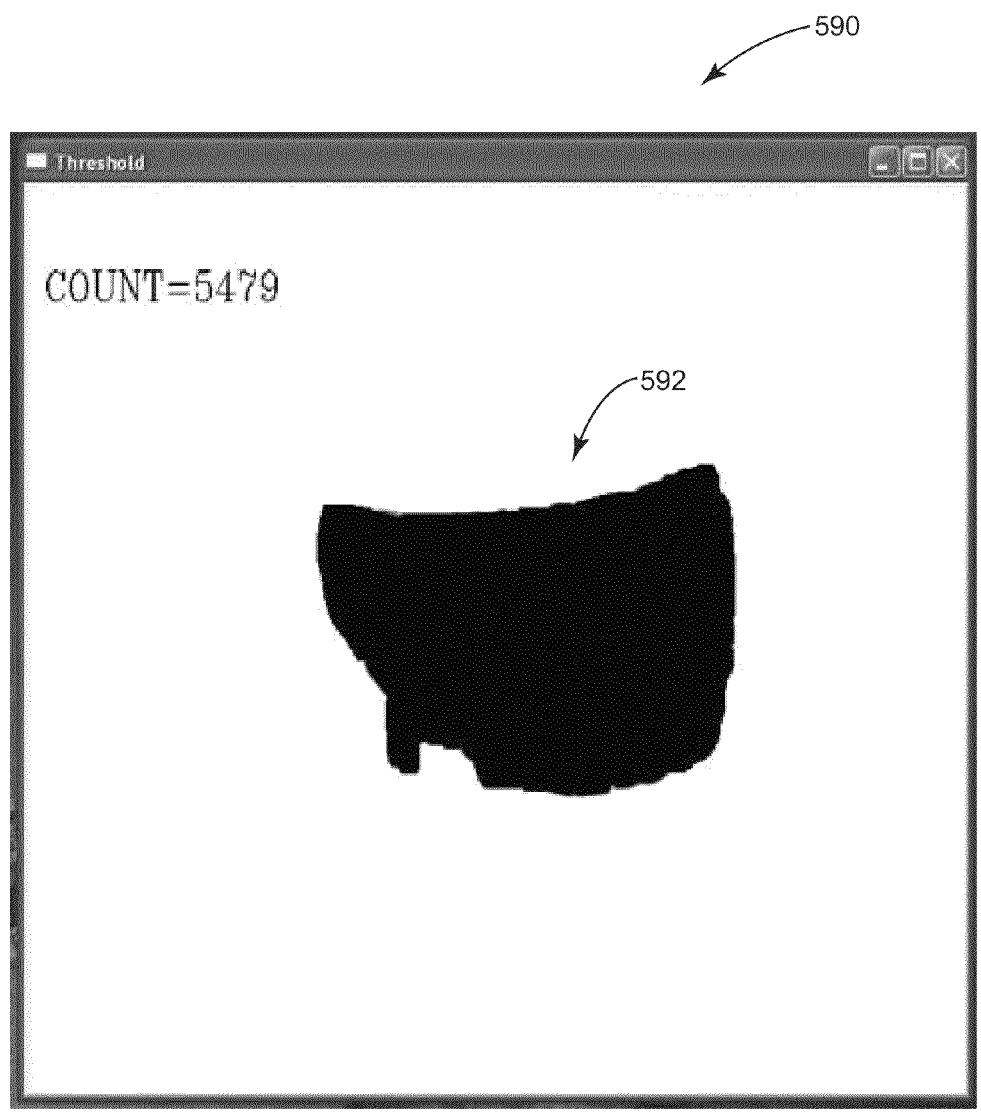
FIG. 41 is an exemplary threshold mask used during pre-processing of the tear film images.

Other results can be displayed on the display 174 of the OSI device 170 that may be used by a physician or technician to judge the LLT and/or ALT measurement results. For example, FIG. 41 illustrates a threshold window 590 illustrating a (inverse) threshold mask 592 that was used during pre-processing of the tear film images. In this example, the threshold window 590 was generated as a result of the show threshold window selection box 482 being selected in the GUI utility 380 of FIG. 27. This may be used by a clinician to humanly evaluate whether the threshold mask looks abnormal. If so, this may have caused the LLT and ALT estimates to be inaccurate and may cause the clinician to discard the results and image the patient's tear film again. The maximum distance between the color of any given pixel among the 31,119 pixels and a color in the TFLT palette 560 was 19.9 in this example.

Figure 42:
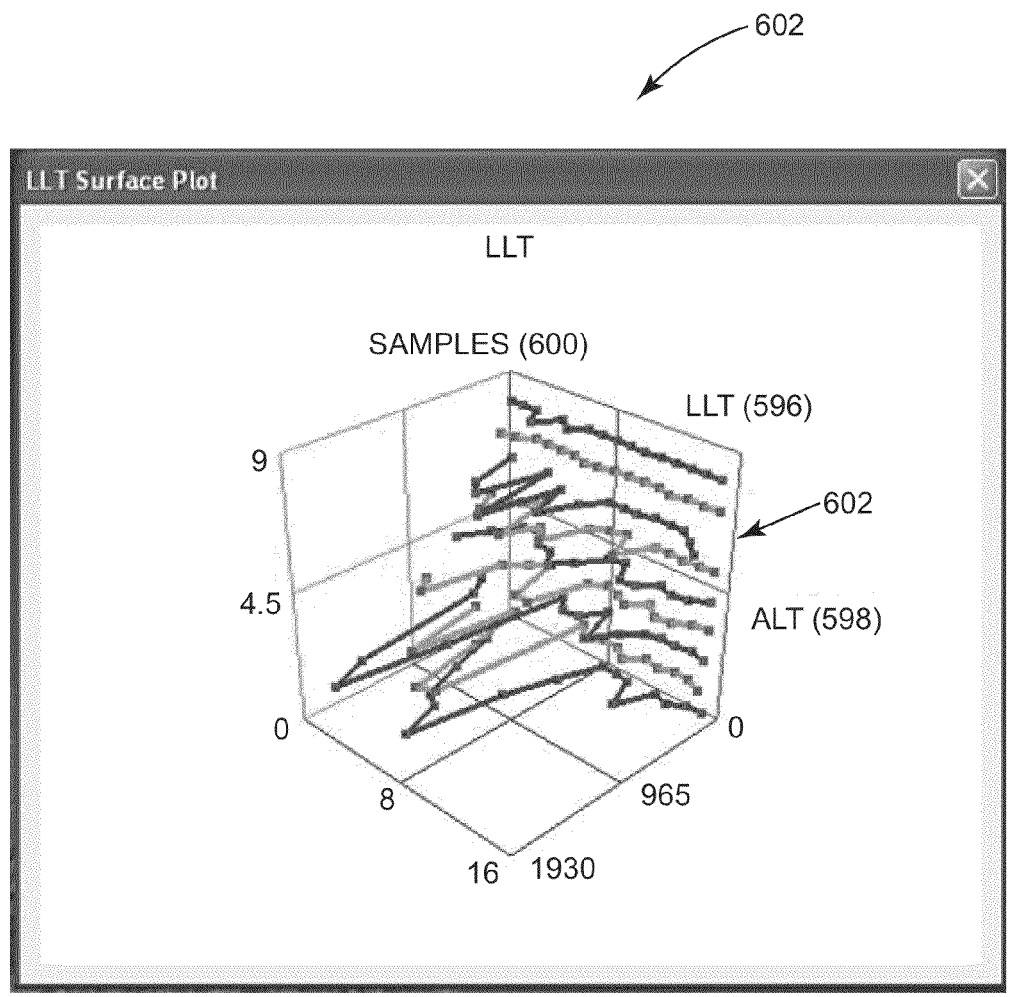
FIG. 42 is an exemplary three-dimensional (3D) surface plot of the measured LLT and ALT thicknesses of a patient's tear film.

FIG. 42 illustrates another histogram that may be displayed on the display 174 and may be useful to a clinician. As illustrated therein, a three-dimensional (3D) histogram plot 460 is illustrated. The clinician can choose whether the OSI device 170 displays this histogram plot 460 by selecting the 3D plot selection box 516 in the GUI utility 380 of FIG. 27, as an example, or the OSI device 170 may automatically display the histogram plot 460. The 3D histogram plot 460 is simply another way to graphically display the fit of the processed pixels from the pre-processed images of the tear film to the TFLT palette 560. The plane defined by the LLT 596 and ALT 598 axes represents the TFLT palette 560. The axis labeled "Samples" 600 is the number of pixels that match a particular color in the TFLT palette 560.

Figure 43:
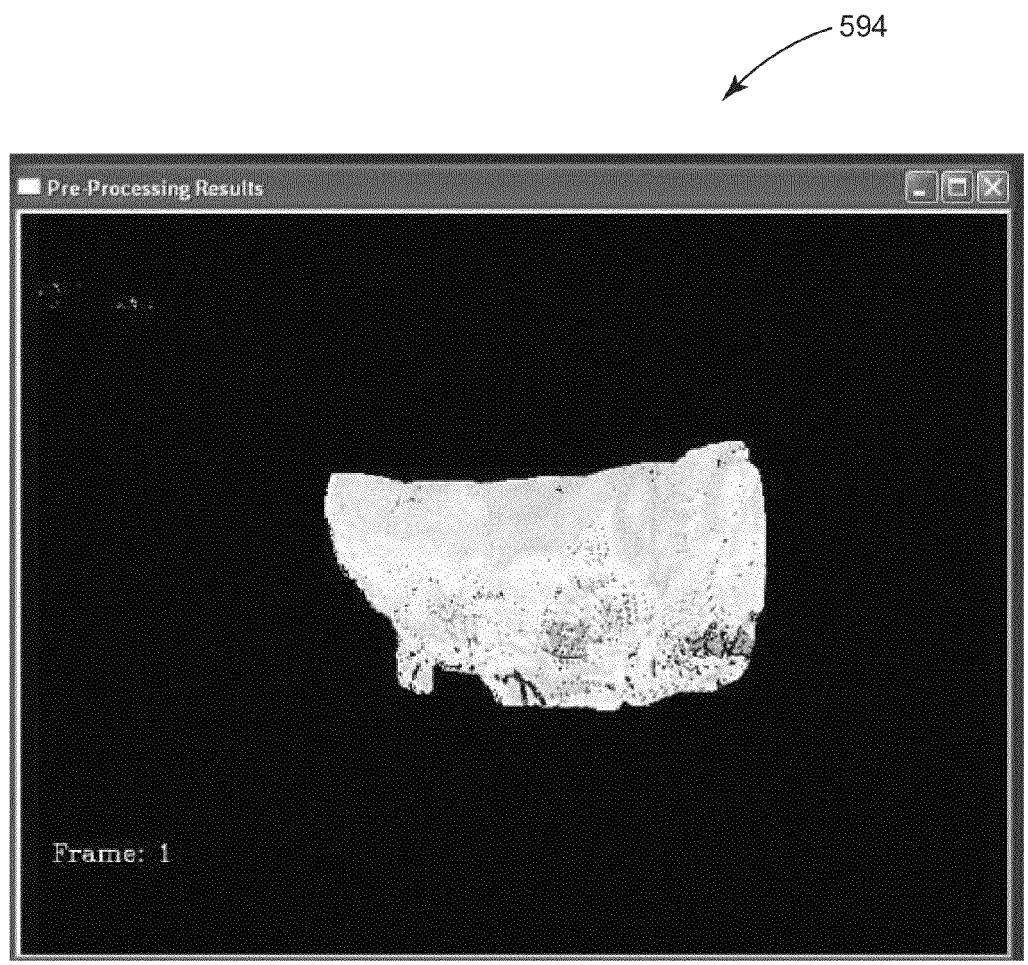
FIG. 43 is an exemplary image representing interference interactions of specularly reflected light from a patient's tear film results window based on replacing a pixel in the tear film image with the closest matching RGB color value in the normalized 3-wave tear film interference model of FIG. 38.

FIG. 43 illustrates a result image 594 of the specularly reflected light from a patient's tear film. However, the actual pixel value for a given area on the tear film is replaced with the determined closest matching color value representation in the TFLT palette 560 to a given pixel for that pixel location in the resulting image of the patient's tear film (block 547 in FIG. 36). This setting can be selected, for example, in the GUI utility 380 of FIG. 27. Therein, a "replace resulting image . . . ." selection box 512 is provided to allow a clinician to choose this option. Visually displaying interference interactions representing the closest matching color value to the interference interactions in the interference signal of the specularly reflected light from a patient's tear film in this manner may be helpful to determine how closely the tear film interference model matches the actual color value representing the resulting image (or pixels in the image).

Ambiguities can arise when calculating the nearest distance between an RGB value of a pixel from a tear film image and RGB values in a TFLT palette, such as TFLT palettes 560 and 560' in FIGS. 37A and 37B as examples. This is because when the theoretical LLT of the TFLT palette is plotted in RGB space for a given ALT in three-dimensional (3D) space, the TFLT palette 604 is a locus that resembles a pretzel like curve, as illustrated with a 2-D representation in the exemplary TFLT palette locus 606 in FIG. 44. Ambiguities can arise when a tear film image RGB pixel value has close matches to the TFLT palette locus 606 at significantly different LLT levels. For example, as illustrated in the TFLT palette locus 606 in FIG. 44, there are three (3) areas of close intersection 608, 610, 612 between RGB values in the TFLT palette locus 606 even though these areas of close intersection 608, 610, 612 represent substantially different LLTs on the TFLT palette locus 606. This is due to the cyclical phenomenon caused by increasing orders of optical wave interference, and in particular, first order versus second order interference for the LLT range in the tear films. Thus, if an RGB value of a tear film image pixel is sufficiently close to two different LLT points in the TFLT palette locus 606, the closest RGB match may be difficult to match. The closest RGB match may be to an incorrect LLT in the TFLT palette locus 606 due to error in the camera and translation of received light to RGB values. Thus, it may be desired to provide further processing when determining the closest RGB value in the TFLT palette locus 606 to RGB values of tear film image pixel values when measuring TFLT.

Figure 44:
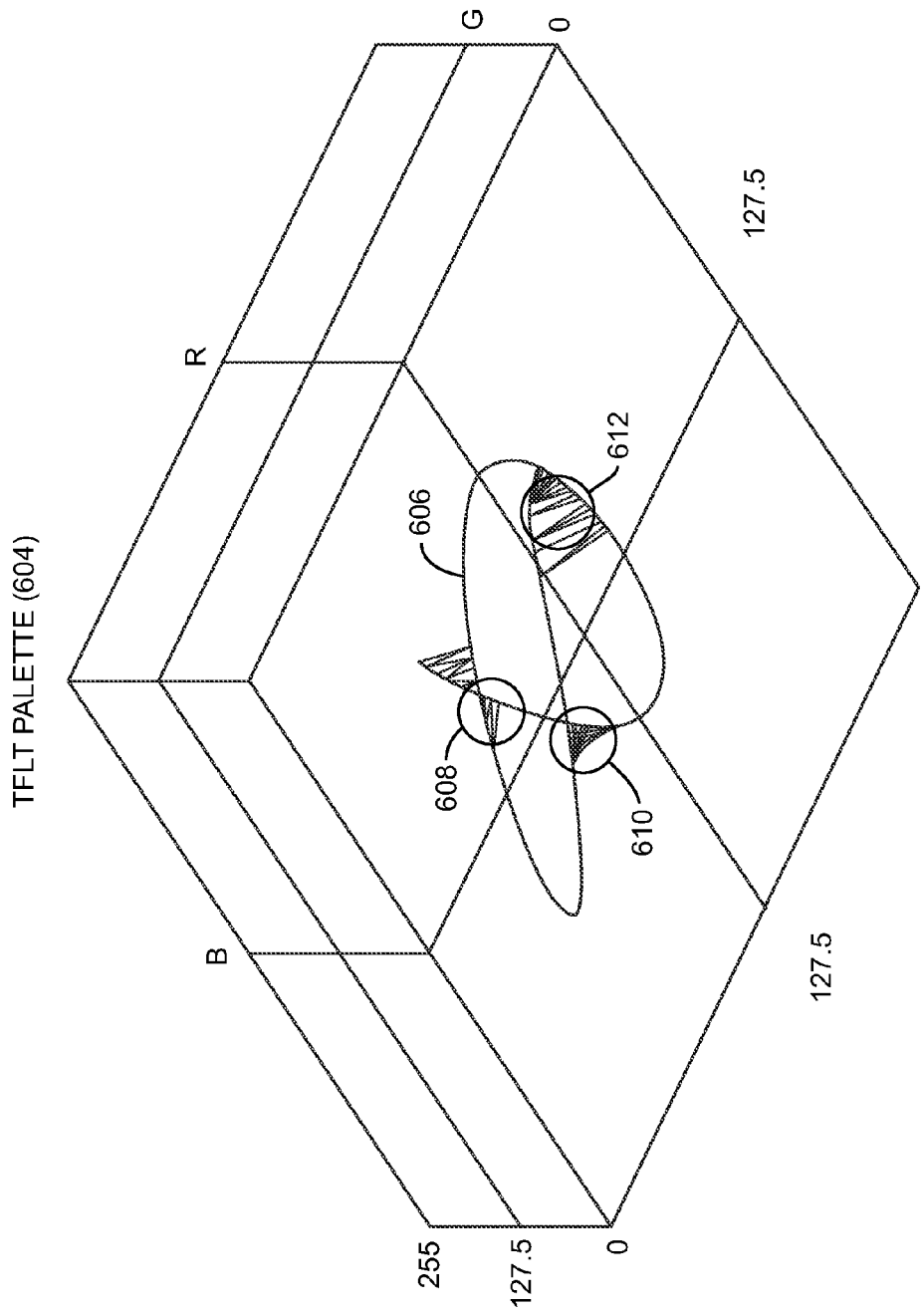
FIG. 44 is an exemplary TFLT palette curve for a TFLT palette of LLTs plotted in RGB space for a given ALT in three-dimensional (3D) space.

In this regard, there are several possibilities that can be employed to avoid ambiguous RGB matches in a TFLT palette. For example, the maximum LLT values in a TFLT palette may be limited. For example, the TFLT palette locus 606 in FIG. 44 includes LLTs between 10 nm and 300 nm. If the TFLT palette locus 606 was limited in LLT range, such as 240 nm as illustrated in the TFLT palette locus 614 in FIG. 45, two areas of close intersection 610 and 612 in the TFLT palette 604 in FIG. 44 are avoided in the TFLT palette 604 of FIG. 45. This restriction of the LLT ranges may be acceptable based on clinical experience since most patients do not exhibit tear film colors above the 240 nm range and dry eye symptoms are more problematic at thinner LLTs. In this scenario, the limited TFLT palette 604 of FIG. 45 would be used as the TFLT palette in the post-processing system 362 in FIG. 36, as an example.

Figure 45:
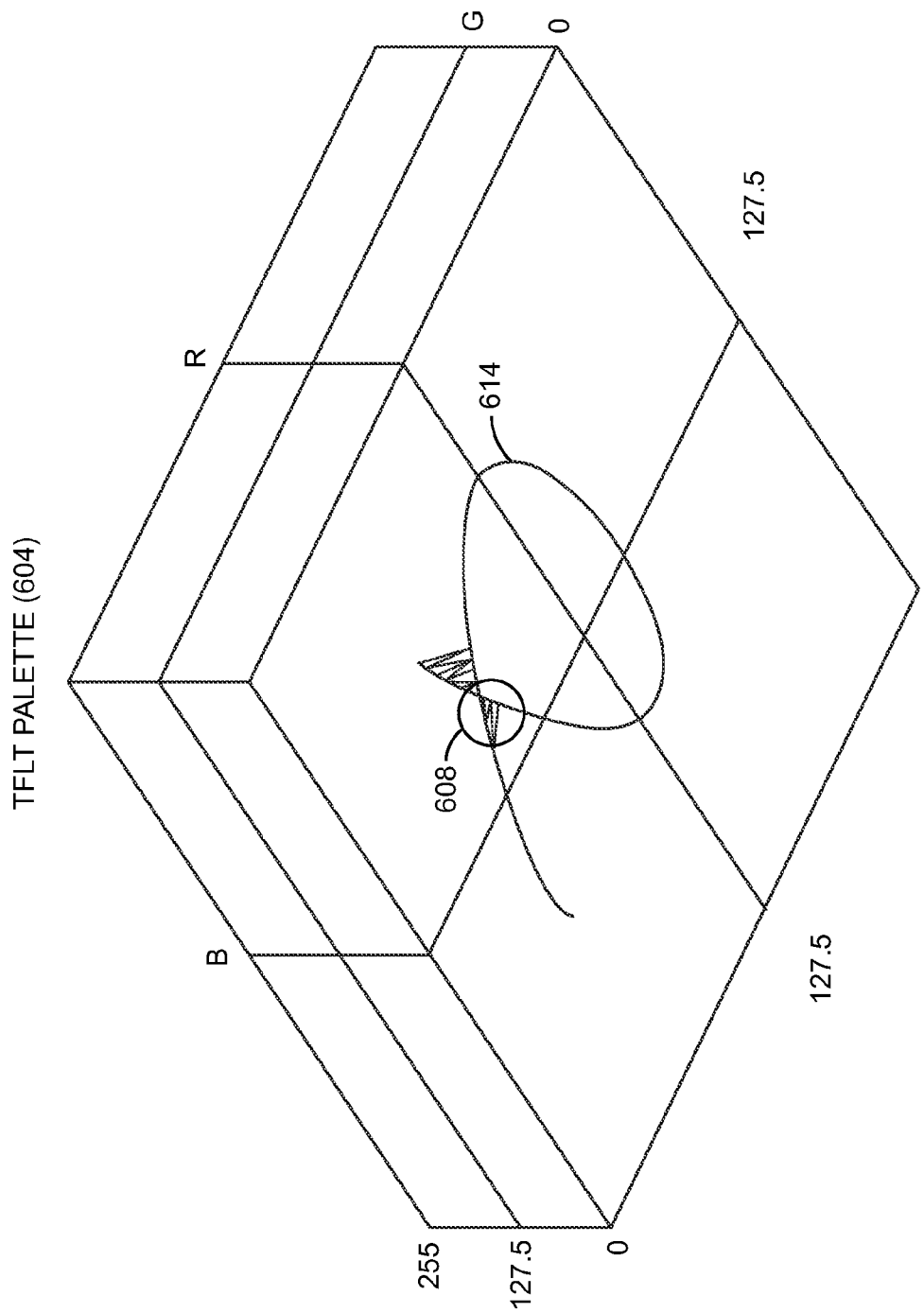
FIG. 45 is an exemplary TFLT palette curve for the TFLT palette of FIG. 44 with LLTs limited to a maximum LLT of 240 nm plotted in RGB space for a given ALT in three-dimensional (3D) space.

Even by eliminating two areas of close intersection 610, 612 in the TFLT palette 604, as illustrated in FIG. 45, the area of close intersection 608 still remains in the TFLT palette locus 614. In this embodiment, the area of close intersection 608 is for LLT values near 20 nm versus 180 nm. In these regions, the maximum distance allowed for a valid RGB match is restricted to a value of about half the distance of the TFLT palette's 604 nearing ambiguity distance. In this regard, RGB values for tear film pixels with match distances exceeding the specified values can be further excluded from the TFLT calculation to avoid tear film pixels having ambiguous corresponding LLT values for a given RGB value to avoid error in TFLT measurement as a result.

Figure 46:
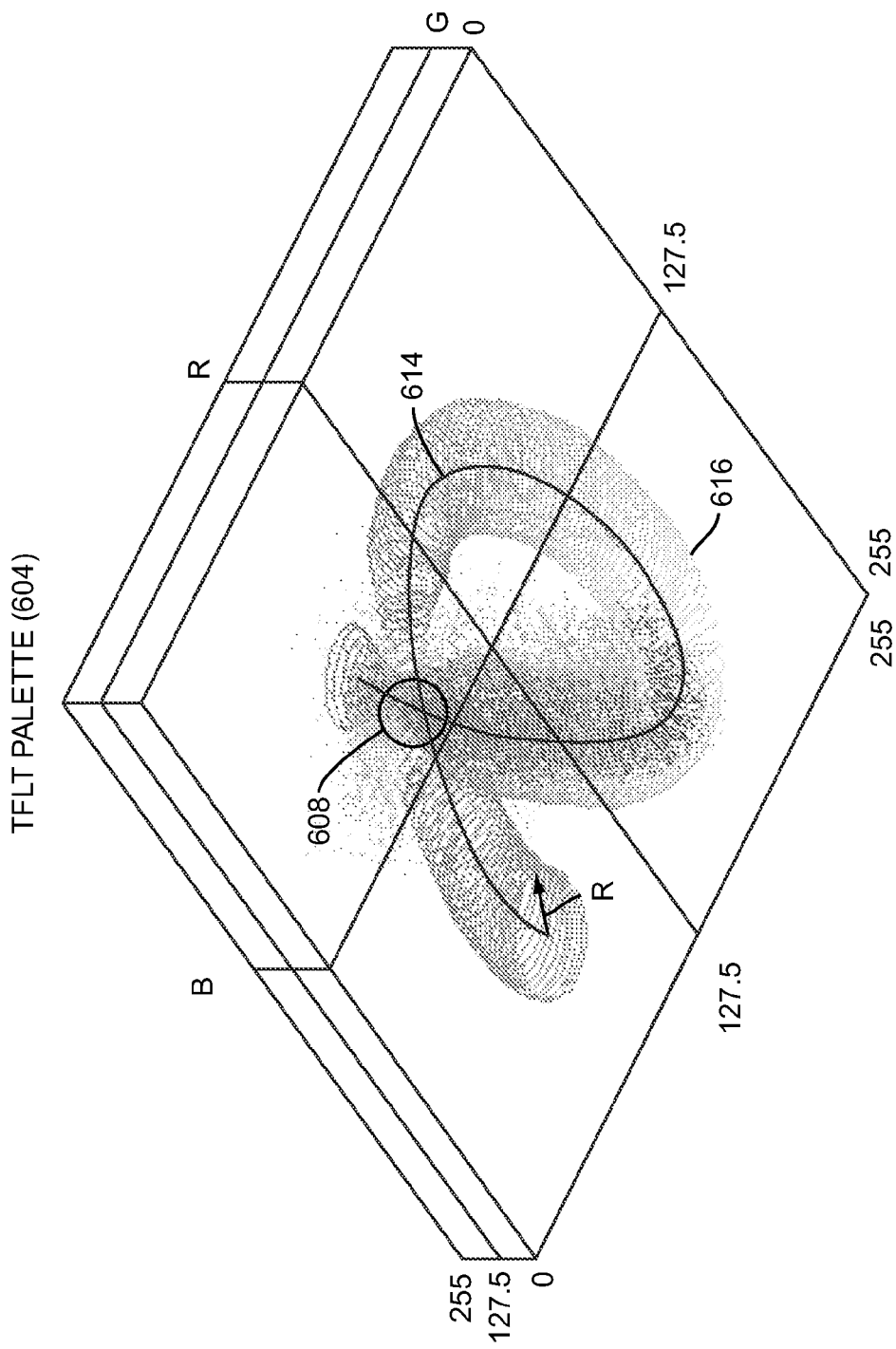
FIG. 46 illustrates the TFLT palette curve of FIG. 45 with an acceptable distance to palette (ADP) filter shown to determine tear film pixel values having RGB values that correspond to ambiguous LLTs.

In this regard, FIG. 46 illustrates the TFLT palette locus 614 in FIG. 45, but with a circle of radius R swept along the path of the TFLT palette locus 614 in a cylinder or pipe 616 of radius R. Radius R is the acceptable distance to palette (ADP), which can be configured in the control system 340. When visualized as a swept volume inside the cylinder or pipe 616, RGB values of tear film image pixels that fall within those intersecting volumes may be considered ambiguous and thus not used in calculating TFLT, including the average TFLT. The smaller the ADP is set, the more poorly matching tear film image pixels that may be excluded in TFLT measurement, but less pixels are available for use in calculation of TFLT. The larger the ADP is set, the less tear film image pixels that may be excluded in TFLT measurement, but it is more possible that incorrect LLTs are included in the TFLT measurement. The ADP can be set to any value desired. Thus, the ADP acts effectively as a filter to filter out RGB values for tear film images that are deemed a poor match and those that may be ambiguous according to the ADP setting. This filtering can be included in the post-processing system 362 in FIG. 36, as an example, and in step 546 therein, as an example.

Graphical User Interface (GUI)

Figure 47:
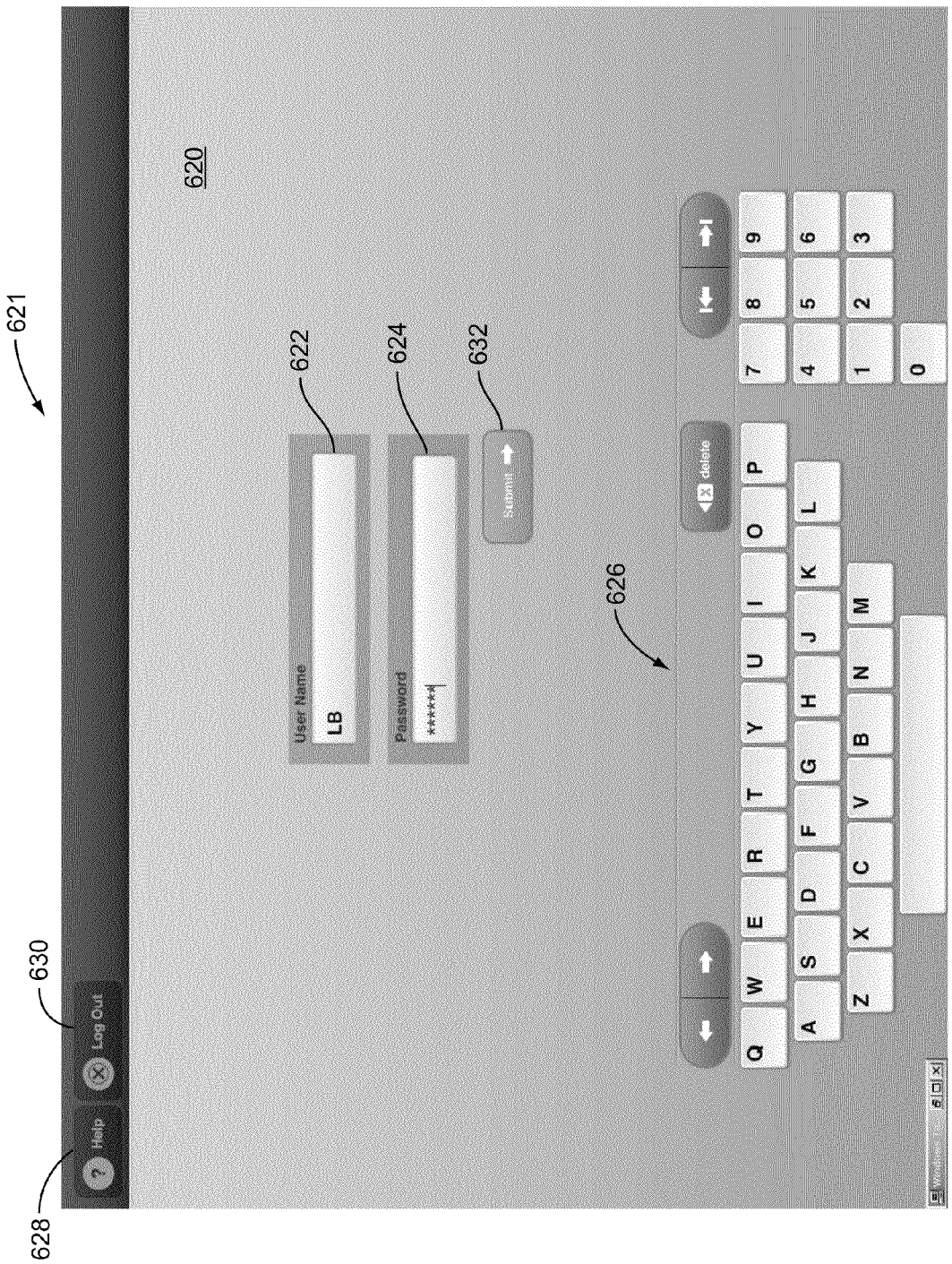
FIG. 47 is an exemplary login screen to a user interface system for controlling and accessing the OSI devices of FIGS. 6A, 6B, 12, 13, 14A, 14B, 19A, 19B, 21A, 21B, 23A, 23B, 24A, and 24B.

In order to operate the OSI device 170, a user interface program may be provided in the user interface system 378 (see FIG. 25A) that drives various graphical user interface (GUI) screens on the display 174 of the OSI device 170 in addition to the GUI utility 380 of FIG. 27 to allow access to the OSI device 170. Some examples of control and accesses have been previously described above. Examples of these GUI screens from this GUI are illustrated in FIGS. 44-48 and described below. The GUI screens allow access to the control system 340 in the OSI device 170 and to features provided therein. As illustrated in FIG. 47, a login GUI screen 620 is illustrated. The login GUI screen 620 may be provided in the form of a GUI window 621 that is initiated when a program is executed. The login GUI screen 620 allows a clinician or other user to log into the OSI device 170. The OSI device 170 may have protected access such that one must have an authorized user name and password to gain access. This may be provided to comply with medical records and privacy protection laws. As illustrated therein, a user can enter their user name in a user name text box 622 and a corresponding password in the password text box 624. A touch or virtual keyboard 626 may be provided to allow alphanumeric entry. To gain access to help or to log out, the user can select the help and log out tabs 628, 630, which may remain resident and available on any of the GUI screens. After the user is ready to login, the user can select the submit button 632. The user name and password entered in the user name text box 622 and the password text box 624 are verified against permissible users in a user database stored in the disk memory 368 in the OSI device 170 (see FIG. 25A).

Figure 48:
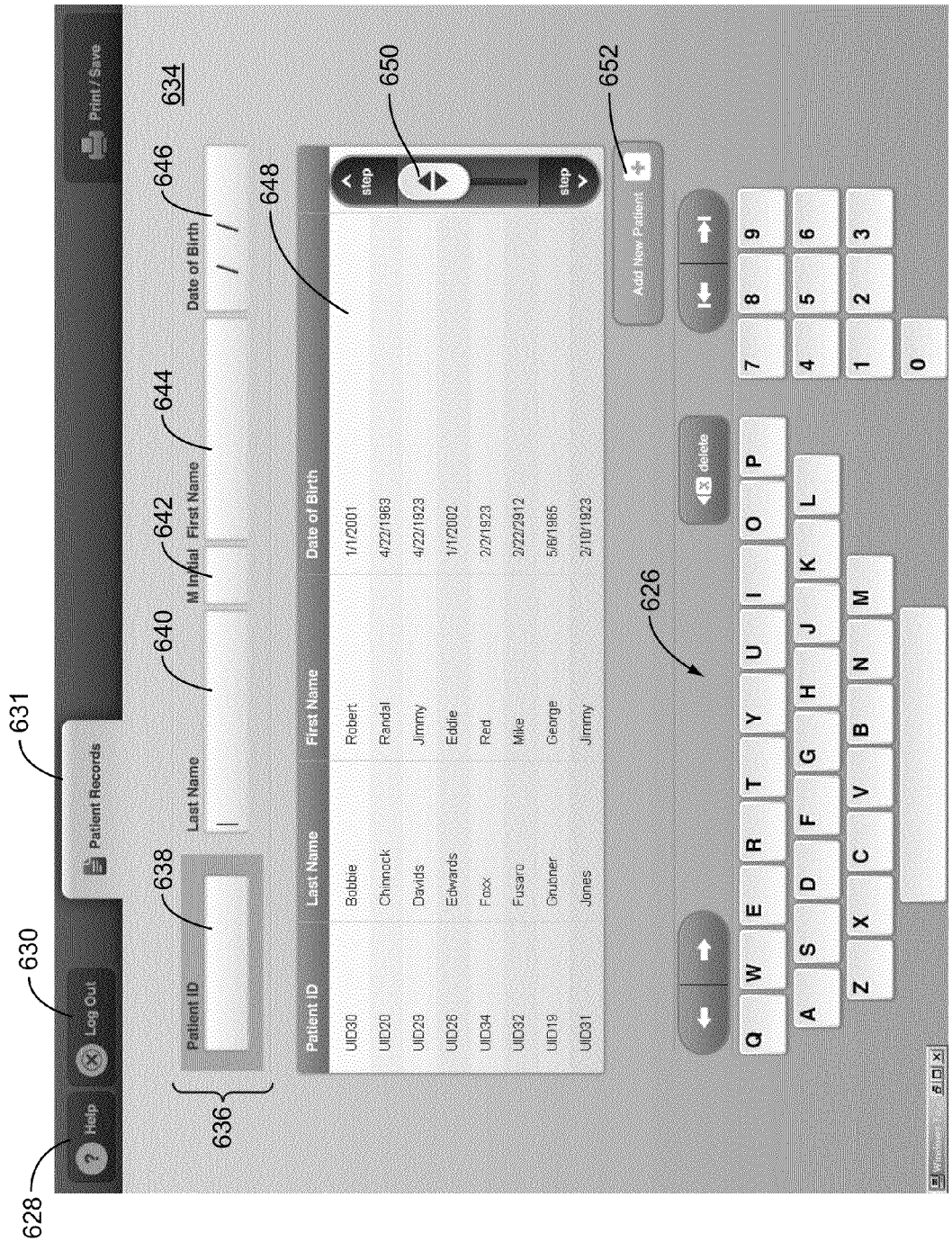
FIG. 48 illustrates an exemplary interface screen for accessing a patient database interface in the OSI devices of FIGS. 6A, 6B, 12, 13, 14A, 14B, 19A, 19B, 21A, 21B, 23A, 23B, 24A, and 24B.

If a user successfully logs into the OSI device 170, a patient GUI screen 634 appears on the display 174 with the patient records tab 631 selected, as illustrated in FIG. 48. The patient GUI screen 634 allows a user to either create a new patient or to access an existing patient. A new patient or patient search information can be entered into any of the various patient text boxes 636 that correspond to patient fields in a patient database. Again, the information can be entered through the virtual keyboard 626, facilitated with a mouse pointing device (not shown), a joystick, or with a touch screen covering on the display 174. These include a patient ID text box 638, patient last name text box 640, patient middle initial text box 642, a patient first name text box 644, and a date of birth text box 646. This data can be entered for a new patient, or used to search a patient database on the disk memory 368 (see FIG. 25A) to access an existing patient's records. The OSI device 170 may contain disk memory 368 with enough storage capability to store information and tear film images regarding a number of patients. Further, the OSI device 170 may be configured to store patient information outside of the OSI device 170 on a separate local memory storage device or remotely. If the patient data added in the patient text boxes 636 is for a new patient, the user can select the add new patient button 652 to add the new patient to the patient database. The patients in the patient database can also be reviewed in a scroll box 648. A scroll control 650 allows up and down scrolling of the patient database records. The patient database records are shown as being sorted by last name, but may be sortable by any of the patient fields in the patient database.

Figure 49:
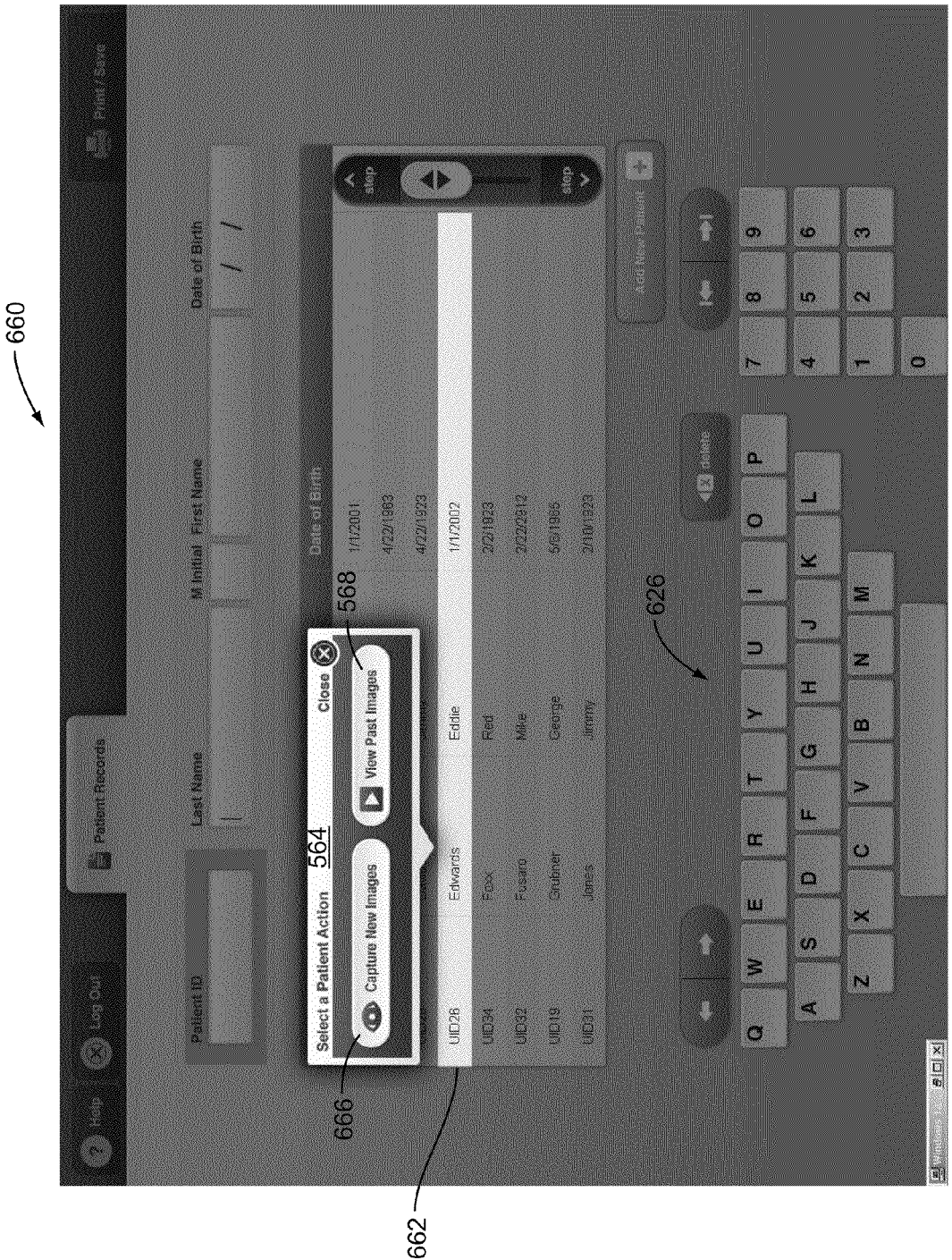
FIG. 49 illustrates a patient action control box for selecting to either capture new tear film images of a patient in the patient database or view past captured images of the patient from the OSI devices of FIGS. 6A, 6B, 12, 13, 14A, 14B, 19A, 19B, 21A, 21B, 23A, 23B, 24A, and 24B.
Figure 50:
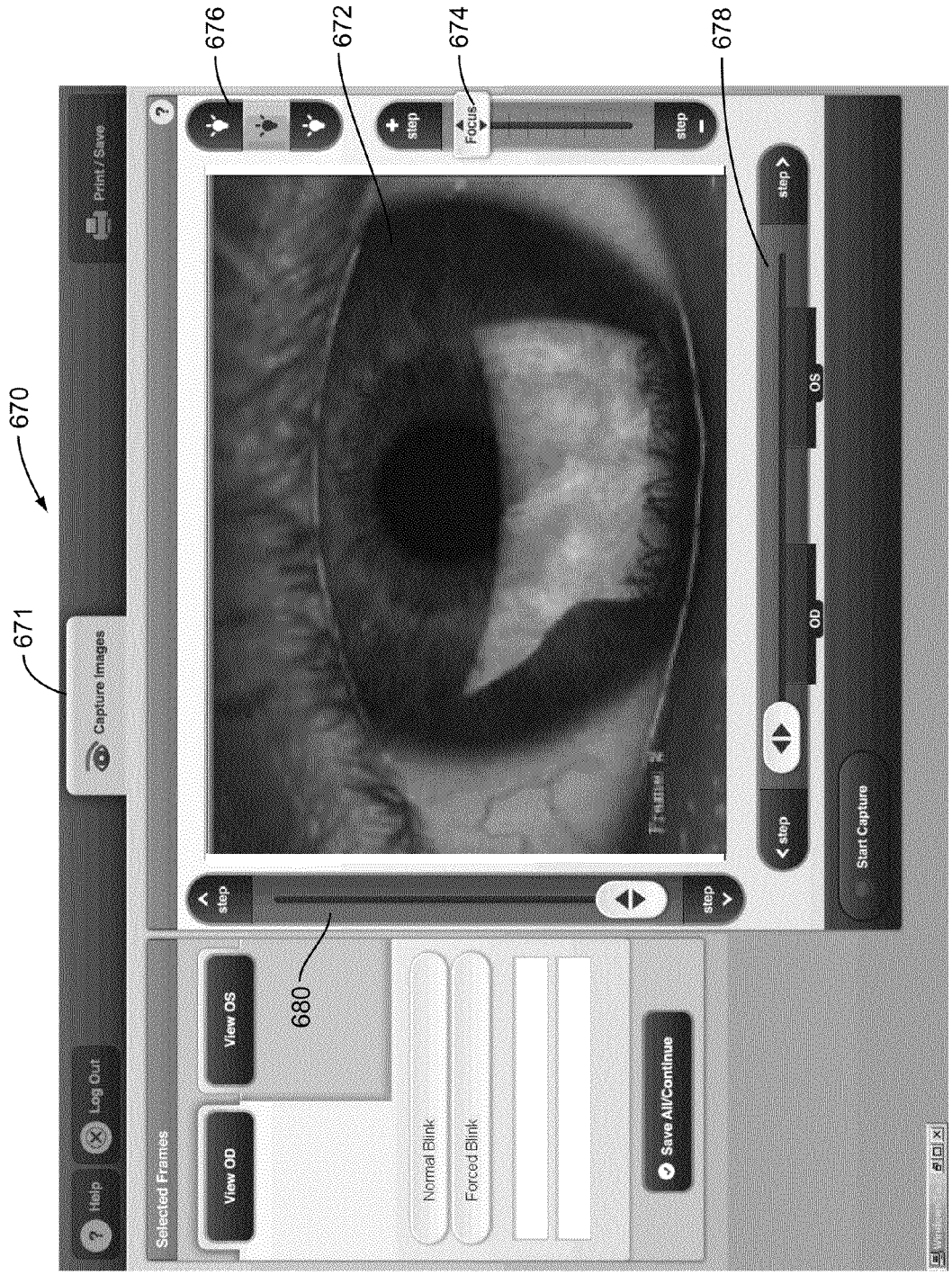
FIG. 50 illustrates a viewing interface for viewing a patient's tear film either captured in real-time or previously captured by the OSI devices of FIGS. 6A, 6B, 12, 13, 14A, 14B, 19A, 19B, 21A, 21B, 23A, 23B, 24A, and 24B.

If a patient is selected in the scroll box 648, which may be an existing or just newly added patient, as illustrated in the GUI screen 660 in FIG. 49, the user is provided with an option to either capture new tear film images of the selected patient or to view past images, if past tear film images are stored for the selected patient on disk memory 368. In this regard, the selected patient is highlighted 662 in the patient scroll box 648, and a select patient action pop-up box 664 is displayed. The user can either select the capture new images button 666 or the view past images button 668. If the capture new images button 666 is selected, the capture images GUI 670 is displayed to the user under the capture images tab 671 on the display 174, which is illustrated in FIG. 50. As illustrated therein, a patient eye image viewing area 672 is provided, which is providing images of the patient's eye and tear film obtained by the video camera 198 in the OSI device 170. In this example, the image is of an overlay of the subtracted first and second pattern images of the patient's tear film onto the raw image of the patient's eye and tear film, as previously discussed. The focus of the image can be adjusted via a focus control 674. The brightness level of the image in the viewing area 672 is controlled via a brightness control 676. The user can control the position of the video camera 198 to align the camera lens with the tear film of interest whether the lens is aligned with the patient's left or right eye via an eye selection control 678. Each frame of the patient's eye captured by the video camera 198 can be stepped via a stepping control 680. Optionally, or in addition, a joystick may be provided in the OSI device 170 to allow control of the video camera 198.

Figure 51:
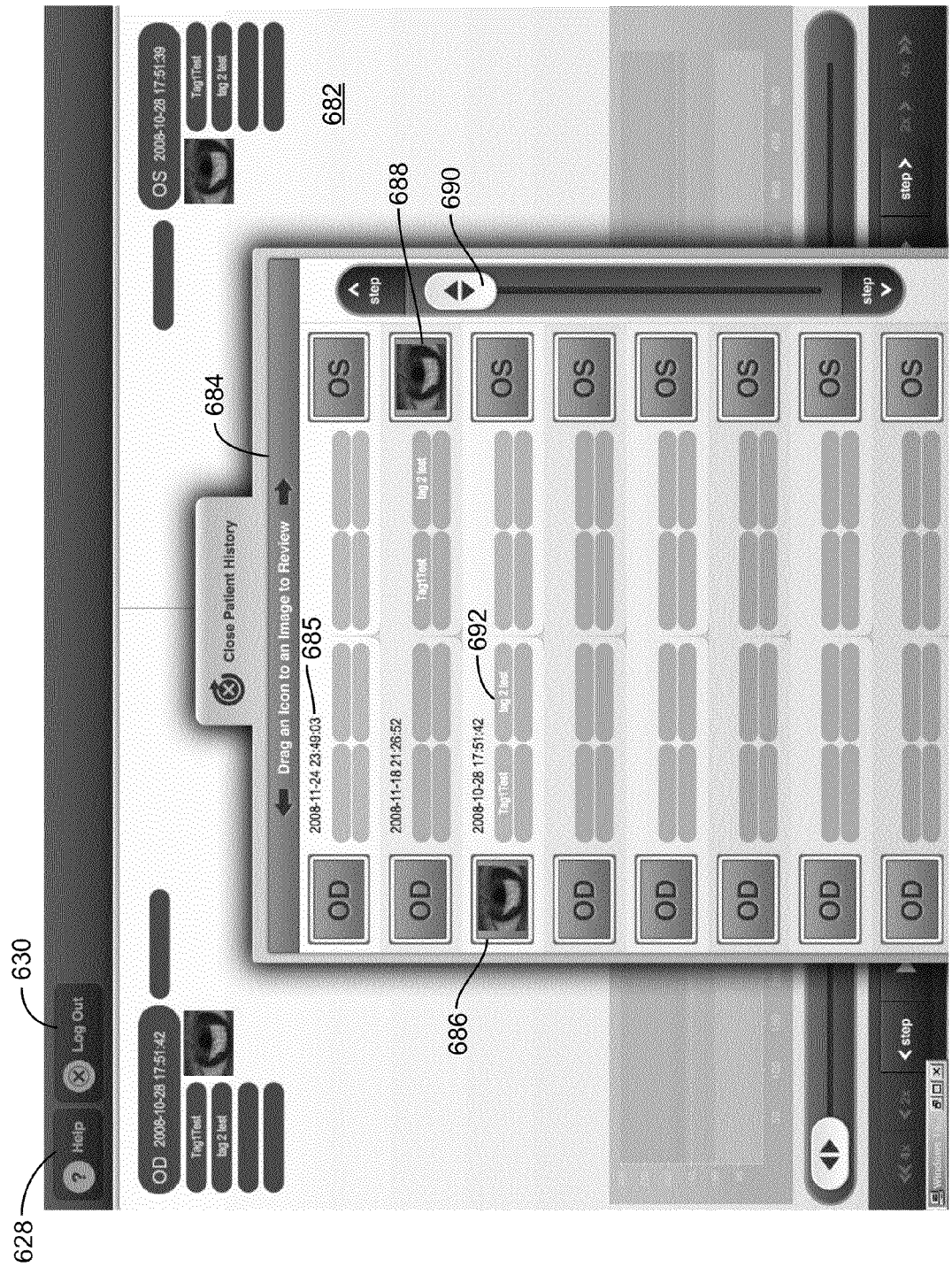
FIG. 51 illustrates a tear film image database for a patient.

The stored images of the patient's eye and tear film can also be accessed from a patient history database stored in disk memory 368. FIG. 51 illustrates a patient history GUI screen 682 that shows a pop-up window 684 showing historical entries for a given patient. For each tear film imaging, a time and date stamp 685 is provided. The images of a patient's left and right eye can be shown in thumbnail views 686, 688 for ease in selection by a user. The stored images can be scrolled up and down in the pop-up window 684 via a step scroll bar 690. Label names in tag boxes 692 can also be associated with the images. Once a desired image is selected for display, the user can select the image to display the image in larger view in the capture images GUI 670 in FIG. 50. Further, two tear film images of a patient can be simultaneously displayed from any current or prior examinations for a single patient, as illustrated in FIG. 52.

Figure 52:
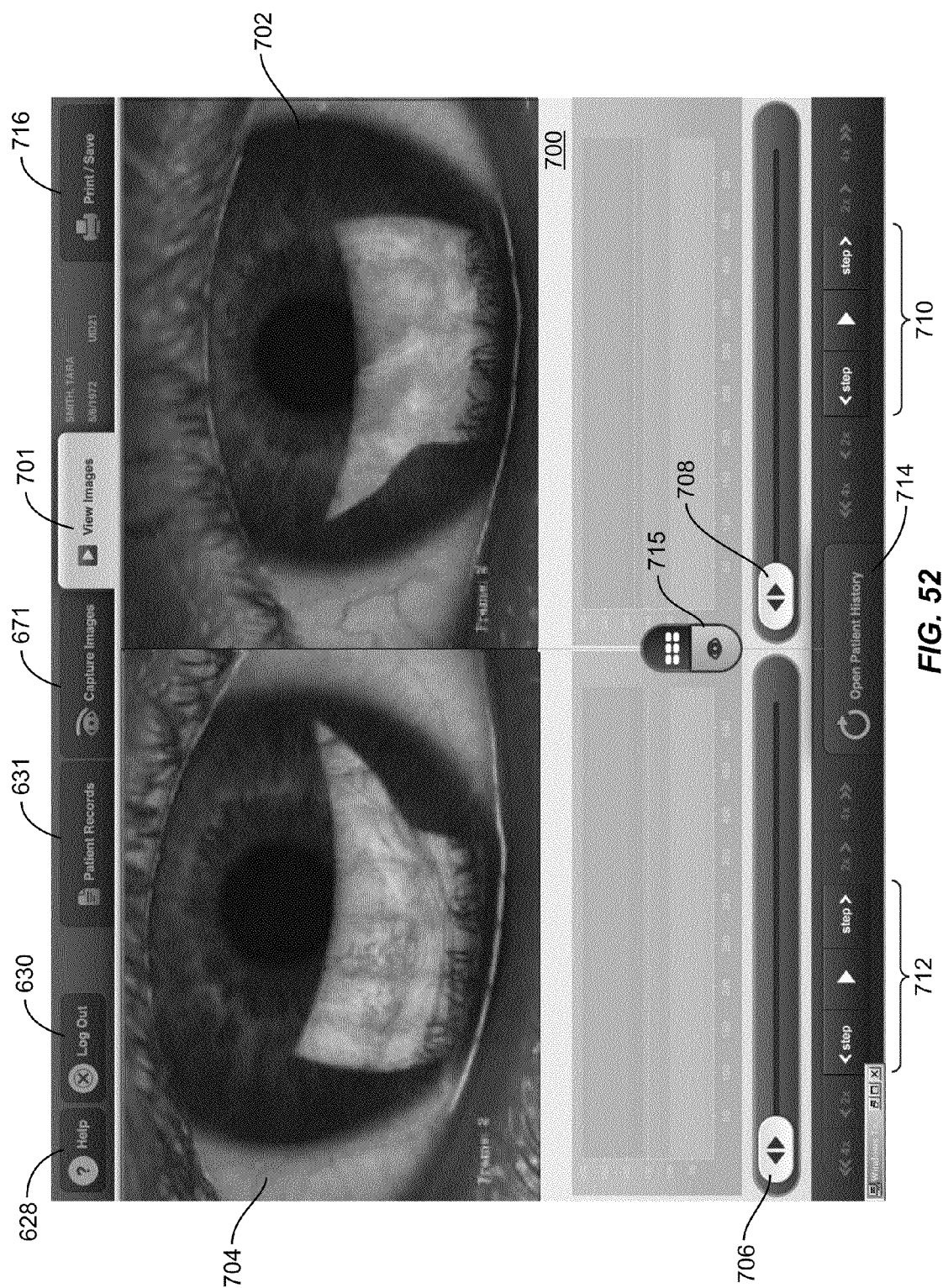
FIG. 52 illustrates a view images GUI screen showing an overlaid image of interference interactions of the interference signals from specularly reflected light from a patient's tear film overtop an image of the patient's eye for both the patient's left and right eyes side by side.
Figure 53:
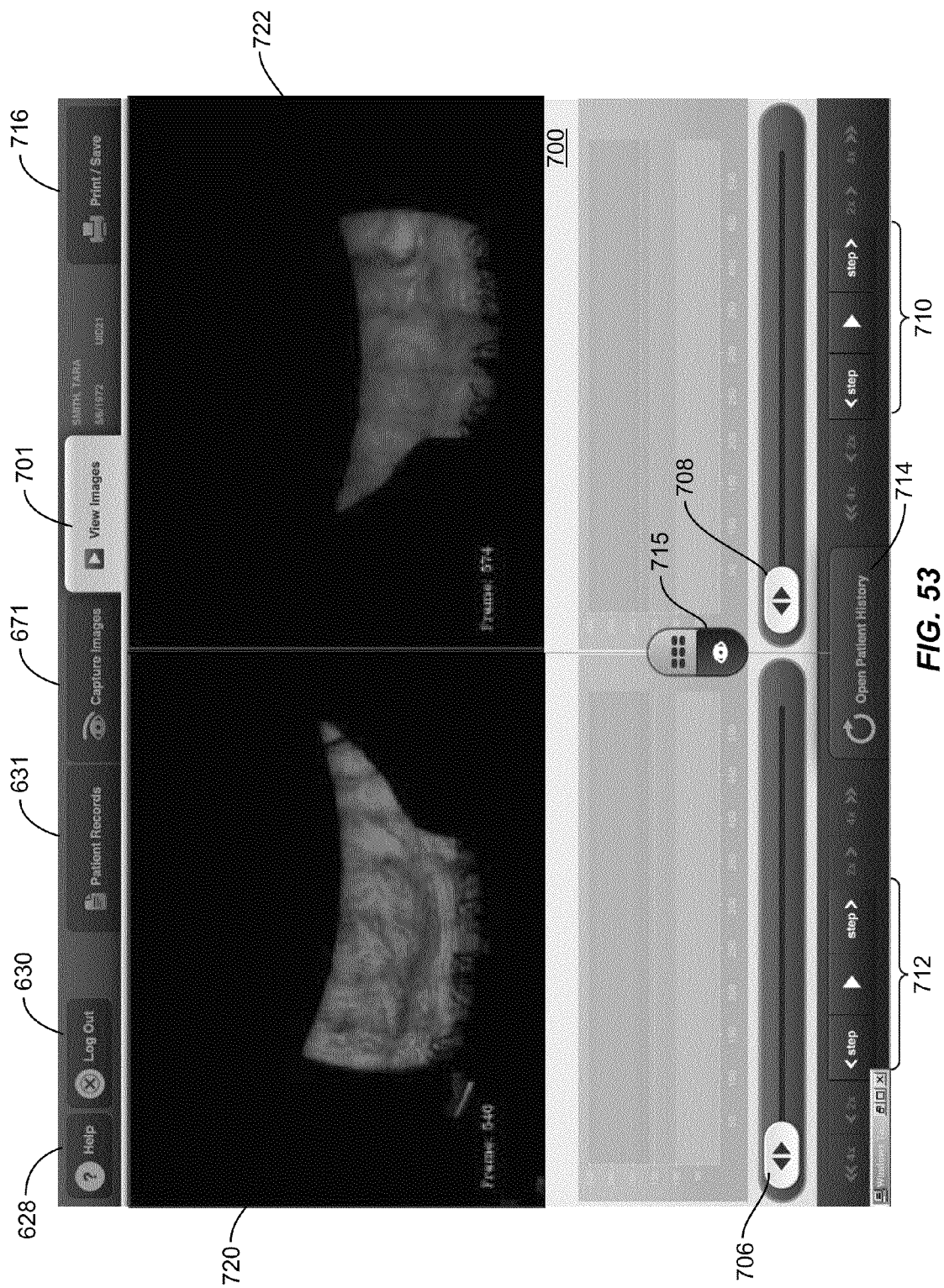
FIG. 53 illustrates the GUI screen of FIG. 52 with the images of the patient's eye toggled to show only the interference interactions of the interference signals from specularly reflected light from a patient's tear film.

As illustrated in FIG. 52, a view images GUI screen 700 is shown, wherein a user has selected a view images tab 701 to display images of a patient's ocular tear film. In this view images GUI screen 700, both images of the patient's left eye 702 and right eye 704 are illustrated side by side. In this example, the images 702, 704 are overlays of the subtracted first and second pattern images of the patients tear film onto the raw image of the patient's tear eye and tear film, as previously discussed. Scroll buttons 706, 708 can be selected to move a desired image among the video of images of the patient's eye for display in the view images GUI screen 700. Further, step and play controls 710, 712 allow the user to control playing a stored video of the patient's tear film images and stepping through the patient's tear film images one at a time, if desired. The user can also select an open patient history tab 714 to review information stored regarding the patient's history, which may aid in analysis and determining whether the patient's tear film has improved or degraded. A toggle button 715 can be selected by the user to switch the images 702, 704 from the overlay view to just the images 720, 722, of the resulting interference interactions of specularly reflected light from the patient's tear films, as illustrated in FIG. 53. As illustrated in FIG. 53, only the resulting interference interactions from the patient's tear film are illustrated. The user may select this option if it is desired to concentrate the visual examination of the patient's tear film solely to the interference interactions.

Figure 54:
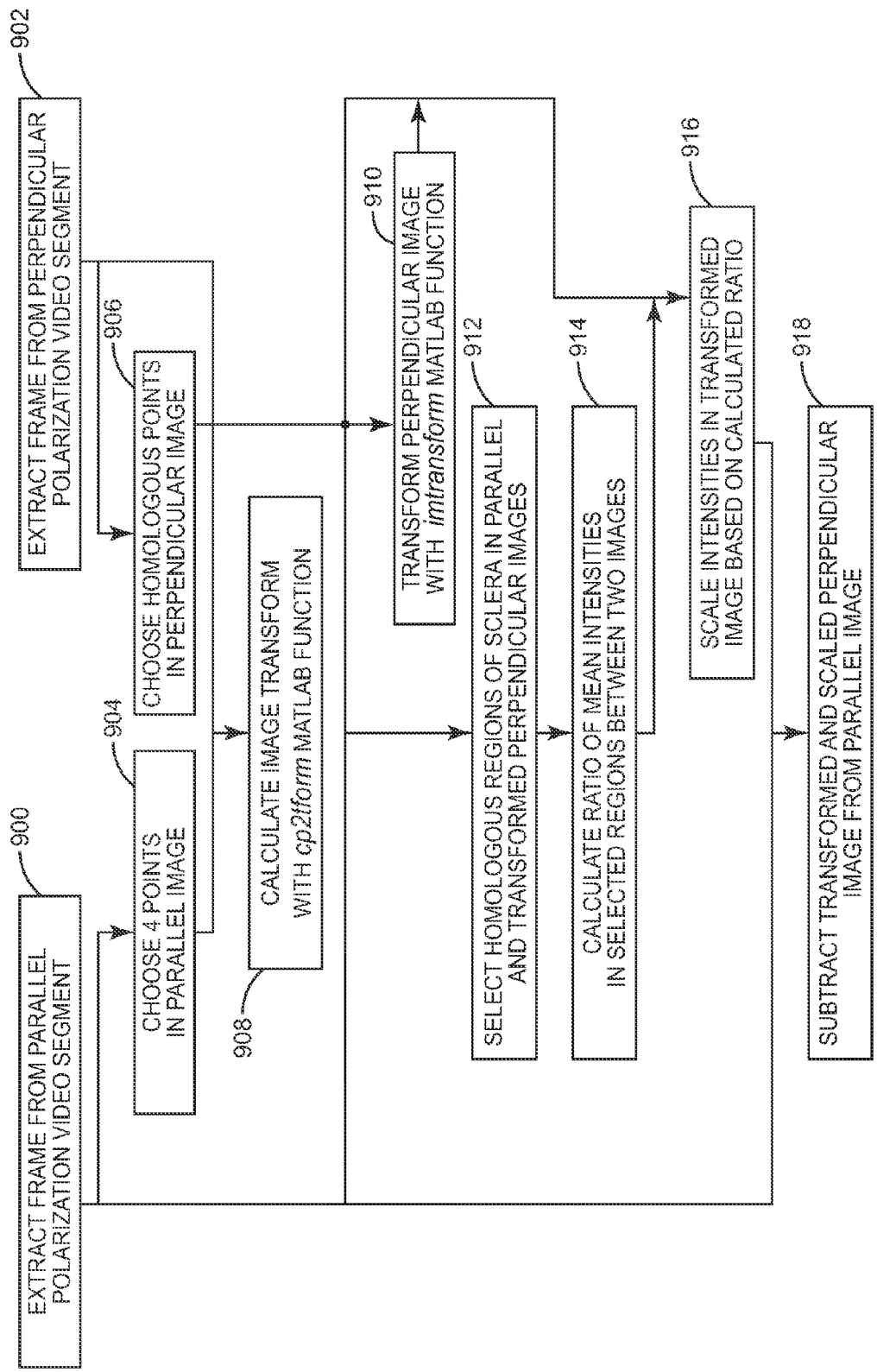
FIG. 54 is a flow chart that illustrates step-by-step processing of a polarization subtraction technique of the present disclosure.
Figure 55A:
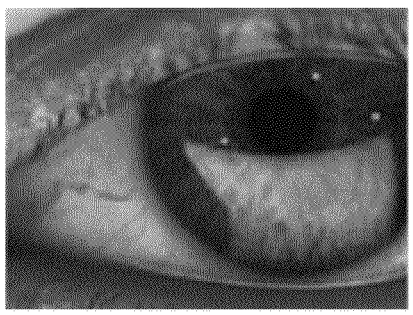
FIGS. 55A-F are examples of the images selected to implement the step-by-step processing of FIG. 54.
Figure 55B:
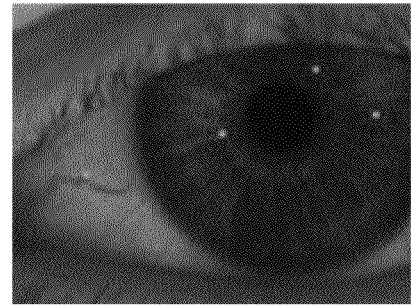

In yet another embodiment, a polarization subtraction algorithm improves isolation of a tear film interference pattern from a background signal. FIG. 54 is a flow chart that illustrates step-by-step computerized processing of the polarization subtraction algorithm of the present disclosure. A first image frame shown in FIG. 55A is automatically extracted from a polarization video segment (block 900). A second image frame shown in FIG. 55B is automatically extracted from a perpendicular polarization video segment (block 902). The polarization subtraction algorithm automatically then selects a plurality of points (e.g., pixels) within the first image frame (block 904). In the exemplary case of FIG. 55A, four selected points are highlighted in green. Next, the polarization subtraction algorithm automatically selects homologous points. The homologous points are highlighted in green in the second image frame shown in FIG. 55B.

Once the homologous points are selected, an imaging processing tool invoked by the polarization subtraction algorithm uses pairs of the plurality of points and pairs of the homologous points to calculate a spatial transformation (block 904). For example, this processing step could be performed using the Matlab® function "cp2tform." After the spatial transformation has been calculated, the polarization subtraction algorithm transforms the second image frame by invoking an imaging processing tool that transforms the second image in accordance with the previously calculated spatial transformation (block 910). In this case, the process of block (910) could be performed using the Matlab® function "imtransform." FIG. 55C illustrates the resulting transformation of the second image frame.

Figure 55C:
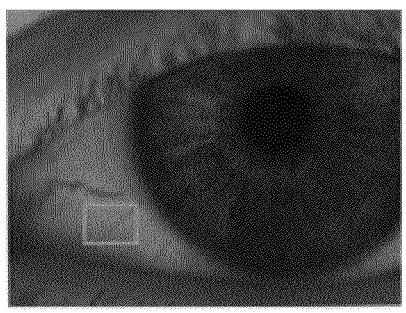
Figure 55D:
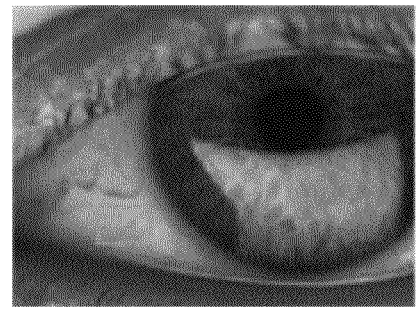

Next, the polarization subtraction algorithm automatically selects homologous regions of a sclera captured in the transformed first image frame shown in FIG. 55C and the first image frame shown in FIG. 55D (block 912). Once the homologous regions are selected, the polarization subtraction algorithm automatically calculates a ratio of mean intensities in the selected homologous regions between the first image frame and the second image frame is calculated (block 914).

Figure 55E:
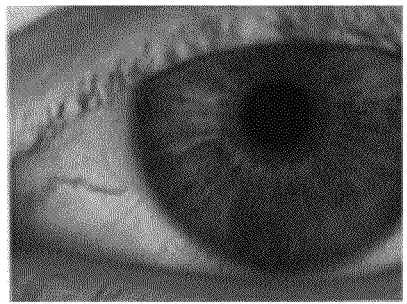
Figure 55F:
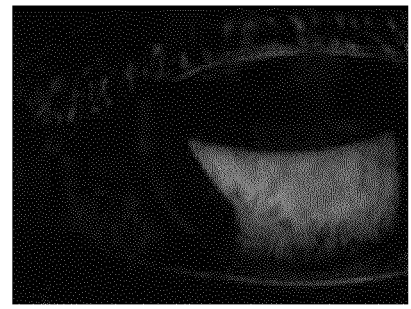

Next, based on the calculated intensity ratio, the intensities in the second image frame are scaled automatically by the polarization subtraction algorithm (block 916). FIG. 55E shows an example of a resulting transformed and intensity scaled second image frame. At this point, the polarizer subtraction algorithm subtracts the transformed and intensity scaled second image frame from the first image frame, which results in a polarization subtraction image such as the polarization subtraction image shown in FIG. 55FF.

Many modifications and other embodiments of the present disclosure set forth herein will come to mind to one skilled in the art to which the disclosure pertains having the benefit of the teachings presented in the foregoing descriptions and the associated drawings. These modifications include, but are not limited to, the type of light source or illuminator, the number of polarizers, the type of imaging device, image device settings, the relationship between the illuminator and an imaging device, the control system, the type of tear film interference model, and the type of electronics or software employed therein, the display, the data storage associated with the OSI device for storing information, which may also be stored separately in a local or remotely located remote server or database from the OSI device, any input or output devices, settings, including pre-processing and post-processing settings. Note that subtracting the second image from the first image as disclosed herein includes combining the first and second images, wherein like signals present in the first and second images are cancelled when combined. Further, the present disclosure is not limited to illumination of any particular area on the patient's tear film or use of any particular color value representation scheme.

Therefore, it is to be understood that the present disclosure is not to be limited to the specific embodiments disclosed and that modifications and other embodiments are intended to be included within the scope of the appended claims. It is intended that the present disclosure cover the modifications and variations of this disclosure provided they come within the scope of the appended claims and their equivalents. Although specific terms are employed herein, they are used in a generic and descriptive sense only and not for purposes of limitation.

What is claimed is:

1. An apparatus for imaging an ocular tear film, comprising:
   a control system configured to:
   (a) receive at least one first image containing optical wave interference of specularly reflected light in a first polarization plane along with a background signal from a region of interest (ROI) of an ocular tear film captured by an imaging device while illuminated by a multi-wavelength light source;
   (b) receive at least one second image containing only the background signal in a second polarization plane perpendicular or substantially perpendicular to the first polarization plane from the ROI of the ocular tear film captured by an imaging device;
   (c) subtract the at least one second image from the at least one first image to generate at least one resulting image containing the optical wave interference of specularly reflected light from the ROI of the ocular tear film with the background signal removed or reduced.

2. The apparatus of claim 1, further comprising an imaging device configured to capture the at least one first image and capture the at least one second image.

3. The apparatus of claim 2, further comprising a polarizer disposed in an imaging path of the imaging device,
   wherein the polarizer has a center axis and is selectively rotatable about the center axis to provide a first polarization axis relative to the first polarization plane of the specularly reflected light from the ROI of the ocular tear film during a capture of the at least one first image, and wherein the polarizer is selectively rotatable to provide a second polarization axis that is perpendicular or substantially perpendicular relative to the first polarization axis during the capture of the at least one second image.

4. The apparatus of claim 2, further comprising a rotatable wheel having a first polarizer and second polarizer, the rotatable wheel selectively rotatable such that the first polarizer is disposed in an imaging path of the imaging device during the capture of the at least one first image, and wherein the second polarizer is alternately disposed in the imaging path of the imaging device during the capture of the at least one second image.

5. The apparatus of claim 4, wherein the first polarizer has a first polarization axis that is parallel or substantially parallel to the first polarization plane of the specularly reflected light from the ROI of the ocular tear film to pass or substantially pass the specularly reflected light to the imaging device while reducing the background signal.

6. The apparatus of claim 4, wherein the second polarizer has a second polarization axis that is perpendicular or substantially perpendicular to the second polarization plane of the specularly reflected light from the ROI of the ocular tear film to reduce or eliminate the specularly reflected light while passing a portion of the background signal to the imaging device.

7. The apparatus of claim 4, wherein the first polarizer has a first polarization axis that is parallel or substantially parallel to the polarization plane of the specularly reflected light from the ROI of the ocular tear film to pass or substantially pass the specularly reflected light to the imaging device while reducing the background signal, and
wherein the second polarizer has a second polarization axis that is perpendicular or substantially perpendicular to the polarization plane of the specularly reflected light from the ROI of the ocular tear film to eliminate or substantially eliminate the specularly reflected light while passing a portion of background signal to the imaging device.

8. The apparatus of claim 2, further comprising:
a first polarizer selectively disposable in an imaging path of the imaging device during a capture of the at least one first image; and
a second polarizer selectively disposable in the imaging path of the imaging device during the capture of the at least one second image.

9. The apparatus of claim 8, wherein the first polarizer has a first polarization axis that is parallel or substantially parallel to the first polarization plane of the specularly reflected light from the ROI of the ocular tear film to pass or substantially pass the specularly reflected light to the imaging device while reducing the background signal before the background signal reaches the imaging device.

10. The apparatus of claim 8, wherein the second polarizer has a second polarization axis that is perpendicular or substantially perpendicular to the second polarization plane of the specularly reflected light from the ROI of the ocular tear film to reduce or eliminate the specularly reflected light before the specularly reflected light reaches the imaging device while passing a portion of the background signal.

11. The apparatus of claim 8, further comprising:
a first polarizer selectively disposed in the imaging path of the imaging device,
wherein the first polarizer has a polarization axis that is parallel or substantially parallel to the first polarization plane of the specularly reflected light from the ROI of the ocular tear film to pass or substantially pass the specularly reflected light to the imaging device while reducing the background signal before the background signal reaches the imaging device; and
a second polarizer alternately disposed in the imaging path of the imaging device,
wherein the second polarizer has a polarization axis that is perpendicular or substantially perpendicular to the second polarization plane of the specularly reflected light from the ROI of the ocular tear film to reduce or eliminate the specularly reflected light while passing a portion of background signal to the imaging device.

12. The apparatus of claim 8, wherein the first polarizer and the second polarizer are alternately translatable into the imaging path of the imaging device.

13. The apparatus of claim 8, wherein the first polarizer and the second polarizer are alternately rotatable into the imaging path of the imaging device.

14. The apparatus of claim 1, further comprising a first imaging device configured to capture the at least one first image, and a second imaging device configured to capture the at least one second image.

15. The apparatus of claim 14, further comprising a non-polarizing beam splitter configured to direct a first portion of the specularly reflected light including the background signal to the first imaging device while simultaneously directing a second portion of the specularly reflected light including the background signal to the second imaging device.

16. The apparatus of claim 15, further comprising a first polarizer disposed in an imaging path of the first imaging device during a capture of the at least one first image.

17. The apparatus of claim 16, wherein the first polarizer has a first polarization axis parallel or substantially parallel to the first polarization plane of the specularly reflected light directed to the imaging device from the ROI of the ocular tear film to pass or substantially pass the specularly reflected light to the first imaging device while reducing the background signal before the background signal reaches the first imaging device.

18. The apparatus of claim 15, further comprising a second polarizer disposed in an imaging path of the second imaging device during a capture of the at least one second image.

19. The apparatus of claim 18, wherein the second polarizer has a second polarization axis perpendicular or substantially perpendicular to the second polarization plane of the specularly reflected light from the ROI of the ocular tear film to reduce or eliminate the specularly reflected light before the specularly reflected light reaches the second imaging device while passing a portion of the background signal to the second imaging device.

20. The apparatus of claim 15, further comprising:
a first polarizer disposed in an imaging path of the first imaging device,
wherein the first polarizer has a first polarization axis that is parallel or substantially parallel to the first polarization plane of the specularly reflected light from the ROI of the ocular tear film to pass or substantially pass the specularly reflected light to the first imaging device while reducing the background signal; and
a second polarizer disposed in the imaging path of the second imaging device,
wherein the second polarizer has a second polarization axis that is perpendicular or substantially perpendicular to the polarization plane of the specularly reflected light from the ROI of the ocular tear film to reduce or eliminate the specularly reflected light while passing a portion of background signal to the second imaging device.

21. The apparatus of claim 14, further comprising a polarizing beam splitter configured to direct a portion of the specularly reflected light and the background signal to the first imaging device while simultaneously directing the background signal to the second imaging device reducing or eliminating the specularly reflected light.

22. The apparatus of claim 1, further comprising a polarizer disposed in an illumination path of the multi-wavelength light source and configured to polarize light emitted from the multi-wavelength light source illuminating the ROI of the ocular tear film.

23. The apparatus of claim 22, wherein the polarizer is a circular polarizer.

24. The apparatus of claim 1, wherein the background signal includes at least one of stray light and ambient light.

25. The apparatus of claim 1, wherein the imaging device is configured to capture the at least one second image when the multi-wavelength light source is illuminating the ROI of the ocular tear film.

26. The apparatus of claim 25, wherein the background signal includes diffusely reflected light resulting from illumination of the ocular tear film.

27. The apparatus of claim 26, wherein the background signal includes diffusely reflected light from an iris of an eye.

28. The apparatus of claim 1, wherein the control system is further configured to sequentially control an imaging device to capture the optical wave interference of specularly reflected light and the background signal in the at least one first image to provide a plurality of first images, and capture the background signal in the at least one second image to provide a plurality of second images interleaved with the plurality of first images to provide a plurality of first and second image pairs.

29. The apparatus of claim 28, wherein the control system is configured to subtract the at least one second images from the plurality of first and second image pairs from the corresponding at least one first images from the plurality of first and second image pairs to generate a plurality of resulting images each containing the optical wave interference of specularly reflected light from the ROI of the ocular tear film with the background signal removed or reduced.

30. The apparatus of claim 1, wherein the multi-wavelength light source is comprised of a multi-wavelength Lambertian light source configured to uniformly or substantially uniformly illuminate the ROI of the ocular tear film.

31. The apparatus of claim 1, wherein the control system is further configured to display at least one of the at least one first image, the at least one second image, or the at least one resulting image on a visual display.

32. A method of imaging an ocular tear film, comprising:
   illuminating a region of interest (ROI) of an ocular tear film with a multi-wavelength light source;
   capturing optical wave interference of specularly reflected light in a first polarization plane including a background signal from the ROI of the ocular tear film while illuminated by the multi-wavelength light source in at least one first image by an imaging device;
   capturing only the background signal in a second polarizing plane perpendicular or substantially perpendicular to the first polarization plane from the ROI of the ocular tear film in at least one second image by an imaging device; and
   subtracting the at least one second image from the at least one first image to generate at least one resulting image containing the optical wave interference of specularly reflected light from the ROI of the ocular tear film with the background signal removed or reduced.

* * * * *